(12) United States Patent
Mackernan

(10) Patent No.: US 11,428,687 B2
(45) Date of Patent: *Aug. 30, 2022

(54) MOLECULAR SENSORS

(71) Applicant: University College Dublin, National University of Ireland, Dublin, Dublin (IE)

(72) Inventor: Donal Mackernan, Dublin (IE)

(73) Assignee: University College Dublin, National University of Ireland, Dublin, Belfield (IE)

( * ) Notice: Subject to any disclaimer, the term of this patent is extended or adjusted under 35 U.S.C. 154(b) by 58 days.

This patent is subject to a terminal disclaimer.

(21) Appl. No.: 16/331,327

(22) PCT Filed: Sep. 8, 2017

(86) PCT No.: PCT/IB2017/055432
§ 371 (c)(1),
(2) Date: Mar. 7, 2019

(87) PCT Pub. No.: WO2018/047110
PCT Pub. Date: Mar. 15, 2018

(65) Prior Publication Data
US 2019/0227057 A1    Jul. 25, 2019

(30) Foreign Application Priority Data
Sep. 8, 2016 (GB) .................... 1615296

(51) Int. Cl.
*G01N 33/542* (2006.01)
*G01N 21/64* (2006.01)
(Continued)

(52) U.S. Cl.
CPC ....... *G01N 33/542* (2013.01); *G01N 21/6428* (2013.01); *G01N 33/5308* (2013.01); *G01N 33/582* (2013.01); *G01N 2021/6439* (2013.01)

(58) Field of Classification Search
CPC ............ G01N 33/542; G01N 21/6428; G01N 33/5308; G01N 33/582
See application file for complete search history.

(56) References Cited

FOREIGN PATENT DOCUMENTS

| WO | WO2008020823 A2 | 2/2008 |
| WO | WO2013155553 A1 | 10/2013 |
| WO | WO2016139643 A2 | 9/2016 |

OTHER PUBLICATIONS

Sanyal et al. (I) Mol. Biosyt. 2016 vol. 12, p. 2988-2991 "How Flexible is a Protein: Simple Estimates Using FRET Microscopy" (Year: 2016).*

(Continued)

*Primary Examiner* — Changhwa J Cheu
(74) *Attorney, Agent, or Firm* — Lee & Hayes, P.C.

(57) ABSTRACT

The invention relates to a sensor molecule for detecting a target molecule comprising: (a) a rod-like molecule L and a rod-like molecule R connected to each other by a joint molecule C to form a hinge; (b) a target binding molecule A bonded to the end of rod-like molecule L opposite to the joint molecule C; (c) a binding molecule A' bonded to the end of rod-like molecule R opposite the joint molecule C; wherein the target binding molecule A is arranged to bind to an epitope or nucleic acid sequence of the target molecule to be detected, and binding molecule A' is arranged to bind to the same epitope or same nucleic acid sequence, or portion thereof of the target molecule as target binding molecule A; and wherein the hinge is biased into an open position, such that target binding molecule A and binding molecule A' are biased apart by the hinge. The invention also relates to analyte dependent activation of pharmaceuticals and chemotoxins.

21 Claims, 25 Drawing Sheets

Specification includes a Sequence Listing.

(51) Int. Cl.
  *G01N 33/53* (2006.01)
  *G01N 33/58* (2006.01)

(56) References Cited

OTHER PUBLICATIONS

Sanyal et al. (II) J. Phys. Conf. Ser. 2015 vol. 640, p. 1-6 "Multiscale Modelling of UniMolecular FRET Probes Using Monte Carlo Simulations". (Year: 2015).*
Lee (Mol. Biol. Rep. 2013 40:3953-3960) (Year: 2013).*
Soleimani (Res Pharm Sci 2016 11:187-199) (Year: 2016).*
Biosciences Biotechnology Asia 2015 12 :725-730) (Year: 2015).*
International search report and written opinion dated Dec. 22, 2017, in International application No. PCT/IB2017/055432, 12 pages.

\* cited by examiner

Loop

MOLECULAR SENSORS

CROSS REFERENCE TO RELATED APPLICATIONS

This application is a U.S. National Phase Application of International Application No. PCT/IB2017/055432, filed Sep. 8, 2017, which claims priority to Great Britain patent Application No. 1615296.9 filed Sep. 8, 2016, which are incorporated herein by reference in their entirety.

Sequence Listing Information

The Sequence Listing associated with this application is provided in text format in lieu of a paper copy and is hereby incorporated by reference into the specification. The name of the text file containing the Sequence Listing is JD85293P.WOP sequence listing_ST25.txt. The text file is 187 KB, was created on Jan. 4, 2022, and is being submitted electronically via EFS-Web.

TECHNICAL FIELD

The invention relates generally to the field of molecular biology, food and health science and metabolomics. More specifically, the invention relates to molecular sensors, such as unimolecular sensors, and methods using intramolecular resonance energy transfer (RET) and fluorescence for detecting the presence of analytes or ligand binding in assays and in vivo, including the use of immunoassays to detect analytes such as antigens and antibodies in the life and environmental sciences and related industries. The invention also relates to analyte dependent activation of pharmaceuticals and chemo-toxins.

BACKGROUND

A variety of genetic biosensors have been developed since the discovery of green fluorescent protein (FP) and its subsequent cloning from the jellyfish *Aequorea victoria*. These biosensors have permitted the investigation of cellular mechanisms using optical microscopy, permitting the tracking of analytes (i.e. cellular proteins and other signalling molecules) within their endogenous environment (as described for example in reference NP1), and in vitro. The FP's when built into appropriate sensors can effectively illuminate the internal workings of the cell. As the sensors are proteins, they can be inserted within the cellular compartments to report on local concentrations of analytes or ligands of interest, which is known as genetic targeting, through "off the shelf" biotechnology kits, provided appropriate sequences of amino-acid residues have been determined, or designed. It is this design step which arguably now has become the most demanding and rewarding, and created, for instance, opportunities to investigate signalling networks in living cells. The range of application of such biosensors includes use as neurotransmitter sensors, in high-throughput screening drug discovery, the observation of turnover of select metabolites at the single cell level in real time, and the visualization of specific macromolecular machines within the cellular environment.

Biosensors can be designed to respond to changes in local analyte concentrations, by changing their internal structures, which in turn can be observed optically, through changes in the fluorescence properties of individual FP's, or changes in the resonance energy transfer (RET) rates between pairs of FP's, termed the donor and acceptor. Sensors designed to exploit RET are particularly capable of providing fine scale spatial and temporal information within cellular compartments. In some cases the light source for these probes is endogenous, coming from naturally bio-luminescent proteins, so called BRET probes. However, most require an external light source, and are termed FRET probes (described generally in references NP2, NP3, NP4).

In each case, the quantum mechanism used is the same. If the donor is in a suitable optically excited state, and if the distance r between it and the other chromophore (the acceptor) is sufficiently close (1-10 nm) (see reference NP5) RET can take place. As RET efficiency typically has an $r^{-6}$ dependence, changes in r can effectively switch RET on and off. It is the nature and design of this molecular and genetically targetable switch that lies at the heart of the success of FRET based microscopy in biology.

The following six representative examples of genetic biosensors devised to monitor/report on local intracellular concentrations serve to explain the context of the present invention, and in particular the problem it addresses and solves.

The first example is provided by the biosensor cameleon-1 (see reference NP6), which was the first genetically encodable $Ca^{2+}$ indicator. It was created by placing a protein composed of the C-terminus of calmodulin (CaM) and the CaM binding peptide M13, between the FRET pair Cyan Fluorescent Protein (CFP) and Green Fluorescent Protein (GFP). Changes in the intracellular concentration of the indicator induce conformational changes between CAM and M13, corresponding changes in the distance and relative orientation between CFP and GFP, and ensuing variation in the FRET rate. Through various mutations, derivatives of cameleon-1 can now measure $Ca^{2+}$ molar concentrations ranging from $10^{-7}$ to $10^{-4}$ M in a variety of cellular compartments.

The second example is provided by Allen and Zhang (see references NP7, NP8), who, motivated by a desire to track cAMP activity, for example at the inner side of the plasma membrane, cytoplasm, nucleus, and mitochondria in living cells, systematically optimized probes through circular permutation (cp).

The third example is provided by Lissandron et al (see reference NP9) who improved cAMP unimolecular probes combining molecular simulation with experiment to optimise linkers through mutation of selective residues, and thereby almost doubled FRET efficiency and substantially improved "dynamic range" (a measure of the signal to noise ratio).

The fourth example is provided by Pertz et al. (see reference NP10), who by focusing on the Rho family of GTPases (G proteins) which regulate the actin and adhesion dynamics that control cell migration, developed a fluorescent biosensor to visualize the spatiotemporal dynamics of RhoA activity during cell migration, and subsequently engineered a library of probes (see reference NP4) by varying several geometrical parameters, such as fluorophore distance (using linkers of different length), dipole orientation (using cp mutants in both the acceptor and donor fluorophores), and sensing module domain topology.

Despite the widespread use and development of RET reporters such as those mentioned above, various difficulties remain. For instance, a strong RET signal, and a strong signal to noise ratio, can be achieved by increasing the tendency of the FP's to bind in the ON state (i.e., when the analyte binds to the ligand binding domain as a result of its intracellular concentration going beyond an effective threshold value.) But this tends also to increase the perturbation of the endogenous system, making it more difficult to track fine scale changes in time and space. For instance, the over-expression of the biosensors designed to measure analytes such as $Ca^{2+}$ can interfere with the proper function of endogenous CaM molecules. As another illustration of the difficulty, consider the demands made of a probe to monitor protein kinases activity which are often dynamically regulated. It is desirable that the probe can continuously track up and down regulation of kinase activities whilst maintaining a strong RET signal and a high signal to noise ratio, yet is difficult to realise in practice, as pointed out by a fifth set of examples of the (see references NP1, NP11.)

A sixth example of over-expression of bio-sensors is found in the work of Palmer et al., who employed a "bump and hole" strategy to diminish interactions between wild-type CaM and the M13 peptide in the sensor, while maintaining the sensitivity of the reporter (see reference NP12). But despite their success in overcoming such difficulties for a particular reporter, an approach and associated general purpose mechanism applicable to a large and quite wide class of reporters has remained elusive.

In effect the ligand binding domain and sensor domain remain in the ON state long after they should have separated if they were to be able to respond sensitively to up and down variations of the analyte concentration corresponding to the endogenous system. As a consequence, the FRET signal remains high long after it should desirably have dropped.

Immunoassays are biochemical tests used to measure the presence and concentration of analytes using antibodies or immunoglobulin. A wide variety of macromolecules can be detected, including antigens, and antibodies. In general, the detection of the analyte involves one or more antibodies binding to it, with at least one antibody being "labelled" with some form of marker molecule, frequently a fluorescent protein, a dye, or an enzyme. For instance, the enzyme-linked immunosorbent assay (ELISA) is a test that is extensively used as a diagnostic tool in wide variety of applications from medicine and plant pathology to environmental science and food industry. In the simplest version of this test, known as Direct ELISA, a microtiter surface is exposed to an antigen solution for enough time that the antigen bonds to the surface, to which subsequently is added a primary antibody conjugated with an enzyme. After some time, a substrate is also added to the microtiter, which reacts with the enzyme, thereby changing colour. The microtiter is then washed to remove the excess—leaving the effectively stained antibodies bound to the plastic surface. Indirect ELISA is similar to Direct ELISA, except that the primary antibody is not conjugated. Instead an additional secondary antibody conjugated with an enzyme is added, which binds to the primary antibody. In yet another assay known as Sandwich ELISA, a primary antibody is anchored to a microtiter surface, to which is added a solution containing the antigen, and another primary antibody capable of binding to a different epitope on the antigen. The excess antibody is washed away, and another solution containing an enzyme conjugated secondary antibody which binds to the primary antibodies. In sandwich ELISA, the presence of the antigen effectively turns on an attractive indirect interaction between the two primary antibodies. In competitive ELISA, like Direct ELISA, the unlabelled primary antigen is incubated with the antigen in a microtiter so that it binds to the surface. In the next step, a solution including unconjugated antigens and primary antibodies is added to microtiter, and incubated. The surface is then washed to remove unbound antigens and antibody, and then an enzyme conjugated secondary antibody is added which binds to the primary antibody-antigen complex. The key feature of this technique is the competition between the antigens attached to the microtiter surface and antigens in solution to bind to primary antibodies. The above ELISA tests can be used to detect either antigens, or antibodies, and are described in detail in reference NP28.

Immunofluorescence is an alternative method to measure the presence of antigens, where the role of the enzyme in ELISA tests is instead played by fluorescent proteins or dyes. Thus, in direct immunofluorescence, a fluorescent molecule or dye is conjugated to the primary antibody, which can be viewed through a microscope. In indirect, sandwich and competitive immunofluorescence, a fluorescent molecule or dye is conjugated to the secondary antibody, which can be viewed through a microscope. As in ELISA, many washing and incubating steps are required in the above immunofluorescence assays, and are described in detail in reference NP29.

Western Blot is another form of immunoassay where the target analytes are proteins, and which combines immuno-fluorescence with gel electrophoresis to more easily identify different analytes according to their molecular weight. NP30.

To reduce the problem of unintended cross interactions between antibodies and other immune-interactions, it is also possible to use specific fragments of antibodies such as IgG and IgM, capable of binding to one or more epitopes on the antigen, such as F(ab')2, Fab, Fab' and Fv as described in references NP31 and NP32.

In both ELISA based assays and immunofluorescence, it is necessary to conjugate antibodies with appropriate labels, such as dyes (Cyanine Dyes, Fluoroscine, Rhodamine, Texas red, Aminomethylcoumarin and Phycoetherine), enzymes or fluorescent proteins. Other methods such as split GFP (or split *Gaussia* Luciferase) can also be used for tagging, where the two moieties fluoresce (or bioluminesce) only when they are brought together to form again a functional GFP (or bioluminescent molecule). Further details are given, for instance, described in references NP33 and NP34.

These conjugation methods target specific chemical groups available in the antibodies including tyrosine, lysine, glutamate, aspartate, methionine, serine, histidine, and arginine. The most common chemical reactions used target primary amines (—NH2), carboxyls (—CHO) and thiolates (SH). Lysine, which contains a primary amine, is a very common residue on practically all antibodies, and is the primary targeting site for conjugation. However this conjugation method can on occasion reduce the ability of the antibody to recognise corresponding antigen(s) due to accidental unintended labelling at the F(ab) region of the antibody. For this, and other reasons, carboxyls are perhaps the second most common labelling target, where typically the (—CHO) conjugation sites are on the Fc region of the antibody, without significantly affecting the antigen-binding capacity. In the case of antibody fragments (e.g. F(ab)$_2$, Fc, Fv), thiolates are the typical choice of labelling target.

The standard methods and reagents used for conjugation are described in references NP31 and NP35, and for the specific case of sulfhydryls, see also references NP36 and NP33. The standard chemistry for labelling of amines uses either heterobifunctional reagents, or NHS esters, or carbodiimides, or sodium periodate. In the case of carboxyls, the carbohydrates must first be oxidized to create reactive aldehydes. In the case of carboxyls, the carbohydrates must first be oxidized to create reactive aldehydes. If primary amines are accessible on the label, the reacted aldehyde in the carbohydrates can be conjugated using reductive amination. In the absence of accessible primary amines on the label, the reacted aldehyde in the carbohydrates can be conjugated using hydrazide groups. For example, if the label is a protein, the hydrazide group can be functionalised selectively on either its C or N terminals. In the case that two different types of antibodies (for example a primary and a secondary antibody) are to be bound to the C and N terminals of a protein respectively, a blocked hydrazide group can be added to the C terminal of the protein, which can be subsequently chemically unblocked after conjugation of the first antibody at the N terminal of the protein (or vice-versa). Conjugation at sulphur atoms requires that the thiols exist as free sulfhydryls (—S) (using for instance reagents such as DTT and TCEP), which can be reacted to the label activated with maleimide or iodoacetyl groups.

Although the assay methods described above are widely used, they have a number of difficulties. Typically they require several washing steps to remove excess antibodies which have not bonded to their target antigens or primary antibodies, and as a consequence are laborious or require specialised, bulky and expensive equipment. Estimating the actual concentration of the analyte(s) present in a sample is generally difficult, indirect and not accurate. Measurements cannot easily be made to track real time changes in the concentration of analytes, other than by taking consecutive samples and running each sample through complex protocols of washing, and addition of various reagents etc.

The microtiter described above can be of various shapes and sizes, including Micro and Macro arrays, Micro-well arrays, Micro-zone arrays fabricated in paper and Microfluidic chips (described generally in references NP37, NP38 and NP39).

Binding in these assays is frequently detected using, for instance, confocal scanning microscopy, and more recently with desktop scanners. Confocal microscopy uses a laser scanner (described in reference PT2) and a microscope to build up a three dimensional image of a sample through a series of two dimensional images of the sample made at various depths. In the context of immunoassays, the corresponding images can be at a cellular or sub-cellular level. The main drawback of this complex and rather fragile machinery is cost. Desktop scanning cannot be easily used to make three dimensional images. However for surface imagery, it is much cheaper than confocal microscopy, largely because the laser and complex optical lenses and mirrors used in the latter are replaced by a either a single LED of a single wavelength or a combination of Red-Green-Blue LEDs producing the target wavelength, and an ordinary CCD camera. Another method of measuring immunofluorescence uses single or multiple LED's as combined with photomultiplier diode chips.

Chromophores including fluorescent proteins can be combined with quenching nanoparticles such as gold (described in reference NP41) and antibodies to detect analytes, and to heat tissue in living samples (described in reference NP42).

As an alternative to localised tissue heat treatment, photodynamic therapy uses photosensitizer or photosensitizing agents such as porphyrin and phthalocyanin, to expose, for instance cancerous cells to reactive oxygen species upon exposure of the photosensitizing agent to electro-magnetic fields/light of appropriate wavelengths (described in reference NP43). Photodynamic therapy can also be used to treat microbial infection (described in reference NP44). It is also possible to combine photosensitizing agents with antibodies targeting specific antigens, and even to form larger complexes such as antibody-phthalocyanine-gold nanoparticle conjugates.

An aim of the present invention is to provide an improved molecular sensor that is capable of overcoming some of the problems of the above described sensors and methods.

According to a first aspect of the invention, there is provided a sensor molecule for detecting a target molecule comprising:
 (a) a rod-like molecule L and a rod-like molecule R connected to each other by a joint molecule C to form a hinge;
 (b) a target binding molecule A bonded to the end of rod-like molecule L opposite to the joint molecule C;
 (c) a binding molecule A' bonded to the end of rod-like molecule R opposite the joint molecule C;
 wherein the target binding molecule A is arranged to bind to an epitope or nucleic acid sequence of the target molecule to be detected, and binding molecule A' is arranged to bind to the same epitope or same nucleic acid sequence, or portion thereof of the target molecule as target binding molecule A; and
 wherein the hinge is biased into an open position, such that target binding molecule A and binding molecule A' are biased apart by the hinge.

In one embodiment, the presence and binding of a target molecule by target binding molecule A, and the binding of binding molecule A' to the target molecule is arranged to bias the hinge into a closed position in opposition to the force of the hinge, which is biased to an open position.

The sensor molecule may comprise a state denoted as the ON state wherein A is attracted towards A' and the hinge is arranged to repeatedly open and close. For example, the hinge will close due to A and A' being brought into closer proximity by both binding to the target molecule, by temporally overcoming the bias energy of the hinge to open. The bias energy of the hinge to open can temporarily force A and A' apart. Therefore, the sensor molecule is in a state of dynamic switching to an open and closed position in the presence and detection of a target molecule. This dynamic state is designated the ON state.

The sensor molecule may comprise a state denoted as the OFF state wherein the hinge is in an open position and A is not attracted towards A'.

The ON and/or OFF state may be detectable. Additionally or alternatively, a transition between the ON and OFF states may be detectable. In one embodiment, the ON state is detectable.

The binding of target binding molecule A to the target molecule may be direct binding or through one or more intermediate molecules. Additionally, the binding of binding molecule A' to the target molecule may be direct binding or through one or more intermediate molecules.

A characteristic feature of the present invention is that it solves the problem of the prior art described above (of the ligand binding domain and sensor domain remaining in the ON state long after they should have separated if they were to be able to respond sensitively to up and down variations of the analyte concentration corresponding to the endogenous system) in a counter-intuitive way by not requiring the ligand binding domain and sensor domain to be tightly bound to each other in the ON state. Instead the ON state is characterised by frequent transitions from a bound conformation (where the ligand binding domain and sensor domain are essentially in contact) to an unbound conformation (where the ligand binding domain and sensor domain are far from being in contact) and vice-versa. The OFF state is essentially always unbound.

An advantage of targeting only a single epitope is that only complimentary portions of the heavy and light chains of an antibody, or equivalents thereof, are necessary to form an epitope binding pair as opposed to an antibody on both arms, which has the advantage that the overall sensor molecule is significantly smaller. Other advantages include that the sensor can disassociate more quickly from the target epitope when the local concentration of the target drops—thus reducing latency so that faster changes in the concentration of the target to be tracked in time; smaller protein based sensors when can be expressed in cells; smaller sensors can penetrate barriers, such as intra and inter cellular barriers, and the blood brain barrier more easily; and their small size can allow them to be eliminated more quickly in the case of living organisms In one embodiment, the target binding molecule A and/or the binding molecule A' are capable of emitting a signal for detection when they are in proximity to each other, or bound to each other. Alternatively, the sensor may further comprise a signal molecule B and a signal molecule B'.

The detectable ON state signal may be provided by the pair of signal molecules B and B' being brought into sufficient proximity to cause a detectable ON state signal to be emitted.

The signal molecule B and/or B' may comprise a chromophore, fluorophore or bioluminescent molecule. In another embodiment, the target binding molecule A and/or binding molecule A' may comprise a chromophore, fluorophore or bioluminescent molecule. The fluorophores or bioluminescent molecules may be photo-activatable (such as PA-mRFP1 or PA-mCherry1), photo-convertible convertible (such as Kaede or Dendra2), photo-switchable (such as Dronpa or Pardon), fluorescent protein timers (such as DsRed-E5 or Fast-FT), or phosphorescent. One example is to use the reversible photoswitching of Dronpa mutant K145N (see Zhou et. al. Optical Control of Protein Activity by Fluorescent Protein Domains. *Science*. 2012 Nov. 9; 338(6108): 810-814) and thereby the light dependent association-disassociation could be used to trigger the ON and OFF state of the biosensor. When used in association with a sensor and ligand binding domain these can be used to get a better signal to noise, as well as measure the binding energy.

In one embodiment, the detectable ON state signal is provided by resonance energy transfer (RET) between signal molecule B and signal molecule B'. In another embodiment, the detectable ON state signal is provided by resonance energy transfer (RET) between target binding molecule A and binding molecule A'. Signal molecules B and B' may undergo measurable resonance energy transfer when sufficiently close to each other when the sensor molecule is in the ON state (e.g. when A' and A are closer together). The resonance energy transfer (RET) may be Förster resonance energy transfer (FRET) or bioluminescent resonance energy transfer (BRET).

The signal molecule B may be bound to ligand binding molecule A and the signal molecule B' may be bound to binding molecule A' (or vice versa). Alternatively, the signal molecule B may be bound to the end of rod-like molecule L opposite the joint molecule C and the signal molecule B' may be bound to the end of the rod-like molecule R opposite the joint molecule C (or vice versa). In embodiments wherein B and B' are respectively bound to A and A' (or vice versa), the binding may be direct, or via a spacer molecule. The binding may be covalent.

In one embodiment, sensor molecules B and B' each comprise a part of a split molecule. A split molecule may be a functioning molecule that can be split into two or more parts to a non-functioning state, and can be rejoined when the two or more parts are brought back together, such that the function is restored. For example, when brought close together due to the close presence of the target molecule, the split molecule parts may undergo resonance energy transfer in the presence of a suitable electro-magnetic field of external or endogenous origin. In one embodiment the split molecule is a bioluminescent molecule, which is capable of being split into parts, whereby the re-joining (or at least the close proximity) of the parts can lead to a restored bioluminescent function. In one embodiment, the split molecule may comprise a split enzyme, such as a split horseradish peroxidase whereby the re-joining (or at least the close proximity) of the parts can lead to a restored peroxidase function. The horseradish peroxidase may comprise the horseradish peroxidase described herein, or split versions of the horseradish peroxidase sequence described herein (i.e. left and right portions described herein).

The split molecule may comprise a split fluorescent protein. Examples of split fluorescent proteins are well known in the art. For example the split fluorescent protein may comprise green fluorescent protein (GFP). A cleavage/split site of GFP is known to be between strand 10 and 11 of GFP. In another embodiment, the split fluorescent protein may comprise yellow fluorescent protein (YFP) or cyan fluorescent protein (CFP). Examples are described in US 20120282643 A1.

In one embodiment, the sensor molecule B comprises FP1 described herein (FP1: MSKGEELFTGVVPILVELDGD-VNGHKFSVSGEGEGDATYGKLTLKFICTTGKLPV PWPTLVTTLVQCFSRYPDHMKRHDFFKSAMP-EGYVQERTIFFKDDGNYKTRAEV KFEGDTLVNRI-ELKGIDFKEDGNILGHKLEYNYISHNVYITAD-KQKNGIKANFKIR HNIEDGSVQLADHYQQNTPIG-DGPVLLPDNHYLSTQSALSKDPNEKRDHMVLLE FVTAAGI—SEQ ID NO: 14).

The sensor molecule B' may comprise FP2 described herein (FP2: MSKGEELFTGVVPILVELDGDVNGHK-FSVSGEGEGDATYGKLTLKFICTTGKLPV PWPTLVTT-FLQCFARYPDHMKRHDFFKSAMPEGYVQERTI-FFKDDGNYKTRAEV KFEGDTLVNRIELKGIDFKEDG-NILGHKLEYNYNSQNVYIMADKQKNGIKVNFKI RHNIEDGSVQLADHYQQNTPIGDGPVLLPDNHYL-SYQSALSKDPNEKRDHMVLL EFVTAAGI—SEQ ID NO: 15).

The sensor molecule B may comprise FP1 and the sensor molecule B' may comprise FP2. Alternatively, the sensor molecule B may comprise FP2 and the sensor molecule B' may comprise FP1.

An advantage of the sensor molecule of the invention is that it makes the use of split FP's or split bioluminescent proteins reversible. Previously in the art, irreversibility (i.e. the tendency of the split pair once reunited not to come apart) has limited their use in the tracking of time dependent changes in analyte concentration. In this invention, the sensor molecule pulls them apart, provided an adequate bias has been selected for the hinge to open.

In another embodiment, the split molecule may comprise a biological active molecule that can be split into two or more parts, such that when the parts are brought back together in the presence of a target molecule of the sensor molecule, the function of the biological active molecule is restored.

The biologically active molecule may comprise an active drug, a pro-drug, an enzyme, or a co-factor.

In one embodiment, the split biologically active molecule may comprise a DNA or RNA modifying enzyme, such as SNASE (such as SNASE DELTA +PHS). The modification may comprise cleavage. The SNASE may comprise the SNASE sequence described herein, or split versions thereof as described herein (i.e. left and right portions described herein).

An embodiment of the invention providing a split molecule that is a biological active molecule is that a target effect can be provided. For example, an active drug can be provided upon the detection of a target molecule, such that the split molecule is brought back together and the active drug is provided. Localised or timed effects can be provided in this embodiment. For example, the split molecule may only become active when a target molecule is present. Therefore, the effects of the target molecule are latent until levels of the target molecule increase. For localisation, the split molecule may only be switched on in locations where a target molecule is present, for example only in specific cells, or cell compartments, or only in specific tissues that a target molecule is present.

In one embodiment, the activated drug may comprise an activated chemo-toxin.

In another embodiment, the split molecule may comprise a catalyst that initiates or enhances a chemical reaction in the presence of the target molecule. In another embodiment, the split molecule may comprise a molecule that releases heat through quenching in the presence of the target molecule and a suitable electro-magnetic field. In another embodiment, the split molecule may comprise a molecule that becomes an activated photosensitizer complex producing oxygen radicals in the presence of the target molecule and a light source.

In another embodiment, signal molecule B and signal molecule B' may comprise reactive compounds that produce a chemical reaction in the presence of the target molecule.

The split molecule may comprise a toxin. For example the toxin may be the A and B components of an AB protein toxin, for example Diphtheria toxin. When A and B components of the toxin are brought together in the presence of a target molecule (for example on a target cell), the toxin is capable of binding and penetrating a target cell. In another example of the diphtheria toxin, the B component is split into two components B1 and B2 such that B1 remains fused to A. When A-B1 and B2 components of the toxin are brought together in the presence of the target molecule (for example on a target cell), the toxin A-B1-B2 is capable of binding and penetrating a target cell. The split molecule may comprise Diph1-495 (SEQ ID NO: 22) on one side of the hinge and Diph496-535 (SEQ ID NO: 23) on the other side of the hinge.

In some embodiments, the roles/function of molecules A and A' relative to molecules B and B' may be reversed. In the hinge, A may substantially oppose B or B'. Similarly A' may substantially oppose B or B'. In one embodiment, molecule A or A' will be positioned further from the joint molecule C relative to B or B'. In an alternative embodiment, molecule B or B' will be positioned further from the joint molecule C than A or A'. The skilled person can design the relative positioning of the molecules, A, A', B and B' to suit the particular target molecule and sensor system required.

The spacer molecule may comprise a peptide, such as a polypeptide. In one embodiment, the spacer molecule may also contribute to the energy to bias the hinge apart. The spacer molecule may comprise a flexible polymer or a rigid polymer or rod. The length and flexibility of the spacer molecule may be designed/tuneable to accommodate the hinge open and closed dimensions for any given sensor molecule. The length of the spacer molecule may not exceed the sum of the lengths of each arm of the hinge, half of that value is the typical choice. For example, the ON state may be controlled by providing a higher flexibility to the spacer molecule in order for it to flex into an appropriate position sufficient for interaction of B and B' to provide a signal. In one embodiment the spacer molecule comprises or consists of the sequence $[GSG]^m$ or the sequence $A[GSG]^mA$, wherein m is 1, 2, 3, 4, 5, or more. In one embodiment the spacer molecule comprises or consists of the sequence $[GSG]^m$ or the sequence $A[GSG]^mA$, wherein m is 6, 7, 8, 9, 10, 11, 12, or more. The spacer molecule may be flexible. The spacer molecule may comprise or consist of amino acids. The spacer molecule may comprise or consist of the amino acid glycine. The spacer molecule may comprise the amino acid sequence SGS or GS. In another embodiment, the spacer molecule may comprise a repeat of SGS or SG, for example $[SGS]^m$ or $[SG]^m$, wherein m is selected from 2, 3, 4, 5, 6, 7, 8, 9, or 10. In another embodiment, the spacer molecule may comprise a repeat of SGS or SG, for example $[SGS]^m$ or $[SG]^m$, wherein m is selected from 11, 12, 13, 14, 15, 16, 17, 18, 19, 20, 21, or 22. The spacer molecule may comprise the amino acid sequence GGGGSGGGGS. The spacer molecule may comprise the amino acid sequence AGSGGSGGSGA. The spacer molecule may comprise the amino acid sequence AGSGA. The spacer molecule may comprise the amino acid sequence SGSSGS. The spacer molecule may comprise the amino acid sequence SGSSGSSGSSGS. The spacer molecule may be between 2 and 60 amino acids in length.

The skilled person will recognise that if one or more of the modules/units A, B, A' or B' is large, it may be advantageous to increase the length of the flexible linker connecting it to other modules so as to overcome any steric effects. For example in the case of split proteins, as they need to be able to come together and become functional when the hinge is closed. If for instance B or B' is very big, and the flexible linker connecting them to A or A' is short, A and A' may be sterically hindered to bind and become functional. This may be overcome by increasing the length of the linker connecting A to B or B to A' (or both), and the aggregate length of the two flexible linkers will be greater than the end to end distance of BB' (lying between A and A'). If the flexible linker is long, the length of the hinge may be increased to ensure that the sensor still acts as an on-off switch. In one embodiment, the flexible linkers described herein may be increased in length, such as doubled in length (except for any flexible linker in the centre of the hinge).

A skilled person will understand that if an additional SGS is added to the flexible linker between the arms of the hinge to increase flexibility, it may weaken the bias of the hinge to be open by a few Kcal/Mol. Therefore, the molecule may then require additional charged residues to be added to either rod molecule L and/or R to increase the electrostatic repulsion between either arm of the hinge when closed for instance, EAAAKEAAKSGSSGSKAAAEKAAAE to EAKAKEAAKSGSSGSKAAAEKAKAE. Adding charged residues to increase bias/repulsion may also be provided to accommodate different pH and salt conditions of the solvent (for example in different cellular compartments/organelles or in assays such as may occur in non-physiological conditions, or split proteins (e.g. split FP) binding with greater binding energy. The objective is that in the absence of the target molecule the hinge will open, and in its presence it will open and close. This provides guidance on whether additional charged residues are required to increase the tendency for the hinge top open.

The rod-like molecules L and R may have a high aspect ratio (i.e. substantially longer than its width). For example, the aspect ratio of the rod-like molecules L and R may be about 6-10:1 (length to width). The aspect ratio of the rod-like molecules L and R may be at least about 6:1 (length to width). This is to ensure that the sensor will not significantly interfere with the chemistry it is designed to monitor (or in the case of drug/toxin delivery, be precise in its manipulation of the endogenous system). In one embodiment, the rod-like molecules L and R may each be at least 40 Ångströms in length. In another embodiment, the rod-like molecules L and R may each be at least 50 Ångströms in length. In another embodiment, the rod-like molecules L and R may each be at least 60 Ångströms in length. The rod-like molecules L and R may each be between about 40 and about 100 Ångströms in length. Alternatively, the rod-like molecules L and R may each be between about 50 and about 100 Ångströms in length. Alternatively, the rod-like molecules L and R may each be between about 60 and about 100 Ångströms in length. Alternatively, the rod-like molecules L and R may each be between about 60 and about 90 Ångströms in length. Alternatively, the rod-like molecules L and R may each be between about 60 and about 80 Ångströms in length.

The rod-like molecules L and R may each be between about 6 and about 8 Ångströms in width. The rod-like molecules L and R may each be between about 40 and about 100 Ångströms in length and between about 6 and 8 Ångströms in width. In another embodiment, the rod-like molecules L and R may each be between about 50 and about 100 Ångströms in length and between about 6 and 8 Ångströms in width. In another embodiment, the rod-like molecules L and R may each be between about 60 and about 100 Ångströms in length and between about 6 and 8 Ångströms in width. In another embodiment, the rod-like molecules L and R may each be between about 60 and about 90 Ångströms in length and between about 6 and 8 Ångströms in width. In another embodiment, the rod-like molecules L and R may each be between about 60 and about 80 Ångströms in length and between about 6 and 8 Ångströms in width.

Furthermore, the rod-like molecules L and R may not be so flexible that the rod easily folds. For example, the rod-like molecules L and R may be substantially rigid. This can be measured in terms of the average length of the molecule (along the most extended axis) and the fluctuations from the average length. For example, the length of the rod-like molecules L and R should not fluctuate by more than 20% to 30%. The length of the rod-like molecules L and R may not fluctuate by more than 25%. The length of the rod-like molecules L and R may not fluctuate by more than 30%.

In one embodiment, the rod-like molecule L and/or rod-like molecule R may comprise a polypeptide. The polypeptide may form an alpha-helical structure. Therefore, in one embodiment, the rod-like molecule L and/or rod-like molecule R comprise or consist of an alpha-helical polypeptide.

In another embodiment, the rod-like molecule L and/or rod-like molecule R may comprise a carbon nanotube, which has been sufficiently treated or produced to be substantially hydrophilic, and therefore soluble under physiological conditions. A person skilled in the art can select or functionalise carbon nanotubes to match the solvent.

Advantageously, the alpha-helical structure of the rod-like molecules L and R provides an effective rod, which is sufficiently rigid to provide a biased hinge mechanism, when joined by joint molecule C. For example the rods are not flexible to a degree that they can conform to any space or shape under normal physiological conditions. For example, the rod-like molecules L and R may be sufficiently rigid such that they allow the sensor to flex and return to their original shape/conformation. The rigidity of rods can be defined in various ways including: the ratio of the variance of the length of the rod to its average length, or alternatively the Young's modulus. This can be measured through a variety of experimental and theoretical/simulation methods, for example Atomic Force Microscopy, single molecular FRET microscopy, and through molecular simulation.

In one embodiment, the rod-like molecule L and/or rod-like molecule R may comprise an alpha-helical structure of a Leucine Zipper, such as the GCN4 leucine zipper. In one embodiment, the rod-like molecule L and/or rod-like molecule R may comprise an alpha-helical structure of a BAR protein. In one embodiment, the rod-like molecule L and/or rod-like molecule R may comprise collagen.

The rod-like molecule L and/or rod-like molecule R may be about 42 amino acids in length, for example when (EAAAK)6 (see Boersma et. al. Nature Methods, 2015; DOI: 10.1038/nmeth.3257). The rod-like molecule L and/or rod-like molecule R may be between about 35 and about 60 amino acids in length. The rod-like molecule L and/or rod-like molecule R may be between about 40 and about 60 amino acids in length. The rod-like molecule L and/or rod-like molecule R may be between about 40 and about 50 amino acids in length. The rod-like molecule L and/or rod-like molecule R may be between about 40 and about 45 amino acids in length.

The rod-like molecule L may comprise a number N of constituent molecules $q_1, q_2, \ldots, q_N$. The rod-like molecule R may comprise a number N' of constituent molecules $q'_1, q'_2, \ldots, q'_{N'}$.

$q_1, q_2, \ldots, q_N, q'_1, q'_2, \ldots, q'_{N'}$ may be selected to be charged amino acids, or hydrophilic or hydrophobic amino acids, or a combination thereof. For example, the rod-like molecules L and R may comprise an alpha-helical polypeptide, which comprises $q_N$, wherein q is charged, hydrophilic or hydrophobic amino acids, and N is the number of such amino acids typically between 1 and 20.

The rod-like molecules L and R may each comprise separate clusters of constituent molecules (q). For example, the rod-like molecules L and R may each comprise a cluster of constituent molecules $q_1$ and a second cluster of constituent molecules $q_2$. Two, three, four, five, six, seven, eight, nine, ten, eleven, twelve or more clusters (q) may be provided. Each constituent molecule cluster q may comprise the same number of residues and/or the same sequence of residues.

In one embodiment, the rod-like molecules L and R of the sensor molecule are symmetrical. For example, they may comprise similar or identical sequences. For example they may mirror each other when opposed in the hinge of the sensor molecule. Where the rod-like molecule L comprises a specified sequence, the rod-like molecule R may comprise the same sequence in reverse (i.e. a sequence running N to C terminal on one rod would be the same sequence on the opposing rod as the sequence running C to N terminal). The cluster of constituent molecules q of rod-like molecule L may align with the cluster of constituent molecules q of rod-like molecule R, such that they oppose each other in the hinge.

In an embodiment wherein the rod-like molecules L and R of the hinge comprise alpha-helices, the appropriate residue sequences may be provided by the skilled person using information in the literature regarding alpha helices and their stability, for instance, it is common general knowledge for the skilled person that the residue alanine has the highest tendency to form alpha helices when combined together. Further examples of selection criteria that like charges at positions i, and i+4 in the peptide sequence should be avoided; and that the effective charges of the residues depend on their $pK_a$ values and the pH of the solvent. The skilled person will have access to publically available predictive tools online allowing the skilled person to assess the likely stability and solubility of the hinge at different pH conditions. Once a sequence for an appropriate alpha helix is selected, the corresponding structure can be built (as a pdb coordinate file) using bio-informatics tools available online. For example, the server known as IntFold may be used. All of the different peptides are combined together using protein alignment tools such as Modeller. The simulation codes used can be open source, free, and are commonly used in theoretical chemistry/biophysics to estimate free energy properties, with the most commonly used examples in biophysics being NAMD, and GROMACS. The typical fore-fields used in bio-simulations, including in this invention, is CHARMM27 and CHARMM36 including CMAP or Amber.

The choice of residues may be tailored by the skilled person to suit: (a) the solvent or fluid containing the sensor molecule (typically physiological conditions of temperature, pressure, pH and salt, but other conditions may pertain in for example in assays) and (b) the ligand binding and sensor domains binding energy in the ON state—values of which are known in the art (as binding affinities) (see for example table 1 herein) in embodiments wherein the target molecule (ligand) and target binding molecule A are each primary antibodies for specific antigens and their corresponding epitopes. Binding affinities ($K_D$) are typically of the order of μM, and correspond to a Gibbs free energy of the order of 8.5 kcal/mol. Binding affinities ($K_D$) may also be in mM to the nM range.

In one embodiment, the bias energy associated with the hinge opening is 5-20 kcal/mol. In another embodiment, the bias energy associated with the hinge opening is 8-15 kcal/mol. In another embodiment, the bias energy associated with the hinge opening is 8-12 kcal/mol. In another embodiment, the bias energy associated with the hinge opening is 10-12 kcal/mol.

The skilled person will understand that the binding energy of A and A' may be substantially similar to the opposing bias energy of the hinge. Such comparable energies will prevent the hinge from being always closed or always open in the presence of the target molecule (e.g. it allows the dynamic switching between the two open and closed states of the hinge in the ON state).

The hinge may be biased into the open position by the constituent molecules. In particular, the constituent molecules of the rod-like molecule L may repel the constituent molecules of the rod-like molecule R in the presence of the solvent.

In one embodiment, the rod-like molecules L and R comprise an alpha helix of the following repeat residues [EAAAK]$^m$ and [EAAAK]$^m$ respectively, where m is the number of repeats ranging from 6 to 12, and E and K are positively charged at physiological pH condition (e.g. about pH 7.3). In one embodiment, the rod-like molecules L and R comprise an alpha helix of the following repeat residues [EAAAK]$^m$ and [KAAAE]$^m$ respectively, where m is the number of repeats ranging from 6 to 12, and E and K are positively charged at physiological pH condition (e.g. about pH7.3).

In one embodiment, the rod-like molecules L and R comprise an alpha helix of the following repeat residues [EAAAAK]$^m$ and [EAAAAK]$^m$ respectively, where m is the number of repeats ranging from 6 to 12, and E and K are positively charged at physiological pH condition (e.g. about pH7.3). In one embodiment, the rod-like molecules L and R comprise an alpha helix of the following repeat residues [EAAAAK]$^m$ and [KAAAAE]$^m$ respectively, where m is the number of repeats ranging from 6 to 12, and E and K are positively charged at physiological pH condition (e.g. about pH7.3).

In one embodiment, the rod-like molecules L and R comprise an alpha helix of the following repeat residues [EAAAAAK]$^m$ and [EAAAAAK]$^m$ respectively, where m is the number of repeats ranging from 6 to 12, and E and K are positively charged at physiological pH condition (e.g. about pH7.3). In one embodiment, the rod-like molecules L and R comprise an alpha helix of the following repeat residues [EAAAAAK]$^m$ and [KAAAAAE]$^m$ respectively, where m is the number of repeats ranging from 6 to 12, and E and K are positively charged at physiological pH condition (e.g. about pH7.3).

The rod-like molecules L and R may comprise the sequence EAAKAAKA, or the mirror sequence AKAAKAAE at the end immediately adjacent to the joint molecule C. For example, the joint molecule C may be flanked according to the following sequence [EAAAAAK]$^4$ EAAKAAKA-[Joint Molecule C]-AKAAKAAE [KAAAAAE]$^4$. The rod-like molecule L may comprise the sequence EAAAKEAAAKEAAAKEAAAKEAAAK and/or the rod-like molecule R may comprise the sequence KAAAEKAAAEKAAAEKAAAEKAAAE.

The hinge may comprise or consist of the hinge of the FRET crowding sensor molecule of Boersma et. al. (Nature Methods, 2015; DOI: 10.1038/nmeth.3257), or parts thereof.

The sensor molecule may be unimolecular (i.e. a unimolecular sensor). The sensor molecule may be a fusion protein.

In one embodiment the sensor molecule comprises the sequence of any one of SEQ ID NOs: 1 to 13. In one embodiment the sensor molecule comprises the sequence of SEQ ID NO: 1. In another embodiment the sensor molecule comprises the sequence of SEQ ID NO: 2. In another embodiment the sensor molecule comprises the sequence of SEQ ID NO: 3. In another embodiment the sensor molecule comprises the sequence of SEQ ID NO: 4. In another embodiment the sensor molecule comprises the sequence of SEQ ID NO: 5. In another embodiment the sensor molecule comprises the sequence of SEQ ID NO: 6. In another embodiment the sensor molecule comprises the sequence of SEQ ID NO: 7. In another embodiment the sensor molecule comprises the sequence of SEQ ID NO: 8. In another embodiment the sensor molecule comprises the sequence of SEQ ID NO: 9. In another embodiment the sensor molecule comprises the sequence of SEQ ID NO: 10. In another embodiment the sensor molecule comprises the sequence of SEQ ID NO: 11. In another embodiment the sensor molecule comprises the sequence of SEQ ID NO: 12. In another embodiment the sensor molecule comprises the sequence of SEQ ID NO: 13. The skilled person will understand that the individual components of any one of SEQ ID NOs: 1-13 may be used in an alternative sensor molecule, or individual components may be substituted with functional equivalents. Therefore, the present invention provides variants of SEQ ID NOs: 1 to 13, wherein one or more components are substituted for an equivalent functioning component.

In another embodiment the sensor molecule comprises the sequence of SEQ ID NO: 24, 25, 26, 27, 28, 29, 30, or 31.

In one embodiment the sensor molecule comprises the rod-like molecules L and R of any one of the sequences of SEQ ID NO: 1 to 13. In another embodiment the sensor molecule comprises the joint molecule C of any one of the sequences of SEQ ID NO: 1 to 13. In another embodiment the sensor molecule comprises the rod-like molecules L and R, and the joint molecule C of any one of the sequences of SEQ ID NO: 1 to 13.

In another embodiment the sensor molecule comprises the rod-like molecules L and R, and the joint molecule C according to the following sequence EAAAKEAAAKEAAAKEAAAKEAAAKEAAAKSGS-KAAAEKAAAEKAAAEKAAAEKA AAEKAAAE.

In one embodiment, the sensor molecule comprises or consists of the protein sequence FP1-A[GSG]$^{m1}$A-TBM-A [GSG]$^{m2}$AL-[hinge]-RA[GSG]$^{m3}$A-BM-A[GSG]$^{m4}$A-FP2,
wherein FP1 and FP2 are a signal molecule B and B' respectively;
TBM and BM are the target binding molecule A and binding molecule A' respectively;
L and R denote the Left and Right alpha helices of the hinge;
A, S, and G denote the amino acids Alanine, Glycine and Serine; and
m1, m2, m3 and m4 are appropriately selected number of repeats to ensure that the sensor is functional according to the invention.

In one embodiment m1 may be an integer of between 1 and 10. Additionally or alternatively, m2 may be an integer of between 1 and 10.

In one embodiment m=6-9 so that the biased energy of the hinge to be open, is equal to or lower than the binding energy of the target binding molecule A and binding molecule A' in the presence of the target molecule. In several embodiments the hinge [EAAAK]$^6$[SGS][KAAAE]$^6$ can be used which has a biased energy of 12 kcal/mol. This biased energy can be reduced by addition of flexible spacers. The typical reduction in the bias is in the range of 0.05 to 0.15 kcal/mol per Angstrom length of the spacer molecule. The skilled person will readily find the appropriate biased energy of the hinge by simulation or experimentation. Similarly, the binding energy of the target binding molecule A and binding molecule A' in the presence of the target molecule will be known in the prior art (for example, if using a known ligand binding system) or estimated through experiment or molecular simulation by the skilled person.

In one embodiment, the rod-like molecules L and R and joint molecule C (the hinge) are composed of residue sequences such as:
[EAAAK]$^n$A[joint molecule C]$^m$A[KAAAE]$^n$; or
[EAAAK]$^n$A[joint molecule C]$^m$A[KAAAE]$^n$,
wherein E, A, G, S, and K are the single letter codes for amino acids and n and m are non-zero positive integers.
In one embodiment, n ranges from 4 to 24.
In one embodiment a rod-like molecule L or R may comprise the sequence [EAAAAAK]$^4$ EAAKAAKA. The rod-like molecule L and R together with the joint molecule C may comprise the sequence [EAAAAAK]$^4$ EAAKAAKA S G S AKAAKAAE [KAAAAAE]$^4$.

The rod molecules L and R may be neutral. Alternatively, rod molecules L and R may have a substantially low overall charge. In the example directly above the overall net charge is +2 electron Coulomb, under physiological conditions. The overall net charge may be no more than +1, +2, +3, +4, +5, or +10. The rod molecules L and R and/or the joint molecule C may be hydrophilic.

The joint molecule C may be flexible. The joint molecule C may comprise or consist of amino acids. The joint molecule C may comprise or consist of the amino acid glycine. The joint molecule C may comprise the amino acid sequence SGS or GS. In another embodiment, the joint molecule C may comprise a repeat of SGS or SG, for example [SGS]$^m$ or [SG]$^m$, wherein m is selected from 2, 3, 4, 5, 6, 7, 8, 9, or 10.

The target binding molecule A may comprise an antibody fragment or mimic thereof or a protein that can bind to a nucleic acid sequence. The binding molecule A' may comprise an antibody fragment or mimic thereof, or a protein that can bind to a nucleic acid sequence. In another embodiment, the binding molecule A' may comprise an antibody fragment or mimic thereof that binds to the same epitope or portion thereof as target binding molecule A, or a protein that can bind to the same nucleic acid sequence or subsequence thereof as target binding molecule A. In one embodiment the target binding molecule A and binding molecule A' are selected to each be an antibody fragment, or a mimetic thereof, which complement each other to target the same epitope on the same target, such as an analyte or antigen. In one embodiment, the target binding molecule A is one half of a fragment of an antibody, or mimetic thereof, targeting an analyte or antigen, and binding molecule A' is the corresponding other half of the fragment of the antibody, or mimetic thereof. In one embodiment, the target binding molecule A comprises a heavy chain of an antibody fragment, and the binding molecule A' comprises the light chain of the antibody fragment, or vice versa. The target binding molecule A and binding molecule A' may comprise an scFv which is split into two opposing ends of the hinge, for example, the heavy chain on one terminal or arm of the sensor molecule and the light chain on the opposing terminal or arm of the sensor molecule, or vice versa. The target binding molecule A and binding molecule A' may comprise an affibody which is split into two opposing ends of the hinge, for example, one portion on one terminal or arm of the sensor molecule and the complementary portion on the opposing terminal or arm of the sensor molecule. In the presence of an epitope, the target binding molecule A and binding molecule A' are arranged to work together for binding to the same epitope.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb". An antibody mimetic may comprise an affibody.

Affibodies (described by Nord et al (1997. Nature Biotechnology, V15, pp. 772-777), which is herein incorporated by reference) are small proteins that bind to target molecules with a wide variety of applications. As proteins they can be used in the cell, facilitated in part by the lack of cystine bonds, as well as in assays. They comprise three alpha helix type proteins connected by short loops. Starting from the n-terminus, the first two helices bind to the target. The role of third helix is to give structural stability to the affibody, the consensus to date being that it does not bind directly to the target. However, when the third helix is absent in variants of the affibody, the binding to the target is generally lost, unless the first two helices are modified to include a cystine bond.

In the latter case, there is very tentative evidence that the binding to the target is preserved. Extensive libraries of affibodies have been created since their first invention some thirty years ago. Affibodies are the fastest known binders to target molecules, retain their function up to at least 65° C., and are comparatively robust. Affibodies frequently have tags, such as fluorescent proteins, attached to either their N or C ends, without significant effect on their binding properties. The present invention envisages the use of such affibodies for epitope targeting.

In one embodiment the affibody may be derived from the Z domain (the immunoglobulin G binding domain) of protein A. In one embodiment, the affibody comprises a three helical bundle (i.e. prior to splitting for use in the hinge sensor molecule of the invention). The affibody may be split into two opposing ends of the hinge sensor molecule by splitting one or two helices from the remaining helices of the affibody. The split may be provided in the interconnecting loop between the helices. At least the hinge will connect the split helices in the hinge sensor molecule. In one embodiment the hinge sequence is inserted between the helices and may maintain the same natural order as the affibody, i.e. N- to C-terminal. For example, affibody helix 1 may be split/separated from helix 2 and 3, which that they are disposed on opposing arms of the hinge sensor molecule. In particular, affibody domains required for target binding may each be disposed on opposing arms of the hinge sensor molecule.

In one embodiment, the affibody comprises a four helical bundle, where an additional helix has been added to the typical 3-helix affibody structure. The fourth/additional helix may be a duplicate of helices 1, 2, or 3, or fragments thereof. In one embodiment, the fourth/additional helix is a duplicate of affibody helix 3, or a fragment thereof. The fourth additional helix may comprise the sequence PNLNNQSANLLAEAKELNDAQAPK (SEQ ID NO: 21). The skilled person will understand that a number of substitutions/additions to the residues on the fourth helix may be provided to ensure that the 4-helix bundle is such that the helices are approximately parallel to each other, with the fourth helix having approximately the same spatial ordering of hydrophilic or non-polar residues as the third helix from the perspective of the second helix, and that most of the hydrophilic residues of the fourth helix are exposed to the solvent. Residues being used in the substitution/addition may be those likely to produce an alpha helix, which the skilled person can calculate using standard bioinformatics tools or calculations.

Adjacent helices may be joined by interconnecting loops. The affibody may be split into two opposing ends of the hinge sensor molecule by splitting one or two helices from the remaining helices of the affibody. The split may be provided in the interconnecting loop between the helices. At least the hinge will connect the split helices in the hinge sensor molecule. For example, affibody helix 1 may be split/separated from helix 2, 3 and 4, which that they are disposed on opposing arms of the hinge sensor molecule. In another example, affibody helix 1 and 2 may be split/separated from helix 3 and 4, which that they are disposed on opposing arms of the hinge sensor molecule. In an embodiment wherein the fourth helix comprises a charged residue pair KK, the charged residue pair KK may be substituted with LL, KL or LK residues for stability. In an embodiment wherein the fourth helix comprises a charged residue pair KK, the charged residue pair KK may be substituted with LL residues for stability. The skilled person will understand that other residue substitutions are possible, for example KK can be switched to EK, KE, AE or EA, or other.

The affibody, or fragments thereof, may comprise any one of the affibody sequences provided in SEQ ID NOs: 4 to 13. In particular, the target binding molecule A may comprise any one of the affibody helices sequences as described in SEQ ID NOs: 4 to 13. Additionally, the binding molecule A' may comprise any one of the complimentary (i.e. complimentary to the chosen target binding molecule A affibody helices to form a functional binding pair) affibody helices sequences as described in SEQ ID NOs: 4 to 13.

The target binding molecule A or binding molecule A' may comprise the sequence HHLQVDNKFNKEMRNAYWEIALLPN (SEQ ID NO: 16/Affibody Helix 1). The target binding molecule A or binding molecule A' may comprise the sequence HHLQVDNKFNKEMRNAYWEIALLPNLNNQQKRAFIRSLYDDP (SEQ ID NO: 17/Affibody Helices 1,2). The target binding molecule A or binding molecule A' may comprise the sequence LNNQQKRAFIRSLYDDPSQSANLLAEAKKLNDLLPNLNNQSANLLAEAKELNDAQAPK (SEQ ID NO: 18/Affibody Helices 2, 3, 4). The target binding molecule A or binding molecule A' may comprise the sequence LNNQQKRAFIRSLYDDPSQSANLLAEAKKLNDLL (SEQ ID NO: 19/Affibody Helices 2, 3, 4). The target binding molecule A or binding molecule A' may comprise the sequence SQSANLLAEAKKLNDLLPNLNNQSANLLAEAKELNDAQAPK (SEQ ID NO: 20/Affibody Helices 3, 4).

The protein that binds to nucleic acid sequences (such as DNA or RNA) may comprise the DNA binding domains of Transcription Factors, such as concatenations of modules of zinc fingers, Transcription like effectors (Tales), and in the case of RNA, Pumilio and FBF homology' RNA recognition proteins (PUF proteins). Such proteins may be split into two moieties A and A' which bind to complementary portions of a target nucleic acid sequence. The skilled person will recognise that such proteins can be linked to other proteins, for example fluorescent proteins and their moieties, or enzymes that may add, delete, or modify the expression of nucleic acids. The TAL (transcription activator-like) effector may comprise the sequence described herein, or split sequences thereof (i.e. left and right portions described herein). The Zinc finger, such as 2i13, may comprise the sequence described herein, or split sequences thereof (i.e. left and right portions described herein). The Pumilio-Homology Domain From Human Pumiliol (PUF) may comprise the sequence described herein, or split sequences thereof (i.e. left and right portions described herein).

It is possible to take monoclonal and other antibodies and use techniques of recombinant DNA technology to produce other antibodies or chimeric molecules, which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, mimetics, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g., murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [25] which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site; (viii) bispecific single chain Fv dimers (PCT/US92/09965) and; (ix) "diabodies", multivalent or multispecific fragments constructed by gene fusion (WO94/13804; [28]).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associated with each other to form an antigen binding site: antigen binding sites are formed by the association of the first domain of one polypeptide within the multimer with the second domain of another polypeptide within the multimer (WO94/13804).

It may be preferable to use scFv dimers or diabodies rather than whole antibodies. Diabodies and scFv can be constructed without an Fc region, using only variable domains, potentially reducing the effects of anti-idiotypic reaction.

Any known antibody, or fragments or CDRs thereof, that is capable of specifically binding to the desired target molecule may be used in the sensor molecule according to the invention.

The target may comprise amino acid, such as a peptide or protein. In another embodiment, the target may comprise nucleic acid or nucleic acid sequence. The target may comprise a small molecule (i.e. having a MW of less than 900 KDa), such as a hapten. The target may comprise a complex of two or more molecules, such as a complex of sub-units. In one embodiment, the epitope of the target may be formed by a complex of two or more molecules, such as a complex of sub-units. The epitope may comprise a sequence of nucleic acid.

The target may comprise a ligand, a receptor, an analyte, an antibody, or an enzyme, or fragments thereof. In one embodiment, the target may comprise Her2.

In one embodiment the target molecule may comprise glycated hemoglobin and/or glycated albumin. These targets in effect measure the long-time average concentration amount of glucose in an individual's blood, and are excellent indicators of the possible future onset of diabetes, as well as the indicators of how well a given therapy is progressing. Currently these are measured using immunoassays, but could be measured using the sensor molecule of the invention. The appropriate antibodies of each of these target molecules are well known in the art for providing binding molecules A and/or A'.

The sensor molecule according to the invention may be bound to another sensor molecule. For example, a first sensor molecule according to the invention may be bound to a second sensor molecule according to the invention (i.e. a pair of sensor molecules are provided together). The binding may be via any suitable polymer (e.g. polypeptide or nucleic acid), which is capable of associated the two sensor molecules together.

The first and second sensor molecules may be different. For example directed to a different target and/or producing a different signal or effect.

An advantage of providing two sensor molecule bound together is that they may be co-located for a particular assay, or to carry out a specific function in the same area. For example, one sensor molecule may be responsible for reporting/detecting the presence of a target molecule and the other sensor molecule may be responsible for carrying out a reaction.

The sensor molecule may comprise combinations of functions provided by signal molecules B and B'. For example a single sensor molecule may comprise the target binding molecule A and binding molecule A', and two or more sets of sensor molecules B and B'. The two or more sets of B and B' molecules may be different in function. For example, one set may provide a signal function, such as a fluorescence signal, and the second set may provide a split molecule, such as a biological active. Therefore, the working sensor may be visualised as it provides the additional function.

Two or more sensors can be joined in unison to give rise to a collective effect. For example the sensors may form a channel, which opens in the presence of the target molecule allowing passage of other small molecules and conversely in absence of the target molecule prevents there passage. In another embodiment two or more sensors in unison can be used as a scaffold to transport a drug like molecule to a cellular compartment, and in the presence of an analyte open and releases the drug.

According to another aspect of the present invention, there is provided a nucleic acid encoding the sensor molecule of the invention herein.

In one embodiment, the entire sensor molecule may be encoded as a fusion protein. In another embodiment, parts of the sensor molecule may be encoded, for example such that the remaining components can be added at a later stage to form the complete sensor molecule.

The nucleic acid may comprise or consist of a vector. The vector may be an expression vector arranged to express the sensor molecule in a host cell.

According to another aspect of the present invention, there is provided a host cell comprising the nucleic acid according to the invention herein and/or the sensor molecule according to the invention herein.

The host cell may be capable of expressing the sensor molecule of the invention herein.

According to another aspect of the present invention, there is provided an assay method for the detection of a target molecule in sample comprising:
  providing the sample;
  providing the sensor molecule according to the invention in the sample;
  detecting the presence or absence of a signal from the sensor molecule;
  wherein an ON signal confirms the presence of the target molecule in the sample.

The assay method may further comprise determining the level/intensity of the signal. The assay method may further comprise determining the presence or level/intensity of the signal over time. The assay method may further comprise determining the location of the signal.

The sample may comprise biological fluid sample, such as blood, serum, blood plasma, urine, faeces, aspirate, biopsy, growth media, or an environmental sample, such as a water sample.

According to another aspect of the present invention, there is provided a composition comprising the sensor molecule according to the invention.

The composition may comprise two or more different sensor molecules according to the invention. The different sensor molecule may differ in the target molecule being detected, and/or the light signal produced. For example different fluorescent or bioluminescent molecules may be provided on different sensor molecules, which provide different colour light signals.

The composition may be a pharmaceutical composition. The pharmaceutical composition may comprise any pharmaceutically acceptable excipients.

According to another aspect of the present invention, there is provided an assay method for the detection of a target molecule in vivo comprising:
providing the sensor molecule according to the invention in vivo;
detecting the presence or absence of a signal from the sensor molecule;
wherein an ON signal confirms the presence of the target molecule in vivo.

In vivo may comprise in a cell, such as a prokaryote cell or eukaryote cell. In vivo may comprise extracellular environment, for example in a tissue or fluid.

The sensor molecule may be provided in vivo by expression of the sensor molecule in vivo, for example in a cell.

The sensor molecule may be attached and or embedded to a protein, protein matrix, capsid, a cell membrane, subcellular membrane, or an organic/inorganic substrate.

According to another aspect of the present invention, there is provided the use of the sensor molecule according to the invention to visualise or monitor any of the following: (a) the structure and conformation of proteins; (b) the spatial distribution and assembly of protein complexes; (c) protein receptor/ligand interactions including the local concentrations of analytes; (d) the interactions of single molecules; (e) the sequence, structure or conformations of nucleic acids; (f) the distributions and transport of lipids; (g) membrane potential sensing; (h) monitoring fluorogenic protease substrates; (i) local cellular concentrations of cyclic AMP and calcium.

According to another aspect of the present invention, there is provided the use of the sensor molecule according to the invention in the detection of a target analyte, and optionally its concentration, in assays or living cells.

The use may involve tracking the target analytes over time.

According to another aspect of the present invention, there is provided the use of the sensor molecule according to the invention as a drug or drug delivery vehicle to, or within, biological cells, fluids or tissue.

The drug may be a chemo-toxin. The toxin may comprise diphtheria toxin. The diphtheria toxin may be split onto opposing arms/ends of the hinge, such that it is only functional when the hinge is closed into the ON position.

According to another aspect of the present invention, there is provided the use of the sensor molecule according to the invention to provide or catalyse a chemical reaction in the vicinity or within biological cells, organic materials, fluids or tissue.

According to another aspect of the present invention, there is provided the use of the sensor molecule according to the invention to deliver heat in the vicinity or within biological cells, fluids, tissue or organic materials.

According to another aspect of the present invention, there is provided the use of the sensor molecule according to the invention in photodynamic therapy in the vicinity or within biological cells, fluids, tissue, or organic materials.

According to another aspect of the present invention, there is provided the use of the sensor molecule according to the invention for cell killing, wherein the sensor molecule comprises a split molecule that is an active toxin once the parts of the split molecule are brought together in the presence of a target molecule, optionally wherein the target molecule is specific to the cell or cell type.

The uses of the invention may be in vivo or in vitro.

According to another aspect of the present invention, there is provided the use of the sensor molecule according to the invention to perform assays for analytes including titration measure using microtiters or vials, with and without specialised equipment. Such use may have multiple applications including environmental, health, food safety, and security.

According to another aspect of the present invention, there is provided the use of the sensor molecule according to the invention to detect analytes in suitable continuous flow chambers. Such use may have multiple applications including environmental, health, food safety, and security.

According to another aspect of the present invention, there is provided the use of the sensor molecule according to the invention to detect and/or visualise nucleic acid.

The detection and/or visualisation of nucleic acid may be in vitro, for example in a sample, in situ in a cell, or in vivo.

According to another aspect of the present invention, there is provided the use of the sensor molecule according to the invention to modify nucleic acid, such as DNA.

The nucleic acid modification may be in vitro or in vivo. In one embodiment, the nucleic acid modification may comprise gene therapy.

According to another aspect of the present invention, there is provided a method of providing a biological active only in the presence of a target molecule comprising:
providing the sensor molecule according to the invention, wherein the sensor molecule comprises a split molecule, wherein the split molecule is a biological active.

According to another aspect of the present invention, there is provided a method of treatment for a disease in a subject comprising the administration of the sensor molecule or composition according to the invention to a subject, wherein the sensor molecule comprises a biological active in the form of a split molecule, which is capable of becoming an active suitable for treatment of the disease.

The disease may comprise cancer. In an embodiment wherein the disease is cancer, the biological active may comprise a chemo-toxin. The biological active may comprise an AB-toxin. In an embodiment wherein the disease is cancer, the target molecule may comprise a cancer cell specific receptor or cell surface marker. The disease may comprise a genetic disease.

According to another aspect of the present invention, there is provided a method of treatment for a disease in a subject comprising the administration of the sensor molecule or composition according to the invention to a subject, wherein the sensor molecule comprises a split molecule, which is capable of becoming an active suitable for treatment of the disease in the presence of a target molecule.

The disease may comprise a genetic disease. The method of treatment may comprise gene therapy.

The subject may be mammalian. The subject may be human.

In embodiments related to sequences, the skilled person will understand that there can be some sequence variation without substantially affecting or removing the intended function of the sequence. Such variations include mutations, additions, deletions and substitutions of residues or nucleotides. Conservative substitutions may be made. In some embodiment, the sequence can have at least 80% identity with the listed sequence. In another embodiment, the sequence may have 85%, 90%, 95%, 96%, 97% 98%, 99%, or 99.5% sequence identity. Such variants are within the scope of the invention. Sequence identity may be determined using standard NCBI BLASTp or BLASTn parameters.

Definitions

The terms "close proximity" or "near" is understood to mean physical interaction, such as binding, or sufficiently close for the intended function of the molecule. For example, sufficiently close for fluorescence excitation to occur between FRET molecules (for example about 40-60 Ångströms or less). In applications requiring closer proximity, such as in the use of a split molecule (such as a chemo-toxin), the distance may be considered to be close enough for the split molecule to function (e.g. less than 40 Ångströms or less than 20 Ångströms). The skilled person will understand that the distance can vary between different sensor molecule functions and components.

The term "open position" in regard to the hinge is understood to mean that the hinge is apart such that any binding or signal function between molecules, such as FRET, does not occur. The open position may require the molecules A and A' and/or B and B' to be at least 60 Ångströms apart. The term "closed position" in regard to the hinge is understood to mean that the hinge is together such that any binding or signal function, such as FRET, can occur. The closed position may require the molecules A and A' and/or B and B' to be no more than 30 Ångströms apart, or no more than 20 Ångströms apart, alternatively, no more than 10 Ångströms apart.

The term "attracted" used herein is understood to mean that one molecule is drawn towards another molecule through either direct binding or indirect binding, or brought into direct contact or closer proximity.

The sensor molecule may be capable of detection of the target molecule under physiological conditions and/or assay conditions. Furthermore, reference to binding, affinity, attraction, biasing energies or similar molecular interactions may be under physiological conditions and/or assay conditions. The term "physiological conditions" is understood to include physiological pH, physiological salt concentrations, and physiological temperature. The sensor molecule may also be required to work in vitro assay conditions. Such assay conditions may match physiological conditions, for example substantially similar to intracellular or extracellular conditions in vivo. The skilled person can readily adjust the sensor molecule constituents and features within the scope of the invention in order to provide function in any given assay conditions. For example such changes may be based on known molecule pK values.

The sensor molecule may also be referred to as a "Tuneable Multistate Dynamical Unimolecular Hinge Sensor".

Within this document, the terms "target molecule", "ligand" and "analyte" are equivalent and will be used interchangeably, reflecting their usage in the literature.

The terms "connected", "attached" or "attachment" may include a covalent binding.

Reference herein regarding the binding of a molecule to a target molecule may be considered as specific binding. "Specific" is generally used to refer to the situation in which one member of a specific binding pair will not show any significant binding to molecules other than its specific binding partner(s), and, e.g., has less than about 30% cross reactivity with any other molecule. In other embodiments it has less than 20%, 10%, or 1% cross reactivity with any other molecule. The term is also applicable where e.g., an antigen binding domain is specific for a particular epitope which is carried by a number of antigens, in which case, the specific binding member carrying the antigen binding domain will be able to bind to the various antigens carrying the epitope.

In one embodiment, the signalling molecule may comprise the calcium-binding messenger protein Calmodulin. In one embodiment the novel biased hinge substitute's linkers in currently available unimolecular FRET sensors, and such that it is tuned to suitably match its FP's, ligand binding domain and sensor domain.

In another embodiment the novel biased hinge substitutes linkers in currently available unimolecular BRET sensors, and such that it is tuned to suitably match its FP's, ligand binding domain and sensor domain.

In another embodiment, the biased rigid hinge can be tuned for completely new FP's or ligand binding domain or sensor domains, but still in the context of FRET or BRET probes.

In another embodiment the curly element C depicted in FIGS. 2 and 3 is a highly flexible connected linker.

In another embodiment the curly element C depicted in FIGS. 2 and 3 is a combination of consecutive sequences of rigid and flexible peptides.

In another embodiment either the A or A' end of the sensor (see FIGS. 2 and 3) is typically anchored via a short spacer to the C-terminus of a protein close to the cellular locale of interest.

In another embodiment A or A' end of the sensor and fluorescent tags can be attached to target proteins using chemical labelling using covalent bonding (such as amine labelling, thiol labelling) (see reference NP24), enzymatic labelling (Labelling catalysed by post-translational enzyme modification, Labelling with self-modified enzymes like Cutinase or Interin) (see reference NP25) and non-covalent tagging (tetracysteine/biarsenical tag, histidine tag etc., see reference NP26).

In another embodiment FPs can have a variety of manifestations such as photoactivatable (PA-mRFP1, PA-mCherry1), photo-convertible (Kaede, Dendra2), photo-switchable (Dronpa, Pardon), photo-convertible/photo-switchable (IrisFP) and Fluorescent Protein Timers (DsRed-E5, Fast-FT).

The use of multiple acceptor probes provides another embodiment of the sensor, where for instance, one or more acceptor FP's of different colours (but such that RET is possible) are placed on target proteins close to the sensor donor FP. This allows relative changes in position of the FP's to be measured at essentially the same time as variations in the local analyte concentration.

In one embodiment the invention can be used to visualise the structure and conformation of proteins.

In another embodiment the invention can be used to monitor the spatial distribution and assembly of protein complexes.

In another embodiment the invention can be used to monitor receptor/ligand interactions in proteins.

In another embodiment the invention can be used for probing interactions of single molecules.

In another embodiment the invention can be used for probing structure and conformation of nucleic acids.

In another embodiment the invention can be used for monitoring distribution and transport of lipids.

In another embodiment the invention can be used for membrane potential sensing.

In another embodiment the invention can be used for monitoring fluorogenic protease substrates.

In another embodiment the invention can be used for monitoring cyclic AMP, cyclic GMP, calcium, zinc, and Halide ions.

In another embodiment the invention can be used as redox sensors, pH sensors.

In another embodiment the invention can be used as phosphatase activity sensor, and histone acetylation/methylation sensors.

In another embodiment the invention can be used to measure the concentration of glycated haemoglobin in blood.

In another embodiment the invention can be used to measure the concentration of glycated albumin in blood.

In another embodiment the invention can be used to measure the concentration of blood clotting factors 1 to 11.

In another embodiment the invention can be used to measure growth factor such as Epidermal growth factor, fibroblast factor, vascular endothelial growth factor.

In another embodiment the invention can be used to measure insulin, insulin-like growth factor and oxytocin, and steroid hormones.

In another embodiment the invention can be used as cell cycle reporter.

In another embodiment the invention can be used as strain sensors.

In another embodiment the invention can be used as sugar sensors.

In another embodiment the invention can be used in high-throughput screening drug discovery.

In another embodiment the invention can be used in high-throughput screening of agonist and antagonist ligands of taste and olfactory receptors.

In another embodiment the invention can be used in the observation of the turnover of selected metabolites at the single cell level in real time.

In another embodiment the invention can be used in the visualization of specific macromolecular machines within the cellular environment.

In another embodiment the invention can be used to determine the effectiveness of agonist or antagonist ligands acting on G protein receptors.

In another embodiment the invention can be used as light/ligand activated sensors or targeted drug discovery.

In another embodiment the invention can be used as actuators or active agents in the manipulation and control of biological processes and signalling networks.

In another embodiment the invention can be used as an organic or inorganic indicator of the presence and concentration of analytes in analytical chemistry, biochemistry, photochemistry, food, health, and environmental sciences.

In an embodiment where the invention is composed of inorganic or organic components or mixtures thereof, it can be used as electronic sensors, nano-electromechanical systems, memory devices and nano-actuators.

In another embodiment the invention is be used to estimate the binding energies of different ligands to receptors and rank their efficacy as agonist and antagonists with applications in the development of drugs, flavours, perfumes, insecticides, with applications for human, animal and plant health, and the food and perfume industries.

In another embodiment of the invention the detection of analytes such as antigens is made through macromolecules A and A'. Macromolecules A and A' can be selected to be primary antibodies targeting different epitopes on the analyte, which may the same type of epitope but at different locations. Macromolecules B and B' can each consist of one or more selected molecules or moieties of split molecules, which when brought close together produce a variety of selected effects: (a) resonance energy transfer in the presence of a suitable electro-magnetic field; (b) fluorescence in the presence of a suitable electro-magnetic field; (c) bioluminescence; (d) activated drug; (e) activated chemo toxin; (f) chemical reaction; (g) catalysed chemical reaction; (h) in the presence of a suitable electro-magnetic field the release of heat through quenching; (i) in the presence of a suitable electro-magnetic field either of an external or endogenous source, the production of reactive oxygen. In addition several of these effects can be combined in the same sensor. These effects take place in the vicinity on the sensor, which can be close to or within cells, cellular compartments, or in vitro.

Another embodiment of the invention can be used in the detection and measurement of the concentration of analytes in assays and in living cells and their tracking over time using pairs of primary antibodies or fragments thereof targeting epitopes on corresponding antigens.

Another embodiment the invention can be used in the detection of analytes and measurement of the concentration in immunoassays and in living cells and their tracking over time, using a primary antibody or suitable fragments thereof targeting an epitope, and a corresponding secondary antibody.

Another embodiment of the invention can be used in the detection and measurement of concentration of primary antibodies in immunoassays and in living cells and their tracking over time using a corresponding antigen or antigen fragment and a corresponding secondary antibody.

Another embodiment of the invention can be used in the activation of pharmaceutically active molecules and toxins on the detection of target analytes on and within living cells.

Another embodiment of the invention can be used in the activation of pharmaceutically active molecules and chemotoxins, catalysts and other chemical reactions on the detection of target analytes on and within living cells, and simultaneous measurement including optical marking of the location and of said analytes, and their tracking over time.

Another embodiment of the invention can be used on the presence of target analytes for the heating of local cellular and subcellular regions.

Another embodiment of the invention can be used for photodynamic therapy targeting, for example, cancerous cells and various pathogens in living tissue.

Another embodiment of the invention can be used in the field for immunoassays for analytes using microtiters or vials, and without specialised equipment, and at low cost for several applications including environmental, health, food safety, and security.

Another embodiment of the invention can be used in the field immunoassays for analytes including titration measurements using microtiters or vials, with and without specialised equipment, and at low cost for several applications including environmental, health, food safety, and security.

Another embodiment of the invention can be used in the detection of analytes in suitable continuous flow chambers for several applications including environmental, health, food safety, and security.

Applications

The sensor molecule according to the invention may be used in any one or more of the following applications.

Kits for bio-chemistry/bio-molecular/molecular medicine research.

Pharmaceuticals and Biopharmaceuticals—Drug discovery—including high throughput discovery for human and animal health. FRET assays are often used with additional techniques like robotic, ultra-high throughput screening systems to screen for potential drugs. The sensitivity of these assays can be increased using the sensor or the invention, thereby giving lower false positives.

Medical diagnostics—for human and animal health. FRET is used in designing diagnostic assays to measure analytes relevant to human health like insulin and growth factors etc. Our sensor can render them more accurate.

Food industry—including high throughput discovery of flavours and functional foods for humans and animals Perfume and cosmetics industry—including high throughput discovery of perfumes Biotechnology industry—Membrane fusion assays. Stuck et. al. showed the interaction of the lipid rafts could be studied as a function of addition of an analyte concentration, when a sensor domain embedded partially within a lipid rafts is attached to a FP and connected by a dynamical hinge to a FP and ligand binding domain either inside or outside the cellular compartment. Struck. D. K., D. Hoekstra, and R. E. Pagano. 1981. *Use of resonance energy transfer to monitor membrane fusion. Biochemistry.* 20: 4093-4099.

Biopharmaceuticals/pharmaceuticals industries—immunoassays. Immunoassay using flexible linkers are often used in assays. One can increase the signal to noise by using a dynamical hinge instead of a flexible linker.

Biopharmaceuticals/pharmaceuticals industries/medical diagnostics/forensics—automated DNA sequencing, and Real-time PCR assays and SNP detection, and detection of nucleic acid hybridization. PCR is often used as a tool to amplify the peptide based analyte. However the ability of the sensor of the invention to detect lower concentration of analytes will allow the diagnostic process to skip the intensive PCR step altogether.

Electronics, Semiconductors Industries, Quantum Computing

Health Sciences Industries—Development of testing kits in immunology for use in the health-science industry. In the case of enzyme-linked immunosorbent assay (ELISA) is often used to measure antibodies, antigens, proteins and glycoproteins, for example to diagnose HIV, test pregnancy, and measurement of cytokines or soluble receptors in cell supernatant or serum. ELISA assays are generally carried out in 96 well plates, allowing multiple samples to be measured in a single experiment. The sensor of the invention can make ELISA more accurate. Other assays include cell based (Lymphoproliferative assays to phytohaemagglutinin (PHA), pokeweed mitogen (PWM) and Candida, Natural Killer Cell) and flow based assays (AssaysFlow cytometric, single platform CD4 counts).

Security industry, for example, detection of chemicals and explosives for security purposes). Explosive sensing often involves using FRET molecules where the explosive binds to the system and disrupts FRET. The sensor of the invention can be incorporated in such sensing to increase sensitivity. For example, PETN and RDX using a FRET-based fluorescence sensor system.

Food and Cosmetics industries—detection of pathogens and allergens in foods and cosmetics. FRET assays are often used for sensing toxins, or allergens in food. The sensor can be incorporated in such to increase sensitivity.

Assays in the environmental industry (e.g. testing of air and water purity, detection of pathogens and allergens in foods and cosmetics). FRET is used in detection of chemicals, which in even in minute quantities act as allergens etc. The sensor can be incorporated in such to increase sensitivity.

Life science associated industries: real time visualization of analytes in assays and in vivo. FRET is widely used to measure spatio-temporally the effect of signalling molecule like Calcium etc inside a live cell. The sensor can be incorporated in such to increase sensitivity.

Pharmaceutical industry—delivery and activation of drugs, catalysts and chemo-toxins, photodynamic therapeutics. Drug delivery is a priority area in biomedical sciences, our sensors both individually or in unison can be used to deliver drugs in presence of a target molecule.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

SUMMARY

Resonance Energy Transfer (RET) based probes are widely used to understand spatiotemporal dynamics of protein pairs both in-vivo and in-vitro. It is well known that the choice of molecular linker connecting FP's in such probes can have a very strong effect on its overall performance. The approach taken here is to invent a radically new type of sensor by focusing on the structural properties required of the biased hinge mechanism to complement any give pair of sensor and ligand binding domain and associated pair of FP's and ligand of interest, thereby facilitating real time tracking of biochemical events, combined with strong signal and signal to noise characteristics. Our linker design is different in several key aspects from those devised hitherto, including flexible linkers of Matsuda et al.

The mechanism can be understood as a radical change of the basic model of Komatsu et al, realizable when the flexible linker connecting the sensor and ligand binding domain is replaced by a biased hinge. The biased hinge in the latter context is designed to be in an open conformation (where the FP's are far apart and the FRET signal is low or negligible) in the OFF state see FIG. 2, and in the ON state oscillating between an open and closed conformation frequently enough to allow local concentration of analytes to remain close to endogenous levels see FIG. 3. In the rest of this document the sensor that results from this replacement will be referred to as a multistate dynamical unimolecular hinge sensor, or simply as the sensor in contexts when what is intended is clear.

Figure 1:
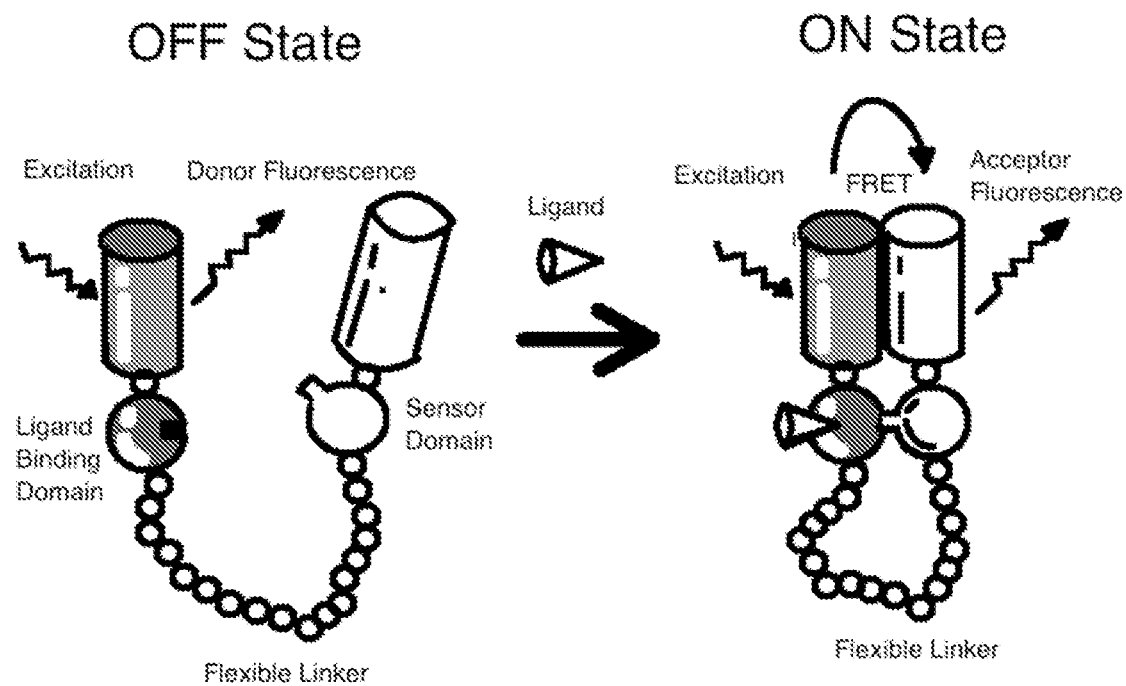
FIG. 1 Schematic description of FRET unimolecular sensor using a flexible linker as described in reference PT1 by Matsuda et al. The OFF state of the sensor corresponding to the absence of the ligand or analyte is displayed in the left panel, where ligand binding domain and sensor domain are on average far apart, and as a consequence the RET signal intensity is low. The donor and acceptor fluorophore proteins are depicted as cylinders. The ON state of the sensor corresponding to the presence of the ligand or analyte is displayed in the right panel, where ligand binding domain and sensor domain are on average in close contact, and as a consequence the RET signal intensity is high.
Figure 2:
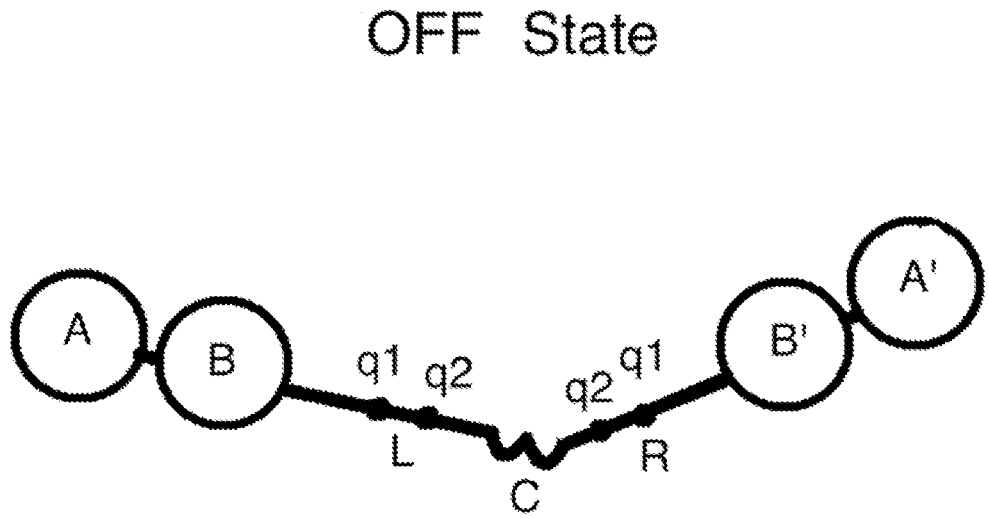
FIG. 2 Schematic description of a multistate dynamical unimolecular hinge sensor of the present invention in the OFF state corresponding to the absence of the ligand.

An example of the unimolecular FRET or BRET sensor that is realizable using this biased hinge linker is drawn schematically in FIG. 2. The spheres represent macromolecules, interconnecting straight-lines denote rigid peptides labelled L and R respectively, while the curly element C denotes a highly flexible connected linker. The points labelled q1 and q2 denote charged or hydrophilic or hydrophobic residues (note the number 2 of such residues on L and on R is illustrative, there can be more and the number per peptide need not be the same). Not shown are short peptides acting as spacers between the macromolecules and linkers, or possible additional genetic sequences used for expression of the sensor in target organelles. The residues q1, q2, . . . and their locations are selected so that the probability of the hinge being open (i.e. the angle BCB' approximately equals 180 degrees) in the ON state is approximately the same as being closed (i.e. the angle BCB' approximately 0 degrees).

In one arrangement, the FP pair are depicted as macromolecules A and A', and the ligand binding domain and sensor domain are depicted as macromolecules B and B'. In another, different arrangement, the FP pair can be depicted as macromolecules B and B', and the ligand binding domain and sensor domain are depicted as macromolecules A and A'.

In the case that q1, q2, . . . are charged residues, their corresponding charges can be positive (arginine, histidine, lysine) or negative (aspartic and glutamic acid), for instance at a physiological pH corresponding to the selection of amino acid sequence. The alpha-helical propensity of these molecules vary with arginine (0.21), histidine (0.61), lysine (0.26), aspartic Acid (0.69) and glutamic Acid (0.40) making histidine and aspartic acids possible choices (see reference NP14).

Test results obtained through Metropolis Monte Carlo simulation of an example of a unimolecular RET sensor (referred to as prototype 1) at physiological temperature (36° C.) are given in FIGS. 4-7 where the RET signal intensity, signal to noise ratio, and related probability distributions are displayed. The numerical model of prototype 1 consists of a potential $V(r_1, r_2)=V_s(r_1, r_2)+V_1(r_1, r_2)$ where $V_s(r_1, r_2)$ represents a switchable interaction between the ligand binding domain and sensor domain, and $(r_1, r_2)$ are the position vectors of the idealized spheres modelling the ligand binding domain and donor FP, and the sensor domain and acceptor FP respectively, each of diameter $\sigma$. In the OFF state, i.e. in the absence of the ligand or analyte $V_s(r_1, r_2)$ ensures that the two spheres cannot overlap, which mathematically is implemented by the constraint that the distance r between the spheres is never less than $\sigma$, $r>\sigma$; in the ON state, it ensures that the two spheres do not overlap, but also experience a uniform attractive interaction of depth $\varepsilon$ for $\sigma<r\leq\sigma+\delta$. The potential $V_1(r_1, r_2)=D_e(1-\exp(\alpha(\theta-180)))^2$ models a biased hinge, using a Morse potential of depth $D_e$ and inverse-width $\alpha$, where $\theta$ is the angle between $r_1$ and $r_2$. The values of the parameters $\varepsilon$, $\sigma$, $\delta$ are generally selected to be close to the values of the real system of interest, for instance typically $\varepsilon$ is between 2 and 10 Kcal/mol, $\sigma$ is ~2.4 nm, $\delta$ is ~1.5 nm to and a reasonable choice for $D_e \sim \varepsilon$, and $\alpha \sim 3.141/60$.

Prototype 2 is similar to prototype 1, except that in the ON state the attractive interaction of depth $\varepsilon$ is replaced by a Lennard-Jones potential $V_s(r_1, r_2)=4\varepsilon([\sigma/r]^{12}-[\sigma/r]^6)$. The test results are given in FIGS. 8-11 where the RET signal intensity, signal to noise ratio, and related probability distributions are displayed.

Prototype 3 is similar to prototype 1, except that in the OFF state $V_s(r_1, r_2)=0.004([\sigma/r]^{12}-[\sigma/r]^6)$; and in the ON state 1 $V_s(r_1, r_2)=4\varepsilon([\sigma/r]^{12}-[\sigma/r]^6)$. Qualitatively, the main difference between prototype 1 and prototype 3 is the use of a soft (continuous and differentiable interaction rather than a "hard core" interaction. The test results are given in FIGS. 12-15 where the RET signal intensity, signal to noise ratio, and related probability distributions are displayed. The test results are given in FIGS. 12-15 where the RET signal intensity, signal to noise ratio, and related probability distributions are displayed.

Figure 3:
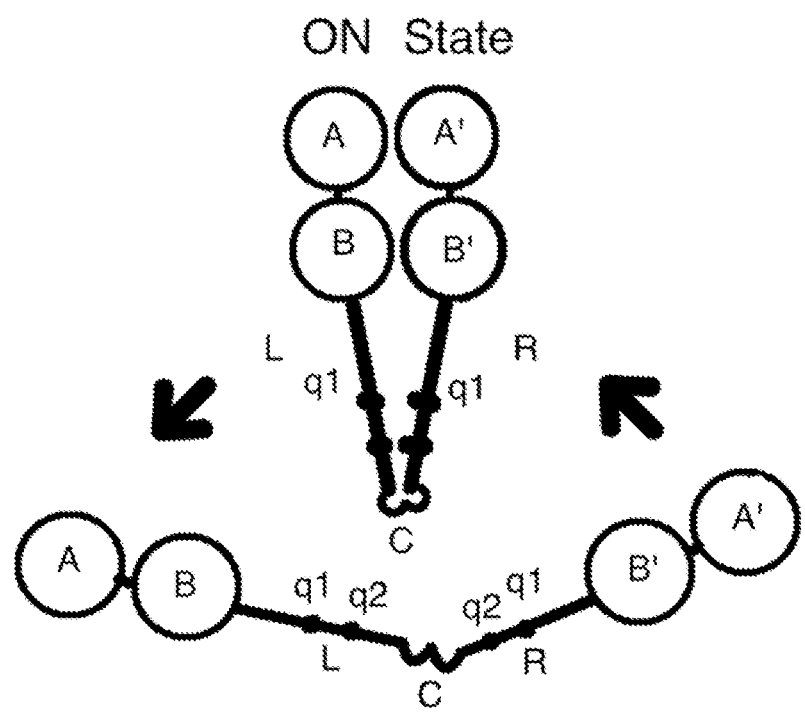
FIG. 3 Schematic description of a multistate dynamical unimolecular hinge sensor of the present invention in the ON state sensor corresponding to the presence of the ligand or analyte.
Figure 4:
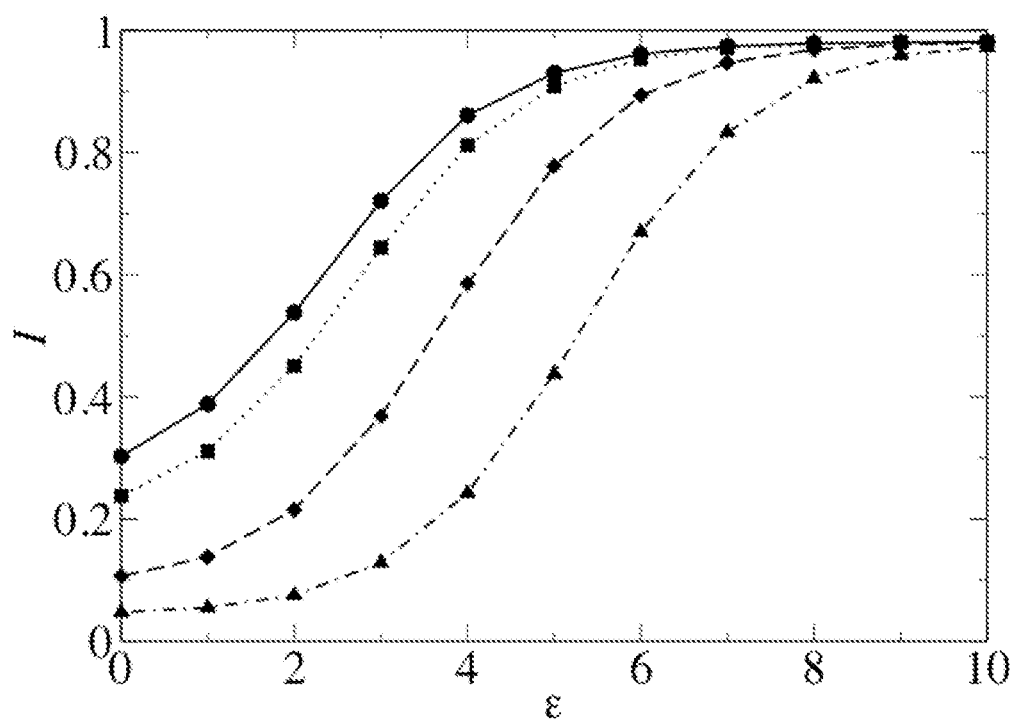
FIG. 4 Test results for prototype 1 of a multistate dynamical unimolecular hinge sensor. The resonance energy transfer signal intensity I at physiological temperature is plotted as a function of binding energy $\Delta\varepsilon$ for different values of the depth of the bias $D_c$: ●=0; ■=1 Kcal/mol; ♦=3 Kcal/mol; ▲=5 Kcal/mol.
Figure 5:
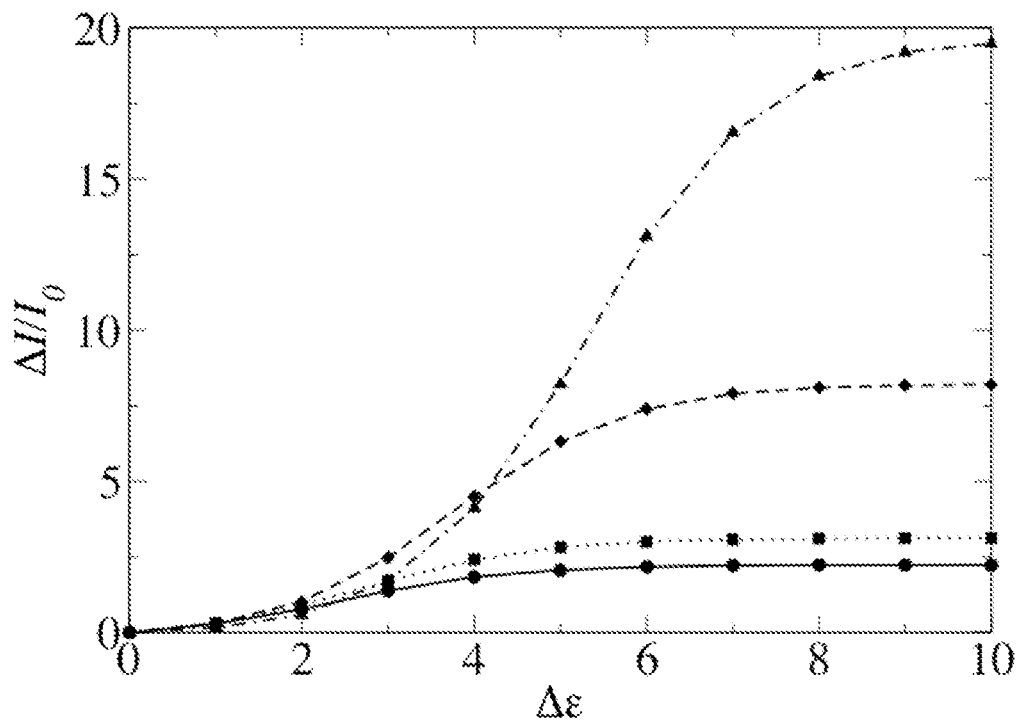
FIG. 5 Test results for prototype 1 of a multistate dynamical unimolecular hinge sensor. The resonance energy transfer signal to noise ratio $(I-I_0)/I_0$ at physiological temperature is plotted as a function of binding energy Δε for different values of the depth of the bias $D_c$: ●=0; ■=1 Kcal/mol; ◆=3 Kcal/mol; ▲=5 Kcal/mol.
Figure 6:
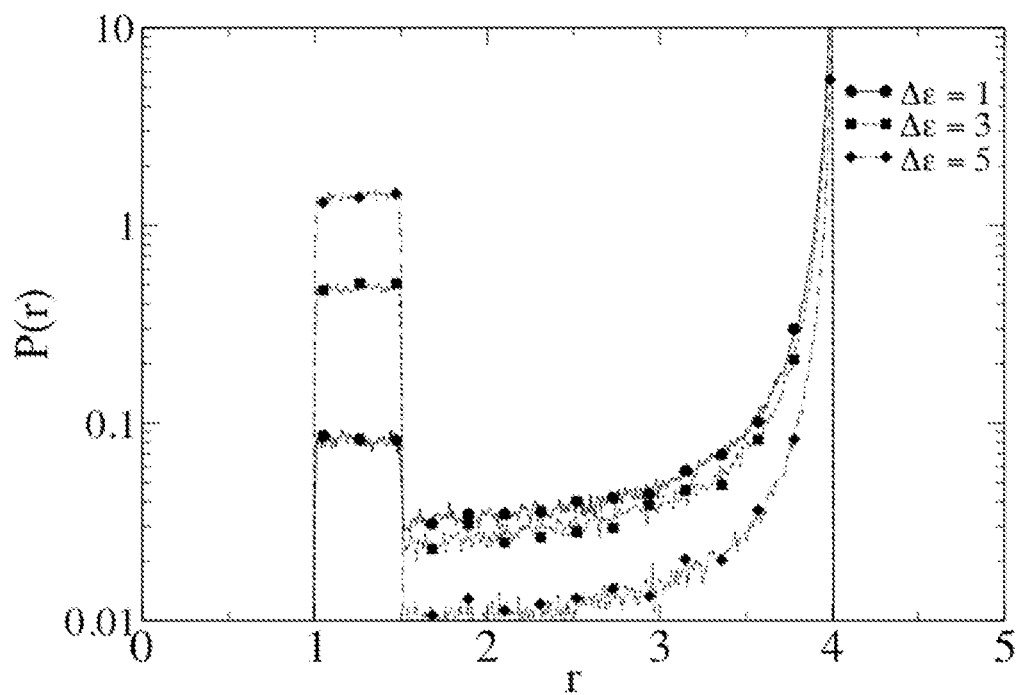
FIG. 6 Test results for prototype 1 of a multistate dynamical unimolecular hinge sensor, where the bias depth $D_c$=4 Kcal/mol. The probability distribution P(r) of inter macromolecule distances r at physiological temperature is plotted for different values of the binding energies Δε●=1 Kcal/mol; ■=3 Kcal/mol; ▲=5 Kcal/mol.
Figure 7:
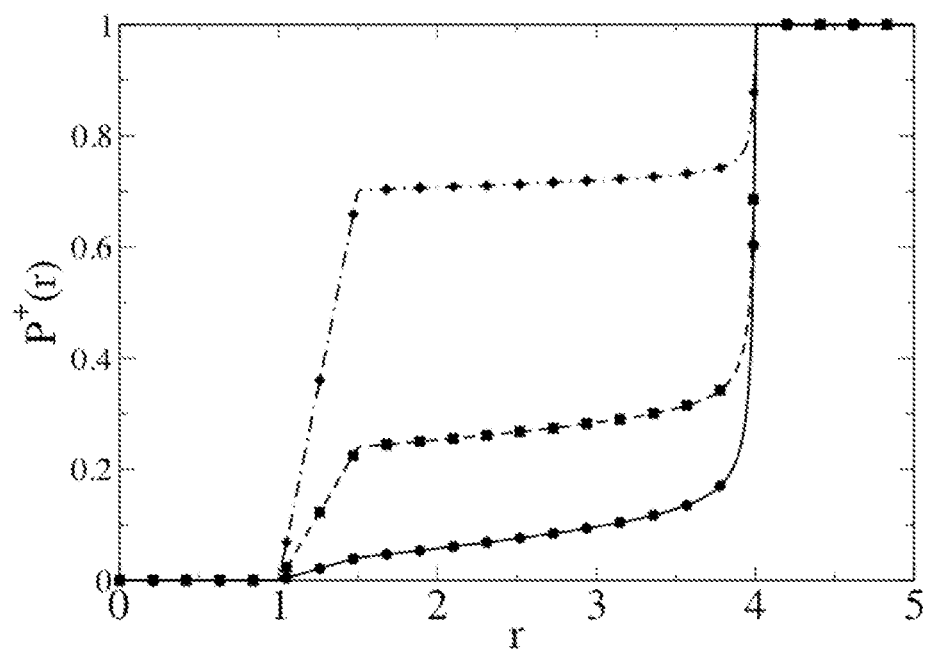
FIG. 7 Test results for prototype 1 of a multistate dynamical unimolecular hinge sensor, where the bias depth $D_c$=4 Kcal/mol. The probability $P^+(r)$ of inter macromolecule distances r at physiological temperature is plotted for different values of the binding energies Δε●=1 Kcal/mol; ■=3 Kcal/mol; ◆=5 Kcal/mol. Note that $P^+(r)$ is simply the integral from 0 to r of P(r) and is otherwise known as the cumulative probability. Here it gives the probability that two spheres of the model are within a distance r of each other.
Figure 8:
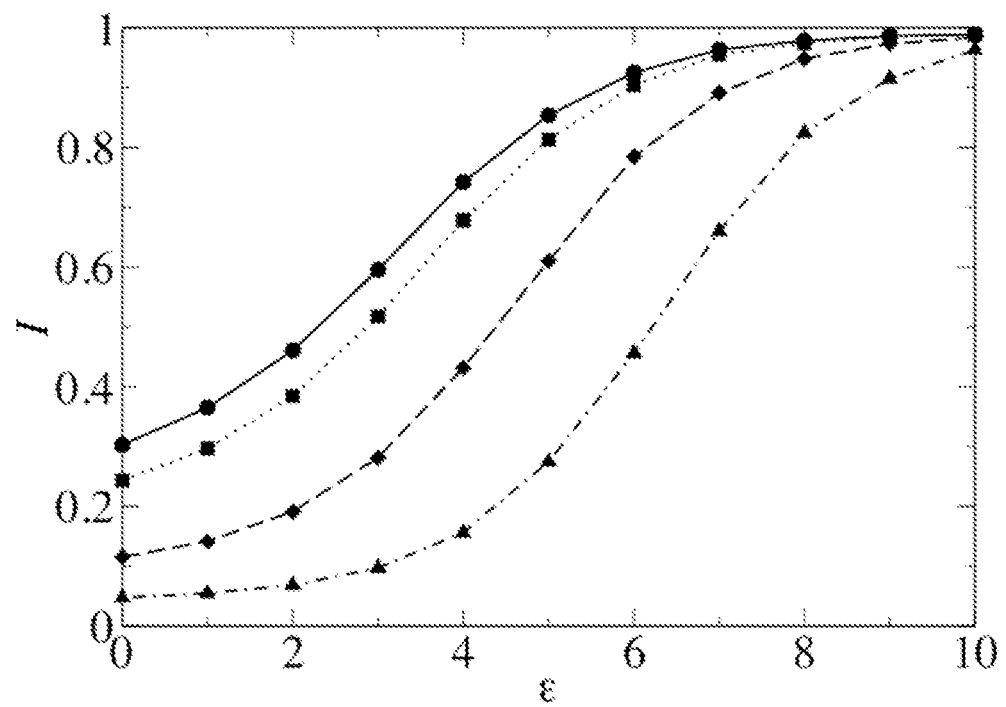
FIG. 8 Test results for prototype 2 of a multistate dynamical unimolecular hinge sensor. The resonance energy transfer signal intensity I at physiological temperature is plotted as a function of binding energy Δε for different values of the depth of the bias $D_c$: ●=0; ■=1 Kcal/mol; ◆=3 Kcal/mol; ◆=5 Kcal/mol.
Figure 9:
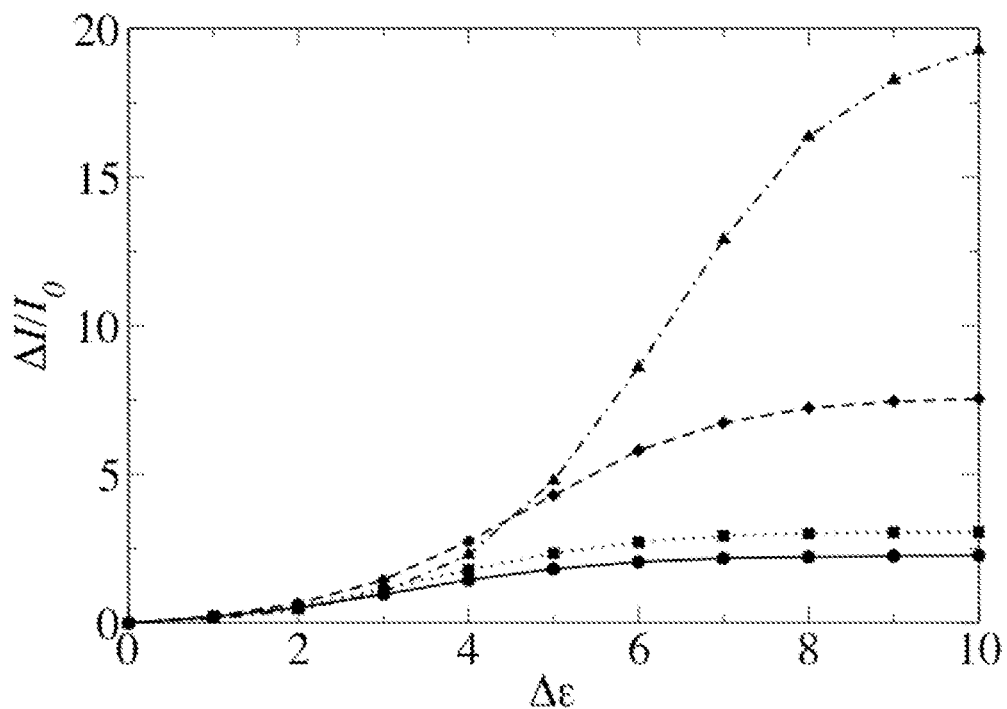
FIG. 9 Test results for prototype 2 of a multistate dynamical unimolecular hinge sensor. The resonance energy transfer signal to noise ratio $(I-I_0)/I_0$ at physiological temperature is plotted as a function of binding energy Δε for different values of the depth of the bias $D_c$: ●=0; ■=1 Kcal/mol; ◆=3 Kcal/mol; ▲=5 Kcal/mol.
Figure 10:
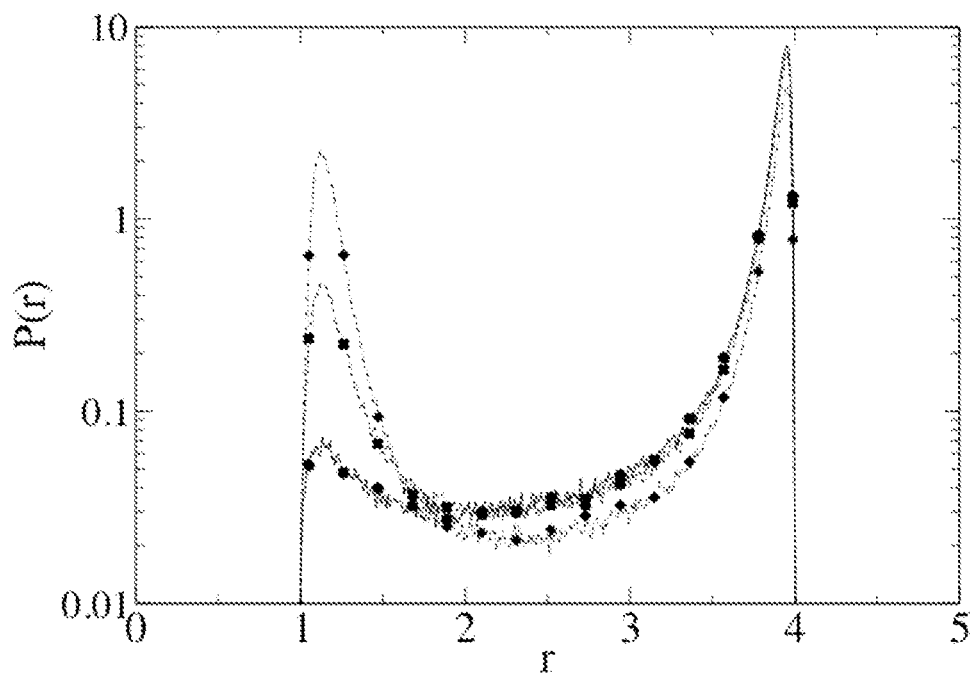
FIG. 10 Test results for prototype 2 of a multistate dynamical unimolecular hinge sensor, where the bias depth $D_c$=4 Kcal/mol. The probability distribution P(r) of inter macromolecule distances r at physiological temperature is plotted for different values of the binding energies Δε●=1 Kcal/mol; ■=3 Kcal/mol; ◆=5 Kcal/mol.
Figure 11:
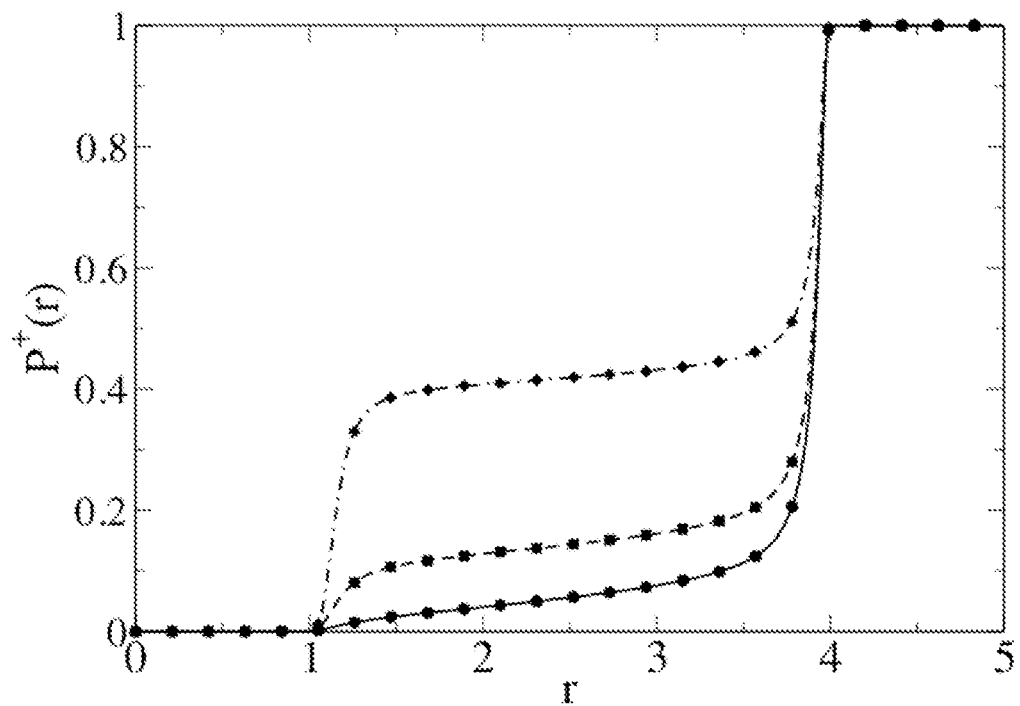
FIG. 11 Test results for prototype 2 of a multistate dynamical unimolecular hinge sensor, where the bias depth $D_c$=4 Kcal/mol. The probability $P^+(r)$ of inter macromolecule distances r at physiological temperature is plotted for different values of the binding energies Δε●=1 Kcal/mol; ■=3 Kcal/mol; ◆=5 Kcal/mol.
Figure 12:
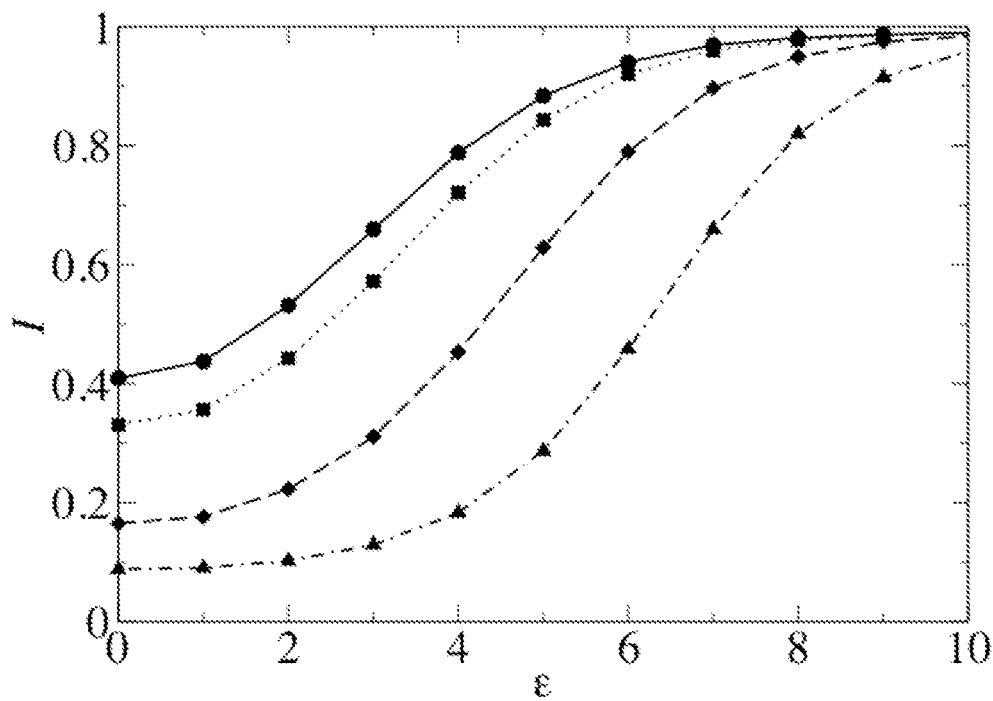
FIG. 12 Test results for prototype 3 of a multistate dynamical unimolecular hinge sensor. The resonance energy transfer signal intensity I at physiological temperature is plotted as a function of binding energy Δε for different values of the depth of the bias $D_c$: ●=0; ■=1 Kcal/mol; ◆=3 Kcal/mol; ◆=5 Kcal/mol.
Figure 13:
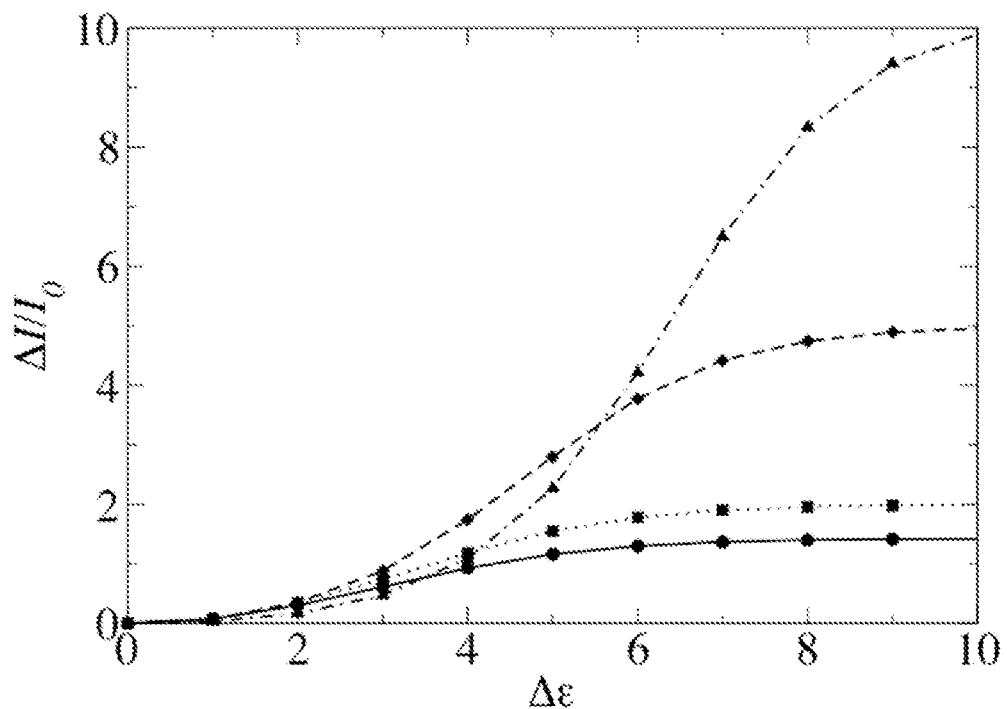
FIG. 13 Test results for prototype 3 of a multistate dynamical unimolecular hinge sensor. The resonance energy transfer signal to noise ratio $(I-I_0)/I_0$ at physiological temperature is plotted as a function of binding energy Δε for different values of the depth of the bias $D_c$: ●=0; ■=1 Kcal/mol; ◆=3 Kcal/mol; ▲=5 Kcal/mol.
Figure 14:
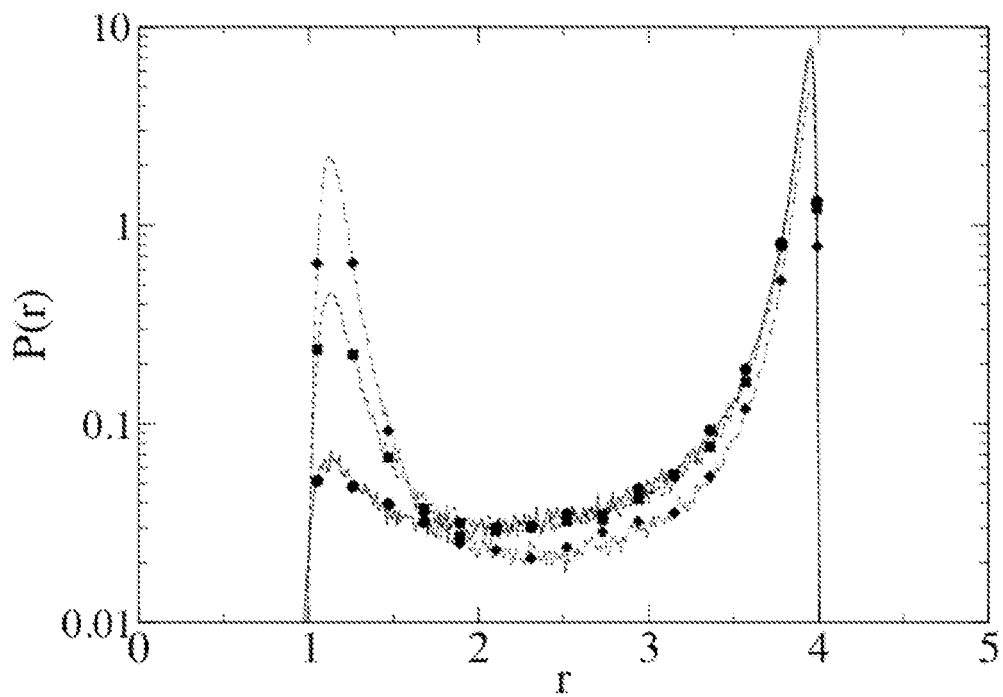
FIG. 14 Test results for prototype 3 of a multistate dynamical unimolecular hinge sensor, where the bias depth $D_c$=4 Kcal/mol. The probability distribution P(r) of inter macromolecule distances r at physiological temperature is plotted for different values of the binding energies Δε●=1 Kcal/mol; ■=3 Kcal/mol; ◆=5 Kcal/mol.
Figure 15:
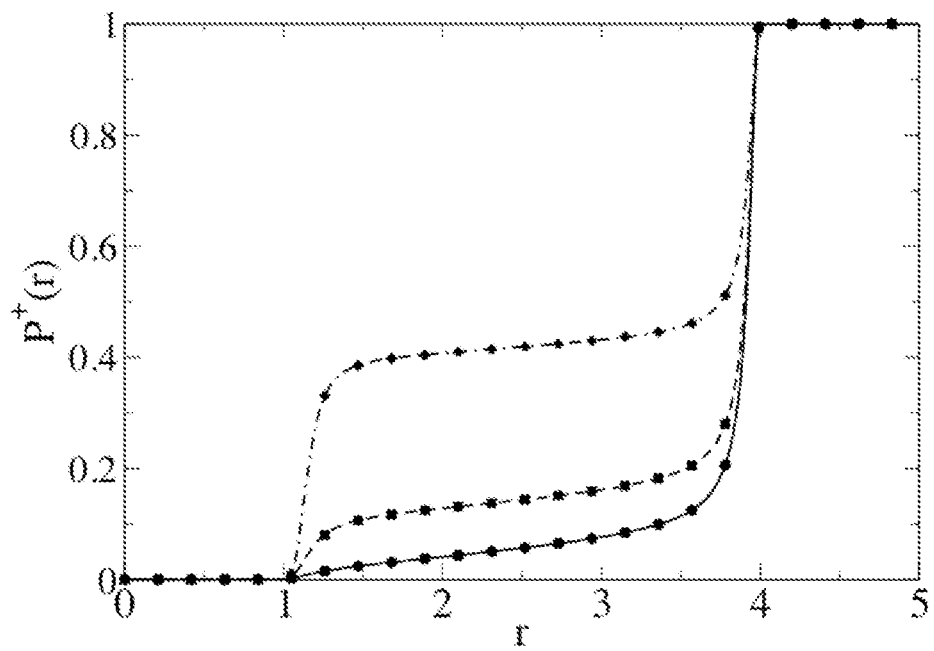
FIG. 15 Test results for prototype 3 of a multistate dynamical unimolecular hinge sensor, where the bias depth $D_c$=4 Kcal/mol. The probability $P^+(r)$ of inter macromolecule distances r at physiological temperature is plotted for different values of the binding energies Δε●=1 Kcal/mol; ■=3 Kcal/mol; ◆=5 Kcal/mol.

Unimolecular sensors having the structural and dynamical features depicted in FIGS. 2 and 3, can be readily generated. First, residue sequences of amino acids giving rise to stiff rod like peptides such as L or R are well known, and are widely available in the literature in the form of long alpha helical proteins such as Basic Leucine Zipper Domain (bZIP domain) found in many DNA binding proteins of almost eukaryotes. One example of bZIP, is a domain found in Maf transcription factor proteins NP15. Other long alpha helical structural motifs include coiled coils, examples include the muscle protein tropomyosin and oncoproteins c-Fos and c-jun (see reference NP16). Shorter alpha-helical motifs include the widely studied villin headpiece (see reference NP17).

Second, short very flexible peptides connecting the rods such as peptide C are also well known. Third, as mentioned above charged amino acids are also well known. Fourth, the proteins which comprise the ligand binding domain, and sensor domains, and FP's can be taken from the literature (see reference NP1). Where estimates of the binding energy between particular ligand binding domains and sensor domains in the ON state in the presence of the ligand are not available, they can be estimated experimentally (see reference NP18), or computed via molecular simulation, using publically available standard force-fields developed for biology such as CHARMM (see reference NP19) or AMBER (see reference NP20), open source and publically available simulation engines such as NAMD (see reference NP21) or GROMACS (see reference NP22) and biased sampling methods such as those available in the open software package PLUMED, (see reference NP23) as well as commercial packages.

Once the binding energy is known (or estimated), the residues q1, q2, ... in FIGS. 2 and 3 and their locations in the residue sequence defining the biased hinge can be optimised, via molecular simulation so that in the ON state the probability of the biased hinge sensor being open is slightly higher or equal to the probability of it being closed.

Another example of a biased hinge type sensor can be constructed where the curly element C in FIGS. 2 and 3 denotes a combination of rigid and flexible peptides rather than only a highly flexible peptide as the interconnecting linker. This example is by design more adaptable to chemical constraints associated with charged residues, and steric effects.

Having determined the full residue sequence of the full biosensor, the sensor can be generated using "off the shelf" biotechnology kits for example those made by: PURExpress® In Vitro Protein Synthesis Kit; Mammalian expression kits such as Jump In™ T-REx™ HEK 293 Kit; Cell-Free Expression Kits such as Expressway™ Maxi Cell-Free E. coli Expression System; and Bacterial expression kits such as Champion™ pET160 Directional TOPO® Expression Kit with Lumio™ Technology. Thus the linker can be tailor-made to match essentially any ligand binding domain and sensor domain, ligand and FP pair.

The ligand binding domain can be designed using various method such as Monoclonal Antibody, Polyclonal antibody or Genomic antibody technologies.

Macromolecules (for example FPs, ligand binding domains, sensor domains and even full unimolecular sensors) can be attached to specific sites of proteins of interest using chemical labelling for example covalent bonding amine labelling, thiol labelling etc. (see reference NP24), enzymatic labelling (labelling catalysed by post-translational enzyme modification, labelling with self-modified enzymes such as cutinase or interin, see reference NP25) and non-covalent tagging (tetracysteine/biarsenical tag, histidine tag, see reference NP26). Other tags can be genetic based which include SNAP and CLIP tags (see reference NP27).

A practical issue in analytical chemistry, biochemistry, related sciences and industry is the perturbative effect of chemical sensors/indicators used to measure the concentrations of analytes of interest. If the sensor is not very sensitive to the target analyte, large volumes of probe may be required. Another frequent situation is that the design of the probe is such that it has a disruptive effect on the system it is designed to monitor, which complicates fine scale measurements, including the tracking of temporal and spatial variations of analyte concentrations. The present invention resolves both of these difficulties.

In parallel with developments of RET sensors using single donor and acceptor FPs, a method using a single FP donor but multiple FP acceptors (of different colours) has been reported, for instance by Sun et al. (see reference NP13). The latter method can be combined with the present invention, where for example the additional acceptor FPs are attached to sites of the protein of interest.

The present invention resolves many of the difficulties in performing immunoassays through the application of Tuneable Multistate Dynamical Unimolecular Hinge Sensors. In the context of immunoassays, the sensors have several novel capabilities, not possible or very difficult to implement with available methods. These include the facility to track in time the local concentrations of target analytes, to turn on pharmaceutically active molecules or toxins, and do not require the complex set of washing steps typically used with conventional immunoassays described above in the background art.

Figure 16:
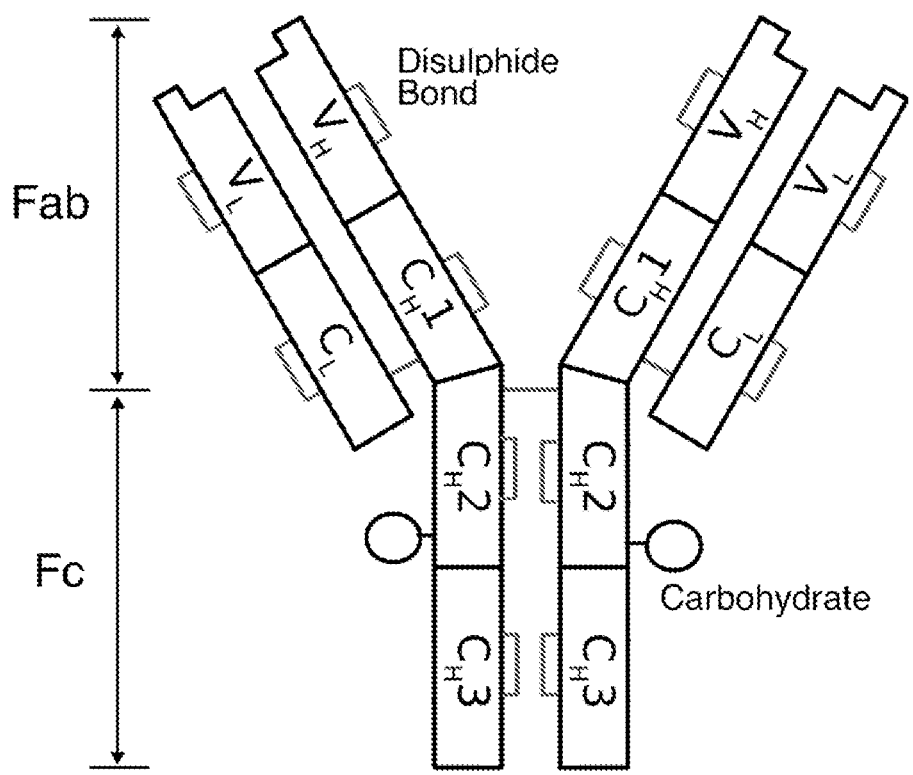
FIG. 16 Schematic description of a primary antibody showing the heavy and light chains, the Fab and Fc regions, as well as the location of disulphide bonds and carbohydrates.
Figure 17:
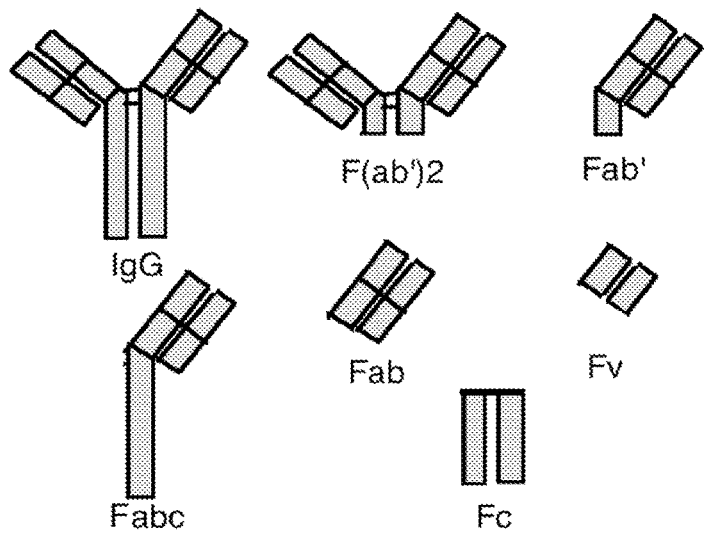
FIG. 17 Schematic description showing different fragments of a primary antibody realizable in experiments.

In this invention the detection of analytes such as antigens or antibodies (see FIG. 16) is made by selecting macromolecules A and A' of the Tuneable Multistate Dynamical Unimolecular Hinge Sensors (see FIG. 2) to be suitable antibody fragments (see FIG. 17). Macromolecules B and B' can be a variety of different types of macromolecules interconnected through a biased hinge. The sensor can be tuned so that in the OFF state (i.e. in the absence of target analytes close to A or A'), the arms of the hinge are open, and in the ON state (i.e. in the presence of target analytes close to A or A'), the arms of the hinge oscillate between open and closed configurations.

B can be conjugated with A through primary amines in the antibody, or through carbohydrates in the Fc region, and similarly B' can be conjugated with A' (with the use of blocking reagents as described above where required). It is also possible to conjugate A with B and A' with B' using the sulfhydryl groups described in the background art.

In variant 1, and other aspects and embodiments, of this invention, macromolecules B and B' are suitable fluorescent proteins or bioluminescent molecules, which can undergo resonance energy transfer when brought together by the action of A and A' on the sensing of a target analyte, such as an antigen or antibody as described above.

In variant 2, and other aspects and embodiments, of this invention, B is a fluorescent protein or bioluminescent molecule or dye molecule capable of absorbing light from an external field and B' to be a quencher macromolecule, for instance made from a metal such as gold, such that when A and A' come together in their ON state, B and B' to so that the energy absorbed by B is transferred non-radiatively to B' and released locally in the form of heat on or close to the target analyte within or close to a cell or cellular compartment.

In variant 3, and other aspects and embodiments, of this invention, B or B' are macromolecules which are the reactants of a chemical reaction such that when B and B' are far apart the reaction cannot take place (in OFF state of A and A'), and when A and A' come together in their ON state, the reaction can take place to produce products which may be pharmaceutical active or chemo-toxic. It is also possible that B consists of reactants which require a catalyst to react, and B' consists of the corresponding catalyst, such that when A and A' come together in their ON state, the resulting the products of the catalysed reaction are active drugs or chemo-toxic on or close to the target analyte within or close to a cell or cellular compartment.

In variant 4, and other aspects and embodiments, of this invention, B and B' are each a moiety of a split single fluorophore (or split bioluminescent molecule) such that in the OFF state they are far apart and do not fluoresce (or bio-luminesce), and in the ON when A and A' can come together, B and B' are also brought together and fluoresce when illuminated at appropriate wavelengths (or bio-luminesce) on or close to the target analyte within or close to a cell or cellular compartment.

In variant 5, and other aspects and embodiments, of this invention, B and B' are each the moieties of a split macromolecule which is pharmaceutically inactive (or non-chemo-toxic or non-photosensitizing) when they are far apart (in the OFF state of A and A'), and when A and A' come together in their ON state due to the presence of the target analyte, B and B' are brought together so that the complex is pharmaceutical active (or chemo-toxic or photosensitizing).

Variant 6 of this invention is a combination of variant 4 and variant 5. B consists of a moiety of a split fluorescent protein or split bioluminescent molecule and the moiety of a split drug or split chemo-toxic or split photosensitizing molecule macromolecule, and B' consists of the other moiety of the split fluorescent protein or split bioluminescent molecule and the other moiety of a split drug or split chemo-toxic molecule, such that when B and B' are apart the complex is inactive, and when B and B' are brought together due to the presence of target analyte by A and A', the complex becomes pharmaceutically active or chemo-toxic or photosensitizing and fluorescent or bioluminescent.

In variant 7, and other aspects and embodiments, of this invention, B consists of the moieties of a split fluorescent protein or split bioluminescent molecule and a quencher molecule, and B' consist of the other moieties of the split fluorescent protein or split bioluminescent molecule and a quencher molecule, such that B and B' are apart they cannot become easily optically excited, for instance by an external field, but when B and B' are brought together due to the recognition of a target analyte by A and A', the resulting complex both easily absorbs energy from an externally applied source and transfers it non-radiatively through the quencher molecule, thereby heating the local cellular or sub-cellular region wherein the analyte is located. It is also possible to divide the quencher into two moieties, with one quencher moiety and one fluorescent moiety in B, and one quencher moiety and one fluorescent moiety in B'.

Variant 8, and other aspects and embodiments, of this invention is a combination of variants 3 and 4. B consists of the moieties of a split fluorescent protein or split bioluminescent molecule and some of the reactants of a chemical reaction and B' consist of the other moieties of the split fluorescent protein or split bioluminescent molecule and the rest of the reactants required for a chemical reaction. It is also possible that B consists of reactants which require a catalyst to react, and B' consists of the corresponding catalyst. When B and B' are apart the they cannot easily fluoresce or bioluminesce, and the chemical reaction cannot easily take place, but when B and B' are brought together due to the recognition of a target analyte by A and A', the resulting complex can fluoresce or bioluminesce, and the chemical reaction can take place at or close to the local cellular or sub-cellular region wherein the analyte is located.

As well as sensors targeting single analytes in the above variants of the invention, multiple sensors targeting different analytes, each using corresponding macromolecules (A, A', B and B') can be used at the same time within a living sample or microtiter testing well or vial. When appropriate, different acceptor fluorophores (or moieties thereof) emitting at different wavelengths can be used so as to allow simultaneous use and/or measurement (using microscopy) of each type of possible analyte present in the sample.

Variants 1, 4, 6 and 8, and other aspects and embodiments, of this invention can be used for performing immunoassays to identify the presence of analytes including antibodies in samples using microscopy and suitable light sources for the selected fluorescent proteins, or no external light sources if the donor fluorescent protein is bioluminescent or chemiluminescent.

Variants 1, 4, 6 and 8, and other aspects and embodiments, of this invention, when combined with confocal scanning microscopy described in the background art, can be used to identify the time dependent concentration and location of analytes in a sample. This includes the capacity to generate three dimensional spatial images of the concentration of analytes and track their position over time, including in living cells.

The invention can also be used to monitor changes in real time in such analyte concentration through the use of appropriate flow chambers, or in living cells.

Desktop scanners or an ordinary CCD camera, and either a single LED of a single wavelength or a combination of Red-Green-Blue LEDs can be combined with variants 1, 4, 6 and 8, and other aspects and embodiments, of this invention to determine the concentration of the analyte in a sample, including its time dependence, to produce multi-dimensional images tracking over time the concentration of the analyte.

Variants 1, 4, 6 and 8, and other aspects and embodiments, of this invention can be combined with either a single LED of a single wavelength or a combination of Red-Green-Blue LEDs and photomultiplier diode chips to measure the photo emission of the sensor, and thereby determine the concentration of the analyte in a sample, including its time dependence, for instance when a three or two dimensional image is not required. This can be used for taking and analysing immunoassays in the field, as well as in specialised laboratories.

Figure 18:
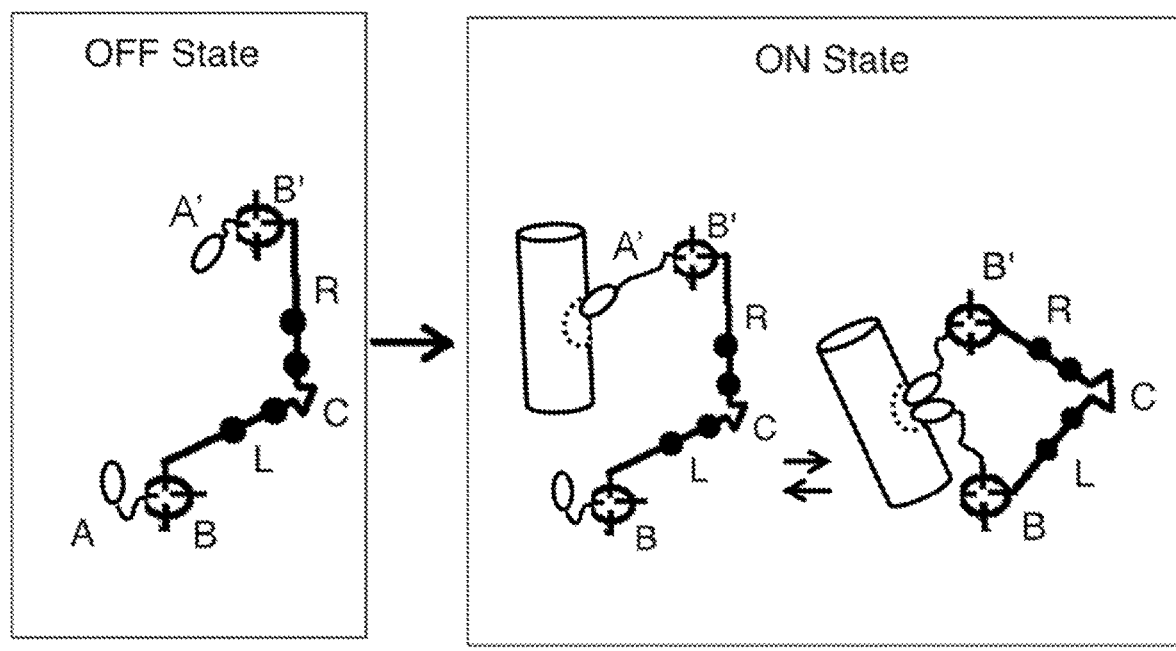
FIG. 18 is Schematic description of Tuneable Multistate Dynamical Unimolecular Hinge Sensors targeting a single epitope according to the invention, when A and A' are complimentary portions of an FIG. 39 DNA cleaving hinge sensor with split SNASE DELTA +PHS variant (built from 3bdc.pdb) moieties of SNASE and DNA recognition zinc finger proteins and longer inter-connecting flexible linkers between moieties.
Figure 19:
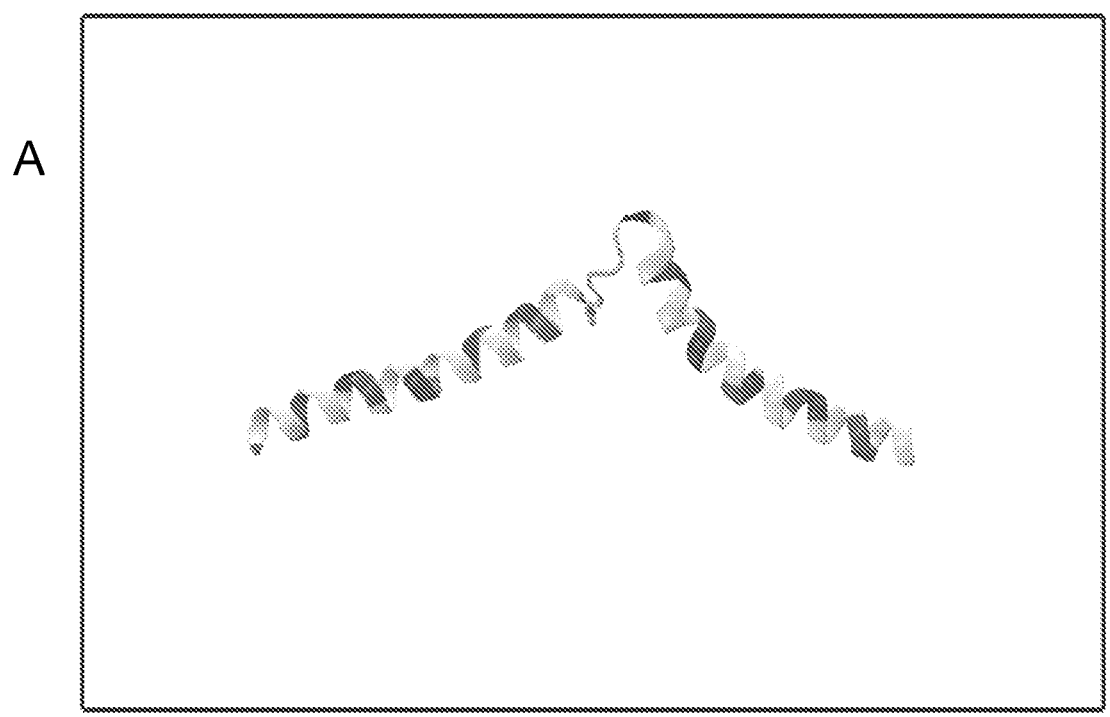
Figure 19:
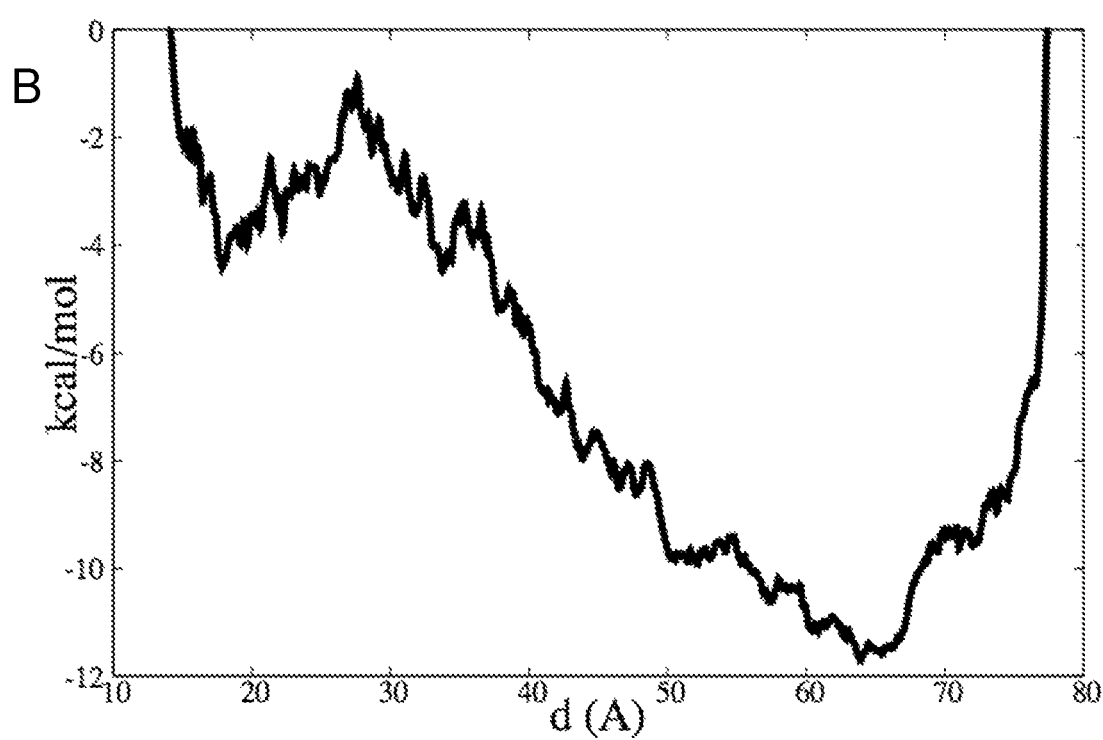
Figure 20:
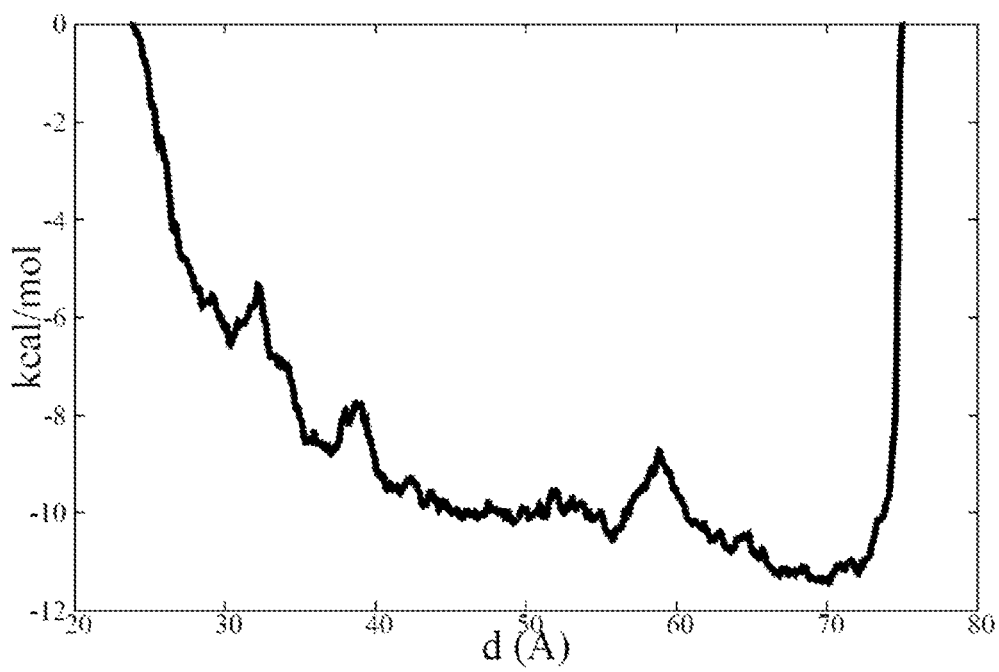

When A or A' is bonded to a suitable surface of a flow chamber, variants 1, 4, 6 and 8, and other aspects and embodiments, of this invention can be used to measure the time dependent concentration of analytes, including their detection in continuous sample measurement (see FIG. 18).

When A or A' is bonded to a suitable surface of a suitable titration vessel, the invention can be used for measuring the concentration of one or multiple analytes during a titration.

When macromolecules B and B' are the moieties of a split bio-luminescent or chemiluminescent molecule, the invention can be combined with low cost microtiter and vials described in the background art, to perform and analyse immunoassays in the field i.e. in non-laboratory conditions and without the use of specialised equipment.

When macromolecules B and B' are the moieties of a split bio-luminescent or chemiluminescent molecule, the invention can be used to deliver light close to the location of analytes, which can be close to or within living cells or cellular compartments, for the purpose of targeted electromagnetic radiation treatment.

When macromolecules B and B' are pairs of chemical reactants which react spontaneously when brought together, and such that the chemical product is either a drug or a chemo-toxin or a chemo-toxin or photosensitizing, the invention can be used as a therapeutic for diseased living cells or sub-cellular compartments, and such that the drug or chemo-toxin becomes activated on the presence of a target analyte. If B also includes either a donor FP or bioluminescent molecule or a moiety of a split FP or a moiety of a split bioluminescent molecule and B' includes a corresponding acceptor FP, or corresponding moiety of a split FP or corresponding moiety of a split bioluminescent, the activation of a drug or chemo-toxin or photosensitizing agent can be marked by the emission of light. When a donor fluorophore is used an external light source is required. When either a non-split fluorophore or non-split bioluminescent molecule is used as a donor, the emission signalling recognition of the analyte is due to resonance energy transfer.

When B is a fluorophore or a chromophore and B' is a quencher, and given a light source, variants 2 and 7, and other aspects and embodiments, of the invention can be used to deliver non-radiative energy in the form of heat at or close to the location of target analytes in living cells.

Discussion

It is well known that the choice of molecular linker connecting FP's in the probe can have a very strong effect on its overall performance. The approach taken here is to invent a radically new type of sensor by focusing on the structural properties required of the linker mechanism to complement any given pair of sensor and ligand binding domain and associated pair of FP's and ligand of interest, thereby facilitating real time tracking of biochemical events, combined with strong signal and signal to noise characteristics. Our biased hinge design and the resulting sensor is different in several key aspects from the one described in references PT1 and NP11.

The highly tuneable multistate dynamical hinge sensor is designed (i.e. biased) to be normally fully open in OFF state (i.e. the absence of the target ligand) so as to ensure the FP pair are far apart and the corresponding RET rate is very low. The sensor is tuned so that when combined with a ligand binding domain and sensor domain and associated FP's, it can open and close frequently in the ON state, but in such a way that it is can be selected to be on average open more often than closed.

This intrinsic fluctuating feature in the ON state accounts for the high signal and signal to noise properties, while allowing concentrations levels of target analyte to be maintained close to endogenous levels. This design feature of choosing the ON state to be fluctuating between two conformations (open and closed) rather than simply closed, is completely counter intuitive, and novel.

The sensor described above need not be protein based, its components can be organic or inorganic or a mixture thereof.

The present invention in the context of immunoassays also creates a series of novel capabilities not possible or very difficult to implement with available methods. In this invention the detection of analytes such as antigens is made through macromolecules A and A' of the Tuneable Multistate Dynamical Unimolecular Hinge Sensors (see FIG. 2). Macromolecules A and A' can be selected to each be the moieties of a primary antibody targeting a single epitope on an antigen through the binding of a pair of moieties of a single antibody/antibody fragment or protein mimetic thereof (FIG. 18). The sensor can be tuned so that in the OFF state (i.e. in the absence of target analytes close to A or A'), the arms of the hinge are open, and in the ON state (i.e. in the presence of target analytes close to A or A'), the arms of the hinge oscillate between open and closed configurations. Macromolecules B and B' can each consist of one or more selected molecules or moieties of split molecules, which when brought close together due to the presence of target analytes can produce a variety of selected effects: (a) resonance energy transfer in the presence of a suitable electro-magnetic radiation field; (b) fluorescence in the presence of a suitable electro-magnetic radiation field; (c) bioluminescence; (d) activated drug; (e) activated chemo toxin; (f) chemical reaction; (g) catalysed chemical reaction; (h) in the presence of a suitable electro-magnetic radiation field, the release of heat through quenching; (i) in the presence of a suitable electro-magnetic radiation field either of an external or endogenous source, the production of reactive oxygen. In addition several of these effects can be combined in the same sensor, including: {C1 (a-c), C2 (a-d), C3 (a-e), C4 (a-f), C5 (a-g), C6 (a-h); C7 (a-i), C8 (b-d), C9 (b-e), C10 (b-f), C11 (b-g), C12 (b-h), C13 (b-i), C14 (c-d), C15 (c-e), C16 (c-f), C17 (c-g), C17 (c-h), C18 (c-i)}. These effects take place in the vicinity on the sensor, which can be close to or within cells, cellular compartments, or in vitro.

Variants of the invention can be used to visualise and track in time analytes in vivo and in vitro in assays to create multi-dimensional images of said analytes using confocal scanning microscopy, desktop scanners, a variety of suitable LEDS and photo cascade chips. In addition variants of the invention can be deployed in the field using microtiters or vials, without specialised equipment, and at low cost for several applications including environmental, health, and food safety. Multiple sensors targeting different analytes can be deployed to measure a single sample simultaneously, and can be used to measure the time dependent concentration of analytes in suitable flow chambers or through titration.

Variants of the invention can be used to deliver payloads to regions close to and within cellular environments which can be specified if required by genetic targeting, and such that the payloads become activated on the presence of target analytes, and are inactive in their absence. The payloads can include drugs, chemo-toxins, chemicals, catalysts, heat through the localised absorption of external electro-magnetic or chemical fields, and hydrogen radicals using photosensitizers coupled with electro-magnetic fields of external or endogenous origin.

The hinge of the highly tuneable multistate dynamical unimolecular hinge sensor is designed (i.e., biased) to be normally fully open in OFF state (i.e. the absence of the target ligand) so as to ensure the FP pair are far apart and the corresponding RET rate is very low. The biased hinge is tuned so that when combined with a ligand binding domain and sensor domain and associated FP's, it can open and close frequently in the ON state, but in such a way that it is can be selected to be on the average open more often than closed. This intrinsic fluctuating feature in the ON state accounts for the high signal and signal to noise properties, while allowing concentrations levels of target analyte to be maintained close to endogenous levels. This design feature of choosing the ON state to be fluctuating between two configurations (open and closed) rather than simply closed, is completely counter intuitive, and novel. A version of this sensor including inorganic components can be used in electronic, semi-conducting and quantum computing industries as electronic sensors, memory devices and nano-actuators. The present invention in the context of immunoassays also creates a series of novel capabilities not possible or very difficult to implement with available methods. Variants of the invention can be used to deliver payloads to regions close to and within cellular environments which can be specified if required by genetic targeting, and such that the payloads become activated on the presence of target analytes, and are inactive in their absence. The payloads can include drugs, chemo-toxins, chemicals, catalysts, heat through the localised absorption of external optical or chemical fields, and oxygen radicals as used in photodynamic therapy.

EXAMPLES

The following examples of the invention target single epitopes rather than pairs of epitopes on an antigen. The binding fragments selected and used in these examples are derived from the optimized biotherapeutic single-chain Fv (scFv) of Tu et al (2015, J Biol Chem. 2016 Jan. 15; 291(3):1267-76. doi: 10.1074/jbc.M115.688010.), namely 5C6W anti-CXCL13 scFv—E10. The sequence of the scFv is set out below:

QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAREP

DYYDSSGYYPIDAFDIWGQGTTVTVSSGGGGSGGGGSGGGGS

QSALTQPASVSASPGQSITISCTGTSSDVGAYDWVSWYQQHPGKAPKLLI

FDVNNRPSGVSHRFSGSKSGNTASLTISGLQAEDEADYYCASATLLDTYV

FGTGTKVTVLGDQEPKSSDKTH

Note on the above sequence: the heavy chain is N terminal, linker is bold and underlined, and the light chain is C terminal.

These examples serve to teach how the sensors are built. It is clear to the skilled person that the spacers/flexible linkers would in general be adjusted to fit specific problems, reflecting steric effects of the constituent components, binding affinities, the bias specific to a given hinge, and pH and salt conditions. The hinge sequences, spacer molecules/flexible linkers, and other molecules depicted in examples 1-3 may each be individually selected as a potential component of the sensor molecule of the invention, or combinations thereof may be selected.

Example 1 Sensor Using Split ScFv but a Pair of FP's

Full sensor using H-[GGGGS]^2-A[GSG]^3-fP1-hinge-A[GSG]^3-fp2-[GGGGS]^2-L

A heavy and light chain are respectively provided from a ScFv antibody fragment in the sensor molecule such that the full system is a single protein (i.e. in effect a single linear chain albeit with two disulphide bonds present in the ScFv. Note that it is also possible for other examples to eliminate the disulphide bonds to facilitate sensor expression in the reductive environment (electron rich) of the cytosol). Using only the heavy and light chains has the advantageous consequence, that the sensor is significantly smaller, targeting a single epitope rather than a pair of epitopes on the same antigen. The example 5C6W was selected because epitope mapping has shown that both the light chain and heavy chain are involved in binding to the epitope—which is necessary for proper functioning of the sensor. The flexible linkers can be shortened/lengthened/mutated to optimise functioning of the sensor, and for that matter, additional spacer type alpha helices can be added where required.

The sequence of the example hinge sensor molecule is provided below in the N to C terminal direction (the combined sequences of this molecule are also known as SEQ ID NO: 1):

Heavy chain
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAREP

DYYDSSGYYPIDAFDIWGQGTTVTVSS

Flexible Linker/spacer molecule
GGGGSGGGGS

FP1
MSKGEELFTGVVPILVELDGDVNGHKFSVSGEGEGDATYGKLTLKFICTT

GKLPVPWPTLVTTLVQCFSRYPDHMKRHDFFKSAMPEGYVQERTIFFKDD

GNYKTRAEVKFEGDTLVNRIELKGIDFKEDGNILGHKLEYNYISHNVYIT

ADKQKNGIKANFKIRHNIEDGSVQLADHYQQNTPIGDGPVLLPDNHYLST

QSALSKDPNEKRDHMVLLEFVTAAGI

Flexible Linker/spacer molecule
AGSGGSGGSGA

Hinge (pair of rod-like molecules linked through a joint molecule C)
EAAAKEAAAKEAAAKEAAAKEAAAKEAAAKAGSGAKAAAEKAAAEKAAAE

KAAAEKAAAEKAAAE

Flexible Linker/spacer molecule
AGSGGSGGSGA

FP2
MSKGEELFTGVVPILVELDGDVNGHKFSVSGEGEGDATYGKLTLKFICTT

GKLPVPWPTLVTTFLQCFARYPDHMKRHDFFKSAMPEGYVQERTIFFKDD

GNYKTRAEVKFEGDTLVNRIELKGIDFKEDGNILGHKLEYNYNSQNVYIM

ADKQKNGIKVNFKIRHNIEDGSVQLADHYQQNTPIGDGPVLLPDNHYLSY

QSALSKDPNEKRDHMVLLEFVTAAGI

Flexible Linker/spacer molecule
GGGGSGGGGS

Light Chain
QSALTQPASVSASPGQSITISCTGTSSDVGAYDWVSWYQQHPGKAPKLLI

FDVNNRPSGVSHRFSGSKSGNTASLTISGLQAEDEADYYCASATLLDTYV

FGTGTKVTVLGDQEPKSSDKTH

Figure 21:
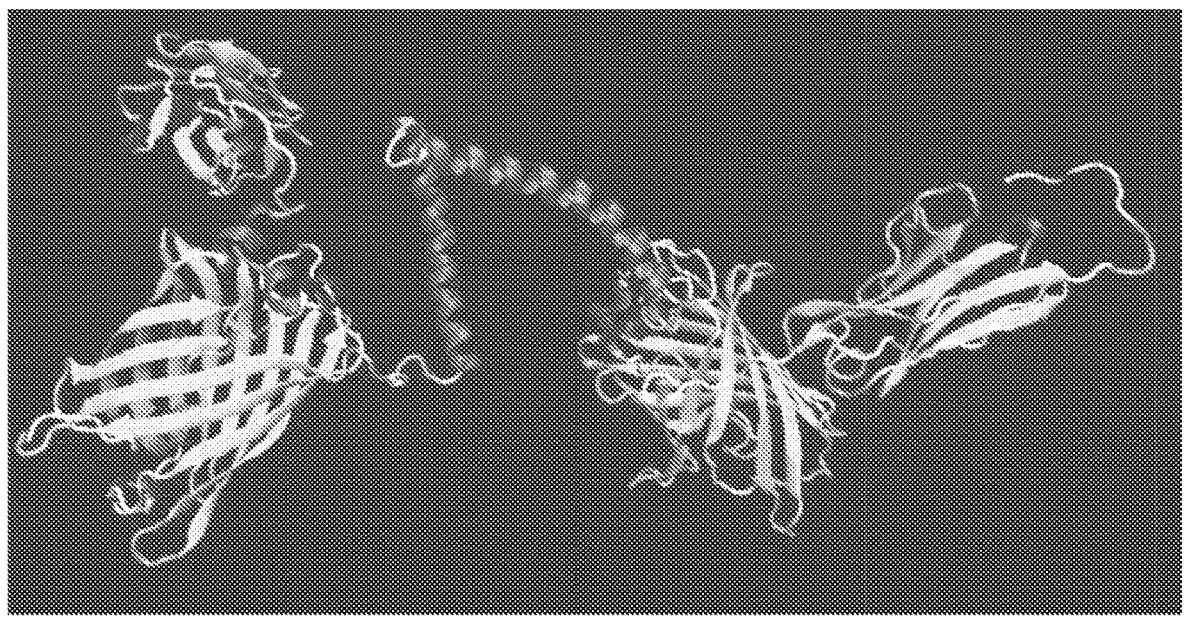

A 3D model of the above molecule is shown in FIG. 21.

Example 2 Sensor Using Split ScFv and the Two Moities of a Split Yellow FP

Full sensor using H-[GGGGS]^2-A[GSG]^3-split-YFP-left-hinge-A[GSG]^3-split-YFP-right-[GGGGS]^2-L A heavy and light chain are respectively provided from a ScFv antibody fragment in the sensor molecule such that the full system is a single protein (i.e. in effect a single linear chain albeit with two disulphide bonds present in the ScFv. Note that it is also possible for other examples to eliminate the disulphide bonds to facilitate sensor expression in the reductive environment (electron rich) of the cytosol). Using only the heavy and light chains has the advantageous consequence, that the sensor is significantly smaller, targeting a single epitope rather than a pair of epitopes on the same antigen. The example 5C6W was selected because epitope mapping has shown that both the light chain and heavy chain are involved in binding to the epitope—which is necessary for proper functioning of the sensor. The yellow fluorescent protein pdb code used is 1F09 (as before).

The flexible linkers can be shortened/lengthened/mutated to optimise functioning of the sensor, and for that matter, additional spacer type alpha helices can be added where required.

The sequence of the example hinge sensor molecule is provided below in the N to C terminal direction (the combined sequences of this molecule are also known as SEQ ID NO: 2):

```
Heavy chain
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAREP

DYYDSSGYYPIDAFDIWGQGTTVTVSS

Flexible Linker/spacer molecule
GGGGSGGGGS

FP1
MSKGEELFTGVVPILVELDGDVNGHKFSVSGEGEGDATYGKLTLKFICTT

GKLPVPWPTLVTTFGXGLQCFARYPDHMKRHDFFKSAMPEGYVQERTIFF

KDDGNYKTRAEVKFEGDTLVNRIELKGIDFKEDGNILGHK

Flexible Linker/spacer molecule
AGSGGSGGSGA

Hinge (pair of rod-like molecules linked through
a joint molecule C)
EAAAKEAAAKEAAAKEAAAKEAAAKSGSKAAAEKAAAEKAAAEKA

AAEKAAAEKAAAE

Flexible Linker/spacer molecule
AGSGGSGGSGA

FP2
LEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK

Flexible Linker/spacer molecule
GGGGSGGGGS

Light chain
QSALTQPASVSASPGQSITISCTGTSSDVGAYDWVSWYQQHPGKAPKLLI

FDVNNRPSGVSHRFSGSKSGNTASLTISGLQAEDEADYYCASATLLDTYV

FGTGTKVTVLGDQEPKSSDKTH
```

Figure 22:
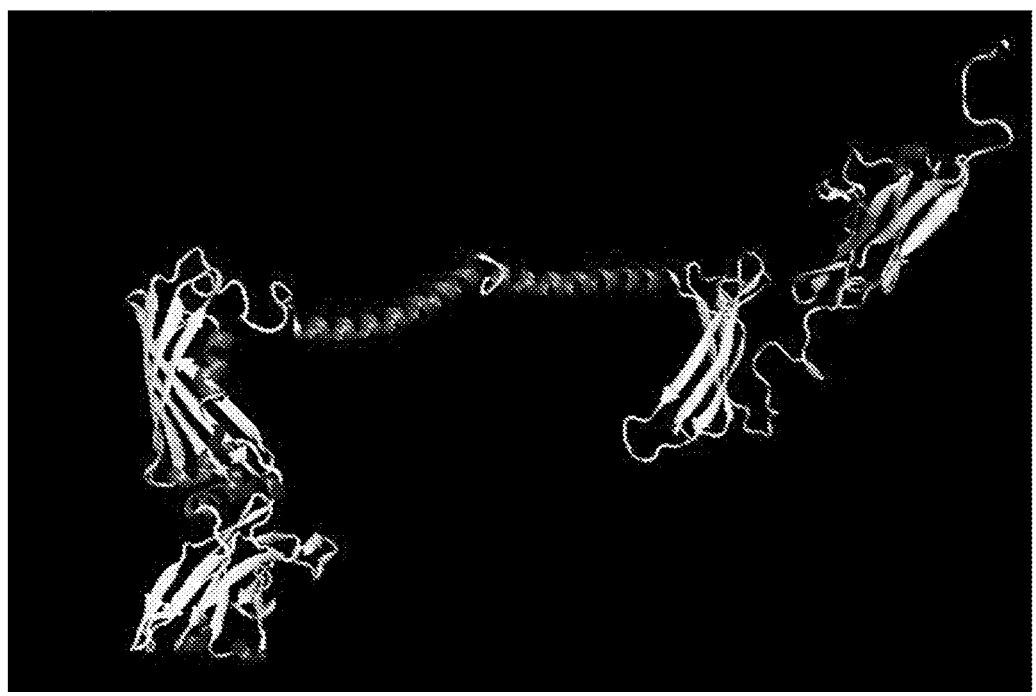

A 3D model of the above molecule is shown in FIG. 22.

Example 3 Sensor Using Split ScFv and the Split Diphtheria Toxin

Based on pdb files 5c6w and 1xdt

Full sensor using diph1-495-[GGGGS]^2-A[GSG]^3-H-hinge-A[GSG]^3-L-[GGGGS]^2-diph496-535

The sequence of the example hinge sensor molecule is provided below in the N to C terminal direction (the combined sequences of this molecule are also known as SEQ ID NO: 3):

```
Diph1-495
                                    (SEQ ID NO: 22)
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSS

Flexible Linker/spacer molecule
AGSGA

Heavy chain
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAREP

DYYDSSGYYPIDAFDIWGQGTTVTVSS

Flexible Linker/spacer molecule
AGSGGSGGSGA

Hinge (pair of rod-like molecules linked
through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
AGSGGSGGSGA

Light chain
QSALTQPASVSASPGQSITISCTGTSSDVGAYDWVSWYQQHPGKAPKLLI

FDVNNRPSGVSHRFSGSKSGNTASLTISGLQAEDEADYYCASATLLDTYV

FGTGTKVTVLGDQEPKSSDKTH

Flexible Linker/spacer molecule
AGSGA

Diph496-535
                                    (SEQ ID NO: 23)
SEKIHSNEISSDSIGVLGYQKTVDHTKVNSKLSLFFEIKS
```

Figure 23:

A 3D model of the above molecule is shown in FIG. 23.

Example 4—Using Affibodies for Targeting

Affibodies are small proteins that bind to target molecules with a wide variety of applications. As proteins they can be used in the cell, facilitated in part by the lack of cystine bonds, as well as in assays. They comprise three alpha helix type proteins connected by short loops. Starting from the n-terminus, the first two helices bind to the target. The role of third helix is to give structural stability to the affibody, the consensus to date being that it does not bind directly to the target. (reference 1). However, when the third helix is absent in variants of the affibody, the binding to the target is generally lost, unless the first two helices are modified to include a cystine bond. In the latter case, there is very tentative evidence that the binding to the target is preserved. Extensive libraries of affibodies have been created since their first invention some thirty years ago. Affibodies are the fastest known binders to target molecules, retain their function up to at least 65 degrees C., and are comparatively robust. (reference 2) Affibodies frequently have tags, such as fluorescent proteins, attached to either their N or C ends, without significant effect on their binding properties.

4 helix alpha helices are quite common in biology, and are known to be robust. (reference 3)

Molecular dynamics simulations of proteins having secondary structures such as alpha helices, turns and loops can be performed using a variety of publically available simulation codes, such as Gromacs, namd, CHARMM and Amber. For simulation of proteins in water under physiological conditions, sufficiently accurate force-fields are available which preserve key secondary and tertiary structures. These include GROMOS 54a7 and CHARMM 36, and appropriate models of water, protonation and salt levels.

Example Zher 2 Affibody pdb sequence 2kzi
fasta single letter sequence:

*MGSSHHHHHHLQ*VDNKFNKEMRNAYWEIALLPNLNNQQKRAFIRSLYDDP

SQSANLLAEAKKLNDAQAPK

Main structure (corresponding sequence is bold and underlined) determined using NMR (see 2kzi pdb file entry for experimental details; also see Eigenbrot et al. (2010) Proc. Natl. Acad. Sci. USA 107: 15039-15044), which is herein incorporated by reference). The missing structure (i.e. MGSSHHHHHHLQ) highlighted by italics is disordered and believed not to be involved in binding to the target. The residues associated with helices directly binding to target are underlined (i.e. VDNKFNKEMRNAYWE-IALLPNLNNQQKRAFIRSLY), and the third helix required for stability of the complex is bold and underlined (i.e. DDPSQSANLLAEAKKLNDAQAPK).

Figure 24:
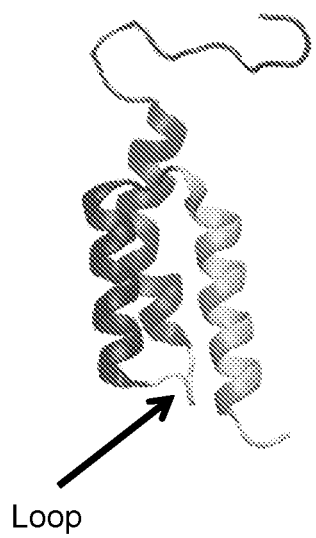

The full protein was reconstructed using modeller, and molecular dynamics simulations (Gromacs with SPC water and the GROMOS 54a7 Forcefield). The structure observed in simulation was consistent with NMR. An earlier attempt to simulate the protein using CHARMM 22 forcefield and TIP3 model of water failed to reproduce NMR data—indicating that accurate forcefields are important here. A snap shot of the full protein we obtained after one nanosecond of molecular dynamics simulation is given in FIG. 24 with an appropriate rendering emphasizing the secondary structure.

Design of a 4-Helix Complex Comprising an Affibody with an Additional Helix and Associated Interconnecting Loop One letter sequence:

*MGSSHHHHHHLQ*VDNKFNKEMRNAYWEIALLPNLNNQQKRAFIRSLYDDP

SQSANLLAEAKL*NDLLPNLNNQSANLLAEAKELNDAQAPK*

The associated interconnecting loop is highlighted by italics and underlined (i.e. <u>NDLLPNLNNQSANLLAEAKELNDAQAPK</u>).

The loop and helix were selected to as to ensure a 4-helix bundle structure, and the stability of the affibody in 3 steps. In the first step, the loop (residues: LLPNLN, see FIG. 24: arrow) was copied and added to the end of helix 3 (such a modification is herein generally applicable for aspects and embodiments of the invention herein, which may require a fourth helix). Second a large segment of helix 3 was added to the end of the loop. The segment was selected by visual inspection of the original affibody, to determine the most complementary segment, and subsequent homology computations using modeller (using the structure of the affibody of interest i.e Zher pdb) to see if the resulting structure corresponded to a 4-helix bundle. An alignment used to generate the structure is given below.

The third step involved simulating the structure in water using molecular dynamics. This resulted initially in the destruction of the first alpha helix. Upon close examination, it was found at the charged residue pair KK copied to fourth helix plays a critical role in determining the stability of the Zher 2 affibody. Replacing K with L resulted in a stable structure. Additional residue substitutions may result in further optimization of the structure, in particular so as to enhance binding to target and stability.

Building the Affibody Based Sensor.

Steps—mutation and assembly of fusion protein and validation—basic algorithm

1. Split the residue sequence of the affibody (or its 4-helix bundle derivative) in the middle of the loop between helix 1 and helix 2 into two, and insert there the biased hinge sequence in the same natural order as the affibody (i.e. n-terminus to c-terminus).

In the case of the sequence 2kzi, the loop is in the sequence LLPNLN, i.e. on either side of the/close to corresponding proline residue 2. Attach appropriate modules ends of extended hinge 1 and 4.

1b An alternative to step 1 is to cut the loop between helix 2 and helix 3 into two and glue onto biased hinge.

Each step is validated using homology modelling and simulation before the subsequent step. If the structure that emerges at each step is unsuccessful, the trial mutation and partial assembly is rejected and a new variant is proposed until a successful one is obtained. If at the end of step 3 a sequence giving a successful structure is not realized, the process is repeated from step 1 with a modified sequence. Typical modifications are: (a) addition of a hydrophilic flexible linker spacer (repeats of SGS or deletions of short loops not involved in binding; (b) addition/deletion of residues to regulate overall charge (c) addition/deletion of turns involving proline (d) addition deletion of residues with a high probability to participate in an alpha helix so as to induce or remove an approximate 60 degree turn etc. Mutations such as these are best done one at a time once an approximate satisfactory structure is obtained. Note that, in general, the skilled person would avoid as much as possible mutations to residues known to be directly involved with binding to epitopes/target ligands, so as to preserve their binding to target propensity. When adding sub-sequences (e.g. an additional alpha helix), the skilled person would try to use, as much as possible, sequences that are believed not to bind to the target.

Example 4a—4-Helix Bundle Modified Her 2
Affibody Based Example Combined with the
Biased Hinge and Pair of Fluorescent Proteins FP1
and FP2

Sensor based 4 helix affibody modified version of (2kzi), biased hinge and pair of FPs sequence:hinge2kzi36:::::composed from L and R:from Intfold: 1.90: 0.19

The sequence of the example hinge sensor molecule is provided below in the N to C terminal direction (the combined sequences of this molecule are also known as SEQ ID NO: 4):

```
FP1
MSKGEELFTGVVPILVELDGDVNGHKFSVSGEGEGDATYGKLTLKFICTT

GKLPVPWPTLVTTLTWGVQCFSRYPDHMKRHDFFKSAMPEGYVQERTIFF

KDDGNYKTRAEVKFEGDTLVNRIELKGIDFKEDGNILGHKLEYNYISHNV

YITADKQKNGIKANFKIRHNIEDGSVQLADHYQQNTPIGDGPVLLPDNHY

LSTQSALSKDPNEKRDHMVLL

Flexible Linker/spacer molecule
SGSSGS

Affibody Helix 1
HHLQVDNKFNKEMRNAYWEIALLPN

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3, 4
LNNQQKRAFIRSLYDDPSQSANLLAEAKKLNDLLPNLNNQSANLLAEAKE

LNDAQAPK

Flexible Linker/spacer molecule
SGSSGSSGSSGS

FP2
SKGEELFTGVVPILVELDGDVNGHKFSVSGEGEGDATYGKLTLKFICTTG

KLPVPWPTLVTTFGYGLQCFARYPDHMKRHDFFKSAMPEGYVQERTIFFK

DDGNYKTRAEVKFEGDTLVNRIELKGIDFKEDGNILGHKLEYNYNSQNVY

IMADKQKNGIKVNFKIRHNIEDGSVQLADHYQQNTPIGDGPVLLPDNHYL

SYQSALSKDPNEKRDHMVLLEFVTAAGI
```

Figure 25:
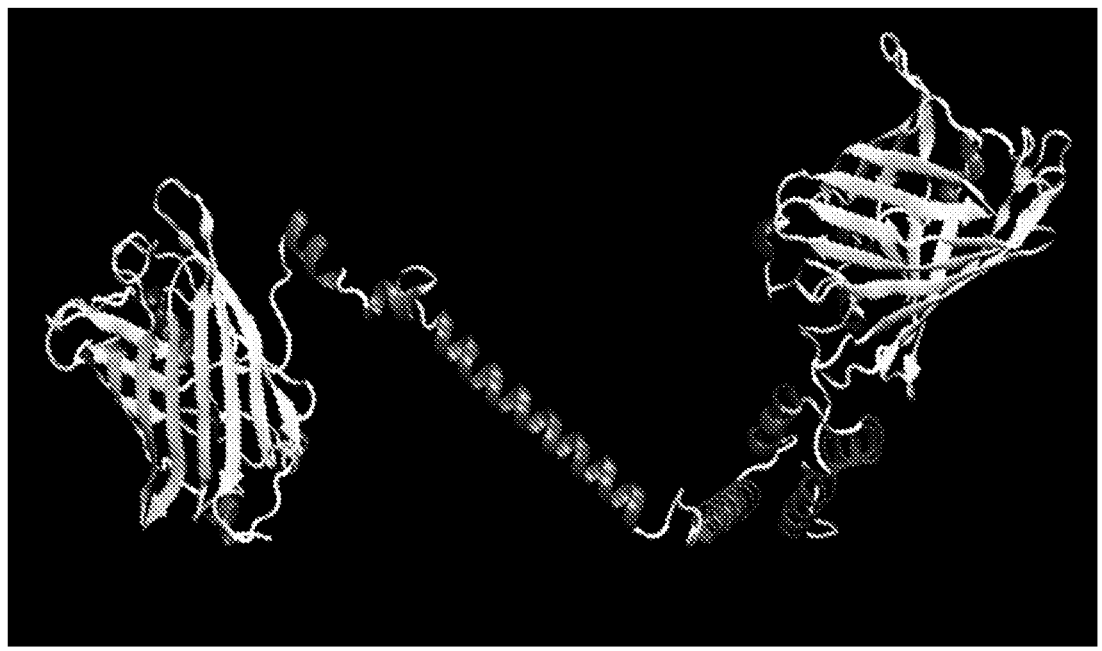

A 3D model of the above molecule is shown in FIG. 25.

Example 4b—3-Helix Bundle Modified her 2 Affibody Based Example Combined with the Biased Hinge and Pair of Fluorescent Proteins FP1 and FP2

Sensor based 3-helix affibody (2kzi), biased hinge and pair of FPs

The sequence of the example hinge sensor molecule is provided below in the N to C terminal direction (the combined sequences of this molecule are also known as SEQ ID NO: 5):

```
FP1
MSKGEELFTGVVPILVELDGDVNGHKFSVSGEGEGDATYGKLTLKFICTT

GKLPVPWPTLVTTLTWGVQCFSRYPDHMKRHDFFKSAMPEGYVQERTIFF

KDDGNYKTRAEVKFEGDTLVNRIELKGIDFKEDGNILGHKLEYNYISHNV

YITADKQKNGIKANFKIRHNIEDGSVQLADHYQQNTPIGDGPVLLPDNHY

LSTQSALSKDPNEKRDHMVLL

Flexible Linker/spacer molecule
SGSSGS

Affibody Helix 1
HHLQVDNKFNKEMRNAYWEIALLPN

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3
LNNQQKRAFIRSLYDDPSQSANLLAEAKKLNDLL

Flexible Linker/spacer molecule
SGSSGSSGSSGS

FP2
SKGEELFTGVVPILVELDGDVNGHKFSVSGEGEGDATYGKLTLKFICTTG

KLPVPWPTLVTTFGYGLQCFARYPDHMKRHDFFKSAMPEGYVQERTIFFK

DDGNYKTRAEVKFEGDTLVNRIELKGIDFKEDGNILGHKLEYNYNSQNVY

IMADKQKNGIKVNFKIRHNIEDGSVQLADHYQQNTPIGDGPVLLPDNHYL

SYQSALSKDPNEKRDHMVLLEFVTAAGI
```

Figure 26:
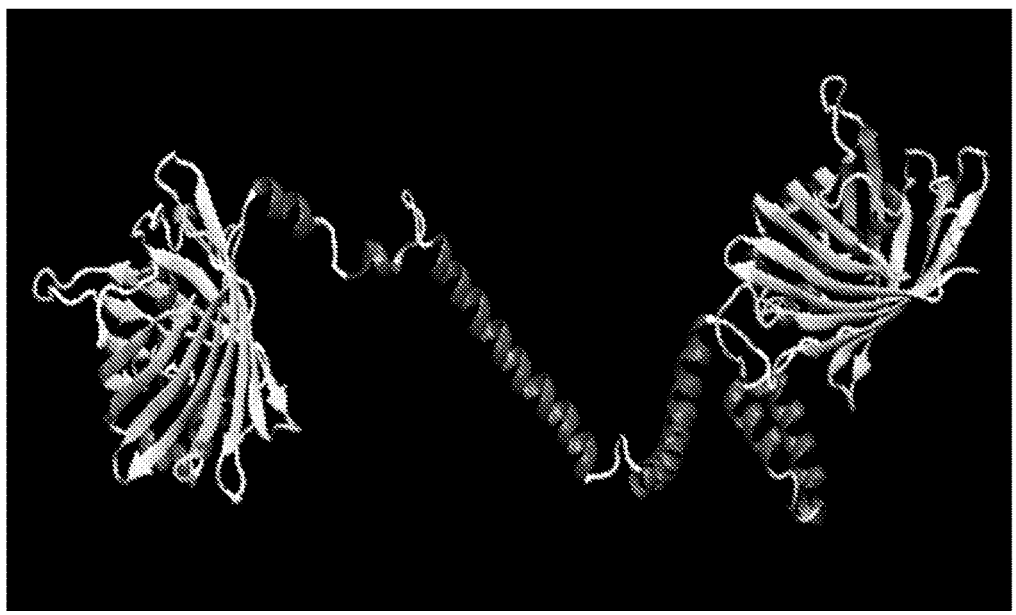

A 3D model of the above molecule is shown in FIG. 26.

Example 4c—Sensor Based on 4-Helix Version of Affibody 2Kzi and Split YFP (Pdb 1F09)

sequence:sensor-2kzi-splitYFP:::::composed from L and R:from Intfold: 1.90: 0.19

The sequence of the example hinge sensor molecule is provided below in the N to C terminal direction (the combined sequences of this molecule are also known as SEQ ID NO: 6):

```
FP1
MSKGEELFTGVVPILVELDGDVNGHKFSVSGEGEGDATYGKLTLKFICTT

GKLPVPWPTLVTTFGYGLQCFARYPDHMKRHDFFKSAMPEGYVQERTIFF

KDDGNYKTRAEVKFEGDTLVNRIELKGIDFKEDGNILGHK

Flexible linker/joint
SGSSGS

Affibody Helix 1
HHLQVDNKFNKEMRNAYWEIALLPN

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3, 4
LNNQQKRAFIRSLYDDPSQSANLLAEAKKLNDLLPNLNNQSANLLAEAKE

LNDAQAPK

Flexible Linker/spacer molecule
SGSSGSSGSSGS
```

```
FP2
LEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK
```

Figure 27:
Figure 28:
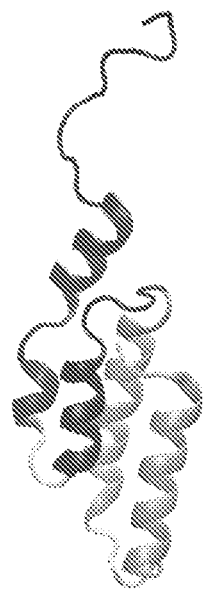

A 3D model of the above molecule is shown in FIG. 27. A snap shot of the full protein obtained after one nanosecond of molecular dynamics simulation is given in FIG. 28 with an appropriate rendering emphasizing the secondary structure.

Example 4d—Sensor Based on 3-Helix Version of Affibody 2Kzi and Split YFP (Pdb 1F09)

The sequence of the example hinge sensor molecule is provided below in the N to C terminal direction (the combined sequences of this molecule are also known as SEQ ID NO: 7):

```
FP1
MSKGEELFTGVVPILVELDGDVNGHKFSVSGEGEGDATYGKLTLKFICTT

GKLPVPWPTLVTTFGYGLQCFARYPDHMKRHDFFKSAMPEGYVQERTIFF

KDDGNYKTRAEVKFEGDTLVNRIELKGIDFKEDGNILGHK

Flexible Linker/spacer molecule
SGSSGS

Affibody Helix 1
HHLQVDNKFNKEMRNAYWEIALLPN

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3
LNNQQKRAFIRSLYDDPSQSANLLAEAKKLNDLL

Flexible Linker/spacer molecule
SGSSGSGSSGS

FP2
LEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK
```

Figure 29:
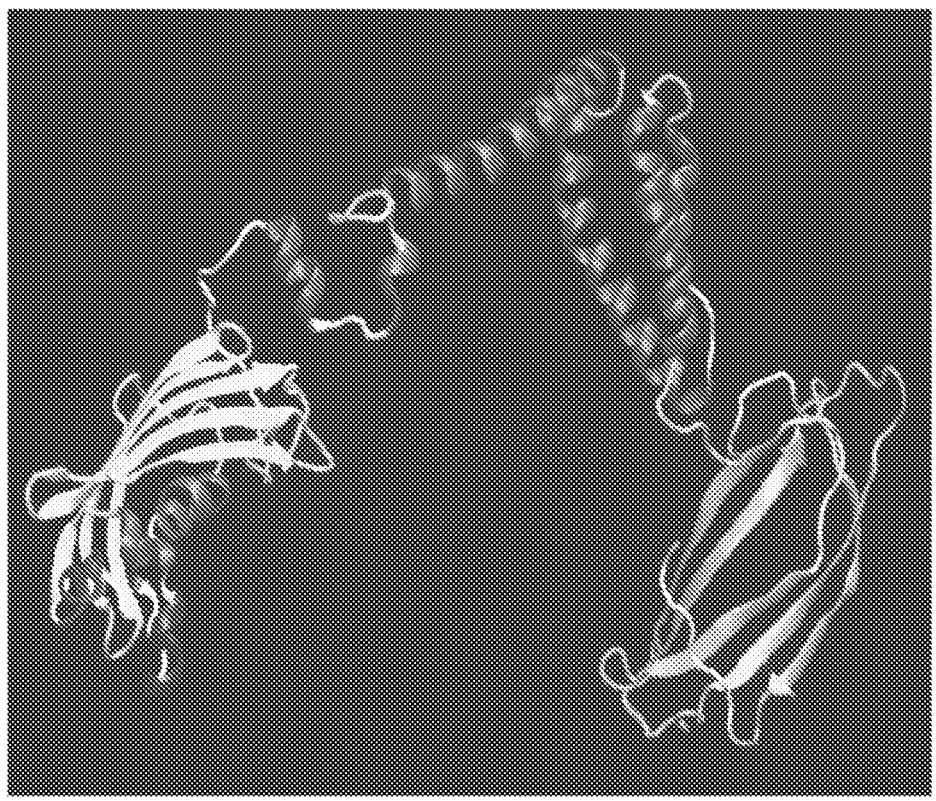

A 3D model of the above molecule is shown in FIG. 29.

Example 4e—Sensor Based on 4-Helix Version of Affibody 2Kzi and Split Diphtheria (pdb 1xdt)

The sequence of the example hinge sensor molecule is provided below in the N to C terminal direction (the combined sequences of this molecule are also known as SEQ ID NO: 8):

```
1xdt residues 1-496
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSS

Flexible Linker/spacer molecule
SGSSGS

Affibody Helix 1
HHLQVDNKFNKEMRNAYWEIALLPN

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3, 4
LNNQQKRAFIRSLYDDPSQSANLLAEAKKLNDLLPNLNNQSANLLAEAKE

LNDAQAPK

Flexible Linker/spacer molecule
SGSSGSSGSSGS

1xdt residues 496-535
SEKIHSNEISSDSIGVLGYQKTVDHTKVNSKLSLFFEIKS
```

Figure 30:
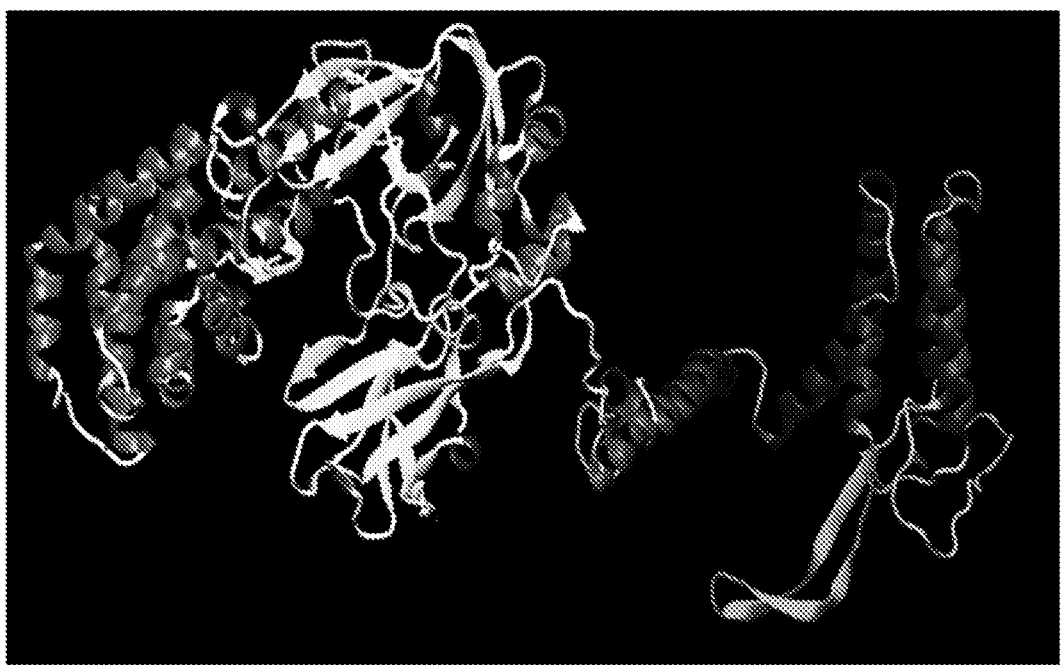

A 3D model of the above molecule is shown in FIG. 30.

Example 4f—Sensor Based on 3-Helix Version of Affibody 2Kzi and Split Diphtheria (Pdb 1xdt)

The sequence of the example hinge sensor molecule is provided below in the N to C terminal direction (the combined sequences of this molecule are also known as SEQ ID NO: 9):

```
1xdt residues 1-496
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSS

Flexible Linker/spacer molecule
SGSSGS

Affibody Helix 1
HHLQVDNKFNKEMRNAYWEIALLPN
```

```
Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 2, 3
LNNQQKRAFIRSLYDDPSQSANLLAEAKKLNDLL

Flexible Linker/spacer molecule
SGSSGSSGSSGS

1xdt residues 496-535
SEKIHSNEISSDSIGVLGYQKTVDHTKVNSKLSLFFEIKS
```

Figure 31:

A 3D model of the above molecule is shown in FIG. 31.

Example 4g—4-Helix Bundle Modified her 2 Affibody Based Example Combined with the Biased Hinge and Pair of Fluorescent Proteins FP1 and FP2

Hinge inserted between second and third helix. Sensor based 4-helix affibody modified version of (2kzi), biased hinge and pair of FP's The sequence of the example hinge sensor molecule is provided below in the N to C terminal direction (the combined sequences of this molecule are also known as SEQ ID NO: 10):

```
FP1
MSKGEELFTGVVPILVELDGDVNGHKFSVSGEGEGDATYGKLTLKFICTT

GKLPVPWPTLVTTLTWGVQCFSRYPDHMKRHDFFKSAMPEGYVQERTIFF

KDDGNYKTRAEVKFEGDTLVNRIELKGIDFKEDGNILGHKLEYNYISHNV

YITADKQKNGIKANFKIRHNIEDGSVQLADHYQQNTPIGDGPVLLPDNHY

LSTQSALSKDPNEKRDHMVLL

Flexible Linker/spacer molecule
SGSSGS

Affibody Helices 1, 2
HHLQVDNKFNKEMRNAYWEIALLPNLNNQQKRAFIRSLYDDP

Flexible Linker/spacer molecule
SGS

Hinge (pair of rod-like molecules
linked through a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 3, 4
SQSANLLAEAKKLNDLLPNLNNQSANLLAEAKELNDAQAPK

Flexible Linker/spacer molecule
SGSSGSSGSSGS

FP2
SKGEELFTGVVPILVELDGDVNGHKFSVSGEGEGDATYGKLTLKFICTTG

KLPVPWPTLVTTFGYGLQCFARYPDHMKRHDFFKSAMPEGYVQERTIFFK

DDGNYKTRAEVKFEGDTLVNRIELKGIDFKEDGNILGHKLEYNYNSQNVY

IMADKQKNGIKVNFKIRHNIEDGSVQLADHYQQNTPIGDGPVLLPDNHYL

SYQSALSKDPNEKRDHMVLLEFVTAAGI
```

Example 4h—Sensor Based on 4-Helix Version of Affibody 2Kzi and Split YFP (Pdb 1F09)

Hinge inserted between second and third helix.

The sequence of the example hinge sensor molecule is provided below in the N to C terminal direction (the combined sequences of this molecule are also known as SEQ ID NO: 11):

```
FP1
MSKGEELFTGVVPILVELDGDVNGHKFSVSGEGEGDATYGKLTLKFICTT

GKLPVPWPTLVTTFGYGLQCFARYPDHMKRHDFFKSAMPEGYVQERTIFF

KDDGNYKTRAEVKFEGDTLVNRIELKGIDFKEDGNILGHK

Flexible Linker/spacer molecule
SGSSGS

Affibody Helices 1, 2
HHLQVDNKFNKEMRNAYWEIALLPNLNNQQKRAFIRSLYDDP

Flexible Linker/spacer molecule
SGS

Hinge (pair of rod-like molecules linked through
a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 3, 4
SQSANLLAEAKKLNDLLPNLNNQSANLLAEAKELNDAQAPK

Flexible Linker/spacer molecule
SGSSGSSGSSGS

FP2
LEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK
```

Example 4i—Sensor Based on 3-Helix Version of Affibody 2Kzi and Split YFP (Pdb 1F09)

Hinge inserted between second and third helix.

The sequence of the example hinge sensor molecule is provided below in the N to C terminal direction (the combined sequences of this molecule are also known as SEQ ID NO: 12):

```
FP1
MSKGEELFTGVVPILVELDGDVNGHKFSVSGEGEGDATYGKLTLKFICTT

GKLPVPWPTLVTTFGYGLQCFARYPDHMKRHDFFKSAMPEGYVQERTIFF

KDDGNYKTRAEVKFEGDTLVNRIELKGIDFKEDGNILGHK

Flexible Linker/spacer molecule
SGSSGS
```

```
Affibody Helices 1, 2
HHLQVDNKFNKEMRNAYWEIALLPNLNNQQKRAFIRSLYDDP

Flexible Linker/spacer molecule
SGS

Hinge (pair of rod-like molecules linked through
a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody helix 3
SQSANLLAEAKKLNDLL

Flexible Linker/spacer molecule
SGSSGSSGSSGS

FP2
LEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK
```

Example 4i—Sensor Based on 4-Helix Version of Affibody 2Kzi and Split Diphtheria (Pdb 1xdt)

Hinge inserted between second and third helix.

The sequence of the example hinge sensor molecule is provided below in the N to C terminal direction (the combined sequences of this molecule are also known as SEQ ID NO: 13):

```
1xdt residues 1-496
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSS

Flexible Linker/spacer molecule
SGSSGS

Affibody Helices 1, 2
HHLQVDNKFNKEMRNAYWEIALLPNLNNQQKRAFIRSLYDDP

Flexible Linker/spacer molecule
SGS

Hinge (pair of rod-like molecules linked through
a joint molecule C)
EAAAKEAAAKEAAAKEAAAKEAAAKEAAAKSGSKAAAEKAAAEKAAAEKA

AAEKAAAEKAAAE

Flexible Linker/spacer molecule
SGS

Affibody Helices 3,4
SQSANLLAEAKKLNDLLPNLNNQSANLLAEAKELNDAQAPK

Flexible Linker/spacer molecule
SGSSGSSGSSGS

1xdt residues 496-535
SEKIHSNEISSDSIGVLGYQKTVDHTKVNSKLSLFFEIKS
```

Example Antibody Binding Affinities

TABLE 1

$K_D$ (the equilibrium dissociation constant between the antibody and its antigen), of 840 Rabbit Monoclonal Antibodies (RabbitMAbs) and 88 MouseAbs expressed as percentage distribution at a given binding affinity from micromolar to femtomolar range.

| $K_D$ Value | RabbitAbs | MouseAbs |
|---|---|---|
| >$10^{-7}$ | 6% | |
| $10^{-7}$ | 11% | |
| $10^{-8}$ | 19% | 1% |
| $10^{-9}$ | 39% | 1% |
| $10^{-10}$ | 10% | 35% |
| $10^{-11}$ | 13% | 54% |
| $10^{-12}$ | 2% | 8% |
| $10^{-13}$ | | 1% |

$K_D$ values for 88 MouseAbs were derived from published literature. The $K_D$ measurement values for the 863 RabbitMAbs were all from the OI-RD measurements. RabbitMAbs appear to be on average 1-2 order of magnitude higher affinity. Origin of data—http://www.abcam.com/index.html?pageconfig=resourcE&rid=15749

| $K_D$ value | Molar concentration (sensitivity) |
|---|---|
| $10^{-4}$ to $10^{-6}$ | Micromolar (uM) |
| $10^{-7}$ to $10^{-9}$ | Nanomolar (nM) |
| $10^{-10}$ to $10^{-12}$ | Picomolar (pM) |
| $10^{-13}$ to $10^{-15}$ | Femtomolar (fM) |

REFERENCES

References discussed herein are incorporated by reference.

Patents and Published Patent Applications

PT1 EP 2623514 A (KYOTO UNIVERSITY) 26 Sep. 2011
PT2 Wang. X. Optical systems for microarray scanning. U.S. Pat. No. 7,706,419 B2. (Apr. 7, 2010)

Non-Patent Literature

NP1 NEWMAN, Robert, et al. Genetically Encodable Fluorescent Biosensors for Tracking Signaling. *Chemical Reviews.* 2011, vol. 111, no. 5, p 3614-3666.
NP2 MIYAWAKI, Atsushi. Visualization of Spatial and Temporal Dynamics on Intracellular Signaling. *Developmental Cell.* 2003, vol. 4, n. 3, p. 295-305.
NP3 MIYAWAKI, Atsushi. Cellular Functions Using Fluorescent Proteins and Fluorescence Resonance Energy Transfer. *Annual Review of Biochemistry.* 2011, vol. 80, p. 357-373.
NP4 FRITZ, Rafael, et al. A Versatile Toolkit to Produce Sensitive FRET Biosensors to Visualize Signaling in Time and Space. *Science* 2013, vol 6, no. 285, p. 1-13.
NP5 LAKOWICZ, Joseph. Principles of Fluorescent Spectroscopy. USA: Springer, 2010. ISBN 0387312781. p. 954.

NP6 MIYAWAKI, Atsushi, et al. Fluorescent indicators for Ca2+ based on green fluorescent proteins and calmodulin. *Nature*. 1997, vol. 388, no. 6645, p 882-7.

NP7 ALLEN, Michael, et al. Subcellular dynamics of protein kinase activity visualized by FRET-based reporters, 2006, *Biochemical and bio-physical research communications*. 2006, vol. 348, no. 2, p. 716-721.

NP8 ZHANG, Jin, et al. FRET-based biosensors for protein kinases: illuminating the kinome. Mol. BioSyst. 2007, vol. 3, no. 11, p. 759-765.

NP9 LISSANDRON, Valentina, et al. Improvement of a fret-based indicator for camp by linker design and stabilization of donor-acceptor interaction. *J. Mol. Biol.* 2005, vol. 354, no. 3, p. 546-55.

NP10 PERTZ, Oliver, et al. Spatiotemporal dynamics of rhoa activity in migrating cells. *Nature.* 2006, vol. 440, p. 1069-1072.

NP11 KOMATSU, Naoki, et al. A Development of an optimized backbone of FRET biosensors for kinases and GTPases. *Molecular Biology of the Cell.* 2011, vol. 22, p. 4647-4658.

NP12 Palmer, Amy, et al. Ca2+ indicators based on computationally redesigned calmodulin-peptide pairs. *Chem. Biol.* 2006, vol. 13, p. 521.

NP13 SUN, Yuansheng, et al. Three-Color Spectral FRET Microscopy Localizes Three Interacting Proteins in Living. *Biophys J.* 2010, vol. 99, no. 4, p. 1274-1283.

NP14 PACE, C, et al. A Helix Propensity Scale Based on Experimental Studies of Peptides and Proteins. *Biophys J.* 2010, vol. 75, no. 1, p. 422-427.

NP15 KUSUNOKI, Hideki, et al. Solution structure of the DNA-binding domain of MafG. *Nat. Struct. Biol.* 2010, vol. 9, no. 4, p. 252-256.

NP16 Mason, Jody, et al. Coiled coil domains: stability, specificity, and biological implications. *Chembiochem.* 2004, vol. 5, no. 2, p. 170-176.

NP17 RIPOLL, Daniel, et al. Folding of the villin headpiece subdomain from random structures. Analysis of the charge distribution as a function of pH. *J Mol Biol.* 2004, vol. 339, no. 4, p. 915-925.

NP18 VREVEN, Thom, et al. Prediction of protein-protein binding free energies. *Protein Sci.* 2012, vol. 21, no. 3, p. 396-404.

NP19 MACKERELL, Alex, et al. All-atom empirical potential for molecular modeling and dynamics studies of proteins. *Journal of Physical Chemistry B.* 1998, vol. 102, p. 3586-3616.

NP20 LINDORFF-LARSEN, Kresten, et al. Improved side-chain torsion potentials for the Amber ff99SB protein force field. *Protein Sci.* 2010, vol. 78, no. 8, p. 1950-1958.

NP21 PHILLIPS, James, et al. Spatiotemporal dynamics of rhoa activity in migrating cells. *Journal of Computational Chemistry.* 2005, vol. 26, p. 1781-1802.

NP22 PRONK, Sander, et al. GROMACS 4.5: a high-throughput and highly parallel open source molecular simulation toolkit. *Bioinformatcs.* 2012, vol. 29, no. 7, p. 845-854.

NP23 Bonomi, Massimiliano, et al. PLUMED: A portable plugin for free-energy calculations with molecular dynamics. *Comp. Phys. Comm.* 2009, vol. 180, no. 10, p. 1961-1972.

NP24 LOMANT, A, et al. Chemical probes of extended biological structures: Synthesis and properties of the cleavable protein cross-linking reagent [35S] dithiobis (succinimidyl propionate) *J. Mol. Biol.* 1976, vol. 104, no. 1, p. 243-261.

NP25 XU Ming-qun, et al. In vitro protein splicing of purified precursor and the identification of a branched intermediate. *Cell.* 1993, vol. 75, no. 7, p. 1371-1377.

NP26 OJIDA, Akido, et al. Oligo-Asp Tag/Zn(II) Complex Probe as a New Pair for Labelling and Fluorescence Imaging of Proteins. *J. Am. Chem. Soc.,* 2006, vol. 128, no. 32, p. 10452-10459.

NP27 GAUTIER, Arnaud, et al. Selective Cross-Linking of Interacting Proteins Using Self-Labelling Tags. *J. Am. Chem. Soc.,* 2009, vol. 131, no. 49, p. 17954-17962.

NP28 LEQUIN, Rudolf. Enzyme Immunoassay (EIA)/Enzyme-Linked Immunosorbent Assay (ELISA). *Clinical Chemistry,* 2005, vol. 51, 2415-2418.

NP29 ODELL, Ian, et al. Immunofluorescence techniques *J. Invest. Dermatology.* 2013, vol. 133, e4.

NP30 MAHMOOD, Tahrin, et al. Western Blot: Technique, Theory, and Trouble Shooting. *North American Journal of Medical Sciences,* 2012, vol. 4, 429-434.

NP31 HERMANSON, Greg. Bioconjugate Techniques. USA: Academic Press, 26 Jul. 2010.

NP32 HUDSON, Philipp, et al. Engineered antibody fragments and the rise of single domains. *Nat. Biotechnol.,* 2005, vol. 23, 1126-1136.

NP33 CABANTOUS, Stephanie, et al. Protein tagging and detection with engineered self-assembling fragments of green fluorescent protein. *Nat. Biotechnol.,* 2005, vol. 23, 102-107.

NP34 LUKER, Kathryn, et al. Split Gaussia Luciferase for Imaging Ligand-Receptor Binding in Bioluminescent Imaging. *Methods in Molecular Biology,* 2013, vol. 1098, 59-69.

NP35 BUCHWALOW, Igor, et al. Immunochemistry: Basics and Methods. Springer: ISBN: 978-3-642-04608-7.

NP36 PALMER, J. L., et al. Reduction and re-oxidation of a critical disulphide bond in rabbit antibody molecule. *J. Biol. Chem.,* 1963, vol. 238, no. 7, p 2369-2398.

NP37 GE, Hui. UPA, a universal protein array system for quantitative detection of protein-protein, protein-DNA, protein-RNA and protein-ligand interactions. *Nucleic Acids Res.* 2000, vol. 28, e3.

NP38 ZHU, Heng, et al. Analysis of yeast protein kinases using protein chips. *Nat. Genet.,* 2000, vol. 26, 283-289.

NP39 COHEN, Claudia, et al. A microchip-based enzyme assay for protein kinase A. *Anal. Biochem.,* 1999, vol. 273, 89.

NP40 CHENG, Chao-Min, et al. Paper-Based ELISA. *Angew. Chem.,* 2010, vol. 49, 4771-4774.

NP41 DULKEITH, E., et al. Fluorescence Quenching of Dye Molecules near Gold Nanoparticles: Radiative and Non-radiative Effects. *Phys. Rev. Lett.,* 2002, vol. 89, 203002.

NP42 SPERLING, Ralph, et al. Biological applications of gold nanoparticles. *Chem. Soc. Rev.,* 2008, vol. 37, 1896-19

NP43 DOLMANS, Dennis, et al. Photodynamic therapy for cancer. *Nature reviews cancer,* 2003, vol. 3, 380-387.

NP44 HAMBLIN, Michael, et al. Photodynamic therapy: a new antimicrobial approach to infectious disease? *Photochem. Photobiol. Sci.,* 2004, vol. 3, 436-450.

Example 5—Nucleic Acid Detection Examples

A large number of proteins are known to bind to DNA, including transcription factors, and in particular: (1) zinc finger proteins; and (2) Transcription like effectors (TALES). See review of Carroll, Dana. *Annual review of*

*biochemistry* 83 (2014): 409-439). Both of these sensing elements are modular proteins, where the modules are concatenated together into a single protein to bind a specific sequence. The protein can be split into two so that each of the two moieties binds to the corresponding part of the sequence of nucleic acids. Thus the two moieties would correspond either to A and A' according to the invention. B and B' according to the invention may denote either two proteins such as two FP's or FP moieties or other proteins or moieties. Example sequences are available on the Protein Data Bank, and include the 2i13 (which targets 18 base pairs) can be split and arranged analogously with previous examples.

In the context of RNA it is now possible to detect RNA using protein sequences in a way which is analogous to TALES, using Pumilio and FBF homology RNA recognition proteins or (PUF) proteins. See Adamala et al., PNAS 2016 (www.pnas.org/cgi/doi/10.1073/pnas.1519368113). That is A and A' according to the invention may correspond to appropriate moieties of a split PUF protein targeting nearby or adjacent nucleic acids in an RNA sequence.

Another protein that can be used to flag the presence of the biomarker is split horseradish peroxidase enzyme but work in an analogous way.

DNA Binding Sensors
hinge-splitYFPs-zfinger2i13

Figure 32:
Figure 33:
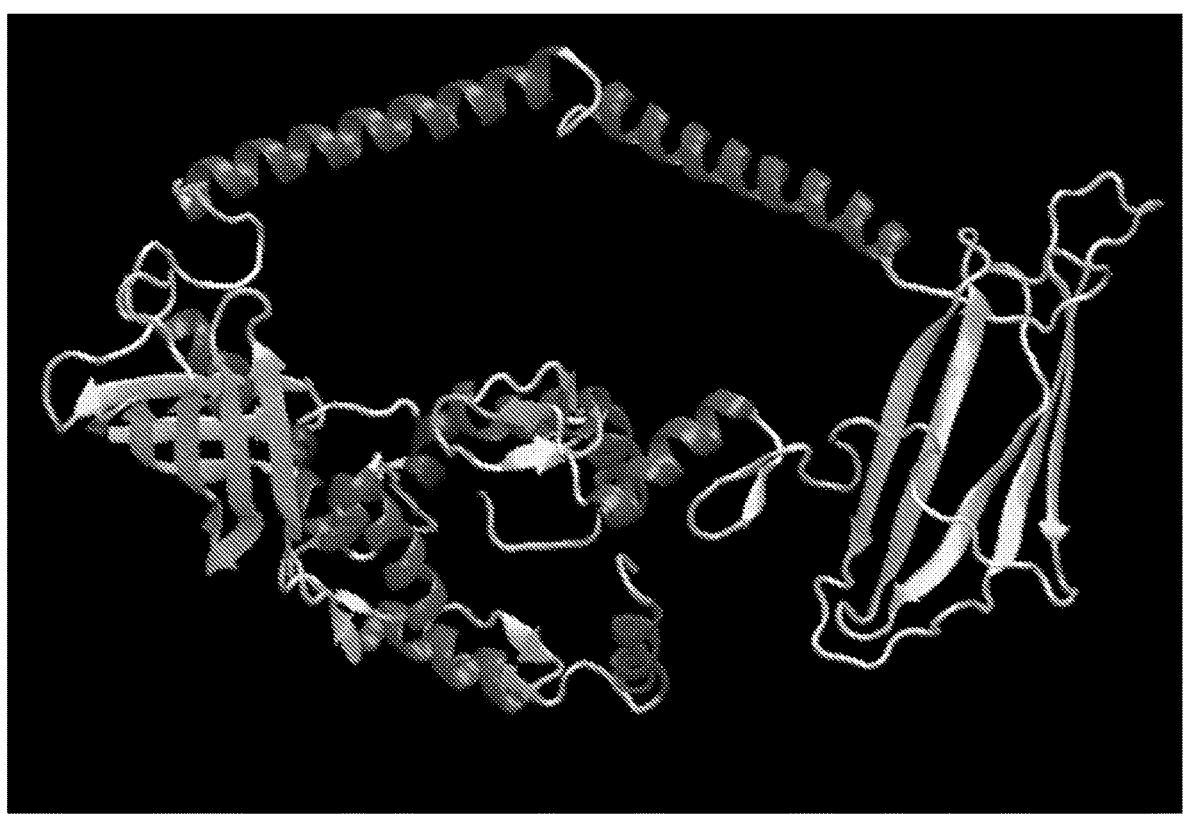

Six zinc fingers split YFP hinge sensor (zfinger based on 2i13.pdb), split YFP (yellow fluorescent protein) same as used in earlier examples. The split 2i13 sequence is based on 2i13 pdb with a split just after GLY 101. The split was chosen so as to not effect as much as possible binding regions of 2i13 either to zinc or to the target DNA as indicated on the Protein Data bank and by visual inspection when bound to the target DNA. Some of the residues and atoms missing in the original pdb file have been recovered using modeller. The sensor can be adjusted by simply shortening/lengthening of the flexible linkers connecting the different protein modules, modification of the charges residues in the hinge, or by the selection of alternative splitting points of 2i13. See FIGS. 32 and 33.

hinge-splitYFPs-zfinger2i13

The sequence of the example hinge sensor molecule is provided below in the N to C terminal direction (the combined sequences of this molecule are also known as SEQ ID NO: 24):

```
Split Zinc finger 2i13 left moiety
FSRSDHLAEHQRTHTGEKPYKCPECGKSFSDKKDLTRHQRTHTGEKPYKC

PECGKSFSQRANLRAHQRTHTG

Flexible Linker/spacer molecule
SGSSGS

Split YFP left moiety
MSKGEELFTGVVPILVELDGDVNGHKFSVSGEGEGDATYGKLTLKFICTT

GKLPVPWPTLVTTFGXGLQCFARYPDHMKRHDFFKSAMPEGYVQERTIFF

KDDGNYKTRAEVKFEGDTLVNRIELKGIDFKEDGNILGHKA

Flexible Linker/spacer molecule
GSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA
```

```
Flexible Linker/spacer molecule
GSGGSGGSG

Split YFP right moiety
ALEYNYNSQNVYIMADKQKNGIKVNFKIRHNIEDGSVQLADHYQQNTPIG

DGPVLLPDNHYLSYQSALSKDPNEKRDHMVLLEFVTAAGITHGMDELYK

Flexible Linker/spacer molecule
SGSSGS

Zinc finger 2i13 right moiety
GEKPYACPECGKSFSQLAHLRAHQRTHTGEKPYKCPECGKSFSREDNLHT

HQRTHTGEKPYKCPECGKSFSRRDALNVHQRTHTGKKTS
```

Hinge-splitYFPs-Tal3ugm

Figure 34A:
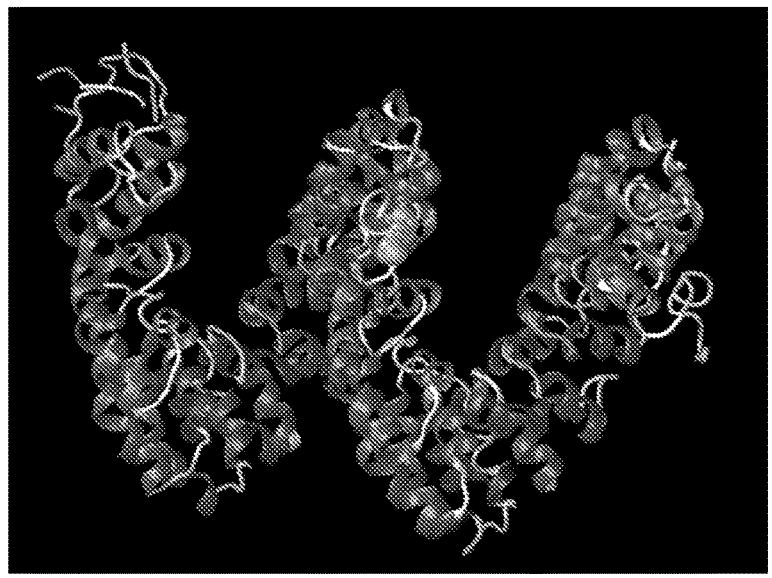

DNA sensor using Tal effector bound to its target DNA (taken from 3ugm.pdb). The splitting point is the residue GLY 628 rendered with VDW atoms. See FIG. 34a.

Figure 34B:
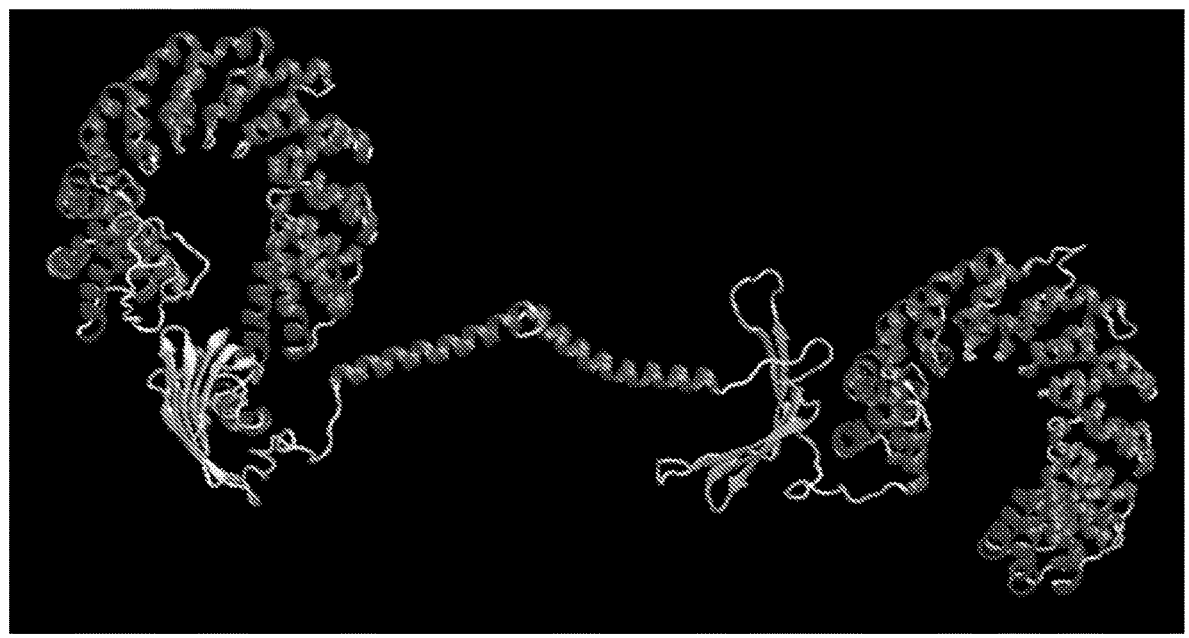

Amino Acid Sequence for Split Tal sensor with split YFPs leftsplit3ugm-leftsplitYFP-hinge-rightsplitYFP-rightsplit3ugm. See FIG. 34b.

The sequence of the example hinge sensor molecule is provided below in the N to C terminal direction (the combined sequences of this molecule are also known as SEQ ID NO: 25):

```
Tal 3ugm left moiety
HIVALSQHPAALGTVAVTYQHIITALPEATHEDIVGVGKQWSGARALEAL

LTDAGELRGPPLQLDTGQLVKIAKRGGVTAMEAVHASRNALTGAPLNLTP

AQVVAIASNNGGKQALETVQRLLPVLCQAHGLTPAQVVAIASHDGGKQAL

ETMQRLLPVLCQAHGLPPDQVVAIASNIGGKQALETVQRLLPVLCQAHGL

TPDQVVAIASHGGGKQALETVQRLLPVLCQAHGLTPDQVVAIASHDGGKQ

ALETVQRLLPVLCQAHGLTPDQVVAIASNGGGKQALETVQRLLPVLCQAH

GLTPDQVVAIASNGGKQALETVQRLLPVLCQAHGLTPDQVVAIASHDGGK

QALETVQRLLPVLCQTHGLTPAQVVAIASHDGGKQALETVQQLLPVLCQA

HGLTPDQVVAIASNIGGKQALATVQRLLPVLCQAHG

Flexible Linker/spacer molecule
SGSSGS

Split YFP left moiety
MSKGEELFTGVVPILVELDGDVNGHKFSVSGEGEGDATYGKLTLKFICTTG

KLPVPWPTLVTTFGXGLQCFARYPDHMKRHDFFKSAMPEGYVQERTIFFKD

DGNYKTRAEVKFEGDTLVNRIELKGIDFKEDGNILGHKA

Flexible Linker/spacer molecule
GSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSG

Split YFP right moiety
ALEYNYNSQNVYIMADKQKNGIKVNFKIRHNIEDGSVQLADHYQQNTPIGD

GPVLLPDNHYLSYQSALSKDPNEKRDHMVLLEFVTAAGITHGMDELYK
```

```
Flexible Linker/spacer molecule
SGSSGS

Tal 3ugm right moiety
GLTPDQVVAIASNGGGKQALETVQRLLPVLCQAHGLTPDQWAIASNGGGK

QALETVQRLLPVLCQAHGLTQVQWAIASNiGGKQALETVQRLLPVLCQAH

GLTPAQVVAIASHDGGKQALETVQRLLPVLCQAHGLTPDQVVAIASNGGG

KQALETVQRLLPVLCOAHGLTQEQVVAIASNNGGKQALETVQRLLPVLCQ

AHGLTPDQVVAIASNGGGKQALETVQRLLPVLCQAHGLTPAQVVAIASNI

GGKQALETVQRLLPVLCQDHGLTLAQVVAIASNIGGKQALETVQRLLPVL

COAHGLTQDQVVAIASNIGGKQALETVQRLLPVLCQDHGLTPDQVVAIAS

NIGGKQALETVQRLLPVLCQOHGLTLDQVVAIASNGGKQALETVQRLLPV

LCQDHGLTPDQVVAIASNSG
```

Example 6—RNA Binding Sensors

Hinge-splitYFPs-PUF1m8x

Figure 35:
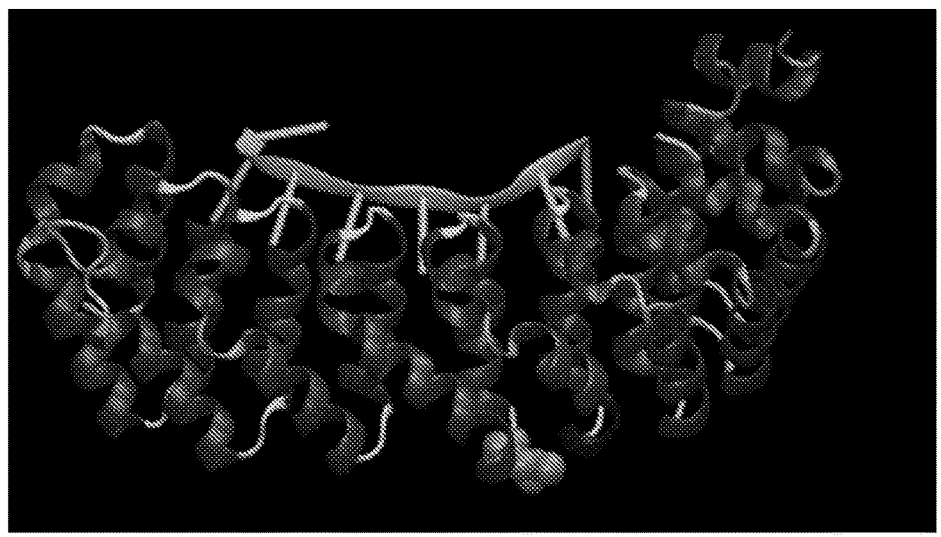
Figure 36:
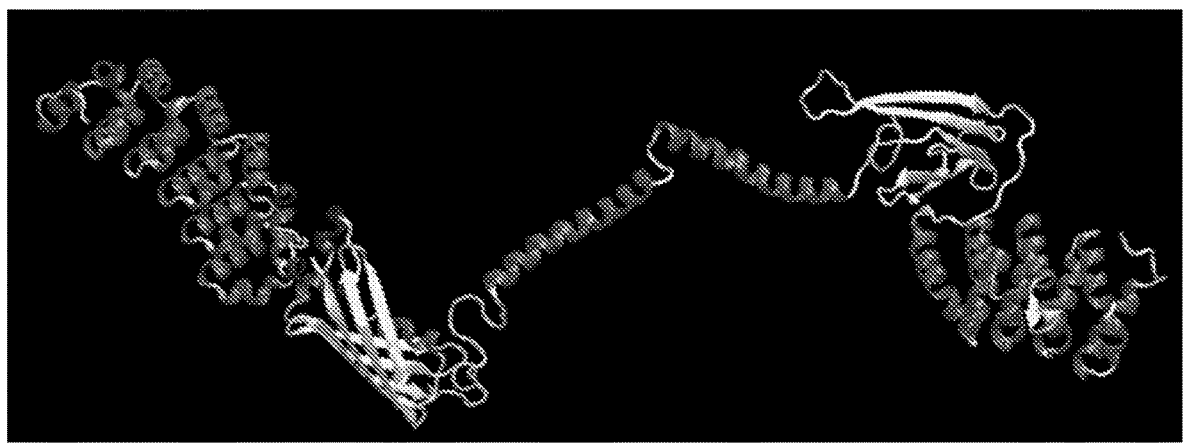

1m8x Pdb file for Pumilio-Homology Domain From Human Pumiliol denoted hereafter as PUF1m8x. Sensor consists of split PUF1m8x flanking split YFP-hinge. See FIGS. 35 and 36 See Adamala, Katarzyna P., et al., *Proceedings of the National Academy of Sciences* 113.19 (2016): E2579-E2588.

The sequence of the example hinge sensor molecule is provided below in the N to C terminal direction (the combined sequences of this molecule are also known as SEQ ID NO: 26):

```
Split PUF 1m8x left moiety
GRSRLLEDFRNNRYPNLQLREIAGHIMEFSQDQHGSRFIQLKLERATPAE

RQLVFNEILQAAYQLMVDVFGNYVIQKFFEFGSLEQKLALAERIRGHVLS

LALQMYGCRVIQKALEFIPSDQQNEMVRELDGHVLKCVKDQNGNHVVQKC

IECVQPQSLQFIIDAFKGQVFALSTHPYGCRVIQRILEHCL

Flexible Linker/spacer molecule
SGSSGS

Split YFP left moiety
MSKGEELFTGVVPILVELDGDVNGHKFSVSGEGEGDATYGKLTLKFICTT

GKLPVPWPTLVTTFGXGLQCFARYPDHMKRHDFFKSAMPEGYVQERTIFF

KDDGNYKTRAEVKFEGDTLVNRIELKGIDFKEDGNILGHKA

Flexible Linker/spacer molecule
GSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSG

Split YFP right moiety
ALEYNYNSQNVYIMADKQKNGIKVNFKIRHNIEDGSVQLADHYQQNTPIG

DGPVLLPDNHYLSYQSALSKDPNEKRDHMVLLEFVTAAGITHGMDELYK

Flexible Linker/spacer molecule
SGSSGS

Split PUF 1m8x rightmoiety
LPDQTLPILEELHQHTEQLVQDQYGNYVIQHVLEHGRPEDKSKIVAEIRG

NVLVLSQHKFASNVVEKCVTHASRTERAVLIDEVCTMNDGPHSALYTMMK

DQYANYVVQKMIDVAEPGQRKIVMHKIRPHIATLRKYTYGKHILAKLEKY

YMKNGVDLG
```

Example 7—DNA and RNA Editing Proteins

Figure 37:
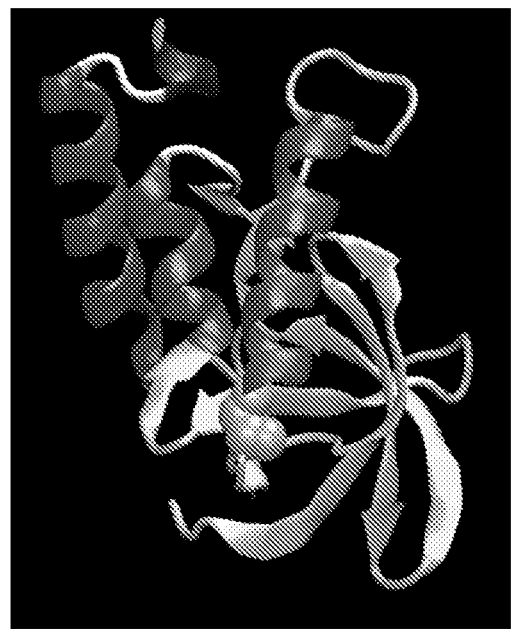

The preceding three examples of a sensor where the presence of a target DNA or RNA sequence switches on (i.e. functionalizes) a split yellow fluorescent protein can be easily modified to functionalise other proteins, where the fluorescent protein moieties are replaced by the moieties of the other protein, such as enzymes that are known to cleave DNA or RNA (for a useful review see a Mino, Takashi, et al. "Gene- and protein-delivered zinc finger-staphylococcal nuclease hybrid for inhibition of DNA replication of human papillomavirus." *PloS one* 8.2 (2013): e56633. A specific example of an enzyme that cleaves both DNA and RNA is SNASE DELTA +PHS variant (from 3bdc.pdb). In the present invention, Ala 69 (63) is chosen as a splitting point so as to separate Arg 87 (81) and Glu 43 (69) which are believed to play a key role in the phosphorodiesterase reaction, while keeping the binding site resides close to one another on the first moiety of the protein. A useful reference is Enzymology Primer for Recombinant DNA Technology chapter 3 pp 165, 166 by Hyone-Myong Eun Academic press 1996 ISBN-13: 978-0122437403. Note the numbering of the residues not in brackets is the convention (to relate different variants of SNASE enzymes to each other) whereas that in brackets corresponds to a purely consecutive ordering used here. Other splitting points are possible, either by design or by trial and error. See FIG. 37.

Hinge-splitSNASE-zfinger2i13

Two versions of this sensor are built, where the flexible linkers connecting the different functional units is doubled in length (excluding central linker in the hinge), so as to allow corresponding moieties sufficient freedom to bind to each other (correctly orientated so as to be functional) in the presence of the target, but not be functional in its absence (i.e. when the hinge is open). Other lengths of the flexible linkers are possible, and depend on the size of the moieties, and the overall length of the arms of the hinge.

Figure 38:
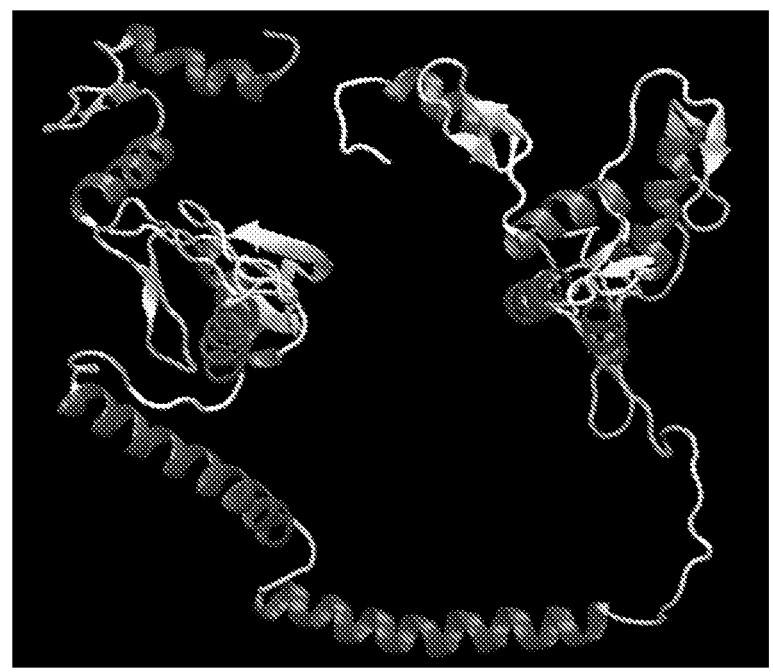

Example of DNA hinge sensor with split SNASE DELTA +PHS variant (built from 3bdc.pdb). and zinc finger moieties (built from 2i13.pdb). See FIG. 38.

The sequence of the example hinge sensor molecule is provided below in the N to C terminal direction (the combined sequences of this molecule are also known as SEQ ID NO: 27):

```
Split zinc finger 2i13 (left moiety)
FSRSDHLAEHQRTHTGEKPYKCPECGKSFSDKKDLTRHQRTHTGEKPYKC

PECGKSFSQRANLRAHQRTHTG

Flexible Linker/spacer molecule
SGSSGS

Split SNASE 3bdc left moiety
ATSTKKLHKEPATLIKAIDGDTVKLMYKGQPMTFRLLLVDTPEFNEKYGP

EASAFTKKMVENAA
```

-continued

Flexible Linker/spacer molecule
GSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSG

Split SNASE 3bdc right moiety
AAKKIEVEFDKGQRTDKYGRGLAYIYADGKMVNEALVRQGLAKVAYVYKG

NNTHEQLLRKAEAQAKKEKLNIWS

Flexible Linker/spacer molecule
SGSSGS

Split zinc finger 2i13 right moiety
GEKPYACPECGKSFSQLAHLRAHQRTHTGEKPYKCPECGKSFSREDNLHT

HQRTHTGEKPYKCPECGKSFSRRDALNVHQRTHTGKKTS*

Figure 39:
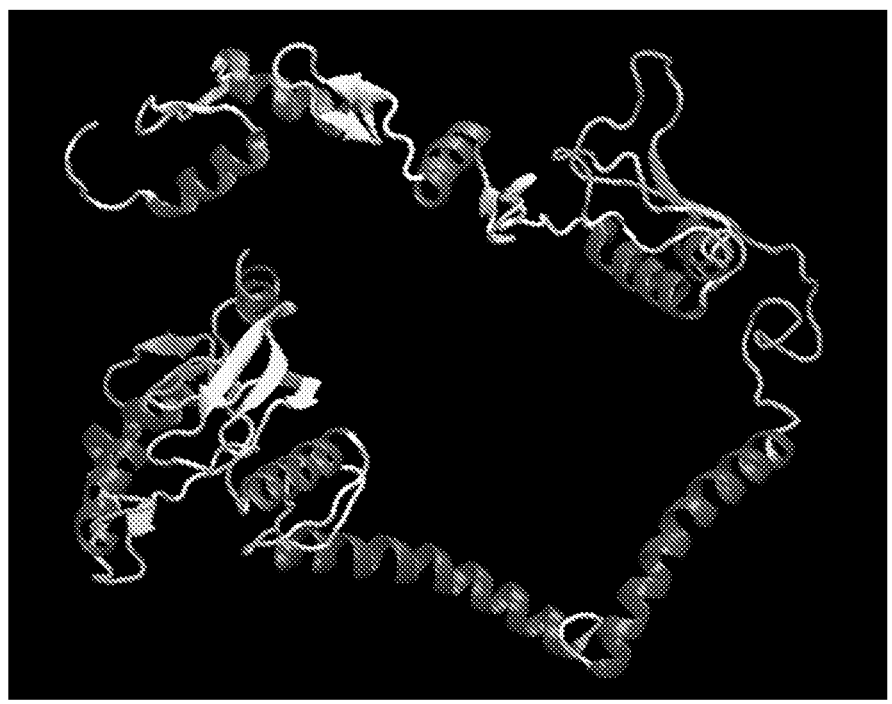

Example of DNA hinge sensor with split SNASE and zinc finger moieties but where the length of the flexible linkers have been doubled with respect to the previous example. See FIG. 39.

The sequence of the example hinge sensor molecule is provided below in the N to C terminal direction (the combined sequences of this molecule are also known as SEQ ID NO: 28):

Split zinc finger 2i13 left moiety
FSRSDHLAEHQRTHTGEKPYKCPECGKSFSDKKDLTRHQRTHTGEKPYKC

PECGKSFSQRANLRAHQRTHTG

Flexible Linker/spacer molecule
SGSSGSSGSSGS

Split SNASE 3bdc left moiety
ATSTKKLHKEPATLIKAIDGDTVKLMYKGQPMTFRLLLVDTPEFNEKYGP

EASAFTKKMVENAA

Flexible Linker/spacer molecule
GSGGSGGSGGSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSGGSGGSGGSG

Split SNASE 3bdc right moiety
AAKKIEVEFDKGQRTDKYGRGLAYIYADGKMVNEALVRQGLAKVAYVYKG

NNTHEQLLRKAEAQAKKEKLNIWS

Flexible Linker/spacer molecule
SGSSGSSGSSGS

Split zinc finger 2i13 right moiety
GEKPYACPECGKSFSQLAHLRAHQRTHTGEKPYKCPECGKSFSREDNLHT

HQRTHTGEKPYKCPECGKSFSRRDALNVHQRTHTGKKTS*

Hinge-splitSNASE-Tal3ugm

Figure 40:
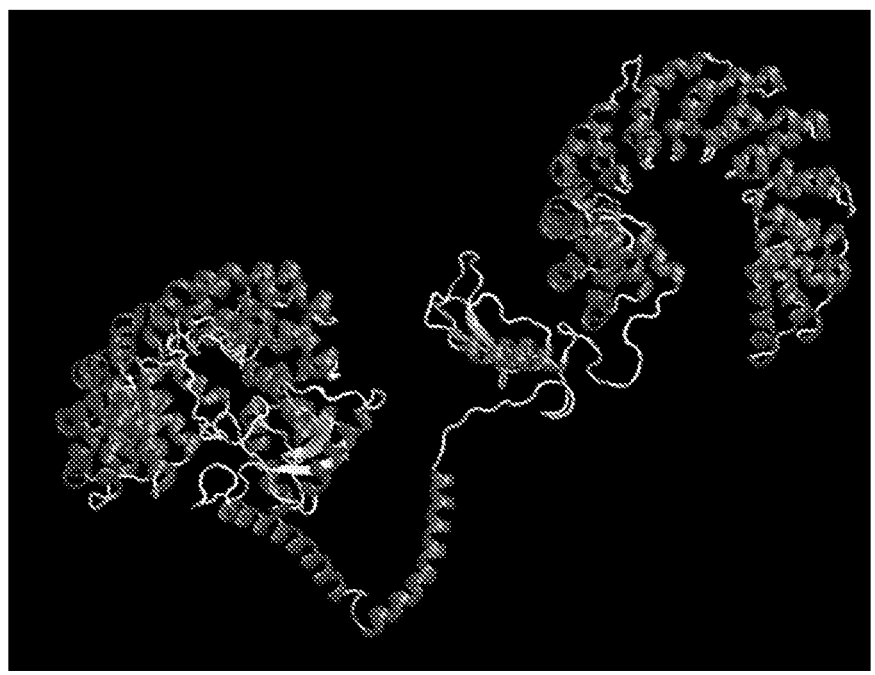
FIG. 40 DNA cleaving hinge sensor with split SNASE DELTA +PHS variant (built from 3bdc.pdb) and Tal DNA recognition proteins (split moieties built from 3ugm.pdb).

Example of DNA cleaving hinge sensor with split SNASE DELTA +PHS variant (built from 3bdc.pdb) and Tal DNA recognition proteins (split moieties built from 3ugm.pdb). See FIG. 40.

The sequence of the example hinge sensor molecule is provided below in the N to C terminal direction (the combined sequences of this molecule are also known as SEQ ID NO: 29):

Split Tal 3ugm left moiety
HIVALSQHPAALGTVAVTYQHIITALPEATHEDIVGVGKQWSGAEALEAL

LTDAGELRGPPLQLDTGQLVKIAKRGGVTAMEAVHASRNALTGAPLNLTP

AQVVAIASNNGGKQALETVQRLLPVLCQAHGLTPAQVVAIASHDGGKQAL

ETMQRLLPVLCQAHGLPPDQVVAIASNIGGKQALETVQRLLPVLCQAHGL

TPDQVVAIASHGGGKQALETVQRLLPVLCQAHGLTPDQVVAIASHDGGKQ

ALETVQRLLPVLCQAHGLTPDQVVAIASNGGGKQALETVQRLLPVLCQAH

GLTPDQVVAIASNGGKQALETVQRLLPVLCQAHGLTPDQVVAIASHDGGK

QALETVQRLLPVLCQTHGLTPAQVVAIASHDGGKQALETVQQLLPVLCQA

HGLTPDQVVAIASNIGGKQALATVQRLLPVLCQAHG

Flexible Linker/spacer molecule
SGSSGSSGSSGS

Split SNASE 3bdc left moiety
ATSTKKLHKEPATLIKAIDGDTVKLMYKGQPMTFRLLLVDTPEFNEKYGP

EASAFTKKMVENAA

Flexible Linker/spacer molecule
GSGGSGGSGGSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSGGSGGSGGSG

Split SNASE 3bdc right moiety
AAKKIEVEFDKGQRTDKYGRGLAYIYADGKMVNEALVRQGLAKVAYVYKG

NNTHEQLLRKAEAQAKKEKLNIWS

Flexible Linker/spacer molecule
SGSSGSSGSSGS

Split Tal3ugm right moiety
GLTPDQVVAIASNGGGKQALETVQRLLPVLCQAHGLTPDQVVAIASNGGG

KQALETVQRLLPVLCQAHGLTQVQVVAIASNIGGKQALETVQRLLPVLCQ

AHGLTPAQVVAIASHDGGKQALETVQRLLPVLCQAHGLTPDQVVAIASNG

GGKQALETVQRLLPVLCQAHGLTQEQVVAIASNNGGKQALETVQRLLPVL

CQAHGLTPDQVVAIASNGGGKQALETVQRLLPVLCQAHGLTPAQVVAIAS

NIGGKQALETVQRLLPVLCQDHGLTLAQVVAIASNIGGKQALETVQRLLP

VLCQAHGLTQDQVVAIASNIGGKQALETVQRLLPVLCQDHGLTPDQVVAI

ASNIGGKQALETVQRLLPVLCQDHGLTLDQVVAIASNGGKQALETVQRLL

PVLCQDHGLTPDQVVAIASNSG

Figure 41:
FIG. 41 RNA cleaving hinge sensor based on split SNASE Delta variant (3bdc.pdb) and split moieties of PUF RNA recognition protein (1m8x.pdb).

Hinge-splitSNAS E-PUF1m8x
RNA hinge sensor
sequence:hinge-splitSNASE3bdc-PUF1m8xL:::::composed from L and R: See FIG. 41.

The sequence of the example hinge sensor molecule is provided below in the N to C terminal direction (the combined sequences of this molecule are also known as SEQ ID NO: 30):

Split PUF 1m8x left moiety
GRSRLLEDFRNNRYPNLQLREIAGHIMEFSQDQHGSRFIQLKLERATPAE

RQLVFNEILQAAYQLMVDVFGNYVIQKFFEFGSLEQKLALAERIRGHVLS

LALQMYGCRVIQKALEFIPSDQQNEMVRELDGHVLKCVKDQNGNHVVQKC

IECVQPQSLQFIIDAFKGQVFALSTHPYGCRVIQRILEHCL

Flexible Linker/spacer molecule
SGSSGSSGSSGS

Split SNASE 3bdc left moiety
ATSTKKLHKEPATLIKAIDGDTVKLMYKGQPMTFRLLLVDTPEFNEKYGP

EASAFTKKMVENAA

Flexible Linker/spacer molecule
GSGGSGGSGGSGGSGGSG

Hinge (pair of rod-like molecules linked through
a joint molecule C)
AEAAAKEAAAKEAAAKEAAAKEAAAKEAAAKSGSKAAAEKAAAEKAAAEK

AAAEKAAAEKAAAEA

Flexible Linker/spacer molecule
GSGGSGGSGGSGGSGGSG

Split SNASE 3bdc left moiety
AAKKIEVEFDKGQRTDKYGRGLAYIYADGKMVNEALVRQGLAKVAYVYKG

NNTHEQLLRKAEAQAKKEKLNIWS

Flexible Linker/spacer molecule
SGSSGSSGSSGS

Split PUF 1m8x right moiety
LPDQTLPILEELHQHTEQLVQDQYGNYVIQHVLEHGRPEDKSKIVAEIRG

NVLVLSQHKFASNVVEKCVTHASRTERAVLIDEVCTMNDGPHSALYTMMK

DQYANYVVQKMIDVAEPGQRKIVMHKIRPHIATLRKYTYGKHILAKLEKY

YMKNGVDLG*

Example 8—Hinge-splitHER-split scFv-5c6w

Figure 42:
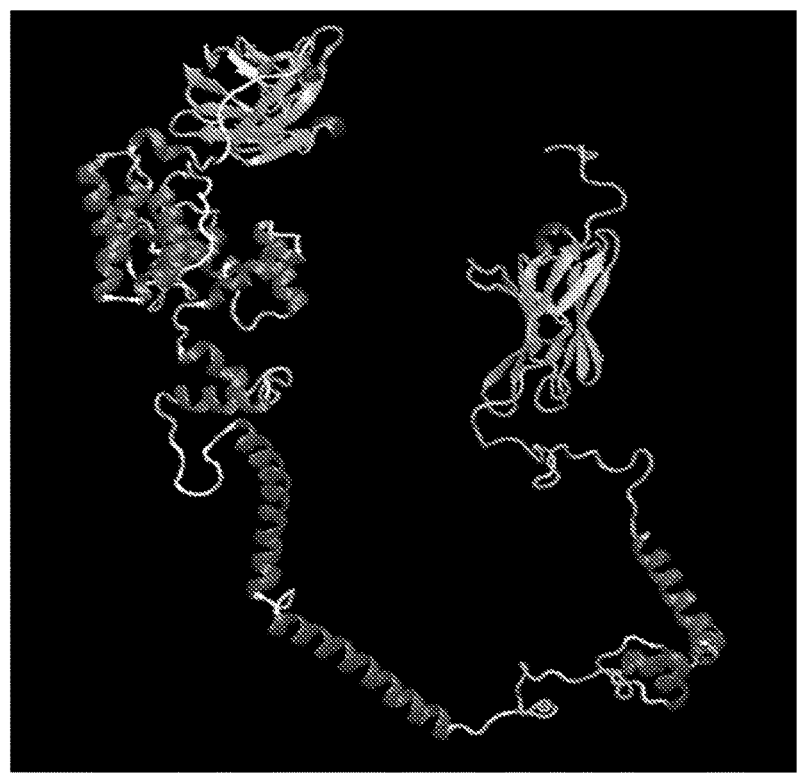
FIG. 42 HER sensor based on split scFv (5c6w.pdb)-based sensor with split horseradish peroxidase (1h5a.pdb).

HER sensor based on split scFv (5c6w.pdb)-based sensor with split horseradish peroxidase (1h5a.pdb). See FIG. 42. For further details on the split enzyme, see Martell, Jeffrey D., et al. "A split horseradish peroxidase for the detection of intercellular protein-protein interactions and sensitive visualization of synapses." Nature biotechnology 34.7 (2016): 774-780.

This illustrates how simple it is to modify the earlier examples that had split yellow fluorescent proteins, through their replacement with split horseradish peroxidase.

The sequence of the example hinge sensor molecule is provided below in the N to C terminal direction (the combined sequences of this molecule are also known as SEQ ID NO: 31):

Split scFv-5c6w left moiety heavy chain
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAREP

DYYDSSGYYPIDAFDIWGQGTTVTVSS

Flexible Linker/spacer molecule
GGGGSGGGGS

Split HER 1h5a left moiety
QLTPTFYDNSCPNVSNIVRDTIVNELRSDPRIAASILRLHFHDCFVNGCD

ASILLDNTTSFRTEKDAFGNANSARGFPVIDRMKAAVESACPRTVSCADL

LTIAAQQSVTLAGGPSWRVPLGRRDSLQAFLDLANANLPAPFFTLPQLKD

SFRNVGLNRSSDLVALSGGHTFGKNQCRFIMDRLYNFSNTGLPDPTLNTT

YLQTLRGLCPLNG

Flexible Linker/spacer molecule
AGSGGSGGSGA

Hinge (pair of rod-like molecules linked through
a joint molecule C)
EAAAKEAAAKEAAAKEAAAKEAAAKEAAAKSGSKAAAEKAAAEKAAAEKA

AAEKAAAEKAAAE

Flexible Linker/spacer molecule
AGSGGSGGSG

Split HER 1h5a right moiety
AGNLSALVDFDLRTPTIFDNKYYVNLEEQKGLIQSDQELFSSPNATDTIP

LVRSFANSTQTFFNAFVEAMDRMGNITPLTGTQGQIRLNCRVVNS

Flexible Linker/spacer molecule
GGGGSGGGGS

Split scFv-5c6w right moiety (light chain)
QSALTQPASVSASPGQSITISCTGTSSDVGAYDWVSWYQQHPGKAPKLLI

FDVNNRPSGVSHRFSGSKSGNTASLTISGLQAEDEADYYCASATLLDTYV

FGTGTKVTVLGDQEPKSSDKTH

---

The invention claimed is:

1. A sensor molecule for detecting a target molecule comprising:
   (a) a rod-like molecule L and a rod-like molecule R connected to each other by a joint molecule C to form a hinge;
   (b) a target binding molecule A bonded to the end of rod-like molecule L opposite to the joint molecule C;
   (c) a binding molecule A' bonded to the end of rod-like molecule R opposite the joint molecule C;
   wherein the target binding molecule A is arranged to bind to an epitope or nucleic acid sequence of the target molecule to be detected, and binding molecule A' is arranged to bind to the same epitope or same nucleic acid sequence, or portion thereof of the target molecule as target binding molecule A;
   wherein the hinge is biased into an open position, such that target binding molecule A and binding molecule A' are biased apart by the hinge; and
   wherein the sensor molecule comprises a state denoted as the ON state wherein A is attracted towards A' by the presence of the target molecule to be detected and the hinge is arranged to repeatedly open and close; and a state denoted as the OFF state wherein the hinge is in an open position and A is not attracted towards A'.

2. The sensor molecule according to claim 1, wherein the binding of a target molecule by target binding molecule A, and the binding of binding molecule A' to the target molecule are arranged to bias the hinge into a closed position in opposition to the force of the hinge, which is biased to an open position.

3. The sensor molecule according to claim 1, wherein the ON state is detectable.

4. The sensor molecule according to claim 1, wherein the sensor further comprises a signal molecule B and a signal molecule B'.

5. The sensor molecule according to claim 4, wherein the detectable ON state signal is provided by the pair of signal molecules B and B' being brought into sufficient proximity to cause a detectable ON state signal to be emitted.

6. The sensor molecule according to claim 4, wherein the signal molecule B and/or B' comprises a chromophore, fluorophore or bioluminescent molecule; and/or
   the target binding molecule A and/or binding molecule A' comprises a chromophore, fluorophore or bioluminescent molecule.

7. The sensor molecule according to claim 4, wherein the signal molecule B is bound either directly or through a spacer molecule to the target binding molecule A and the signal molecule B' is bound either directly or through a spacer molecule to binding molecule A' or vice versa.

8. The sensor molecule according to claim 4, wherein the signal molecules B and B' each comprise a part of a split molecule.

9. The sensor molecule according to claim 1, wherein the length to width ratio of each of the rod-like molecules L and R is about 6-10:1 (length to width).

10. The sensor molecule according to claim 1, wherein the rod-like molecules L and R are substantially rigid.

11. The sensor molecule according to claim 1, wherein the rod-like molecule L and/or rod-like molecule R comprise or consist of polypeptide.

12. The sensor molecule according to claim 1, wherein the rod-like molecule L comprises a number N of constituent molecules q1, q2, . . . , qN; and the rod-like molecule R comprises a number N' of constituent molecules q'1, q'2, . . . , q'N'; and
   wherein q1, q2, . . . , qN, q'1, q'2, . . . , q'N' are selected to be charged amino acids, or hydrophilic or hydrophobic amino acids, or a combination thereof.

13. The sensor molecule according to claim 1, wherein the rod-like molecules L and R comprise an alpha helix of the following repeat residues [EAAAK]$^m$ (SEQ ID NO: 150) and [KAAAE]$^m$ (SEQ ID NO: 151) respectively, where m is the number of repeats ranging from 6 to 12, and E is negatively charged and K is positively charged at physiological pH condition; or
   wherein the rod-like molecules L and R comprise an alpha helix of the following repeat residues and [EAAAAK]$^m$ (SEQ ID NO: 152) and [KAAAAE]$^m$ (SEQ ID NO: 153) respectively, where m is the number of repeats ranging from 6 to 12, and E is negatively charged and K is positively charged at physiological pH condition; or
   wherein the rod-like molecules L and R comprise an alpha helix of the following repeat residues [EAAAAAK]$^m$ (SEQ ID NO: 154) and [KAAAAAE]$^m$ (SEQ ID NO: 155) respectively, where m is the number of repeats ranging from 6 to 12, and E is negatively charged and K is positively charged at physiological pH condition; or
   wherein the rod-like molecules L and R comprise an alpha helix of the following repeat residues [XAAAX]$^m$ (SEQ ID NO: 156) and [XAAAX]$^m$ (SEQ ID NO: 156) respectively, where m is the number of repeats ranging from 1 to 14, and X is negatively or positively charged at physiological pH condition, and wherein the charged residues of the rod-like molecule L are positioned and charged to repel the charged residues of rod-like molecule R; or
   wherein the rod-like molecules L and R comprise an alpha helix of the following repeat residues and [XAAAAX]$^m$ (SEQ ID NO: 157) and [XAAAAX]$^m$ (SEQ ID NO: 157) respectively, where m is the number of repeats ranging from 1 to 14, and X is negatively or positively charged at physiological pH condition, and wherein the charged residues of the rod-like molecule L are positioned and charged to repel the charged residues of rod-like molecule R; or
   wherein the rod-like molecules L and R comprise an alpha helix of the following repeat residues [XAAAAAX]$^m$ (SEQ ID NO: 158) and [XAAAAAX]$^m$ (SEQ ID NO: 158) respectively, where m is the number of repeats ranging from 1 to 14, and X is negatively or positively charged at physiological pH condition, and wherein the charged residues of the rod-like molecule L are positioned and charged to repel the charged residues of rod-like molecule R; or wherein the rod-like molecules L and R comprise an alpha helix of the following repeat residues $[ZAAAZ]^n$ $[XAAAX]^m$ (SEQ ID NO: 159) and $[XAAAX]^m$ $[ZAAAZ]^n$ (SEQ ID NO: 160) respectively, where m is the number of repeats ranging from 1 to 14, and n is the number of repeats ranging from 1 to 14, and X is negatively or positively charged at physiological pH condition, and Z is hydrophilic at physiological pH condition, and wherein the charged residues of the rod-like molecule L are positioned and charged to repel the charged residues of rod-like molecule R; or wherein the rod-like molecules L and R comprise an alpha helix of the following repeat residues $[ZAAAAZ]^n$ $[XAAAAX]^m$ (SEQ ID NO: 161) and $[XAAAAX]^m$ $[ZAAAAZ]^n$ (SEQ ID NO: 162) respectively, where m is the number of repeats ranging from 1 to 14, and n is the number of repeats ranging from 1 to 14, and X is negatively or positively charged at physiological pH condition, and Z is hydrophilic at physiological pH condition, and wherein the charged residues of the rod-like molecule L are positioned and charged to repel the charged residues of rod-like molecule R; or wherein the rod-like molecules L and R comprise an alpha helix of the following repeat residues $[ZAAAAAZ]^n$ $[XAAAAAX]^m$ (SEQ ID NO: 163) and $[XAAAAAX]^m [ZAAAAAZ]^n$ (SEQ ID NO: 164) respectively, where m is the number of repeats ranging from 1 to 14, and n is the number of repeats ranging from 1 to 14, and X is negatively or positively charged at physiological pH condition, and Z is hydrophilic at physiological pH condition, and wherein the charged residues of the rod-like molecule L are positioned and charged to repel the charged residues of rod-like molecule R.

14. The sensor molecule according to claim 1, wherein the sensor molecule is a fusion protein.

15. The sensor molecule according to claim 1, wherein the sensor molecule comprises or consists of the protein sequence
  (i) FP1-$[GSG]^{m1}$-TBM-$[GSG]^{m2}$-[hinge]-$[GSG]^{m3}$-BM-$[GSG]^{m4}$-FP2; or
  (ii) TBM-$[GSG]^{m1}$-FP1-$[GSG]^{m2}$-[hinge]-$[GSG]^{m3}$-FP2-$[GSG]^{m4}$-BM, wherein FP1 and FP2 are a signal molecule B and B' respectively;
  TBM and BM are the target binding molecule A and binding molecule A' respectively;
wherein the rod-like molecule L and a rod-like molecule R of the hinge are each alpha helices;
S and G denote the amino acids Glycine and Serine; and
m1, m2, m3 and m4 are appropriately selected number of repeats to ensure that the sensor is functional according to the invention.

16. The sensor molecule according to claim 1, wherein the joint molecule C is flexible.

17. The sensor molecule according to claim 1, wherein the joint molecule C comprises the amino acid sequence SGS or GS.

18. An assay method for the detection of a target molecule in a sample comprising:
  providing the sample;
  providing the sensor molecule according to claim 1 in the sample;
  detecting the presence or absence of a signal from the sensor molecule;
wherein an ON signal confirms the presence of the target molecule in the sample.

19. A method of providing a biologically active molecule, the method comprising:
  providing the sensor molecule according to claim 1 in the presence of a target molecule, wherein the sensor molecule comprises a split molecule, wherein the split molecule is a biologically active molecule split into separated parts, and which is activated by joining together the split parts of the split molecule when the sensor molecule binds the target molecule, thereby providing the biologically active molecule.

20. The sensor molecule of claim 4, wherein the target binding molecule A is connected to the rod like molecule L at a point relatively closer to the joint molecule C than a signal molecule B, and the binding molecule A' is connected to the rod like molecule R at a point relatively closer to the joint molecule C than a signal molecule B'.

21. The sensor molecule of claim 1, wherein a signal molecule B is connected to the rod like molecule L at a point relatively closer to the joint molecule C than the target binding molecule A, and a signal molecule B' is connected to the rod like molecule R at a point relatively closer to the joint molecule C than the binding molecule A'.

* * * * *

SEQUENCE LISTING

```
<160> NUMBER OF SEQ ID NOS: 164

<210> SEQ ID NO 1
<211> LENGTH: 808
<212> TYPE: PRT
<213> ORGANISM: Artificial Sequence
<220> FEATURE:
<223> OTHER INFORMATION: Fusion molecule

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Glu Pro Asp Tyr Tyr Asp Ser Ser Gly Tyr Tyr Pro Ile Asp
            100                 105                 110
Ala Phe Asp Ile Trp Gly Gln Gly Thr Thr Val Thr Val Ser Ser Gly
            115                 120                 125
Gly Gly Ser Gly Gly Gly Ser Met Ser Lys Gly Glu Glu Leu
        130                 135                 140
Phe Thr Gly Val Val Pro Ile Leu Val Glu Leu Asp Gly Asp Val Asn
145                 150                 155                 160
Gly His Lys Phe Ser Val Ser Gly Glu Gly Glu Gly Asp Ala Thr Tyr
                165                 170                 175
Gly Lys Leu Thr Leu Lys Phe Ile Cys Thr Thr Gly Lys Leu Pro Val
            180                 185                 190
Pro Trp Pro Thr Leu Val Thr Thr Leu Val Gln Cys Phe Ser Arg Tyr
            195                 200                 205
Pro Asp His Met Lys Arg His Asp Phe Phe Lys Ser Ala Met Pro Glu
210                 215                 220
Gly Tyr Val Gln Glu Arg Thr Ile Phe Phe Lys Asp Asp Gly Asn Tyr
225                 230                 235                 240
Lys Thr Arg Ala Glu Val Lys Phe Glu Gly Asp Thr Leu Val Asn Arg
                245                 250                 255
Ile Glu Leu Lys Gly Ile Asp Phe Lys Glu Asp Gly Asn Ile Leu Gly
            260                 265                 270
His Lys Leu Glu Tyr Asn Tyr Ile Ser His Asn Val Tyr Ile Thr Ala
            275                 280                 285
Asp Lys Gln Lys Asn Gly Ile Lys Ala Asn Phe Lys Ile Arg His Asn
290                 295                 300
Ile Glu Asp Gly Ser Val Gln Leu Ala Asp His Tyr Gln Gln Asn Thr
305                 310                 315                 320
Pro Ile Gly Asp Gly Pro Val Leu Leu Pro Asp Asn His Tyr Leu Ser
                325                 330                 335
Thr Gln Ser Ala Leu Ser Lys Asp Pro Asn Glu Lys Arg Asp His Met
            340                 345                 350
Val Leu Leu Glu Phe Val Thr Ala Ala Gly Ile Ala Gly Ser Gly Gly
            355                 360                 365
Ser Gly Gly Ser Gly Ala Glu Ala Ala Ala Lys Glu Ala Ala Lys
        370                 375                 380
Glu Ala Ala Ala Lys Glu Ala Ala Ala Lys Glu Ala Ala Ala Lys Glu
385                 390                 395                 400
Ala Ala Ala Lys Ala Gly Ser Gly Ala Lys Ala Ala Glu Lys Ala
            405                 410                 415
Ala Ala Glu Lys Ala Ala Ala Glu Lys Ala Ala Ala Glu Lys Ala Ala
            420                 425                 430
Ala Glu Lys Ala Ala Ala Glu Ala Gly Ser Gly Gly Ser Gly Gly Ser
            435                 440                 445
Gly Ala Met Ser Lys Gly Glu Glu Leu Phe Thr Gly Val Val Pro Ile
            450                 455                 460
```

Leu Val Glu Leu Asp Gly Asp Val Asn Gly His Lys Phe Ser Val Ser
465                 470                 475                 480

Gly Glu Gly Glu Gly Asp Ala Thr Tyr Gly Lys Leu Thr Leu Lys Phe
                485                 490                 495

Ile Cys Thr Thr Gly Lys Leu Pro Val Pro Trp Pro Thr Leu Val Thr
            500                 505                 510

Thr Phe Leu Gln Cys Phe Ala Arg Tyr Pro Asp His Met Lys Arg His
        515                 520                 525

Asp Phe Phe Lys Ser Ala Met Pro Glu Gly Tyr Val Gln Glu Arg Thr
    530                 535                 540

Ile Phe Phe Lys Asp Asp Gly Asn Tyr Lys Thr Arg Ala Glu Val Lys
545                 550                 555                 560

Phe Glu Gly Asp Thr Leu Val Asn Arg Ile Glu Leu Lys Gly Ile Asp
                565                 570                 575

Phe Lys Glu Asp Gly Asn Ile Leu Gly His Lys Leu Glu Tyr Asn Tyr
            580                 585                 590

Asn Ser Gln Asn Val Tyr Ile Met Ala Asp Lys Gln Lys Asn Gly Ile
        595                 600                 605

Lys Val Asn Phe Lys Ile Arg His Asn Ile Glu Asp Gly Ser Val Gln
    610                 615                 620

Leu Ala Asp His Tyr Gln Gln Asn Thr Pro Ile Gly Asp Gly Pro Val
625                 630                 635                 640

Leu Leu Pro Asp Asn His Tyr Leu Ser Tyr Gln Ser Ala Leu Ser Lys
                645                 650                 655

Asp Pro Asn Glu Lys Arg Asp His Met Val Leu Leu Glu Phe Val Thr
            660                 665                 670

Ala Ala Gly Ile Gly Gly Gly Ser Gly Gly Gly Ser Gln Ser
        675                 680                 685

Ala Leu Thr Gln Pro Ala Ser Val Ser Ala Ser Pro Gly Gln Ser Ile
    690                 695                 700

Thr Ile Ser Cys Thr Gly Thr Ser Ser Asp Val Gly Ala Tyr Asp Trp
705                 710                 715                 720

Val Ser Trp Tyr Gln Gln His Pro Gly Lys Ala Pro Lys Leu Leu Ile
                725                 730                 735

Phe Asp Val Asn Asn Arg Pro Ser Gly Val Ser His Arg Phe Ser Gly
            740                 745                 750

Ser Lys Ser Gly Asn Thr Ala Ser Leu Thr Ile Ser Gly Leu Gln Ala
        755                 760                 765

Glu Asp Glu Ala Asp Tyr Tyr Cys Ala Ser Ala Thr Leu Leu Asp Thr
    770                 775                 780

Tyr Val Phe Gly Thr Gly Thr Lys Val Thr Val Leu Gly Asp Gln Glu
785                 790                 795                 800

Pro Lys Ser Ser Asp Lys Thr His
                805

<210> SEQ ID NO 2
<211> LENGTH: 592
<212> TYPE: PRT
<213> ORGANISM: Artificial Sequence
<220> FEATURE:
<223> OTHER INFORMATION: Fusion molecule
<220> FEATURE:
<221> NAME/KEY: misc_feature
<222> LOCATION: (203)..(203)
<223> OTHER INFORMATION: Xaa can be any naturally occurring amino acid

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Asp Tyr Tyr Asp Ser Gly Tyr Tyr Pro Ile Asp
            100                 105                 110

Ala Phe Asp Ile Trp Gly Gln Gly Thr Thr Val Thr Val Ser Ser Gly
        115                 120                 125

Gly Gly Gly Ser Gly Gly Gly Ser Met Ser Lys Gly Glu Glu Leu
    130                 135                 140

Phe Thr Gly Val Val Pro Ile Leu Val Glu Leu Asp Gly Asp Val Asn
145                 150                 155                 160

Gly His Lys Phe Ser Val Ser Gly Glu Gly Glu Gly Asp Ala Thr Tyr
                165                 170                 175

Gly Lys Leu Thr Leu Lys Phe Ile Cys Thr Thr Gly Lys Leu Pro Val
            180                 185                 190

Pro Trp Pro Thr Leu Val Thr Thr Phe Gly Xaa Gly Leu Gln Cys Phe
        195                 200                 205

Ala Arg Tyr Pro Asp His Met Lys Arg His Asp Phe Phe Lys Ser Ala
    210                 215                 220

Met Pro Glu Gly Tyr Val Gln Glu Arg Thr Ile Phe Phe Lys Asp Asp
225                 230                 235                 240

Gly Asn Tyr Lys Thr Arg Ala Glu Val Lys Phe Glu Gly Asp Thr Leu
                245                 250                 255

Val Asn Arg Ile Glu Leu Lys Gly Ile Asp Phe Lys Glu Asp Gly Asn
            260                 265                 270

Ile Leu Gly His Lys Ala Gly Ser Gly Gly Ser Gly Gly Ser Gly Ala
        275                 280                 285

Glu Ala Ala Ala Lys Glu Ala Ala Ala Lys Glu Ala Ala Ala Lys Glu
    290                 295                 300

Ala Ala Ala Lys Glu Ala Ala Ala Lys Glu Ala Ala Ala Lys Ser Gly
305                 310                 315                 320

Ser Lys Ala Ala Ala Glu Lys Ala Ala Ala Glu Lys Ala Ala Ala Glu
                325                 330                 335

Lys Ala Ala Ala Glu Lys Ala Ala Ala Glu Lys Ala Ala Ala Glu Ala
            340                 345                 350

Gly Ser Gly Gly Ser Gly Gly Ser Gly Ala Leu Glu Tyr Asn Tyr Asn
        355                 360                 365

Ser Gln Asn Val Tyr Ile Met Ala Asp Lys Gln Lys Asn Gly Ile Lys
    370                 375                 380

Val Asn Phe Lys Ile Arg His Asn Ile Glu Asp Gly Ser Val Gln Leu
385                 390                 395                 400

Ala Asp His Tyr Gln Gln Asn Thr Pro Ile Gly Asp Gly Pro Val Leu
                405                 410                 415

-continued

```
Leu Pro Asp Asn His Tyr Leu Ser Tyr Gln Ser Ala Leu Ser Lys Asp
            420                 425                 430

Pro Asn Glu Lys Arg Asp His Met Val Leu Leu Glu Phe Val Thr Ala
            435                 440                 445

Ala Gly Ile Thr His Gly Met Asp Glu Leu Tyr Lys Gly Gly Gly Gly
            450                 455                 460

Ser Gly Gly Gly Gly Ser Gln Ser Ala Leu Thr Gln Pro Ala Ser Val
465                 470                 475                 480

Ser Ala Ser Pro Gly Gln Ser Ile Thr Ile Ser Cys Thr Gly Thr Ser
                485                 490                 495

Ser Asp Val Gly Ala Tyr Asp Trp Val Ser Trp Tyr Gln Gln His Pro
            500                 505                 510

Gly Lys Ala Pro Lys Leu Leu Ile Phe Asp Val Asn Asn Arg Pro Ser
            515                 520                 525

Gly Val Ser His Arg Phe Ser Gly Ser Lys Ser Gly Asn Thr Ala Ser
            530                 535                 540

Leu Thr Ile Ser Gly Leu Gln Ala Glu Asp Glu Ala Asp Tyr Tyr Cys
545                 550                 555                 560

Ala Ser Ala Thr Leu Leu Asp Thr Tyr Val Phe Gly Thr Gly Thr Lys
                565                 570                 575

Val Thr Val Leu Gly Asp Gln Glu Pro Lys Ser Ser Asp Lys Thr His
            580                 585                 590

<210> SEQ ID NO 3
<211> LENGTH: 879
<212> TYPE: PRT
<213> ORGANISM: Artificial Sequence
<220> FEATURE:
<223> OTHER INFORMATION: Fusion molecule

<400> SEQUENCE: 3

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190
```

-continued

```
Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ala
                485                 490                 495

Gly Ser Gly Ala Gln Val Gln Leu Val Gln Ser Gly Ala Glu Val Lys
            500                 505                 510

Lys Pro Gly Ser Ser Val Lys Val Ser Cys Lys Ala Ser Gly Gly Thr
        515                 520                 525

Phe Ser Ser Tyr Ala Ile Ser Trp Val Arg Gln Ala Pro Gly Gln Gly
    530                 535                 540

Leu Glu Trp Met Gly Gly Ile Ile Pro Ile Phe Gly Thr Ala Asn Tyr
545                 550                 555                 560

Ala Gln Lys Phe Gln Gly Arg Val Thr Ile Thr Ala Asp Glu Ser Thr
                565                 570                 575

Ser Thr Ala Tyr Met Glu Leu Ser Ser Leu Arg Ser Glu Asp Thr Ala
            580                 585                 590

Val Tyr Tyr Cys Ala Arg Glu Pro Asp Tyr Tyr Asp Ser Ser Gly Tyr
        595                 600                 605
```

```
Tyr Pro Ile Asp Ala Phe Asp Ile Trp Gly Gln Gly Thr Thr Val Thr
610                 615                 620

Val Ser Ser Ala Gly Ser Gly Gly Ser Gly Gly Ser Gly Ala Glu Ala
625                 630                 635                 640

Ala Ala Lys Glu Ala Ala Lys Glu Ala Ala Lys Glu Ala Ala
            645                 650                 655

Ala Lys Glu Ala Ala Lys Glu Ala Ala Lys Ser Gly Ser Lys
        660                 665                 670

Ala Ala Ala Glu Lys Ala Ala Glu Lys Ala Ala Glu Lys Ala
            675                 680                 685

Ala Ala Glu Lys Ala Ala Glu Lys Ala Ala Glu Ala Gly Ser
        690                 695                 700

Gly Gly Ser Gly Gly Ser Gly Ala Gln Ser Ala Leu Thr Gln Pro Ala
705                 710                 715                 720

Ser Val Ser Ala Ser Pro Gly Gln Ser Ile Thr Ile Ser Cys Thr Gly
                725                 730                 735

Thr Ser Ser Asp Val Gly Ala Tyr Asp Trp Val Ser Trp Tyr Gln Gln
                740                 745                 750

His Pro Gly Lys Ala Pro Lys Leu Leu Ile Phe Asp Val Asn Asn Arg
            755                 760                 765

Pro Ser Gly Val Ser His Arg Phe Ser Gly Ser Lys Ser Gly Asn Thr
770                 775                 780

Ala Ser Leu Thr Ile Ser Gly Leu Gln Ala Glu Asp Glu Ala Asp Tyr
785                 790                 795                 800

Tyr Cys Ala Ser Ala Thr Leu Leu Asp Thr Tyr Val Phe Gly Thr Gly
                805                 810                 815

Thr Lys Val Thr Val Leu Gly Asp Gln Glu Pro Lys Ser Ser Asp Lys
            820                 825                 830

Thr His Ala Gly Ser Gly Ala Ser Glu Lys Ile His Ser Asn Glu Ile
            835                 840                 845

Ser Ser Asp Ser Ile Gly Val Leu Gly Tyr Gln Lys Thr Val Asp His
        850                 855                 860

Thr Lys Val Asn Ser Lys Leu Ser Leu Phe Phe Glu Ile Lys Ser
865                 870                 875

<210> SEQ ID NO 4
<211> LENGTH: 619
<212> TYPE: PRT
<213> ORGANISM: Artificial Sequence
<220> FEATURE:
<223> OTHER INFORMATION: Fusion molecule

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95
```

-continued

```
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Ile Ser His Asn Val Tyr Ile Thr Ala Asp Lys Gln Lys Asn Gly
145                 150                 155                 160
Ile Lys Ala Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Ser Gly Ser
    210                 215                 220
Ser Gly Ser His His Leu Gln Val Asp Asn Lys Phe Asn Lys Glu Met
225                 230                 235                 240
Arg Asn Ala Tyr Trp Glu Ile Ala Leu Leu Pro Asn Ser Gly Ser Glu
                245                 250                 255
Ala Ala Ala Lys Glu Ala Ala Ala Lys Glu Ala Ala Ala Lys Glu Ala
            260                 265                 270
Ala Ala Lys Glu Ala Ala Ala Lys Glu Ala Ala Ala Lys Ser Gly Ser
        275                 280                 285
Lys Ala Ala Ala Glu Lys Ala Ala Ala Glu Lys Ala Ala Ala Glu Lys
    290                 295                 300
Ala Ala Ala Glu Lys Ala Ala Ala Glu Lys Ala Ala Ala Glu Ser Gly
305                 310                 315                 320
Ser Leu Asn Asn Gln Gln Lys Arg Ala Phe Ile Arg Ser Leu Tyr Asp
                325                 330                 335
Asp Pro Ser Gln Ser Ala Asn Leu Leu Ala Glu Ala Lys Lys Leu Asn
            340                 345                 350
Asp Leu Leu Pro Asn Leu Asn Asn Gln Ser Ala Asn Leu Leu Ala Glu
        355                 360                 365
Ala Lys Glu Leu Asn Asp Ala Gln Ala Pro Lys Ser Gly Ser Ser Gly
    370                 375                 380
Ser Gly Ser Ser Gly Ser Ser Lys Gly Glu Glu Leu Phe Thr Gly
385                 390                 395                 400
Val Val Pro Ile Leu Val Glu Leu Asp Gly Asp Val Asn Gly His Lys
                405                 410                 415
Phe Ser Val Ser Gly Glu Gly Glu Gly Asp Ala Thr Tyr Gly Lys Leu
            420                 425                 430
Thr Leu Lys Phe Ile Cys Thr Thr Gly Lys Leu Pro Val Pro Trp Pro
        435                 440                 445
Thr Leu Val Thr Thr Phe Gly Tyr Gly Leu Gln Cys Phe Ala Arg Tyr
    450                 455                 460
Pro Asp His Met Lys Arg His Asp Phe Phe Lys Ser Ala Met Pro Glu
465                 470                 475                 480
Gly Tyr Val Gln Glu Arg Thr Ile Phe Phe Lys Asp Asp Gly Asn Tyr
                485                 490                 495
Lys Thr Arg Ala Glu Val Lys Phe Glu Gly Asp Thr Leu Val Asn Arg
            500                 505                 510
Ile Glu Leu Lys Gly Ile Asp Phe Lys Glu Asp Gly Asn Ile Leu Gly
```

His Lys Leu Glu Tyr Asn Tyr Asn Ser Gln Asn Val Tyr Ile Met Ala
            530                 535                 540

Asp Lys Gln Lys Asn Gly Ile Lys Val Asn Phe Lys Ile Arg His Asn
545                 550                 555                 560

Ile Glu Asp Gly Ser Val Gln Leu Ala Asp His Tyr Gln Gln Asn Thr
                565                 570                 575

Pro Ile Gly Asp Gly Pro Val Leu Leu Pro Asp Asn His Tyr Leu Ser
            580                 585                 590

Tyr Gln Ser Ala Leu Ser Lys Asp Pro Asn Glu Lys Arg Asp His Met
        595                 600                 605

Val Leu Leu Glu Phe Val Thr Ala Ala Gly Ile
    610                 615

<210> SEQ ID NO 5
<211> LENGTH: 595
<212> TYPE: PRT
<213> ORGANISM: Artificial Sequence
<220> FEATURE:
<223> OTHER INFORMATION: Fusion molecule

<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Ser Gly Ser
    210                 215                 220

Ser Gly Ser His His Leu Gln Val Asp Asn Lys Phe Asn Lys Glu Met
225                 230                 235                 240

Arg Asn Ala Tyr Trp Glu Ile Ala Leu Leu Pro Asn Ser Gly Ser Glu
                245                 250                 255

Ala Ala Ala Lys Glu Ala Ala Ala Lys Glu Ala Ala Ala Lys Glu Ala

```
            260                 265                 270
Ala Ala Lys Glu Ala Ala Lys Glu Ala Ala Lys Ser Gly Ser
            275                 280                 285

Lys Ala Ala Glu Lys Ala Ala Glu Lys Ala Ala Glu Lys
            290                 295             300

Ala Ala Ala Glu Lys Ala Ala Glu Lys Ala Ala Glu Ser Gly
305                 310                 315             320

Ser Leu Asn Asn Gln Gln Lys Arg Ala Phe Ile Arg Ser Leu Tyr Asp
                325                 330                 335

Asp Pro Ser Gln Ser Ala Asn Leu Leu Ala Glu Ala Lys Lys Leu Asn
                340                 345                 350

Asp Leu Leu Ser Gly Ser Ser Gly Ser Ser Gly Ser Ser Gly Ser Ser
                355                 360                 365

Lys Gly Glu Glu Leu Phe Thr Gly Val Val Pro Ile Leu Val Glu Leu
            370                 375                 380

Asp Gly Asp Val Asn Gly His Lys Phe Ser Val Ser Gly Glu Gly Glu
385                 390                 395                 400

Gly Asp Ala Thr Tyr Gly Lys Leu Thr Leu Lys Phe Ile Cys Thr Thr
                405                 410                 415

Gly Lys Leu Pro Val Pro Trp Pro Thr Leu Val Thr Thr Phe Gly Tyr
            420                 425                 430

Gly Leu Gln Cys Phe Ala Arg Tyr Pro Asp His Met Lys Arg His Asp
            435                 440                 445

Phe Phe Lys Ser Ala Met Pro Glu Gly Tyr Val Gln Glu Arg Thr Ile
    450                 455                 460

Phe Phe Lys Asp Asp Gly Asn Tyr Lys Thr Arg Ala Glu Val Lys Phe
465                 470                 475                 480

Glu Gly Asp Thr Leu Val Asn Arg Ile Glu Leu Lys Gly Ile Asp Phe
                485                 490                 495

Lys Glu Asp Gly Asn Ile Leu Gly His Lys Leu Glu Tyr Asn Tyr Asn
                500                 505                 510

Ser Gln Asn Val Tyr Ile Met Ala Asp Lys Gln Lys Asn Gly Ile Lys
            515                 520                 525

Val Asn Phe Lys Ile Arg His Asn Ile Glu Asp Gly Ser Val Gln Leu
    530                 535                 540

Ala Asp His Tyr Gln Gln Asn Thr Pro Ile Gly Asp Gly Pro Val Leu
545                 550                 555                 560

Leu Pro Asp Asn His Tyr Leu Ser Tyr Gln Ser Ala Leu Ser Lys Asp
                565                 570                 575

Pro Asn Glu Lys Arg Asp His Met Val Leu Leu Glu Phe Val Thr Ala
            580                 585                 590

Ala Gly Ile
        595

<210> SEQ ID NO 6
<211> LENGTH: 408
<212> TYPE: PRT
<213> ORGANISM: Artificial Sequence
<220> FEATURE:
<223> OTHER INFORMATION: Fusion molecule

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
```

```
                    20                  25                  30
Gly Glu Gly Asp Ala Thr Tyr Gly Lys Leu Thr Leu Lys Phe Ile Cys
                35                  40                  45
Thr Thr Gly Lys Leu Pro Val Pro Trp Pro Thr Leu Val Thr Thr Phe
            50                  55                  60
Gly Tyr Gly Leu Gln Cys Phe Ala Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Ser Gly Ser Ser
            130                 135                 140
Gly Ser His His Leu Gln Val Asp Asn Lys Phe Asn Lys Glu Met Arg
145                 150                 155                 160
Asn Ala Tyr Trp Glu Ile Ala Leu Leu Pro Asn Ser Gly Ser Glu Ala
                165                 170                 175
Ala Ala Lys Glu Ala Ala Lys Glu Ala Ala Lys Glu Ala Ala
            180                 185                 190
Ala Lys Glu Ala Ala Lys Glu Ala Ala Lys Ser Gly Ser Lys
            195                 200                 205
Ala Ala Ala Glu Lys Ala Ala Glu Lys Ala Ala Glu Lys Ala
            210                 215                 220
Ala Ala Glu Lys Ala Ala Glu Lys Ala Ala Glu Ser Gly Ser
225                 230                 235                 240
Leu Asn Asn Gln Gln Lys Arg Ala Phe Ile Arg Ser Leu Tyr Asp Asp
                245                 250                 255
Pro Ser Gln Ser Ala Asn Leu Leu Ala Glu Ala Lys Lys Leu Asn Asp
            260                 265                 270
Leu Leu Pro Asn Leu Asn Asn Gln Ser Ala Asn Leu Leu Ala Glu Ala
            275                 280                 285
Lys Glu Leu Asn Asp Ala Gln Ala Pro Lys Ser Gly Ser Ser Gly Ser
            290                 295                 300
Ser Gly Ser Ser Gly Ser Leu Glu Tyr Asn Tyr Asn Ser Gln Asn Val
305                 310                 315                 320
Tyr Ile Met Ala Asp Lys Gln Lys Asn Gly Ile Lys Val Asn Phe Lys
                325                 330                 335
Ile Arg His Asn Ile Glu Asp Gly Ser Val Gln Leu Ala Asp His Tyr
            340                 345                 350
Gln Gln Asn Thr Pro Ile Gly Asp Gly Pro Val Leu Leu Pro Asp Asn
            355                 360                 365
His Tyr Leu Ser Tyr Gln Ser Ala Leu Ser Lys Asp Pro Asn Glu Lys
            370                 375                 380
Arg Asp His Met Val Leu Leu Glu Phe Val Thr Ala Ala Gly Ile Thr
385                 390                 395                 400
His Gly Met Asp Glu Leu Tyr Lys
                405

<210> SEQ ID NO 7
<211> LENGTH: 384
<212> TYPE: PRT
<213> ORGANISM: Artificial Sequence
```

<220> FEATURE:
<223> OTHER INFORMATION: Fusion molecule

<400> SEQUENCE: 7

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Ser Gly Ser Ser
    130                 135                 140

Gly Ser His His Leu Gln Val Asp Asn Lys Phe Asn Lys Glu Met Arg
145                 150                 155                 160

Asn Ala Tyr Trp Glu Ile Ala Leu Leu Pro Asn Ser Gly Ser Glu Ala
                165                 170                 175

Ala Ala Lys Glu Ala Ala Ala Lys Glu Ala Ala Ala Lys Glu Ala Ala
            180                 185                 190

Ala Lys Glu Ala Ala Ala Lys Glu Ala Ala Ala Lys Ser Gly Ser Lys
        195                 200                 205

Ala Ala Ala Glu Lys Ala Ala Glu Lys Ala Ala Glu Lys Ala
    210                 215                 220

Ala Ala Glu Lys Ala Ala Glu Lys Ala Ala Glu Ser Gly Ser
225                 230                 235                 240

Leu Asn Asn Gln Gln Lys Arg Ala Phe Ile Arg Ser Leu Tyr Asp Asp
                245                 250                 255

Pro Ser Gln Ser Ala Asn Leu Leu Ala Glu Ala Lys Lys Leu Asn Asp
            260                 265                 270

Leu Leu Ser Gly Ser Ser Gly Ser Gly Ser Ser Gly Ser Leu Glu
        275                 280                 285

Tyr Asn Tyr Asn Ser Gln Asn Val Tyr Ile Met Ala Asp Lys Gln Lys
    290                 295                 300

Asn Gly Ile Lys Val Asn Phe Lys Ile Arg His Asn Ile Glu Asp Gly
305                 310                 315                 320

Ser Val Gln Leu Ala Asp His Tyr Gln Gln Asn Thr Pro Ile Gly Asp
                325                 330                 335

Gly Pro Val Leu Leu Pro Asp Asn His Tyr Leu Ser Tyr Gln Ser Ala
            340                 345                 350

Leu Ser Lys Asp Pro Asn Glu Lys Arg Asp His Met Val Leu Leu Glu
        355                 360                 365

Phe Val Thr Ala Ala Gly Ile Thr His Gly Met Asp Glu Leu Tyr Lys
    370                 375                 380

<210> SEQ ID NO 8

<211> LENGTH: 705
<212> TYPE: PRT
<213> ORGANISM: Artificial Sequence
<220> FEATURE:
<223> OTHER INFORMATION: Fusion molecule

<400> SEQUENCE: 8

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380
```

```
Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
        420                 425                 430

Leu Leu Pro Thr Ile Pro Gly Lys Leu Asp Val Asn Lys Ser Lys Thr
    435                 440                 445

His Ile Ser Val Asn Gly Arg Lys Ile Arg Met Arg Cys Arg Ala Ile
450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Gly Ser Ser Gly Ser His His Leu Gln Val Asp Asn Lys Phe Asn Lys
            500                 505                 510

Glu Met Arg Asn Ala Tyr Trp Glu Ile Ala Leu Leu Pro Asn Ser Gly
        515                 520                 525

Ser Glu Ala Ala Ala Lys Glu Ala Ala Lys Glu Ala Ala Lys
    530                 535                 540

Glu Ala Ala Ala Lys Glu Ala Ala Lys Glu Ala Ala Lys Ser
545                 550                 555                 560

Gly Ser Lys Ala Ala Ala Glu Lys Ala Ala Glu Lys Ala Ala
            565                 570                 575

Glu Lys Ala Ala Ala Glu Lys Ala Ala Glu Lys Ala Ala Glu
                580                 585                 590

Ser Gly Ser Leu Asn Asn Gln Gln Lys Arg Ala Phe Ile Arg Ser Leu
            595                 600                 605

Tyr Asp Asp Pro Ser Gln Ser Ala Asn Leu Leu Ala Glu Ala Lys Lys
    610                 615                 620

Leu Asn Asp Leu Leu Pro Asn Leu Asn Asn Gln Ser Ala Asn Leu Leu
625                 630                 635                 640

Ala Glu Ala Lys Glu Leu Asn Asp Ala Gln Ala Pro Lys Ser Gly Ser
                645                 650                 655

Ser Gly Ser Ser Gly Ser Ser Gly Ser Ser Glu Lys Ile His Ser Asn
            660                 665                 670

Glu Ile Ser Ser Asp Ser Ile Gly Val Leu Gly Tyr Gln Lys Thr Val
            675                 680                 685

Asp His Thr Lys Val Asn Ser Lys Leu Ser Leu Phe Phe Glu Ile Lys
            690                 695                 700

Ser
705

<210> SEQ ID NO 9
<211> LENGTH: 681
<212> TYPE: PRT
<213> ORGANISM: Artificial Sequence
<220> FEATURE:
<223> OTHER INFORMATION: Fusion molecule

<400> SEQUENCE: 9

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30
```

```
Lys Gly Ile Gln Lys Pro Lys Ser Gly Thr Gln Gly Asn Tyr Asp Asp
         35                  40                  45

Asp Trp Lys Gly Phe Tyr Ser Thr Asp Asn Lys Tyr Asp Ala Ala Gly
         50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
        210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445
```

His Ile Ser Val Asn Gly Arg Lys Ile Arg Met Arg Cys Arg Ala Ile
            450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Gly Ser Ser Gly Ser His His Leu Gln Val Asp Asn Lys Phe Asn Lys
            500                 505                 510

Glu Met Arg Asn Ala Tyr Trp Glu Ile Ala Leu Leu Pro Asn Ser Gly
            515                 520                 525

Ser Glu Ala Ala Ala Lys Glu Ala Ala Ala Lys Glu Ala Ala Ala Lys
530                 535                 540

Glu Ala Ala Ala Lys Glu Ala Ala Ala Lys Glu Ala Ala Ala Lys Ser
545                 550                 555                 560

Gly Ser Lys Ala Ala Ala Glu Lys Ala Ala Ala Glu Lys Ala Ala Ala
                565                 570                 575

Glu Lys Ala Ala Ala Glu Lys Ala Ala Ala Glu Lys Ala Ala Ala Glu
            580                 585                 590

Ser Gly Ser Leu Asn Asn Gln Gln Lys Arg Ala Phe Ile Arg Ser Leu
            595                 600                 605

Tyr Asp Asp Pro Ser Gln Ser Ala Asn Leu Leu Ala Glu Ala Lys Lys
            610                 615                 620

Leu Asn Asp Leu Leu Ser Gly Ser Ser Gly Ser Gly Ser Ser Gly
625                 630                 635                 640

Ser Ser Glu Lys Ile His Ser Asn Glu Ile Ser Ser Asp Ser Ile Gly
                645                 650                 655

Val Leu Gly Tyr Gln Lys Thr Val Asp His Thr Lys Val Asn Ser Lys
            660                 665                 670

Leu Ser Leu Phe Phe Glu Ile Lys Ser
            675                 680

<210> SEQ ID NO 10
<211> LENGTH: 619
<212> TYPE: PRT
<213> ORGANISM: Artificial Sequence
<220> FEATURE:
<223> OTHER INFORMATION: Fusion molecule

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Ser Gly Ser
210                 215                 220

Ser Gly Ser His His Leu Gln Val Asp Asn Lys Phe Asn Lys Glu Met
225                 230                 235                 240

Arg Asn Ala Tyr Trp Glu Ile Ala Leu Leu Pro Asn Leu Asn Asn Gln
                245                 250                 255

Gln Lys Arg Ala Phe Ile Arg Ser Leu Tyr Asp Asp Pro Ser Gly Ser
            260                 265                 270

Glu Ala Ala Ala Lys Glu Ala Ala Ala Lys Glu Ala Ala Ala Lys Glu
        275                 280                 285

Ala Ala Ala Lys Glu Ala Ala Ala Lys Glu Ala Ala Ala Lys Ser Gly
        290                 295                 300

Ser Lys Ala Ala Ala Glu Lys Ala Ala Ala Glu Lys Ala Ala Ala Glu
305                 310                 315                 320

Lys Ala Ala Ala Glu Lys Ala Ala Ala Glu Lys Ala Ala Ala Glu Ser
                325                 330                 335

Gly Ser Ser Gln Ser Ala Asn Leu Leu Ala Glu Ala Lys Lys Leu Asn
            340                 345                 350

Asp Leu Leu Pro Asn Leu Asn Asn Gln Ser Ala Asn Leu Leu Ala Glu
        355                 360                 365

Ala Lys Glu Leu Asn Asp Ala Gln Ala Pro Lys Ser Gly Ser Ser Gly
        370                 375                 380

Ser Ser Gly Ser Ser Gly Ser Ser Lys Gly Glu Glu Leu Phe Thr Gly
385                 390                 395                 400

Val Val Pro Ile Leu Val Glu Leu Asp Gly Asp Val Asn Gly His Lys
                405                 410                 415

Phe Ser Val Ser Gly Glu Gly Glu Gly Asp Ala Thr Tyr Gly Lys Leu
            420                 425                 430

Thr Leu Lys Phe Ile Cys Thr Thr Gly Lys Leu Pro Val Pro Trp Pro
        435                 440                 445

Thr Leu Val Thr Thr Phe Gly Tyr Gly Leu Gln Cys Phe Ala Arg Tyr
        450                 455                 460

Pro Asp His Met Lys Arg His Asp Phe Phe Lys Ser Ala Met Pro Glu
465                 470                 475                 480

Gly Tyr Val Gln Glu Arg Thr Ile Phe Phe Lys Asp Asp Gly Asn Tyr
                485                 490                 495

Lys Thr Arg Ala Glu Val Lys Phe Glu Gly Asp Thr Leu Val Asn Arg
            500                 505                 510

Ile Glu Leu Lys Gly Ile Asp Phe Lys Glu Asp Gly Asn Ile Leu Gly
        515                 520                 525

His Lys Leu Glu Tyr Asn Tyr Asn Ser Gln Asn Val Tyr Ile Met Ala
        530                 535                 540

Asp Lys Gln Lys Asn Gly Ile Lys Val Asn Phe Lys Ile Arg His Asn
```

```
                545                 550                 555                 560
Ile Glu Asp Gly Ser Val Gln Leu Ala Asp His Tyr Gln Gln Asn Thr
                    565                 570                 575

Pro Ile Gly Asp Gly Pro Val Leu Leu Pro Asp Asn His Tyr Leu Ser
                580                 585                 590

Tyr Gln Ser Ala Leu Ser Lys Asp Pro Asn Glu Lys Arg Asp His Met
                595                 600                 605

Val Leu Leu Glu Phe Val Thr Ala Ala Gly Ile
                610                 615

<210> SEQ ID NO 11
<211> LENGTH: 408
<212> TYPE: PRT
<213> ORGANISM: Artificial Sequence
<220> FEATURE:
<223> OTHER INFORMATION: Fusion molecule

<400> SEQUENCE: 11

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Ser Gly Ser Ser
    130                 135                 140

Gly Ser His His Leu Gln Val Asp Asn Lys Phe Asn Lys Glu Met Arg
145                 150                 155                 160

Asn Ala Tyr Trp Glu Ile Ala Leu Leu Pro Asn Leu Asn Asn Gln Gln
                165                 170                 175

Lys Arg Ala Phe Ile Arg Ser Leu Tyr Asp Asp Pro Ser Gly Ser Glu
            180                 185                 190

Ala Ala Ala Lys Glu Ala Ala Lys Glu Ala Ala Lys Glu Ala
        195                 200                 205

Ala Ala Lys Glu Ala Ala Lys Glu Ala Ala Lys Ser Gly Ser
    210                 215                 220

Lys Ala Ala Ala Glu Lys Ala Ala Ala Glu Lys Ala Ala Ala Glu Lys
225                 230                 235                 240

Ala Ala Ala Glu Lys Ala Ala Ala Glu Lys Ala Ala Ala Glu Ser Gly
                245                 250                 255

Ser Ser Gln Ser Ala Asn Leu Leu Ala Glu Ala Lys Lys Leu Asn Asp
            260                 265                 270

Leu Leu Pro Asn Leu Asn Asn Gln Ser Ala Asn Leu Leu Ala Glu Ala
        275                 280                 285

Lys Glu Leu Asn Asp Ala Gln Ala Pro Lys Ser Gly Ser Ser Gly Ser
```

```
                290                 295                 300
Ser Gly Ser Ser Gly Ser Leu Glu Tyr Asn Tyr Asn Ser Gln Asn Val
305                 310                 315                 320

Tyr Ile Met Ala Asp Lys Gln Lys Asn Gly Ile Lys Val Asn Phe Lys
                325                 330                 335

Ile Arg His Asn Ile Glu Asp Gly Ser Val Gln Leu Ala Asp His Tyr
                340                 345                 350

Gln Gln Asn Thr Pro Ile Gly Asp Gly Pro Val Leu Leu Pro Asp Asn
                355                 360                 365

His Tyr Leu Ser Tyr Gln Ser Ala Leu Ser Lys Asp Pro Asn Glu Lys
370                 375                 380

Arg Asp His Met Val Leu Leu Glu Phe Val Thr Ala Ala Gly Ile Thr
385                 390                 395                 400

His Gly Met Asp Glu Leu Tyr Lys
                405

<210> SEQ ID NO 12
<211> LENGTH: 384
<212> TYPE: PRT
<213> ORGANISM: Artificial Sequence
<220> FEATURE:
<223> OTHER INFORMATION: Fusion molecule

<400> SEQUENCE: 12

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Ser Gly Ser Ser
        130                 135                 140

Gly Ser His His Leu Gln Val Asp Asn Lys Phe Asn Lys Glu Met Arg
145                 150                 155                 160

Asn Ala Tyr Trp Glu Ile Ala Leu Leu Pro Asn Leu Asn Asn Gln Gln
                165                 170                 175

Lys Arg Ala Phe Ile Arg Ser Leu Tyr Asp Asp Pro Ser Gly Ser Glu
                180                 185                 190

Ala Ala Ala Lys Glu Ala Ala Ala Lys Glu Ala Ala Ala Lys Glu Ala
            195                 200                 205

Ala Ala Lys Glu Ala Ala Ala Lys Glu Ala Ala Ala Lys Ser Gly Ser
        210                 215                 220

Lys Ala Ala Ala Glu Lys Ala Ala Ala Glu Lys Ala Ala Ala Glu Lys
225                 230                 235                 240

Ala Ala Ala Glu Lys Ala Ala Ala Glu Lys Ala Ala Ala Glu Ser Gly
```

```
                    245                 250                 255
Ser Ser Gln Ser Ala Asn Leu Leu Ala Glu Ala Lys Lys Leu Asn Asp
                260                 265                 270

Leu Leu Ser Gly Ser Ser Gly Ser Ser Gly Ser Ser Gly Ser Leu Glu
            275                 280                 285

Tyr Asn Tyr Asn Ser Gln Asn Val Tyr Ile Met Ala Asp Lys Gln Lys
        290                 295                 300

Asn Gly Ile Lys Val Asn Phe Lys Ile Arg His Asn Ile Glu Asp Gly
305                 310                 315                 320

Ser Val Gln Leu Ala Asp His Tyr Gln Gln Asn Thr Pro Ile Gly Asp
                325                 330                 335

Gly Pro Val Leu Leu Pro Asp Asn His Tyr Leu Ser Tyr Gln Ser Ala
            340                 345                 350

Leu Ser Lys Asp Pro Asn Glu Lys Arg Asp His Met Val Leu Leu Glu
        355                 360                 365

Phe Val Thr Ala Ala Gly Ile Thr His Gly Met Asp Glu Leu Tyr Lys
    370                 375                 380

<210> SEQ ID NO 13
<211> LENGTH: 705
<212> TYPE: PRT
<213> ORGANISM: Artificial Sequence
<220> FEATURE:
<223> OTHER INFORMATION: Fusion molecule

<400> SEQUENCE: 13

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
```

-continued

```
           225                 230                 235                 240
Glu Lys Ala Lys Gln Tyr Leu Glu Gly Phe His Gln Thr Ala Leu Glu
                245                 250                 255
His Pro Glu Leu Ser Glu Leu Lys Thr Val Thr Gly Thr Asn Pro Val
                260                 265                 270
Phe Ala Gly Ala Asn Tyr Ala Ala Trp Ala Val Asn Val Ala Gln Val
                275                 280                 285
Ile Asp Ser Glu Thr Ala Asp Asn Leu Glu Lys Thr Thr Ala Ala Leu
                290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                325                 330                 335
Ser Leu Met Val Ala Gln Ala Ile Pro Leu Val Gly Glu Leu Val Asp
                340                 345                 350
Ile Gly Phe Ala Ala Tyr Asn Phe Val Glu Ser Ile Ile Asn Leu Phe
                355                 360                 365
Gln Val Val His Asn Ser Tyr Asn Arg Pro Ala Tyr Ser Pro Gly His
                370                 375                 380
Lys Thr Gln Pro Phe Leu His Asp Gly Tyr Ala Val Ser Trp Asn Thr
385                 390                 395                 400
Val Glu Asp Ser Ile Ile Arg Thr Gly Phe Gln Gly Glu Ser Gly His
                405                 410                 415
Asp Ile Lys Ile Thr Ala Glu Asn Thr Pro Leu Pro Ile Ala Gly Val
                420                 425                 430
Leu Leu Pro Thr Ile Pro Gly Lys Leu Asp Val Asn Lys Ser Lys Thr
                435                 440                 445
His Ile Ser Val Asn Gly Arg Lys Ile Arg Met Arg Cys Arg Ala Ile
                450                 455                 460
Asp Gly Asp Val Thr Phe Cys Arg Pro Lys Ser Pro Val Tyr Val Gly
465                 470                 475                 480
Asn Gly Val His Ala Asn Leu His Val Ala Phe His Arg Ser Ser Ser
                485                 490                 495
Gly Ser Ser Gly Ser His His Leu Gln Val Asp Asn Lys Phe Asn Lys
                500                 505                 510
Glu Met Arg Asn Ala Tyr Trp Glu Ile Ala Leu Leu Pro Asn Leu Asn
                515                 520                 525
Asn Gln Gln Lys Arg Ala Phe Ile Arg Ser Leu Tyr Asp Asp Pro Ser
                530                 535                 540
Gly Ser Glu Ala Ala Lys Glu Ala Ala Lys Glu Ala Ala
545                 550                 555                 560
Lys Glu Ala Ala Lys Glu Ala Ala Lys Glu Ala Ala Lys
                565                 570                 575
Ser Gly Ser Lys Ala Ala Glu Lys Ala Ala Glu Lys Ala
                580                 585                 590
Ala Glu Lys Ala Ala Glu Lys Ala Ala Glu Lys Ala Ala
                595                 600                 605
Glu Ser Gly Ser Ser Gln Ser Ala Asn Leu Leu Ala Glu Ala Lys Lys
                610                 615                 620
Leu Asn Asp Leu Leu Pro Asn Leu Asn Gln Ser Ala Asn Leu Leu
625                 630                 635                 640
Ala Glu Ala Lys Glu Leu Asn Asp Ala Gln Ala Pro Lys Ser Gly Ser
                645                 650                 655
```

```
Ser Gly Ser Ser Gly Ser Ser Gly Ser Ser Glu Lys Ile His Ser Asn
            660                 665                 670

Glu Ile Ser Ser Asp Ser Ile Gly Val Leu Gly Tyr Gln Lys Thr Val
            675                 680                 685

Asp His Thr Lys Val Asn Ser Lys Leu Ser Leu Phe Glu Ile Lys
            690                 695                 700

Ser
705

<210> SEQ ID NO 14
<211> LENGTH: 226
<212> TYPE: PRT
<213> ORGANISM: Artificial Sequence
<220> FEATURE:
<223> OTHER INFORMATION: Protein fragment

<400> SEQUENCE: 14

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Val Gln Cys Phe Ser Arg Tyr Pro Asp His Met Lys Arg His Asp Phe
65                  70                  75                  80

Phe Lys Ser Ala Met Pro Glu Gly Tyr Val Gln Glu Arg Thr Ile Phe
                85                  90                  95

Phe Lys Asp Asp Gly Asn Tyr Lys Thr Arg Ala Glu Val Lys Phe Glu
            100                 105                 110

Gly Asp Thr Leu Val Asn Arg Ile Glu Leu Lys Gly Ile Asp Phe Lys
        115                 120                 125

Glu Asp Gly Asn Ile Leu Gly His Lys Leu Glu Tyr Asn Tyr Ile Ser
    130                 135                 140

His Asn Val Tyr Ile Thr Ala Asp Lys Gln Lys Asn Gly Ile Lys Ala
145                 150                 155                 160

Asn Phe Lys Ile Arg His Asn Ile Glu Asp Gly Ser Val Gln Leu Ala
                165                 170                 175

Asp His Tyr Gln Gln Asn Thr Pro Ile Gly Asp Gly Pro Val Leu Leu
            180                 185                 190

Pro Asp Asn His Tyr Leu Ser Thr Gln Ser Ala Leu Ser Lys Asp Pro
        195                 200                 205

Asn Glu Lys Arg Asp His Met Val Leu Leu Glu Phe Val Thr Ala Ala
    210                 215                 220

Gly Ile
225

<210> SEQ ID NO 15
<211> LENGTH: 226
<212> TYPE: PRT
<213> ORGANISM: Artificial Sequence
<220> FEATURE:
<223> OTHER INFORMATION: Protein fragment

<400> SEQUENCE: 15

Met Ser Lys Gly Glu Glu Leu Phe Thr Gly Val Val Pro Ile Leu Val
```

```
              1               5                  10                 15
        Glu Leu Asp Gly Asp Val Asn Gly His Lys Phe Ser Val Ser Gly Glu
                         20                 25                 30
        Gly Glu Gly Asp Ala Thr Tyr Gly Lys Leu Thr Leu Lys Phe Ile Cys
                     35                 40                 45
        Thr Thr Gly Lys Leu Pro Val Pro Trp Pro Thr Leu Val Thr Thr Phe
                 50                 55                 60
        Leu Gln Cys Phe Ala Arg Tyr Pro Asp His Met Lys Arg His Asp Phe
        65                 70                 75                 80
        Phe Lys Ser Ala Met Pro Glu Gly Tyr Val Gln Glu Arg Thr Ile Phe
                         85                 90                 95
        Phe Lys Asp Asp Gly Asn Tyr Lys Thr Arg Ala Glu Val Lys Phe Glu
                        100                105                110
        Gly Asp Thr Leu Val Asn Arg Ile Glu Leu Lys Gly Ile Asp Phe Lys
                        115                120                125
        Glu Asp Gly Asn Ile Leu Gly His Lys Leu Glu Tyr Asn Tyr Asn Ser
                        130                135                140
        Gln Asn Val Tyr Ile Met Ala Asp Lys Gln Lys Asn Gly Ile Lys Val
        145                150                155                160
        Asn Phe Lys Ile Arg His Asn Ile Glu Asp Gly Ser Val Gln Leu Ala
                        165                170                175
        Asp His Tyr Gln Gln Asn Thr Pro Ile Gly Asp Gly Pro Val Leu Leu
                        180                185                190
        Pro Asp Asn His Tyr Leu Ser Tyr Gln Ser Ala Leu Ser Lys Asp Pro
                        195                200                205
        Asn Glu Lys Arg Asp His Met Val Leu Leu Glu Phe Val Thr Ala Ala
            210                215                220
        Gly Ile
        225

<210> SEQ ID NO 16
<211> LENGTH: 25
<212> TYPE: PRT
<213> ORGANISM: Artificial Sequence
<220> FEATURE:
<223> OTHER INFORMATION: Protein fragment

<400> SEQUENCE: 16

His His Leu Gln Val Asp Asn Lys Phe Asn Lys Glu Met Arg Asn Ala
1               5                  10                 15
Tyr Trp Glu Ile Ala Leu Leu Pro Asn
            20                 25

<210> SEQ ID NO 17
<211> LENGTH: 42
<212> TYPE: PRT
<213> ORGANISM: Artificial Sequence
<220> FEATURE:
<223> OTHER INFORMATION: Protein fragment

<400> SEQUENCE: 17

His His Leu Gln Val Asp Asn Lys Phe Asn Lys Glu Met Arg Asn Ala
1               5                  10                 15
Tyr Trp Glu Ile Ala Leu Leu Pro Asn Leu Asn Asn Gln Gln Lys Arg
            20                 25                 30
Ala Phe Ile Arg Ser Leu Tyr Asp Asp Pro
            35                 40
```

<210> SEQ ID NO 18
<211> LENGTH: 58
<212> TYPE: PRT
<213> ORGANISM: Artificial Sequence
<220> FEATURE:
<223> OTHER INFORMATION: Protein fragment

<400> SEQUENCE: 18

Leu Asn Asn Gln Gln Lys Arg Ala Phe Ile Arg Ser Leu Tyr Asp Asp
1               5                   10                  15

Pro Ser Gln Ser Ala Asn Leu Leu Ala Glu Ala Lys Lys Leu Asn Asp
            20                  25                  30

Leu Leu Pro Asn Leu Asn Asn Gln Ser Ala Asn Leu Leu Ala Glu Ala
        35                  40                  45

Lys Glu Leu Asn Asp Ala Gln Ala Pro Lys
    50                  55

<210> SEQ ID NO 19
<211> LENGTH: 34
<212> TYPE: PRT
<213> ORGANISM: Artificial Sequence
<220> FEATURE:
<223> OTHER INFORMATION: Protein fragment

<400> SEQUENCE: 19

Leu Asn Asn Gln Gln Lys Arg Ala Phe Ile Arg Ser Leu Tyr Asp Asp
1               5                   10                  15

Pro Ser Gln Ser Ala Asn Leu Leu Ala Glu Ala Lys Lys Leu Asn Asp
            20                  25                  30

Leu Leu

<210> SEQ ID NO 20
<211> LENGTH: 41
<212> TYPE: PRT
<213> ORGANISM: Artificial Sequence
<220> FEATURE:
<223> OTHER INFORMATION: Protein fragment

<400> SEQUENCE: 20

Ser Gln Ser Ala Asn Leu Leu Ala Glu Ala Lys Lys Leu Asn Asp Leu
1               5                   10                  15

Leu Pro Asn Leu Asn Asn Gln Ser Ala Asn Leu Leu Ala Glu Ala Lys
            20                  25                  30

Glu Leu Asn Asp Ala Gln Ala Pro Lys
        35                  40

<210> SEQ ID NO 21
<211> LENGTH: 24
<212> TYPE: PRT
<213> ORGANISM: Artificial Sequence
<220> FEATURE:
<223> OTHER INFORMATION: Protein fragment

<400> SEQUENCE: 21

Pro Asn Leu Asn Asn Gln Ser Ala Asn Leu Leu Ala Glu Ala Lys Glu
1               5                   10                  15

Leu Asn Asp Ala Gln Ala Pro Lys
            20

<210> SEQ ID NO 22
<211> LENGTH: 495
<212> TYPE: PRT

<213> ORGANISM: Artificial Sequence
<220> FEATURE:
<223> OTHER INFORMATION: Protein fragment

<400> SEQUENCE: 22

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65              70                  75                  80

Val Lys Val Thr Tyr Pro Gly Leu Thr Lys Val Leu Ala Leu Lys Val
            85                  90                  95

Asp Asn Ala Glu Thr Ile Lys Lys Glu Leu Gly Leu Ser Leu Thr Glu
        100                 105                 110

Pro Leu Met Glu Gln Val Gly Thr Glu Glu Phe Ile Lys Arg Phe Gly
    115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
    195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
    275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
        340                 345                 350

Ile Gly Phe Ala Ala Tyr Asn Phe Val Glu Ser Ile Ile Asn Leu Phe
    355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
```

```
                385                 390                 395                 400
Val Glu Asp Ser Ile Ile Arg Thr Gly Phe Gln Gly Glu Ser Gly His
                    405                 410                 415

Asp Ile Lys Ile Thr Ala Glu Asn Thr Pro Leu Pro Ile Ala Gly Val
                    420                 425                 430

Leu Leu Pro Thr Ile Pro Gly Lys Leu Asp Val Asn Lys Ser Lys Thr
                    435                 440                 445

His Ile Ser Val Asn Gly Arg Lys Ile Arg Met Arg Cys Arg Ala Ile
                    450                 455                 460

Asp Gly Asp Val Thr Phe Cys Arg Pro Lys Ser Pro Val Tyr Val Gly
                    465                 470                 475                 480

Asn Gly Val His Ala Asn Leu His Val Ala Phe His Arg Ser Ser
                    485                 490                 495

<210> SEQ ID NO 23
<211> LENGTH: 40
<212> TYPE: PRT
<213> ORGANISM: Artificial Sequence
<220> FEATURE:
<223> OTHER INFORMATION: Protein fragment

<400> SEQUENCE: 23

Ser Glu Lys Ile His Ser Asn Glu Ile Ser Ser Asp Ser Ile Gly Val
1               5                   10                  15

Leu Gly Tyr Gln Lys Thr Val Asp His Thr Lys Val Asn Ser Lys Leu
                20                  25                  30

Ser Leu Phe Phe Glu Ile Lys Ser
            35                  40

<210> SEQ ID NO 24
<211> LENGTH: 496
<212> TYPE: PRT
<213> ORGANISM: Artificial Sequence
<220> FEATURE:
<223> OTHER INFORMATION: Fusion molecule
<220> FEATURE:
<221> NAME/KEY: misc_feature
<222> LOCATION: (144)..(144)
<223> OTHER INFORMATION: Xaa can be any naturally occurring amino acid

<400> SEQUENCE: 24

Phe Ser Arg Ser Asp His Leu Ala Glu His Gln Arg Thr His Thr Gly
1               5                   10                  15

Glu Lys Pro Tyr Lys Cys Pro Glu Cys Gly Lys Ser Phe Ser Asp Lys
                20                  25                  30

Lys Asp Leu Thr Arg His Gln Arg Thr His Thr Gly Glu Lys Pro Tyr
                35                  40                  45

Lys Cys Pro Glu Cys Gly Lys Ser Phe Ser Gln Arg Ala Asn Leu Arg
            50                  55                  60

Ala His Gln Arg Thr His Thr Gly Ser Gly Ser Ser Gly Ser Met Ser
65                  70                  75                  80

Lys Gly Glu Glu Leu Phe Thr Gly Val Val Pro Ile Leu Val Glu Leu
                85                  90                  95

Asp Gly Asp Val Asn Gly His Lys Phe Ser Val Ser Gly Glu Gly Glu
                100                 105                 110

Gly Asp Ala Thr Tyr Gly Lys Leu Thr Leu Lys Phe Ile Cys Thr Thr
            115                 120                 125

Gly Lys Leu Pro Val Pro Trp Pro Thr Leu Val Thr Thr Phe Gly Xaa
        130                 135                 140
```

Gly Leu Gln Cys Phe Ala Arg Tyr Pro Asp His Met Lys Arg His Asp
145                 150                 155                 160

Phe Phe Lys Ser Ala Met Pro Glu Gly Tyr Val Gln Glu Arg Thr Ile
            165                 170                 175

Phe Phe Lys Asp Asp Gly Asn Tyr Lys Thr Arg Ala Glu Val Lys Phe
        180                 185                 190

Glu Gly Asp Thr Leu Val Asn Arg Ile Glu Leu Lys Gly Ile Asp Phe
    195                 200                 205

Lys Glu Asp Gly Asn Ile Leu Gly His Lys Ala Gly Ser Gly Gly Ser
210                 215                 220

Gly Gly Ser Gly Ala Glu Ala Ala Ala Lys Glu Ala Ala Ala Lys Glu
225                 230                 235                 240

Ala Ala Ala Lys Glu Ala Ala Ala Lys Glu Ala Ala Ala Lys Glu Ala
            245                 250                 255

Ala Ala Lys Ser Gly Ser Lys Ala Ala Ala Glu Lys Ala Ala Ala Glu
        260                 265                 270

Lys Ala Ala Ala Glu Lys Ala Ala Ala Glu Lys Ala Ala Ala Glu Lys
    275                 280                 285

Ala Ala Ala Glu Ala Gly Ser Gly Gly Ser Gly Gly Ser Gly Ala Leu
290                 295                 300

Glu Tyr Asn Tyr Asn Ser Gln Asn Val Tyr Ile Met Ala Asp Lys Gln
305                 310                 315                 320

Lys Asn Gly Ile Lys Val Asn Phe Lys Ile Arg His Asn Ile Glu Asp
            325                 330                 335

Gly Ser Val Gln Leu Ala Asp His Tyr Gln Gln Asn Thr Pro Ile Gly
        340                 345                 350

Asp Gly Pro Val Leu Leu Pro Asp Asn His Tyr Leu Ser Tyr Gln Ser
    355                 360                 365

Ala Leu Ser Lys Asp Pro Asn Glu Lys Arg Asp His Met Val Leu Leu
370                 375                 380

Glu Phe Val Thr Ala Ala Gly Ile Thr His Gly Met Asp Glu Leu Tyr
385                 390                 395                 400

Lys Ser Gly Ser Ser Gly Ser Gly Glu Lys Pro Tyr Ala Cys Pro Glu
            405                 410                 415

Cys Gly Lys Ser Phe Ser Gln Leu Ala His Leu Arg Ala His Gln Arg
        420                 425                 430

Thr His Thr Gly Glu Lys Pro Tyr Lys Cys Pro Glu Cys Gly Lys Ser
    435                 440                 445

Phe Ser Arg Glu Asp Asn Leu His Thr His Gln Arg Thr His Thr Gly
450                 455                 460

Glu Lys Pro Tyr Lys Cys Pro Glu Cys Gly Lys Ser Phe Ser Arg Arg
465                 470                 475                 480

Asp Ala Leu Asn Val His Gln Arg Thr His Thr Gly Lys Lys Thr Ser
            485                 490                 495

<210> SEQ ID NO 25
<211> LENGTH: 1193
<212> TYPE: PRT
<213> ORGANISM: Artificial Sequence
<220> FEATURE:
<223> OTHER INFORMATION: Fusion molecule
<220> FEATURE:
<221> NAME/KEY: misc_feature
<222> LOCATION: (508)..(508)
<223> OTHER INFORMATION: Xaa can be any naturally occurring amino acid

```
<400> SEQUENCE: 25

His Ile Val Ala Leu Ser Gln His Pro Ala Leu Gly Thr Val Ala
1               5                   10                  15

Val Thr Tyr Gln His Ile Ile Thr Ala Leu Pro Glu Ala Thr His Glu
            20                  25                  30

Asp Ile Val Gly Val Gly Lys Gln Trp Ser Gly Ala Arg Ala Leu Glu
            35                  40                  45

Ala Leu Leu Thr Asp Ala Gly Glu Leu Arg Gly Pro Pro Leu Gln Leu
        50                  55                  60

Asp Thr Gly Gln Leu Val Lys Ile Ala Lys Arg Gly Gly Val Thr Ala
65                  70                  75                  80

Met Glu Ala Val His Ala Ser Arg Asn Ala Leu Thr Gly Ala Pro Leu
                85                  90                  95

Asn Leu Thr Pro Ala Gln Val Val Ala Ile Ala Ser Asn Asn Gly Gly
            100                 105                 110

Lys Gln Ala Leu Glu Thr Val Gln Arg Leu Leu Pro Val Leu Cys Gln
            115                 120                 125

Ala His Gly Leu Thr Pro Ala Gln Val Val Ala Ile Ala Ser His Asp
        130                 135                 140

Gly Gly Lys Gln Ala Leu Glu Thr Met Gln Arg Leu Leu Pro Val Leu
145                 150                 155                 160

Cys Gln Ala His Gly Leu Pro Pro Asp Gln Val Val Ala Ile Ala Ser
                165                 170                 175

Asn Ile Gly Gly Lys Gln Ala Leu Glu Thr Val Gln Arg Leu Leu Pro
            180                 185                 190

Val Leu Cys Gln Ala His Gly Leu Thr Pro Asp Gln Val Val Ala Ile
            195                 200                 205

Ala Ser His Gly Gly Gly Lys Gln Ala Leu Glu Thr Val Gln Arg Leu
        210                 215                 220

Leu Pro Val Leu Cys Gln Ala His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Ala His Gly Leu Thr Pro Asp Gln
            260                 265                 270

Val Val Ala Ile Ala Ser Asn Gly Gly Lys Gln Ala Leu Glu Thr
            275                 280                 285

Val Gln Arg Leu Leu Pro Val Leu Cys Gln Ala His Gly Leu Thr Pro
290                 295                 300

Asp Gln Val Val Ala Ile Ala Ser Asn Gly Gly Lys Gln Ala Leu Glu
305                 310                 315                 320

Thr Val Gln Arg Leu Leu Pro Val Leu Cys Gln Ala His Gly Leu Thr
                325                 330                 335

Pro Asp Gln Val Val Ala Ile Ala Ser His Asp Gly Gly Lys Gln Ala
            340                 345                 350

Leu Glu Thr Val Gln Arg Leu Leu Pro Val Leu Cys Gln Thr His Gly
            355                 360                 365

Leu Thr Pro Ala Gln Val Val Ala Ile Ala Ser His Asp Gly Gly Lys
        370                 375                 380

Gln Ala Leu Glu Thr Val Gln Gln Leu Leu Pro Val Leu Cys Gln Ala
385                 390                 395                 400

His Gly Leu Thr Pro Asp Gln Val Val Ala Ile Ala Ser Asn Ile Gly
                405                 410                 415
```

```
Gly Lys Gln Ala Leu Ala Thr Val Gln Arg Leu Leu Pro Val Leu Cys
            420                 425                 430

Gln Ala His Gly Ser Gly Ser Gly Ser Met Ser Lys Gly Glu Glu
            435                 440                 445

Leu Phe Thr Gly Val Val Pro Ile Leu Val Glu Leu Asp Gly Asp Val
450                 455                 460

Asn Gly His Lys Phe Ser Val Ser Gly Glu Gly Glu Gly Asp Ala Thr
465                 470                 475                 480

Tyr Gly Lys Leu Thr Leu Lys Phe Ile Cys Thr Thr Gly Lys Leu Pro
                485                 490                 495

Val Pro Trp Pro Thr Leu Val Thr Thr Phe Gly Xaa Gly Leu Gln Cys
            500                 505                 510

Phe Ala Arg Tyr Pro Asp His Met Lys Arg His Asp Phe Phe Lys Ser
            515                 520                 525

Ala Met Pro Glu Gly Tyr Val Gln Glu Arg Thr Ile Phe Phe Lys Asp
            530                 535                 540

Asp Gly Asn Tyr Lys Thr Arg Ala Glu Val Lys Phe Glu Gly Asp Thr
545                 550                 555                 560

Leu Val Asn Arg Ile Glu Leu Lys Gly Ile Asp Phe Lys Glu Asp Gly
                565                 570                 575

Asn Ile Leu Gly His Lys Ala Gly Ser Gly Gly Ser Gly Gly Ser Gly
            580                 585                 590

Ala Glu Ala Ala Ala Lys Glu Ala Ala Lys Glu Ala Ala Lys
            595                 600                 605

Glu Ala Ala Lys Glu Ala Ala Lys Glu Ala Ala Lys Ser
            610                 615                 620

Gly Ser Lys Ala Ala Glu Lys Ala Ala Glu Lys Ala Ala
625                 630                 635                 640

Glu Lys Ala Ala Ala Glu Lys Ala Ala Ala Glu Lys Ala Ala Ala Glu
                645                 650                 655

Ala Gly Ser Gly Gly Ser Gly Gly Ser Gly Ala Leu Glu Tyr Asn Tyr
            660                 665                 670

Asn Ser Gln Asn Val Tyr Ile Met Ala Asp Lys Gln Lys Asn Gly Ile
            675                 680                 685

Lys Val Asn Phe Lys Ile Arg His Asn Ile Glu Asp Gly Ser Val Gln
            690                 695                 700

Leu Ala Asp His Tyr Gln Gln Asn Thr Pro Ile Gly Asp Gly Pro Val
705                 710                 715                 720

Leu Leu Pro Asp Asn His Tyr Leu Ser Tyr Gln Ser Ala Leu Ser Lys
                725                 730                 735

Asp Pro Asn Glu Lys Arg Asp His Met Val Leu Leu Glu Phe Val Thr
            740                 745                 750

Ala Ala Gly Ile Thr His Gly Met Asp Glu Leu Tyr Lys Ser Gly Ser
            755                 760                 765

Ser Gly Ser Gly Leu Thr Pro Asp Gln Val Val Ala Ile Ala Ser Asn
770                 775                 780

Gly Gly Gly Lys Gln Ala Leu Glu Thr Val Gln Arg Leu Leu Pro Val
785                 790                 795                 800

Leu Cys Gln Ala His Gly Leu Thr Pro Asp Gln Val Val Ala Ile Ala
                805                 810                 815

Ser Asn Gly Gly Gly Lys Gln Ala Leu Glu Thr Val Gln Arg Leu Leu
            820                 825                 830
```

Pro Val Leu Cys Gln Ala His Gly Leu Thr Gln Val Gln Val Val Ala
            835                 840                 845

Ile Ala Ser Asn Ile Gly Gly Lys Gln Ala Leu Glu Thr Val Gln Arg
    850                 855                 860

Leu Leu Pro Val Leu Cys Gln Ala His Gly Leu Thr Pro Ala Gln Val
865                 870                 875                 880

Val Ala Ile Ala Ser His Asp Gly Gly Lys Gln Ala Leu Glu Thr Val
                885                 890                 895

Gln Arg Leu Leu Pro Val Leu Cys Gln Ala His Gly Leu Thr Pro Asp
            900                 905                 910

Gln Val Val Ala Ile Ala Ser Asn Gly Gly Lys Gln Ala Leu Glu
            915                 920                 925

Thr Val Gln Arg Leu Leu Pro Val Leu Cys Gln Ala His Gly Leu Thr
930                 935                 940

Gln Glu Gln Val Val Ala Ile Ala Ser Asn Asn Gly Gly Lys Gln Ala
945                 950                 955                 960

Leu Glu Thr Val Gln Arg Leu Leu Pro Val Leu Cys Gln Ala His Gly
                965                 970                 975

Leu Thr Pro Asp Gln Val Val Ala Ile Ala Ser Asn Gly Gly Gly Lys
            980                 985                 990

Gln Ala Leu Glu Thr Val Gln Arg  Leu Leu Pro Val Leu  Cys Gln Ala
            995                1000                1005

His Gly  Leu Thr Pro Ala Gln  Val Val Ala Ile Ala  Ser Asn Ile
    1010                1015                1020

Gly Gly Lys Gln Ala Leu Glu  Thr Val Gln Arg Leu  Leu Pro Val
    1025                1030                1035

Leu Cys  Gln Asp His Gly Leu  Thr Leu Ala Gln Val  Val Ala Ile
    1040                1045                1050

Ala Ser  Asn Ile Gly Gly Lys  Gln Ala Leu Glu Thr  Val Gln Arg
    1055                1060                1065

Leu Leu  Pro Val Leu Cys Gln  Ala His Gly Leu Thr  Gln Asp Gln
    1070                1075                1080

Val Val  Ala Ile Ala Ser Asn  Ile Gly Gly Lys Gln  Ala Leu Glu
    1085                1090                1095

Thr Val  Gln Arg Leu Leu Pro  Val Leu Cys Gln Asp  His Gly Leu
    1100                1105                1110

Thr Pro  Asp Gln Val Val Ala  Ile Ala Ser Asn Ile  Gly Gly Lys
    1115                1120                1125

Gln Ala  Leu Glu Thr Val Gln  Arg Leu Leu Pro Val  Leu Cys Gln
    1130                1135                1140

Asp His  Gly Leu Thr Leu Asp  Gln Val Val Ala Ile  Ala Ser Asn
    1145                1150                1155

Gly Gly  Lys Gln Ala Leu Glu  Thr Val Gln Arg Leu  Leu Pro Val
    1160                1165                1170

Leu Cys  Gln Asp His Gly Leu  Thr Pro Asp Gln Val  Val Ala Ile
    1175                1180                1185

Ala Ser  Asn Ser Gly
    1190

<210> SEQ ID NO 26
<211> LENGTH: 685
<212> TYPE: PRT
<213> ORGANISM: Artificial Sequence
<220> FEATURE:
<223> OTHER INFORMATION: Fusion molecule
<220> FEATURE:
<221> NAME/KEY: misc_feature
<222> LOCATION: (263)..(263)
<223> OTHER INFORMATION: Xaa can be any naturally occurring amino acid

<400> SEQUENCE: 26

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Ser
            180                 185                 190

Gly Ser Ser Gly Ser Met Ser Lys Gly Glu Glu Leu Phe Thr Gly Val
        195                 200                 205

Val Pro Ile Leu Val Glu Leu Asp Gly Asp Val Asn Gly His Lys Phe
    210                 215                 220

Ser Val Ser Gly Glu Gly Glu Gly Asp Ala Thr Tyr Gly Lys Leu Thr
225                 230                 235                 240

Leu Lys Phe Ile Cys Thr Thr Gly Lys Leu Pro Val Pro Trp Pro Thr
                245                 250                 255

Leu Val Thr Thr Phe Gly Xaa Gly Leu Gln Cys Phe Ala Arg Tyr Pro
            260                 265                 270

Asp His Met Lys Arg His Asp Phe Phe Lys Ser Ala Met Pro Glu Gly
        275                 280                 285

Tyr Val Gln Glu Arg Thr Ile Phe Phe Lys Asp Asp Gly Asn Tyr Lys
    290                 295                 300

Thr Arg Ala Glu Val Lys Phe Glu Gly Asp Thr Leu Val Asn Arg Ile
305                 310                 315                 320

Glu Leu Lys Gly Ile Asp Phe Lys Glu Asp Gly Asn Ile Leu Gly His
                325                 330                 335

Lys Ala Gly Ser Gly Gly Ser Gly Gly Ser Gly Ala Glu Ala Ala Ala
            340                 345                 350

Lys Glu Ala Ala Ala Lys Glu Ala Ala Ala Lys Glu Ala Ala Ala Lys
        355                 360                 365

Glu Ala Ala Ala Lys Glu Ala Ala Ala Lys Ser Gly Ser Lys Ala Ala
    370                 375                 380
```

```
Ala Glu Lys Ala Ala Ala Glu Lys Ala Ala Glu Lys Ala Ala Ala
385                 390                 395                 400

Glu Lys Ala Ala Ala Glu Lys Ala Ala Glu Ala Gly Ser Gly Gly
            405                 410                 415

Ser Gly Gly Ser Gly Ala Leu Glu Tyr Asn Tyr Asn Ser Gln Asn Val
        420                 425                 430

Tyr Ile Met Ala Asp Lys Gln Lys Asn Gly Ile Lys Val Asn Phe Lys
        435                 440                 445

Ile Arg His Asn Ile Glu Asp Gly Ser Val Gln Leu Ala Asp His Tyr
450                 455                 460

Gln Gln Asn Thr Pro Ile Gly Asp Gly Pro Val Leu Leu Pro Asp Asn
465                 470                 475                 480

His Tyr Leu Ser Tyr Gln Ser Ala Leu Ser Lys Asp Pro Asn Glu Lys
            485                 490                 495

Arg Asp His Met Val Leu Leu Glu Phe Val Thr Ala Ala Gly Ile Thr
            500                 505                 510

His Gly Met Asp Glu Leu Tyr Lys Ser Gly Ser Ser Gly Ser Leu Pro
            515                 520                 525

Asp Gln Thr Leu Pro Ile Leu Glu Glu Leu His Gln His Thr Glu Gln
530                 535                 540

Leu Val Gln Asp Gln Tyr Gly Asn Tyr Val Ile Gln His Val Leu Glu
545                 550                 555                 560

His Gly Arg Pro Glu Asp Lys Ser Lys Ile Val Ala Glu Ile Arg Gly
            565                 570                 575

Asn Val Leu Val Leu Ser Gln His Lys Phe Ala Ser Asn Val Val Glu
            580                 585                 590

Lys Cys Val Thr His Ala Ser Arg Thr Glu Arg Ala Val Leu Ile Asp
            595                 600                 605

Glu Val Cys Thr Met Asn Asp Gly Pro His Ser Ala Leu Tyr Thr Met
610                 615                 620

Met Lys Asp Gln Tyr Ala Asn Tyr Val Val Gln Lys Met Ile Asp Val
625                 630                 635                 640

Ala Glu Pro Gly Gln Arg Lys Ile Val Met His Lys Ile Arg Pro His
            645                 650                 655

Ile Ala Thr Leu Arg Lys Tyr Thr Tyr Gly Lys His Ile Leu Ala Lys
            660                 665                 670

Leu Glu Lys Tyr Tyr Met Lys Asn Gly Val Asp Leu Gly
            675                 680                 685

<210> SEQ ID NO 27
<211> LENGTH: 394
<212> TYPE: PRT
<213> ORGANISM: Artificial Sequence
<220> FEATURE:
<223> OTHER INFORMATION: Fusion molecule

<400> SEQUENCE: 27

Phe Ser Arg Ser Asp His Leu Ala Glu His Gln Arg Thr His Thr Gly
1               5                   10                  15

Glu Lys Pro Tyr Lys Cys Pro Glu Cys Gly Lys Ser Phe Ser Asp Lys
            20                  25                  30

Lys Asp Leu Thr Arg His Gln Arg Thr His Thr Gly Glu Lys Pro Tyr
        35                  40                  45

Lys Cys Pro Glu Cys Gly Lys Ser Phe Ser Gln Arg Ala Asn Leu Arg
    50                  55                  60
```

Ala His Gln Arg Thr His Thr Gly Ser Gly Ser Gly Ser Ala Thr
 65                  70                  75                  80

Ser Thr Lys Lys Leu His Lys Glu Pro Ala Thr Leu Ile Lys Ala Ile
                 85                  90                  95

Asp Gly Asp Thr Val Lys Leu Met Tyr Lys Gly Gln Pro Met Thr Phe
            100                 105                 110

Arg Leu Leu Leu Val Asp Thr Pro Glu Phe Asn Glu Lys Tyr Gly Pro
        115                 120                 125

Glu Ala Ser Ala Phe Thr Lys Lys Met Val Glu Asn Ala Ala Gly Ser
    130                 135                 140

Gly Gly Ser Gly Gly Ser Gly Ala Glu Ala Ala Ala Lys Glu Ala Ala
145                 150                 155                 160

Ala Lys Glu Ala Ala Ala Lys Glu Ala Ala Ala Lys Glu Ala Ala Ala
                165                 170                 175

Lys Glu Ala Ala Ala Lys Ser Gly Ser Lys Ala Ala Ala Glu Lys Ala
            180                 185                 190

Ala Ala Glu Lys Ala Ala Ala Glu Lys Ala Ala Ala Glu Lys Ala Ala
        195                 200                 205

Ala Glu Lys Ala Ala Ala Glu Ala Gly Ser Gly Gly Ser Gly Gly Ser
    210                 215                 220

Gly Ala Ala Lys Lys Ile Glu Val Glu Phe Asp Lys Gly Gln Arg Thr
225                 230                 235                 240

Asp Lys Tyr Gly Arg Gly Leu Ala Tyr Ile Tyr Ala Asp Gly Lys Met
                245                 250                 255

Val Asn Glu Ala Leu Val Arg Gln Gly Leu Ala Lys Val Ala Tyr Val
            260                 265                 270

Tyr Lys Gly Asn Asn Thr His Glu Gln Leu Leu Arg Lys Ala Glu Ala
        275                 280                 285

Gln Ala Lys Lys Glu Lys Leu Asn Ile Trp Ser Ser Gly Ser Ser Gly
    290                 295                 300

Ser Gly Glu Lys Pro Tyr Ala Cys Pro Glu Cys Gly Lys Ser Phe Ser
305                 310                 315                 320

Gln Leu Ala His Leu Arg Ala His Gln Arg Thr His Thr Gly Glu Lys
                325                 330                 335

Pro Tyr Lys Cys Pro Glu Cys Gly Lys Ser Phe Ser Arg Glu Asp Asn
            340                 345                 350

Leu His Thr His Gln Arg Thr His Thr Gly Glu Lys Pro Tyr Lys Cys
        355                 360                 365

Pro Glu Cys Gly Lys Ser Phe Ser Arg Arg Asp Ala Leu Asn Val His
    370                 375                 380

Gln Arg Thr His Thr Gly Lys Lys Thr Ser
385                 390

<210> SEQ ID NO 28
<211> LENGTH: 424
<212> TYPE: PRT
<213> ORGANISM: Artificial Sequence
<220> FEATURE:
<223> OTHER INFORMATION: Fusion molecule

<400> SEQUENCE: 28

Phe Ser Arg Ser Asp His Leu Ala Glu His Gln Arg Thr His Thr Gly
1               5                   10                  15

Glu Lys Pro Tyr Lys Cys Pro Glu Cys Gly Lys Ser Phe Ser Asp Lys
            20                  25                  30

```
Lys Asp Leu Thr Arg His Gln Arg Thr His Thr Gly Glu Lys Pro Tyr
            35                  40                  45
Lys Cys Pro Glu Cys Gly Lys Ser Phe Ser Gln Arg Ala Asn Leu Arg
 50                  55                  60
Ala His Gln Arg Thr His Thr Gly Ser Gly Ser Ser Gly Ser Ser Gly
 65                  70                  75                  80
Ser Ser Gly Ser Ala Thr Ser Thr Lys Lys Leu His Lys Glu Pro Ala
                 85                  90                  95
Thr Leu Ile Lys Ala Ile Asp Gly Asp Thr Val Lys Leu Met Tyr Lys
            100                 105                 110
Gly Gln Pro Met Thr Phe Arg Leu Leu Leu Val Asp Thr Pro Glu Phe
            115                 120                 125
Asn Glu Lys Tyr Gly Pro Glu Ala Ser Ala Phe Thr Lys Lys Met Val
130                 135                 140
Glu Asn Ala Ala Gly Ser Gly Gly Ser Gly Gly Ser Gly Gly Ser Gly
145                 150                 155                 160
Gly Ser Gly Gly Ser Gly Ala Glu Ala Ala Lys Glu Ala Ala
                165                 170                 175
Lys Glu Ala Ala Ala Lys Glu Ala Ala Ala Lys Glu Ala Ala Ala Lys
            180                 185                 190
Glu Ala Ala Ala Lys Ser Gly Ser Lys Ala Ala Glu Lys Ala Ala
            195                 200                 205
Ala Glu Lys Ala Ala Ala Glu Lys Ala Ala Ala Glu Lys Ala Ala Ala
            210                 215                 220
Glu Lys Ala Ala Ala Glu Ala Gly Ser Gly Gly Ser Gly Gly Ser Gly
225                 230                 235                 240
Gly Ser Gly Gly Ser Gly Gly Ser Gly Ala Ala Lys Lys Ile Glu Val
                245                 250                 255
Glu Phe Asp Lys Gly Gln Arg Thr Asp Lys Tyr Gly Arg Gly Leu Ala
            260                 265                 270
Tyr Ile Tyr Ala Asp Gly Lys Met Val Asn Glu Ala Leu Val Arg Gln
            275                 280                 285
Gly Leu Ala Lys Val Ala Tyr Val Tyr Lys Gly Asn Asn Thr His Glu
290                 295                 300
Gln Leu Leu Arg Lys Ala Glu Ala Gln Ala Lys Lys Glu Lys Leu Asn
305                 310                 315                 320
Ile Trp Ser Ser Gly Ser Ser Gly Ser Ser Gly Ser Ser Gly Ser Gly
                325                 330                 335
Glu Lys Pro Tyr Ala Cys Pro Glu Cys Gly Lys Ser Phe Ser Gln Leu
            340                 345                 350
Ala His Leu Arg Ala His Gln Arg Thr His Thr Gly Glu Lys Pro Tyr
            355                 360                 365
Lys Cys Pro Glu Cys Gly Lys Ser Phe Ser Arg Glu Asp Asn Leu His
370                 375                 380
Thr His Gln Arg Thr His Thr Gly Glu Lys Pro Tyr Lys Cys Pro Glu
385                 390                 395                 400
Cys Gly Lys Ser Phe Ser Arg Arg Asp Ala Leu Asn Val His Gln Arg
                405                 410                 415
Thr His Thr Gly Lys Lys Thr Ser
            420

<210> SEQ ID NO 29
<211> LENGTH: 1121
<212> TYPE: PRT
```

<213> ORGANISM: Artificial Sequence
<220> FEATURE:
<223> OTHER INFORMATION: Fusion molecule

<400> SEQUENCE: 29

```
His Ile Val Ala Leu Ser Gln His Pro Ala Leu Gly Thr Val Ala
1               5                   10                  15

Val Thr Tyr Gln His Ile Ile Thr Ala Leu Pro Glu Ala Thr His Glu
            20                  25                  30

Asp Ile Val Gly Val Gly Lys Gln Trp Ser Gly Ala Arg Ala Leu Glu
        35                  40                  45

Ala Leu Leu Thr Asp Ala Gly Glu Leu Arg Gly Pro Pro Leu Gln Leu
50                  55                  60

Asp Thr Gly Gln Leu Val Lys Ile Ala Lys Arg Gly Gly Val Thr Ala
65                  70                  75                  80

Met Glu Ala Val His Ala Ser Arg Asn Ala Leu Thr Gly Ala Pro Leu
                85                  90                  95

Asn Leu Thr Pro Ala Gln Val Val Ala Ile Ala Ser Asn Asn Gly Gly
            100                 105                 110

Lys Gln Ala Leu Glu Thr Val Gln Arg Leu Leu Pro Val Leu Cys Gln
        115                 120                 125

Ala His Gly Leu Thr Pro Ala Gln Val Val Ala Ile Ala Ser His Asp
    130                 135                 140

Gly Gly Lys Gln Ala Leu Glu Thr Met Gln Arg Leu Leu Pro Val Leu
145                 150                 155                 160

Cys Gln Ala His Gly Leu Pro Pro Asp Gln Val Val Ala Ile Ala Ser
                165                 170                 175

Asn Ile Gly Gly Lys Gln Ala Leu Glu Thr Val Gln Arg Leu Leu Pro
            180                 185                 190

Val Leu Cys Gln Ala His Gly Leu Thr Pro Asp Gln Val Val Ala Ile
        195                 200                 205

Ala Ser His Gly Gly Gly Lys Gln Ala Leu Glu Thr Val Gln Arg Leu
    210                 215                 220

Leu Pro Val Leu Cys Gln Ala His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Ala His Gly Leu Thr Pro Asp Gln
            260                 265                 270

Val Val Ala Ile Ala Ser Asn Gly Gly Gly Lys Gln Ala Leu Glu Thr
        275                 280                 285

Val Gln Arg Leu Leu Pro Val Leu Cys Gln Ala His Gly Leu Thr Pro
    290                 295                 300

Asp Gln Val Val Ala Ile Ala Ser Asn Gly Gly Lys Gln Ala Leu Glu
305                 310                 315                 320

Thr Val Gln Arg Leu Leu Pro Val Leu Cys Gln Ala His Gly Leu Thr
                325                 330                 335

Pro Asp Gln Val Val Ala Ile Ala Ser His Asp Gly Gly Lys Gln Ala
            340                 345                 350

Leu Glu Thr Val Gln Arg Leu Leu Pro Val Leu Cys Gln Thr His Gly
        355                 360                 365

Leu Thr Pro Ala Gln Val Val Ala Ile Ala Ser His Asp Gly Gly Lys
    370                 375                 380

Gln Ala Leu Glu Thr Val Gln Gln Leu Leu Pro Val Leu Cys Gln Ala
```

```
                385                 390                 395                 400
            His Gly Leu Thr Pro Asp Gln Val Val Ala Ile Ala Ser Asn Ile Gly
                            405                 410                 415

Gly Lys Gln Ala Leu Ala Thr Val Gln Arg Leu Leu Pro Val Leu Cys
                        420                 425                 430

Gln Ala His Gly Ser Gly Ser Gly Ser Ser Gly Ser Ser Gly Ser
                            435                 440                 445

Ala Thr Ser Thr Lys Lys Leu His Lys Glu Pro Ala Thr Leu Ile Lys
            450                 455                 460

Ala Ile Asp Gly Asp Thr Val Lys Leu Met Tyr Lys Gly Gln Pro Met
            465                 470                 475                 480

Thr Phe Arg Leu Leu Leu Val Asp Thr Pro Glu Phe Asn Glu Lys Tyr
                            485                 490                 495

Gly Pro Glu Ala Ser Ala Phe Thr Lys Lys Met Val Glu Asn Ala Ala
                        500                 505                 510

Gly Ser Gly Gly Ser Gly Gly Ser Gly Gly Ser Gly Gly Ser Gly Gly
                        515                 520                 525

Ser Gly Ala Glu Ala Ala Ala Lys Glu Ala Ala Ala Lys Glu Ala Ala
                530                 535                 540

Ala Lys Glu Ala Ala Ala Lys Glu Ala Ala Ala Lys Glu Ala Ala Ala
            545                 550                 555                 560

Lys Ser Gly Ser Lys Ala Ala Glu Lys Ala Ala Glu Lys Ala
                            565                 570                 575

Ala Ala Glu Lys Ala Ala Ala Glu Lys Ala Ala Ala Glu Lys Ala Ala
                        580                 585                 590

Ala Glu Ala Gly Ser Gly Gly Ser Gly Gly Ser Gly Gly Ser Gly Gly
                        595                 600                 605

Ser Gly Gly Ser Gly Ala Ala Lys Lys Ile Glu Val Glu Phe Asp Lys
                    610                 615                 620

Gly Gln Arg Thr Asp Lys Tyr Gly Arg Gly Leu Ala Tyr Ile Tyr Ala
            625                 630                 635                 640

Asp Gly Lys Met Val Asn Glu Ala Leu Val Arg Gln Gly Leu Ala Lys
                            645                 650                 655

Val Ala Tyr Val Tyr Lys Gly Asn Asn Thr His Glu Gln Leu Leu Arg
                        660                 665                 670

Lys Ala Glu Ala Gln Ala Lys Lys Glu Lys Leu Asn Ile Trp Ser Ser
                    675                 680                 685

Gly Ser Ser Gly Ser Ser Gly Ser Ser Gly Ser Gly Leu Thr Pro Asp
                    690                 695                 700

Gln Val Val Ala Ile Ala Ser Asn Gly Gly Gly Lys Gln Ala Leu Glu
            705                 710                 715                 720

Thr Val Gln Arg Leu Leu Pro Val Leu Cys Gln Ala His Gly Leu Thr
                            725                 730                 735

Pro Asp Gln Val Val Ala Ile Ala Ser Asn Gly Gly Gly Lys Gln Ala
                        740                 745                 750

Leu Glu Thr Val Gln Arg Leu Leu Pro Val Leu Cys Gln Ala His Gly
                    755                 760                 765

Leu Thr Gln Val Gln Val Ala Ile Ala Ser Asn Ile Gly Gly Lys
                770                 775                 780

Gln Ala Leu Glu Thr Val Gln Arg Leu Leu Pro Val Leu Cys Gln Ala
            785                 790                 795                 800

His Gly Leu Thr Pro Ala Gln Val Val Ala Ile Ala Ser His Asp Gly
                            805                 810                 815
```

```
Gly Lys Gln Ala Leu Glu Thr Val Gln Arg Leu Leu Pro Val Leu Cys
            820                 825                 830

Gln Ala His Gly Leu Thr Pro Asp Gln Val Val Ala Ile Ala Ser Asn
        835                 840                 845

Gly Gly Gly Lys Gln Ala Leu Glu Thr Val Gln Arg Leu Leu Pro Val
850                 855                 860

Leu Cys Gln Ala His Gly Leu Thr Gln Gln Val Val Ala Ile Ala
865                 870                 875                 880

Ser Asn Asn Gly Gly Lys Gln Ala Leu Glu Thr Val Gln Arg Leu Leu
                885                 890                 895

Pro Val Leu Cys Gln Ala His Gly Leu Thr Pro Asp Gln Val Val Ala
            900                 905                 910

Ile Ala Ser Asn Gly Gly Gly Lys Gln Ala Leu Glu Thr Val Gln Arg
        915                 920                 925

Leu Leu Pro Val Leu Cys Gln Ala His Gly Leu Thr Pro Ala Gln Val
    930                 935                 940

Val Ala Ile Ala Ser Asn Ile Gly Gly Lys Gln Ala Leu Glu Thr Val
945                 950                 955                 960

Gln Arg Leu Leu Pro Val Leu Cys Gln Asp His Gly Leu Thr Leu Ala
                965                 970                 975

Gln Val Val Ala Ile Ala Ser Asn Ile Gly Gly Lys Gln Ala Leu Glu
            980                 985                 990

Thr Val Gln Arg Leu Leu Pro Val Leu Cys Gln Ala His Gly Leu Thr
        995                1000                1005

Gln Asp Gln Val Val Ala Ile Ala Ser Asn Ile Gly Gly Lys Gln
    1010                1015                1020

Ala Leu Glu Thr Val Gln Arg Leu Leu Pro Val Leu Cys Gln Asp
    1025                1030                1035

His Gly Leu Thr Pro Asp Gln Val Val Ala Ile Ala Ser Asn Ile
    1040                1045                1050

Gly Gly Lys Gln Ala Leu Glu Thr Val Gln Arg Leu Leu Pro Val
    1055                1060                1065

Leu Cys Gln Asp His Gly Leu Thr Leu Asp Gln Val Val Ala Ile
    1070                1075                1080

Ala Ser Asn Gly Gly Lys Gln Ala Leu Glu Thr Val Gln Arg Leu
    1085                1090                1095

Leu Pro Val Leu Cys Gln Asp His Gly Leu Thr Pro Asp Gln Val
    1100                1105                1110

Val Ala Ile Ala Ser Asn Ser Gly
    1115                1120

<210> SEQ ID NO 30
<211> LENGTH: 613
<212> TYPE: PRT
<213> ORGANISM: Artificial Sequence
<220> FEATURE:
<223> OTHER INFORMATION: Fusion molecule

<400> SEQUENCE: 30

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45
```

```
Ala Glu Arg Gln Leu Val Phe Asn Glu Ile Leu Gln Ala Ala Tyr Gln
 50                  55                  60

Leu Met Val Asp Val Phe Gly Asn Tyr Val Ile Gln Lys Phe Phe Glu
 65                  70                  75                  80

Phe Gly Ser Leu Glu Gln Lys Leu Ala Leu Ala Glu Arg Ile Arg Gly
                 85                  90                  95

His Val Leu Ser Leu Ala Leu Gln Met Tyr Gly Cys Arg Val Ile Gln
                100                 105                 110

Lys Ala Leu Glu Phe Ile Pro Ser Asp Gln Gln Asn Glu Met Val Arg
                115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Ser
                180                 185                 190

Gly Ser Ser Gly Ser Ser Gly Ser Ser Gly Ser Ala Thr Ser Thr Lys
                195                 200                 205

Lys Leu His Lys Glu Pro Ala Thr Leu Ile Lys Ala Ile Asp Gly Asp
210                 215                 220

Thr Val Lys Leu Met Tyr Lys Gly Gln Pro Met Thr Phe Arg Leu Leu
225                 230                 235                 240

Leu Val Asp Thr Pro Glu Phe Asn Glu Lys Tyr Gly Pro Glu Ala Ser
                245                 250                 255

Ala Phe Thr Lys Lys Met Val Glu Asn Ala Ala Gly Ser Gly Gly Ser
                260                 265                 270

Gly Gly Ser Gly Gly Ser Gly Gly Ser Gly Gly Ser Gly Ala Glu Ala
                275                 280                 285

Ala Ala Lys Glu Ala Ala Ala Lys Glu Ala Ala Ala Lys Glu Ala Ala
290                 295                 300

Ala Lys Glu Ala Ala Ala Lys Glu Ala Ala Ala Lys Ser Gly Ser Lys
305                 310                 315                 320

Ala Ala Ala Glu Lys Ala Ala Glu Lys Ala Ala Ala Glu Lys Ala
                325                 330                 335

Ala Ala Glu Lys Ala Ala Ala Glu Lys Ala Ala Ala Glu Ala Gly Ser
                340                 345                 350

Gly Gly Ser Gly Gly Ser Gly Gly Ser Gly Gly Ser Gly Gly Ser Gly
                355                 360                 365

Ala Ala Lys Lys Ile Glu Val Glu Phe Asp Lys Gly Gln Arg Thr Asp
370                 375                 380

Lys Tyr Gly Arg Gly Leu Ala Tyr Ile Tyr Ala Asp Gly Lys Met Val
385                 390                 395                 400

Asn Glu Ala Leu Val Arg Gln Gly Leu Ala Lys Val Ala Tyr Val Tyr
                405                 410                 415

Lys Gly Asn Asn Thr His Glu Gln Leu Leu Arg Lys Ala Glu Ala Gln
                420                 425                 430

Ala Lys Lys Glu Lys Leu Asn Ile Trp Ser Ser Gly Ser Ser Gly Ser
                435                 440                 445

Ser Gly Ser Ser Gly Ser Leu Pro Asp Gln Thr Leu Pro Ile Leu Glu
450                 455                 460
```

```
Glu Leu His Gln His Thr Glu Gln Leu Val Gln Asp Gln Tyr Gly Asn
465                 470                 475                 480

Tyr Val Ile Gln His Val Leu Glu His Gly Arg Pro Glu Asp Lys Ser
            485                 490                 495

Lys Ile Val Ala Glu Ile Arg Gly Asn Val Leu Val Leu Ser Gln His
        500                 505                 510

Lys Phe Ala Ser Asn Val Val Glu Lys Cys Val Thr His Ala Ser Arg
    515                 520                 525

Thr Glu Arg Ala Val Leu Ile Asp Glu Val Cys Thr Met Asn Asp Gly
530                 535                 540

Pro His Ser Ala Leu Tyr Thr Met Met Lys Asp Gln Tyr Ala Asn Tyr
545                 550                 555                 560

Val Val Gln Lys Met Ile Asp Val Ala Glu Pro Gly Gln Arg Lys Ile
            565                 570                 575

Val Met His Lys Ile Arg Pro His Ile Ala Thr Leu Arg Lys Tyr Thr
        580                 585                 590

Tyr Gly Lys His Ile Leu Ala Lys Leu Glu Lys Tyr Tyr Met Lys Asn
    595                 600                 605

Gly Val Asp Leu Gly
        610

<210> SEQ ID NO 31
<211> LENGTH: 661
<212> TYPE: PRT
<213> ORGANISM: Artificial Sequence
<220> FEATURE:
<223> OTHER INFORMATION: Fusion molecule

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Asp Tyr Tyr Asp Ser Ser Gly Tyr Tyr Pro Ile Asp
            100                 105                 110

Ala Phe Asp Ile Trp Gly Gln Gly Thr Thr Val Thr Val Ser Ser Gly
        115                 120                 125

Gly Gly Gly Ser Gly Gly Gly Ser Gln Leu Thr Pro Thr Phe Tyr
130                 135                 140

Asp Asn Ser Cys Pro Asn Val Ser Asn Ile Val Arg Asp Thr Ile Val
145                 150                 155                 160

Asn Glu Leu Arg Ser Asp Pro Arg Ile Ala Ala Ser Ile Leu Arg Leu
                165                 170                 175

His Phe His Asp Cys Phe Val Asn Gly Cys Asp Ala Ser Ile Leu Leu
            180                 185                 190

Asp Asn Thr Thr Ser Phe Arg Thr Glu Lys Asp Ala Phe Gly Asn Ala
        195                 200                 205
```

```
Asn Ser Ala Arg Gly Phe Pro Val Ile Asp Arg Met Lys Ala Ala Val
    210                 215                 220

Glu Ser Ala Cys Pro Arg Thr Val Ser Cys Ala Asp Leu Leu Thr Ile
225                 230                 235                 240

Ala Ala Gln Gln Ser Val Thr Leu Ala Gly Gly Pro Ser Trp Arg Val
                245                 250                 255

Pro Leu Gly Arg Arg Asp Ser Leu Gln Ala Phe Leu Asp Leu Ala Asn
            260                 265                 270

Ala Asn Leu Pro Ala Pro Phe Phe Thr Leu Pro Gln Leu Lys Asp Ser
        275                 280                 285

Phe Arg Asn Val Gly Leu Asn Arg Ser Ser Asp Leu Val Ala Leu Ser
    290                 295                 300

Gly Gly His Thr Phe Gly Lys Asn Gln Cys Arg Phe Ile Met Asp Arg
305                 310                 315                 320

Leu Tyr Asn Phe Ser Asn Thr Gly Leu Pro Asp Pro Thr Leu Asn Thr
                325                 330                 335

Thr Tyr Leu Gln Thr Leu Arg Gly Leu Cys Pro Leu Asn Gly Ala Gly
            340                 345                 350

Ser Gly Gly Ser Gly Gly Ser Gly Ala Glu Ala Ala Ala Lys Glu Ala
        355                 360                 365

Ala Ala Lys Glu Ala Ala Ala Lys Glu Ala Ala Ala Lys Glu Ala Ala
    370                 375                 380

Ala Lys Glu Ala Ala Lys Ser Gly Ser Lys Ala Ala Ala Glu Lys
385                 390                 395                 400

Ala Ala Ala Glu Lys Ala Ala Glu Lys Ala Ala Ala Glu Lys Ala
                405                 410                 415

Ala Ala Glu Lys Ala Ala Glu Ala Gly Ser Gly Gly Ser Gly Gly
            420                 425                 430

Ser Gly Ala Gly Asn Leu Ser Ala Leu Val Asp Phe Asp Leu Arg Thr
        435                 440                 445

Pro Thr Ile Phe Asp Asn Lys Tyr Tyr Val Asn Leu Glu Glu Gln Lys
    450                 455                 460

Gly Leu Ile Gln Ser Asp Gln Glu Leu Phe Ser Ser Pro Asn Ala Thr
465                 470                 475                 480

Asp Thr Ile Pro Leu Val Arg Ser Phe Ala Asn Ser Thr Gln Thr Phe
                485                 490                 495

Phe Asn Ala Phe Val Glu Ala Met Asp Arg Met Gly Asn Ile Thr Pro
            500                 505                 510

Leu Thr Gly Thr Gln Gly Gln Ile Arg Leu Asn Cys Arg Val Val Asn
    515                 520                 525

Ser Gly Gly Gly Gly Ser Gly Gly Gly Ser Gln Ser Ala Leu Thr
530                 535                 540

Gln Pro Ala Ser Val Ser Ala Ser Pro Gly Gln Ser Ile Thr Ile Ser
545                 550                 555                 560

Cys Thr Gly Thr Ser Ser Asp Val Gly Ala Tyr Asp Trp Val Ser Trp
                565                 570                 575

Tyr Gln Gln His Pro Gly Lys Ala Pro Lys Leu Leu Ile Phe Asp Val
            580                 585                 590

Asn Asn Arg Pro Ser Gly Val Ser His Arg Phe Ser Gly Ser Lys Ser
        595                 600                 605

Gly Asn Thr Ala Ser Leu Thr Ile Ser Gly Leu Gln Ala Glu Asp Glu
    610                 615                 620

Ala Asp Tyr Tyr Cys Ala Ser Ala Thr Leu Leu Asp Thr Tyr Val Phe
```

```
                625                 630                 635                 640
Gly Thr Gly Thr Lys Val Thr Val Leu Gly Asp Gln Glu Pro Lys Ser
                    645                 650                 655
Ser Asp Lys Thr His
            660

<210> SEQ ID NO 32
<211> LENGTH: 6
<212> TYPE: PRT
<213> ORGANISM: Artificial Sequence
<220> FEATURE:
<223> OTHER INFORMATION: Fragment

<400> SEQUENCE: 32

Gly Ser Gly Gly Ser Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Fragment

<400> SEQUENCE: 33

Gly Ser Gly Gly Ser Gly Gly Ser Gly
1               5

<210> SEQ ID NO 34
<211> LENGTH: 12
<212> TYPE: PRT
<213> ORGANISM: Artificial Sequence
<220> FEATURE:
<223> OTHER INFORMATION: Fragment

<400> SEQUENCE: 34

Gly Ser Gly Gly Ser Gly Gly Ser Gly Gly Ser Gly
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Fragment

<400> SEQUENCE: 35

Gly Ser Gly Gly Ser Gly Gly Ser Gly Gly Ser Gly Gly Ser Gly
1               5                   10                  15

<210> SEQ ID NO 36
<211> LENGTH: 5
<212> TYPE: PRT
<213> ORGANISM: Artificial Sequence
<220> FEATURE:
<223> OTHER INFORMATION: Fragment

<400> SEQUENCE: 36

Ala Gly Ser Gly Ala
1               5

<210> SEQ ID NO 37
<211> LENGTH: 8
<212> TYPE: PRT
<213> ORGANISM: Artificial Sequence
<220> FEATURE:
```

<223> OTHER INFORMATION: Fragment

<400> SEQUENCE: 37

Ala Gly Ser Gly Gly Ser Gly Ala
1               5

<210> SEQ ID NO 38
<211> LENGTH: 11
<212> TYPE: PRT
<213> ORGANISM: Artificial Sequence
<220> FEATURE:
<223> OTHER INFORMATION: Fragment

<400> SEQUENCE: 38

Ala Gly Ser Gly Gly Ser Gly Gly Ser Gly Ala
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Fragment

<400> SEQUENCE: 39

Ala Gly Ser Gly Gly Ser Gly Gly Ser Gly Gly Ser Gly Ala
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Fragment

<400> SEQUENCE: 40

Ala Gly Ser Gly Gly Ser Gly Gly Ser Gly Gly Ser Gly Gly Ser Gly
1               5                   10                  15

Ala

<210> SEQ ID NO 41
<211> LENGTH: 20
<212> TYPE: PRT
<213> ORGANISM: Artificial Sequence
<220> FEATURE:
<223> OTHER INFORMATION: Fragment

<400> SEQUENCE: 41

Ala Gly Ser Gly Gly Ser Gly Gly Ser Gly Gly Ser Gly Gly Ser Gly
1               5                   10                  15

Gly Ser Gly Ala
            20

<210> SEQ ID NO 42
<211> LENGTH: 23
<212> TYPE: PRT
<213> ORGANISM: Artificial Sequence
<220> FEATURE:
<223> OTHER INFORMATION: Fragment

<400> SEQUENCE: 42

Ala Gly Ser Gly Gly Ser Gly Gly Ser Gly Gly Ser Gly Gly Ser Gly
1               5                   10                  15

Gly Ser Gly Gly Ser Gly Ala
            20

```
<210> SEQ ID NO 43
<211> LENGTH: 26
<212> TYPE: PRT
<213> ORGANISM: Artificial Sequence
<220> FEATURE:
<223> OTHER INFORMATION: Fragment

<400> SEQUENCE: 43

Ala Gly Ser Gly Gly Ser Gly Gly Ser Gly Gly Ser Gly Gly Ser Gly
1               5                   10                  15

Gly Ser Gly Gly Ser Gly Gly Ser Gly Ala
            20                  25

<210> SEQ ID NO 44
<211> LENGTH: 29
<212> TYPE: PRT
<213> ORGANISM: Artificial Sequence
<220> FEATURE:
<223> OTHER INFORMATION: Fragment

<400> SEQUENCE: 44

Ala Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Ala
            20                  25

<210> SEQ ID NO 45
<211> LENGTH: 32
<212> TYPE: PRT
<213> ORGANISM: Artificial Sequence
<220> FEATURE:
<223> OTHER INFORMATION: Fragment

<400> SEQUENCE: 45

Ala Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Ala
            20                  25                  30

<210> SEQ ID NO 46
<211> LENGTH: 35
<212> TYPE: PRT
<213> ORGANISM: Artificial Sequence
<220> FEATURE:
<223> OTHER INFORMATION: Fragment

<400> SEQUENCE: 46

Ala Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Ala
        35

<210> SEQ ID NO 47
<211> LENGTH: 38
<212> TYPE: PRT
<213> ORGANISM: Artificial Sequence
<220> FEATURE:
<223> OTHER INFORMATION: Fragment

<400> SEQUENCE: 47

Ala Gly Ser Gly Gly Ser Gly Gly Ser Gly Gly Ser Gly Gly Ser Gly
```

```
                 1               5                  10                  15
Gly Ser Gly Gly Ser Gly Gly Ser Gly Ser Gly Gly Ser Gly Gly
                20                  25                  30

Ser Gly Gly Ser Gly Ala
                35

<210> SEQ ID NO 48
<211> LENGTH: 6
<212> TYPE: PRT
<213> ORGANISM: Artificial Sequence
<220> FEATURE:
<223> OTHER INFORMATION: Fragment

<400> SEQUENCE: 48

Ser Gly Ser Ser Gly Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Fragment

<400> SEQUENCE: 49

Ser Gly Ser Ser Gly Ser Ser Gly Ser
1               5

<210> SEQ ID NO 50
<211> LENGTH: 12
<212> TYPE: PRT
<213> ORGANISM: Artificial Sequence
<220> FEATURE:
<223> OTHER INFORMATION: Fragment

<400> SEQUENCE: 50

Ser Gly Ser Ser Gly Ser Ser Gly Ser Ser Gly Ser
1               5                  10

<210> SEQ ID NO 51
<211> LENGTH: 15
<212> TYPE: PRT
<213> ORGANISM: Artificial Sequence
<220> FEATURE:
<223> OTHER INFORMATION: Fragment

<400> SEQUENCE: 51

Ser Gly Ser Ser Gly Ser Ser Gly Ser Ser Gly Ser Ser Gly Ser
1               5                  10                  15

<210> SEQ ID NO 52
<211> LENGTH: 18
<212> TYPE: PRT
<213> ORGANISM: Artificial Sequence
<220> FEATURE:
<223> OTHER INFORMATION: Fragment

<400> SEQUENCE: 52

Ser Gly Ser Ser Gly Ser Ser Gly Ser Ser Gly Ser Ser Gly Ser
1               5                  10                  15

Gly Ser

<210> SEQ ID NO 53
<211> LENGTH: 21
<212> TYPE: PRT
```

<213> ORGANISM: Artificial Sequence
<220> FEATURE:
<223> OTHER INFORMATION: Fragment

<400> SEQUENCE: 53

Ser Gly Ser Ser Gly Ser Ser Gly Ser Ser Gly Ser Ser Gly Ser Ser
1               5                   10                  15

Gly Ser Ser Gly Ser
            20

<210> SEQ ID NO 54
<211> LENGTH: 24
<212> TYPE: PRT
<213> ORGANISM: Artificial Sequence
<220> FEATURE:
<223> OTHER INFORMATION: Fragment

<400> SEQUENCE: 54

Ser Gly Ser Ser Gly Ser Ser Gly Ser Ser Gly Ser Ser Gly Ser Ser
1               5                   10                  15

Gly Ser Ser Gly Ser Ser Gly Ser
            20

<210> SEQ ID NO 55
<211> LENGTH: 27
<212> TYPE: PRT
<213> ORGANISM: Artificial Sequence
<220> FEATURE:
<223> OTHER INFORMATION: Fragment

<400> SEQUENCE: 55

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser
            20                  25

<210> SEQ ID NO 56
<211> LENGTH: 30
<212> TYPE: PRT
<213> ORGANISM: Artificial Sequence
<220> FEATURE:
<223> OTHER INFORMATION: Fragment

<400> SEQUENCE: 56

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser
            20                  25                  30

<210> SEQ ID NO 57
<211> LENGTH: 33
<212> TYPE: PRT
<213> ORGANISM: Artificial Sequence
<220> FEATURE:
<223> OTHER INFORMATION: Fragment

<400> SEQUENCE: 57

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser

```
<210> SEQ ID NO 58
<211> LENGTH: 36
<212> TYPE: PRT
<213> ORGANISM: Artificial Sequence
<220> FEATURE:
<223> OTHER INFORMATION: Fragment

<400> SEQUENCE: 58

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser
        35

<210> SEQ ID NO 59
<211> LENGTH: 39
<212> TYPE: PRT
<213> ORGANISM: Artificial Sequence
<220> FEATURE:
<223> OTHER INFORMATION: Fragment

<400> SEQUENCE: 59

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser
        35

<210> SEQ ID NO 60
<211> LENGTH: 42
<212> TYPE: PRT
<213> ORGANISM: Artificial Sequence
<220> FEATURE:
<223> OTHER INFORMATION: Fragment

<400> SEQUENCE: 60

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser
        35                  40

<210> SEQ ID NO 61
<211> LENGTH: 45
<212> TYPE: PRT
<213> ORGANISM: Artificial Sequence
<220> FEATURE:
<223> OTHER INFORMATION: Fragment

<400> SEQUENCE: 61

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser
        35                  40                  45

<210> SEQ ID NO 62
<211> LENGTH: 48
<212> TYPE: PRT
```

```
<213> ORGANISM: Artificial Sequence
<220> FEATURE:
<223> OTHER INFORMATION: Fragment

<400> SEQUENCE: 62

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser Ser Gly Ser
        35                  40                  45

<210> SEQ ID NO 63
<211> LENGTH: 51
<212> TYPE: PRT
<213> ORGANISM: Artificial Sequence
<220> FEATURE:
<223> OTHER INFORMATION: Fragment

<400> SEQUENCE: 63

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser Ser Gly Ser
        35                  40                  45

Ser Gly Ser
    50

<210> SEQ ID NO 64
<211> LENGTH: 54
<212> TYPE: PRT
<213> ORGANISM: Artificial Sequence
<220> FEATURE:
<223> OTHER INFORMATION: Fragment

<400> SEQUENCE: 64

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser Ser Gly Ser
        35                  40                  45

Ser Gly Ser Ser Gly Ser
    50

<210> SEQ ID NO 65
<211> LENGTH: 57
<212> TYPE: PRT
<213> ORGANISM: Artificial Sequence
<220> FEATURE:
<223> OTHER INFORMATION: Fragment

<400> SEQUENCE: 65

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser Ser Gly Ser
        35                  40                  45

Ser Gly Ser Ser Gly Ser Ser Gly Ser
```

<210> SEQ ID NO 66
<211> LENGTH: 60
<212> TYPE: PRT
<213> ORGANISM: Artificial Sequence
<220> FEATURE:
<223> OTHER INFORMATION: Fragment

<400> SEQUENCE: 66

Ser Gly Ser Ser Gly Ser Ser Gly Ser Ser Gly Ser Ser Gly Ser Ser
1               5                   10                  15
Gly Ser Ser Gly Ser Ser Gly Ser Ser Gly Ser Ser Gly Ser Ser Gly
            20                  25                  30
Ser Ser Gly Ser Ser Gly Ser Ser Gly Ser Ser Gly Ser Ser Gly Ser
        35                  40                  45
Ser Gly Ser Ser Gly Ser Ser Gly Ser Ser Gly Ser
    50                  55                  60

<210> SEQ ID NO 67
<211> LENGTH: 63
<212> TYPE: PRT
<213> ORGANISM: Artificial Sequence
<220> FEATURE:
<223> OTHER INFORMATION: Fragment

<400> SEQUENCE: 67

Ser Gly Ser Ser Gly Ser Ser Gly Ser Ser Gly Ser Ser Gly Ser Ser
1               5                   10                  15
Gly Ser Ser Gly Ser Ser Gly Ser Ser Gly Ser Ser Gly Ser Ser Gly
            20                  25                  30
Ser Ser Gly Ser Ser Gly Ser Ser Gly Ser Ser Gly Ser Ser Gly Ser
        35                  40                  45
Ser Gly Ser Ser Gly Ser Ser Gly Ser Ser Gly Ser Ser Gly Ser
    50                  55                  60

<210> SEQ ID NO 68
<211> LENGTH: 66
<212> TYPE: PRT
<213> ORGANISM: Artificial Sequence
<220> FEATURE:
<223> OTHER INFORMATION: Fragment

<400> SEQUENCE: 68

Ser Gly Ser Ser Gly Ser Ser Gly Ser Ser Gly Ser Ser Gly Ser Ser
1               5                   10                  15
Gly Ser Ser Gly Ser Ser Gly Ser Ser Gly Ser Ser Gly Ser Ser Gly
            20                  25                  30
Ser Ser Gly Ser Ser Gly Ser Ser Gly Ser Ser Gly Ser Ser Gly Ser
        35                  40                  45
Ser Gly Ser Ser Gly Ser Ser Gly Ser Ser Gly Ser Ser Gly Ser Ser
    50                  55                  60
Gly Ser
65

<210> SEQ ID NO 69
<211> LENGTH: 4
<212> TYPE: PRT
<213> ORGANISM: Artificial Sequence
<220> FEATURE:
<223> OTHER INFORMATION: Fragment

```
<400> SEQUENCE: 69

Ser Gly Ser Gly
1

<210> SEQ ID NO 70
<211> LENGTH: 6
<212> TYPE: PRT
<213> ORGANISM: Artificial Sequence
<220> FEATURE:
<223> OTHER INFORMATION: Fragment

<400> SEQUENCE: 70

Ser Gly Ser Gly Ser Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Fragment

<400> SEQUENCE: 71

Ser Gly Ser Gly Ser Gly Ser Gly
1               5

<210> SEQ ID NO 72
<211> LENGTH: 10
<212> TYPE: PRT
<213> ORGANISM: Artificial Sequence
<220> FEATURE:
<223> OTHER INFORMATION: Fragment

<400> SEQUENCE: 72

Ser Gly Ser Gly Ser Gly Ser Gly Ser Gly
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Fragment

<400> SEQUENCE: 73

Ser Gly Ser Gly Ser Gly Ser Gly Ser Gly Ser Gly
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Fragment

<400> SEQUENCE: 74

Ser Gly Ser Gly Ser Gly Ser Gly Ser Gly Ser Gly Ser Gly
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Fragment

<400> SEQUENCE: 75
```

Ser Gly Ser Gly Ser Gly Ser Gly Ser Gly Ser Gly Ser Gly Ser Gly
1               5                   10                  15

<210> SEQ ID NO 76
<211> LENGTH: 18
<212> TYPE: PRT
<213> ORGANISM: Artificial Sequence
<220> FEATURE:
<223> OTHER INFORMATION: Fragment

<400> SEQUENCE: 76

Ser Gly Ser Gly Ser Gly Ser Gly Ser Gly Ser Gly Ser Gly Ser Gly
1               5                   10                  15

Ser Gly

<210> SEQ ID NO 77
<211> LENGTH: 20
<212> TYPE: PRT
<213> ORGANISM: Artificial Sequence
<220> FEATURE:
<223> OTHER INFORMATION: Fragment

<400> SEQUENCE: 77

Ser Gly Ser Gly Ser Gly Ser Gly Ser Gly Ser Gly Ser Gly Ser Gly
1               5                   10                  15

Ser Gly Ser Gly
            20

<210> SEQ ID NO 78
<211> LENGTH: 22
<212> TYPE: PRT
<213> ORGANISM: Artificial Sequence
<220> FEATURE:
<223> OTHER INFORMATION: Fragment

<400> SEQUENCE: 78

Ser Gly Ser Gly Ser Gly Ser Gly Ser Gly Ser Gly Ser Gly Ser Gly
1               5                   10                  15

Ser Gly Ser Gly Ser Gly
            20

<210> SEQ ID NO 79
<211> LENGTH: 24
<212> TYPE: PRT
<213> ORGANISM: Artificial Sequence
<220> FEATURE:
<223> OTHER INFORMATION: Fragment

<400> SEQUENCE: 79

Ser Gly Ser Gly Ser Gly Ser Gly Ser Gly Ser Gly Ser Gly Ser Gly
1               5                   10                  15

Ser Gly Ser Gly Ser Gly Ser Gly
            20

<210> SEQ ID NO 80
<211> LENGTH: 26
<212> TYPE: PRT
<213> ORGANISM: Artificial Sequence
<220> FEATURE:
<223> OTHER INFORMATION: Fragment

<400> SEQUENCE: 80

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly
        20                  25

<210> SEQ ID NO 81
<211> LENGTH: 28
<212> TYPE: PRT
<213> ORGANISM: Artificial Sequence
<220> FEATURE:
<223> OTHER INFORMATION: Fragment

<400> SEQUENCE: 81

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly
        20                  25

<210> SEQ ID NO 82
<211> LENGTH: 30
<212> TYPE: PRT
<213> ORGANISM: Artificial Sequence
<220> FEATURE:
<223> OTHER INFORMATION: Fragment

<400> SEQUENCE: 82

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
        20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Fragment

<400> SEQUENCE: 83

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
        20                  25                  30

<210> SEQ ID NO 84
<211> LENGTH: 34
<212> TYPE: PRT
<213> ORGANISM: Artificial Sequence
<220> FEATURE:
<223> OTHER INFORMATION: Fragment

<400> SEQUENCE: 84

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
        20                  25                  30

Ser Gly

<210> SEQ ID NO 85
<211> LENGTH: 36
<212> TYPE: PRT
<213> ORGANISM: Artificial Sequence
<220> FEATURE:
<223> OTHER INFORMATION: Fragment

<400> SEQUENCE: 85

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
                20                  25                  30

Ser Gly Ser Gly
        35

<210> SEQ ID NO 86
<211> LENGTH: 38
<212> TYPE: PRT
<213> ORGANISM: Artificial Sequence
<220> FEATURE:
<223> OTHER INFORMATION: Fragment

<400> SEQUENCE: 86

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
                20                  25                  30

Ser Gly Ser Gly Ser Gly
        35

<210> SEQ ID NO 87
<211> LENGTH: 40
<212> TYPE: PRT
<213> ORGANISM: Artificial Sequence
<220> FEATURE:
<223> OTHER INFORMATION: Fragment

<400> SEQUENCE: 87

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
                20                  25                  30

Ser Gly Ser Gly Ser Gly Ser Gly
        35                  40

<210> SEQ ID NO 88
<211> LENGTH: 42
<212> TYPE: PRT
<213> ORGANISM: Artificial Sequence
<220> FEATURE:
<223> OTHER INFORMATION: Fragment

<400> SEQUENCE: 88

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
                20                  25                  30

Ser Gly Ser Gly Ser Gly Ser Gly Ser Gly
        35                  40

<210> SEQ ID NO 89
<211> LENGTH: 44
<212> TYPE: PRT
<213> ORGANISM: Artificial Sequence
<220> FEATURE:
<223> OTHER INFORMATION: Fragment

<400> SEQUENCE: 89

Ser Gly Ser Gly Ser Gly Ser Gly Ser Gly Ser Gly Ser Gly Ser Gly
1               5                   10                  15

```
Ser Gly Ser Gly Ser Gly Ser Gly Ser Gly Ser Gly Ser Gly
        20                  25                  30

Ser Gly Ser Gly Ser Gly Ser Gly Ser Gly Ser Gly
        35                  40

<210> SEQ ID NO 90
<211> LENGTH: 10
<212> TYPE: PRT
<213> ORGANISM: Artificial Sequence
<220> FEATURE:
<223> OTHER INFORMATION: Fragment

<400> SEQUENCE: 90

Gly Gly Gly Gly Ser Gly Gly Gly Gly Ser
1               5                   10

<210> SEQ ID NO 91
<211> LENGTH: 25
<212> TYPE: PRT
<213> ORGANISM: Artificial Sequence
<220> FEATURE:
<223> OTHER INFORMATION: Fusion molecule

<400> SEQUENCE: 91

Glu Ala Ala Ala Lys Glu Ala Ala Lys Ser Gly Ser Ser Gly Ser Lys
1               5                   10                  15

Ala Ala Ala Glu Lys Ala Ala Ala Glu
            20                  25

<210> SEQ ID NO 92
<211> LENGTH: 25
<212> TYPE: PRT
<213> ORGANISM: Artificial Sequence
<220> FEATURE:
<223> OTHER INFORMATION: Fusion molecule

<400> SEQUENCE: 92

Glu Ala Lys Ala Lys Glu Ala Ala Lys Ser Gly Ser Ser Gly Ser Lys
1               5                   10                  15

Ala Ala Ala Glu Lys Ala Lys Ala Glu
            20                  25

<210> SEQ ID NO 93
<211> LENGTH: 30
<212> TYPE: PRT
<213> ORGANISM: Artificial Sequence
<220> FEATURE:
<223> OTHER INFORMATION: Fragment

<400> SEQUENCE: 93

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys
            20                  25                  30

<210> SEQ ID NO 94
<211> LENGTH: 35
<212> TYPE: PRT
<213> ORGANISM: Artificial Sequence
<220> FEATURE:
<223> OTHER INFORMATION: Fragment

<400> SEQUENCE: 94

Glu Ala Ala Ala Lys Glu Ala Ala Ala Lys Glu Ala Ala Ala Lys Glu
```

```
                1               5                   10                  15
Ala Ala Ala Lys Glu Ala Ala Lys Glu Ala Ala Lys Glu Ala
                20                  25                  30

Ala Ala Lys
        35

<210> SEQ ID NO 95
<211> LENGTH: 40
<212> TYPE: PRT
<213> ORGANISM: Artificial Sequence
<220> FEATURE:
<223> OTHER INFORMATION: Fragment

<400> SEQUENCE: 95

Glu Ala Ala Ala Lys Glu Ala Ala Ala Lys Glu Ala Ala Ala Lys Glu
1               5                   10                  15

Ala Ala Ala Lys Glu Ala Ala Lys Glu Ala Ala Lys Glu Ala
                20                  25                  30

Ala Ala Lys Glu Ala Ala Ala Lys
        35                  40

<210> SEQ ID NO 96
<211> LENGTH: 45
<212> TYPE: PRT
<213> ORGANISM: Artificial Sequence
<220> FEATURE:
<223> OTHER INFORMATION: Fragment

<400> SEQUENCE: 96

Glu Ala Ala Ala Lys Glu Ala Ala Ala Lys Glu Ala Ala Ala Lys Glu
1               5                   10                  15

Ala Ala Ala Lys Glu Ala Ala Lys Glu Ala Ala Lys Glu Ala
                20                  25                  30

Ala Ala Lys Glu Ala Ala Ala Lys Glu Ala Ala Ala Lys
        35                  40                  45

<210> SEQ ID NO 97
<211> LENGTH: 50
<212> TYPE: PRT
<213> ORGANISM: Artificial Sequence
<220> FEATURE:
<223> OTHER INFORMATION: Fragment

<400> SEQUENCE: 97

Glu Ala Ala Ala Lys Glu Ala Ala Ala Lys Glu Ala Ala Ala Lys Glu
1               5                   10                  15

Ala Ala Ala Lys Glu Ala Ala Lys Glu Ala Ala Lys Glu Ala
                20                  25                  30

Ala Ala Lys Glu Ala Ala Ala Lys Glu Ala Ala Lys Glu Ala Ala
        35                  40                  45

Ala Lys
    50

<210> SEQ ID NO 98
<211> LENGTH: 55
<212> TYPE: PRT
<213> ORGANISM: Artificial Sequence
<220> FEATURE:
<223> OTHER INFORMATION: Fragment

<400> SEQUENCE: 98

Glu Ala Ala Ala Lys Glu Ala Ala Ala Lys Glu Ala Ala Ala Lys Glu
```

```
                1               5                  10                  15
Ala Ala Ala Lys Glu Ala Ala Lys Glu Ala Ala Lys Glu Ala
                20                  25                  30

Ala Ala Lys Glu Ala Ala Lys Glu Ala Ala Lys Glu Ala Ala
            35                  40                  45

Ala Lys Glu Ala Ala Ala Lys
        50                  55
```

<210> SEQ ID NO 99
<211> LENGTH: 60
<212> TYPE: PRT
<213> ORGANISM: Artificial Sequence
<220> FEATURE:
<223> OTHER INFORMATION: Fragment

<400> SEQUENCE: 99

```
Glu Ala Ala Ala Lys Glu Ala Ala Lys Glu Ala Ala Lys Glu
1               5                  10                  15

Ala Ala Ala Lys Glu Ala Ala Lys Glu Ala Ala Lys Glu Ala
                20                  25                  30

Ala Ala Lys Glu Ala Ala Lys Glu Ala Ala Lys Glu Ala Ala
            35                  40                  45

Ala Lys Glu Ala Ala Lys Glu Ala Ala Lys
        50                  55                  60
```

<210> SEQ ID NO 100
<211> LENGTH: 30
<212> TYPE: PRT
<213> ORGANISM: Artificial Sequence
<220> FEATURE:
<223> OTHER INFORMATION: Fragment

<400> SEQUENCE: 100

```
Lys Ala Ala Ala Glu Lys Ala Ala Ala Glu Lys Ala Ala Ala Glu Lys
1               5                  10                  15

Ala Ala Ala Glu Lys Ala Ala Ala Glu Lys Ala Ala Ala Glu
                20                  25                  30
```

<210> SEQ ID NO 101
<211> LENGTH: 35
<212> TYPE: PRT
<213> ORGANISM: Artificial Sequence
<220> FEATURE:
<223> OTHER INFORMATION: Fragment

<400> SEQUENCE: 101

```
Lys Ala Ala Ala Glu Lys Ala Ala Ala Glu Lys Ala Ala Ala Glu Lys
1               5                  10                  15

Ala Ala Ala Glu Lys Ala Ala Ala Glu Lys Ala Ala Ala Glu Lys Ala
                20                  25                  30

Ala Ala Glu
        35
```

<210> SEQ ID NO 102
<211> LENGTH: 40
<212> TYPE: PRT
<213> ORGANISM: Artificial Sequence
<220> FEATURE:
<223> OTHER INFORMATION: Fragment

<400> SEQUENCE: 102

```
Lys Ala Ala Ala Glu Lys Ala Ala Ala Glu Lys Ala Ala Ala Glu Lys
```

```
                1               5                   10                  15
Ala Ala Ala Glu Lys Ala Ala Ala Glu Lys Ala Ala Ala Glu Lys Ala
                    20                  25                  30

Ala Ala Glu Lys Ala Ala Ala Glu
        35                  40
```

<210> SEQ ID NO 103
<211> LENGTH: 45
<212> TYPE: PRT
<213> ORGANISM: Artificial Sequence
<220> FEATURE:
<223> OTHER INFORMATION: Fragment

<400> SEQUENCE: 103

```
Lys Ala Ala Ala Glu Lys Ala Ala Ala Glu Lys Ala Ala Ala Glu Lys
1               5                   10                  15

Ala Ala Ala Glu Lys Ala Ala Ala Glu Lys Ala Ala Ala Glu Lys Ala
                    20                  25                  30

Ala Ala Glu Lys Ala Ala Ala Glu Lys Ala Ala Ala Glu
        35                  40                  45
```

<210> SEQ ID NO 104
<211> LENGTH: 50
<212> TYPE: PRT
<213> ORGANISM: Artificial Sequence
<220> FEATURE:
<223> OTHER INFORMATION: Fragment

<400> SEQUENCE: 104

```
Lys Ala Ala Ala Glu Lys Ala Ala Ala Glu Lys Ala Ala Ala Glu Lys
1               5                   10                  15

Ala Ala Ala Glu Lys Ala Ala Ala Glu Lys Ala Ala Ala Glu Lys Ala
                    20                  25                  30

Ala Ala Glu Lys Ala Ala Ala Glu Lys Ala Ala Ala Glu Lys Ala Ala
            35                  40                  45

Ala Glu
    50
```

<210> SEQ ID NO 105
<211> LENGTH: 55
<212> TYPE: PRT
<213> ORGANISM: Artificial Sequence
<220> FEATURE:
<223> OTHER INFORMATION: Fragment

<400> SEQUENCE: 105

```
Lys Ala Ala Ala Glu Lys Ala Ala Ala Glu Lys Ala Ala Ala Glu Lys
1               5                   10                  15

Ala Ala Ala Glu Lys Ala Ala Ala Glu Lys Ala Ala Ala Glu Lys Ala
                    20                  25                  30

Ala Ala Glu Lys Ala Ala Ala Glu Lys Ala Ala Ala Glu Lys Ala Ala
            35                  40                  45

Ala Glu Lys Ala Ala Ala Glu
    50                  55
```

<210> SEQ ID NO 106
<211> LENGTH: 60
<212> TYPE: PRT
<213> ORGANISM: Artificial Sequence
<220> FEATURE:
<223> OTHER INFORMATION: Fragment

<400> SEQUENCE: 106

Lys Ala Ala Ala Glu Lys Ala Ala Ala Glu Lys Ala Ala Ala Glu Lys
1               5                   10                  15

Ala Ala Ala Glu Lys Ala Ala Ala Glu Lys Ala Ala Ala Glu Lys Ala
                20                  25                  30

Ala Ala Glu Lys Ala Ala Ala Glu Lys Ala Ala Ala Glu Lys Ala Ala
            35                  40                  45

Ala Glu Lys Ala Ala Ala Glu Lys Ala Ala Ala Glu
        50                  55                  60

<210> SEQ ID NO 107
<211> LENGTH: 36
<212> TYPE: PRT
<213> ORGANISM: Artificial Sequence
<220> FEATURE:
<223> OTHER INFORMATION: Fragment

<400> SEQUENCE: 107

Glu Ala Ala Ala Ala Lys Glu Ala Ala Ala Lys Glu Ala Ala Ala
1               5                   10                  15

Ala Lys Glu Ala Ala Ala Ala Lys Glu Ala Ala Ala Ala Lys Glu Ala
                20                  25                  30

Ala Ala Ala Lys
        35

<210> SEQ ID NO 108
<211> LENGTH: 42
<212> TYPE: PRT
<213> ORGANISM: Artificial Sequence
<220> FEATURE:
<223> OTHER INFORMATION: Fragment

<400> SEQUENCE: 108

Glu Ala Ala Ala Ala Lys Glu Ala Ala Ala Lys Glu Ala Ala Ala
1               5                   10                  15

Ala Lys Glu Ala Ala Ala Ala Lys Glu Ala Ala Ala Ala Lys Glu Ala
                20                  25                  30

Ala Ala Ala Lys Glu Ala Ala Ala Ala Lys
        35                  40

<210> SEQ ID NO 109
<211> LENGTH: 48
<212> TYPE: PRT
<213> ORGANISM: Artificial Sequence
<220> FEATURE:
<223> OTHER INFORMATION: Fragment

<400> SEQUENCE: 109

Glu Ala Ala Ala Ala Lys Glu Ala Ala Ala Lys Glu Ala Ala Ala
1               5                   10                  15

Ala Lys Glu Ala Ala Ala Ala Lys Glu Ala Ala Ala Ala Lys Glu Ala
                20                  25                  30

Ala Ala Ala Lys Glu Ala Ala Ala Ala Lys Glu Ala Ala Ala Lys
        35                  40                  45

<210> SEQ ID NO 110
<211> LENGTH: 54
<212> TYPE: PRT
<213> ORGANISM: Artificial Sequence
<220> FEATURE:
<223> OTHER INFORMATION: Fragment

<400> SEQUENCE: 110

Glu Ala Ala Ala Ala Lys Glu Ala Ala Ala Lys Glu Ala Ala Ala
1               5                   10                  15

Ala Lys Glu Ala Ala Ala Lys Glu Ala Ala Ala Lys Glu Ala
            20                  25                  30

Ala Ala Ala Lys Glu Ala Ala Ala Lys Glu Ala Ala Ala Lys
        35                  40                  45

Glu Ala Ala Ala Ala Lys
    50

<210> SEQ ID NO 111
<211> LENGTH: 60
<212> TYPE: PRT
<213> ORGANISM: Artificial Sequence
<220> FEATURE:
<223> OTHER INFORMATION: Fragment

<400> SEQUENCE: 111

Glu Ala Ala Ala Ala Lys Glu Ala Ala Ala Lys Glu Ala Ala Ala
1               5                   10                  15

Ala Lys Glu Ala Ala Ala Lys Glu Ala Ala Ala Lys Glu Ala
            20                  25                  30

Ala Ala Ala Lys Glu Ala Ala Ala Lys Glu Ala Ala Ala Lys
        35                  40                  45

Glu Ala Ala Ala Lys Glu Ala Ala Ala Lys
    50                  55                  60

<210> SEQ ID NO 112
<211> LENGTH: 66
<212> TYPE: PRT
<213> ORGANISM: Artificial Sequence
<220> FEATURE:
<223> OTHER INFORMATION: Fragment

<400> SEQUENCE: 112

Glu Ala Ala Ala Ala Lys Glu Ala Ala Ala Lys Glu Ala Ala Ala
1               5                   10                  15

Ala Lys Glu Ala Ala Ala Lys Glu Ala Ala Ala Lys Glu Ala
            20                  25                  30

Ala Ala Ala Lys Glu Ala Ala Ala Lys Glu Ala Ala Ala Lys
        35                  40                  45

Glu Ala Ala Ala Lys Glu Ala Ala Ala Lys Glu Ala Ala Ala
    50                  55                  60

Ala Lys
65

<210> SEQ ID NO 113
<211> LENGTH: 72
<212> TYPE: PRT
<213> ORGANISM: Artificial Sequence
<220> FEATURE:
<223> OTHER INFORMATION: Fragment

<400> SEQUENCE: 113

Glu Ala Ala Ala Ala Lys Glu Ala Ala Ala Lys Glu Ala Ala Ala
1               5                   10                  15

Ala Lys Glu Ala Ala Ala Lys Glu Ala Ala Ala Lys Glu Ala
            20                  25                  30

Ala Ala Ala Lys Glu Ala Ala Ala Lys Glu Ala Ala Ala Lys
        35                  40                  45

Glu Ala Ala Ala Lys Glu Ala Ala Ala Lys Glu Ala Ala
    50                  55                  60

Ala Lys Glu Ala Ala Ala Ala Lys
65                  70

<210> SEQ ID NO 114
<211> LENGTH: 42
<212> TYPE: PRT
<213> ORGANISM: Artificial Sequence
<220> FEATURE:
<223> OTHER INFORMATION: Fragment

<400> SEQUENCE: 114

Lys Ala Ala Ala Ala Glu Lys Ala Ala Ala Ala Glu Lys Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Ala Glu
        35                  40

<210> SEQ ID NO 115
<211> LENGTH: 42
<212> TYPE: PRT
<213> ORGANISM: Artificial Sequence
<220> FEATURE:
<223> OTHER INFORMATION: Fragment

<400> SEQUENCE: 115

Lys Ala Ala Ala Ala Glu Lys Ala Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Ala Glu
        35                  40

<210> SEQ ID NO 116
<211> LENGTH: 48
<212> TYPE: PRT
<213> ORGANISM: Artificial Sequence
<220> FEATURE:
<223> OTHER INFORMATION: Fragment

<400> SEQUENCE: 116

Lys Ala Ala Ala Ala Glu Lys Ala Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Ala Glu Lys Ala Ala Ala Ala Glu
        35                  40                  45

<210> SEQ ID NO 117
<211> LENGTH: 54
<212> TYPE: PRT
<213> ORGANISM: Artificial Sequence
<220> FEATURE:
<223> OTHER INFORMATION: Fragment

<400> SEQUENCE: 117

Lys Ala Ala Ala Ala Glu Lys Ala Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

```
Ala Ala Ala Glu Lys Ala Ala Ala Glu Lys Ala Ala Ala Glu
        35                  40                  45

Lys Ala Ala Ala Ala Glu
    50

<210> SEQ ID NO 118
<211> LENGTH: 60
<212> TYPE: PRT
<213> ORGANISM: Artificial Sequence
<220> FEATURE:
<223> OTHER INFORMATION: Fragment

<400> SEQUENCE: 118

Lys Ala Ala Ala Ala Glu Lys Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Glu Lys Ala Ala Ala Glu
        35                  40                  45

Lys Ala Ala Ala Ala Glu Lys Ala Ala Ala Ala Glu
    50                  55                  60

<210> SEQ ID NO 119
<211> LENGTH: 66
<212> TYPE: PRT
<213> ORGANISM: Artificial Sequence
<220> FEATURE:
<223> OTHER INFORMATION: Fragment

<400> SEQUENCE: 119

Lys Ala Ala Ala Ala Glu Lys Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Glu Lys Ala Ala Ala Glu
        35                  40                  45

Lys Ala Ala Ala Ala Glu Lys Ala Ala Ala Ala Glu Lys Ala Ala Ala
    50                  55                  60

Ala Glu
65

<210> SEQ ID NO 120
<211> LENGTH: 72
<212> TYPE: PRT
<213> ORGANISM: Artificial Sequence
<220> FEATURE:
<223> OTHER INFORMATION: Fragment

<400> SEQUENCE: 120

Lys Ala Ala Ala Ala Glu Lys Ala Ala Ala Glu Lys Ala Ala Ala
1               5                   10                  15

Ala Glu Lys Ala Ala Ala Ala Glu Lys Ala Ala Ala Ala Glu Lys Ala
            20                  25                  30

Ala Ala Ala Glu Lys Ala Ala Ala Glu Lys Ala Ala Ala Glu
        35                  40                  45

Lys Ala Ala Ala Ala Glu Lys Ala Ala Ala Ala Glu Lys Ala Ala Ala
    50                  55                  60

Ala Glu Lys Ala Ala Ala Ala Glu
65                  70
```

<210> SEQ ID NO 121
<211> LENGTH: 42
<212> TYPE: PRT
<213> ORGANISM: Artificial Sequence
<220> FEATURE:
<223> OTHER INFORMATION: Fragment

<400> SEQUENCE: 121

Glu Ala Ala Ala Ala Ala Lys Glu Ala Ala Ala Ala Lys Glu Ala
1               5                   10                  15

Ala Ala Ala Ala Lys Glu Ala Ala Ala Lys Glu Ala Ala Ala
            20                  25                  30

Ala Ala Lys Glu Ala Ala Ala Ala Ala Lys
        35                  40

<210> SEQ ID NO 122
<211> LENGTH: 49
<212> TYPE: PRT
<213> ORGANISM: Artificial Sequence
<220> FEATURE:
<223> OTHER INFORMATION: Fragment

<400> SEQUENCE: 122

Glu Ala Ala Ala Ala Ala Lys Glu Ala Ala Ala Ala Lys Glu Ala
1               5                   10                  15

Ala Ala Ala Ala Lys Glu Ala Ala Ala Ala Lys Glu Ala Ala Ala
            20                  25                  30

Ala Ala Lys Glu Ala Ala Ala Ala Lys Glu Ala Ala Ala Ala
        35                  40                  45

Lys

<210> SEQ ID NO 123
<211> LENGTH: 56
<212> TYPE: PRT
<213> ORGANISM: Artificial Sequence
<220> FEATURE:
<223> OTHER INFORMATION: Fragment

<400> SEQUENCE: 123

Glu Ala Ala Ala Ala Ala Lys Glu Ala Ala Ala Ala Lys Glu Ala
1               5                   10                  15

Ala Ala Ala Ala Lys Glu Ala Ala Ala Ala Lys Glu Ala Ala Ala
            20                  25                  30

Ala Ala Lys Glu Ala Ala Ala Ala Lys Glu Ala Ala Ala Ala
        35                  40                  45

Lys Glu Ala Ala Ala Ala Ala Lys
    50                  55

<210> SEQ ID NO 124
<211> LENGTH: 63
<212> TYPE: PRT
<213> ORGANISM: Artificial Sequence
<220> FEATURE:
<223> OTHER INFORMATION: Fragment

<400> SEQUENCE: 124

Glu Ala Ala Ala Ala Ala Lys Glu Ala Ala Ala Ala Lys Glu Ala
1               5                   10                  15

Ala Ala Ala Ala Lys Glu Ala Ala Ala Ala Lys Glu Ala Ala Ala
            20                  25                  30

Ala Ala Lys Glu Ala Ala Ala Ala Ala Lys Glu Ala Ala Ala Ala Ala

```
                35                  40                  45
Lys Glu Ala Ala Ala Ala Lys Glu Ala Ala Ala Ala Lys
    50                  55                  60

<210> SEQ ID NO 125
<211> LENGTH: 70
<212> TYPE: PRT
<213> ORGANISM: Artificial Sequence
<220> FEATURE:
<223> OTHER INFORMATION: Fragment

<400> SEQUENCE: 125

Glu Ala Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Ala
            20                  25                  30

Ala Ala Lys Glu Ala Ala Ala Ala Lys Glu Ala Ala Ala Ala
        35                  40                  45

Lys Glu Ala Ala Ala Ala Lys Glu Ala Ala Ala Ala Lys Glu
    50                  55                  60

Ala Ala Ala Ala Ala Lys
65                  70

<210> SEQ ID NO 126
<211> LENGTH: 77
<212> TYPE: PRT
<213> ORGANISM: Artificial Sequence
<220> FEATURE:
<223> OTHER INFORMATION: Fragment

<400> SEQUENCE: 126

Glu Ala Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Ala
            20                  25                  30

Ala Ala Lys Glu Ala Ala Ala Ala Lys Glu Ala Ala Ala Ala
        35                  40                  45

Lys Glu Ala Ala Ala Ala Lys Glu Ala Ala Ala Ala Lys Glu
    50                  55                  60

Ala Ala Ala Ala Lys Glu Ala Ala Ala Ala Ala Lys
65                  70                  75

<210> SEQ ID NO 127
<211> LENGTH: 84
<212> TYPE: PRT
<213> ORGANISM: Artificial Sequence
<220> FEATURE:
<223> OTHER INFORMATION: Fragment

<400> SEQUENCE: 127

Glu Ala Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Ala
            20                  25                  30

Ala Ala Lys Glu Ala Ala Ala Ala Lys Glu Ala Ala Ala Ala
        35                  40                  45

Lys Glu Ala Ala Ala Ala Lys Glu Ala Ala Ala Ala Lys Glu
    50                  55                  60

Ala Ala Ala Ala Lys Glu Ala Ala Ala Ala Lys Glu Ala Ala
65                  70                  75                  80
```

Ala Ala Ala Lys

<210> SEQ ID NO 128
<211> LENGTH: 42
<212> TYPE: PRT
<213> ORGANISM: Artificial Sequence
<220> FEATURE:
<223> OTHER INFORMATION: Fragment

<400> SEQUENCE: 128

Lys Ala Ala Ala Ala Ala Glu Lys Ala Ala Ala Ala Glu Lys Ala
1               5                   10                  15

Ala Ala Ala Ala Glu Lys Ala Ala Ala Ala Glu Lys Ala Ala Ala
                20                  25                  30

Ala Ala Glu Lys Ala Ala Ala Ala Ala Glu
        35                  40

<210> SEQ ID NO 129
<211> LENGTH: 49
<212> TYPE: PRT
<213> ORGANISM: Artificial Sequence
<220> FEATURE:
<223> OTHER INFORMATION: Fragment

<400> SEQUENCE: 129

Lys Ala Ala Ala Ala Ala Glu Lys Ala Ala Ala Ala Glu Lys Ala
1               5                   10                  15

Ala Ala Ala Glu Lys Ala Ala Ala Ala Glu Lys Ala Ala Ala
                20                  25                  30

Ala Ala Glu Lys Ala Ala Ala Ala Glu Lys Ala Ala Ala Ala
        35                  40                  45

Glu

<210> SEQ ID NO 130
<211> LENGTH: 56
<212> TYPE: PRT
<213> ORGANISM: Artificial Sequence
<220> FEATURE:
<223> OTHER INFORMATION: Fragment

<400> SEQUENCE: 130

Lys Ala Ala Ala Ala Ala Glu Lys Ala Ala Ala Ala Glu Lys Ala
1               5                   10                  15

Ala Ala Ala Glu Lys Ala Ala Ala Ala Glu Lys Ala Ala Ala
                20                  25                  30

Ala Ala Glu Lys Ala Ala Ala Ala Glu Lys Ala Ala Ala Ala
        35                  40                  45

Glu Lys Ala Ala Ala Ala Ala Glu
    50                  55

<210> SEQ ID NO 131
<211> LENGTH: 63
<212> TYPE: PRT
<213> ORGANISM: Artificial Sequence
<220> FEATURE:
<223> OTHER INFORMATION: Fragment

<400> SEQUENCE: 131

Lys Ala Ala Ala Ala Ala Glu Lys Ala Ala Ala Ala Glu Lys Ala
1               5                   10                  15

Ala Ala Ala Glu Lys Ala Ala Ala Ala Glu Lys Ala Ala Ala

```
                 20                  25                  30

Ala Ala Glu Lys Ala Ala Ala Ala Glu Lys Ala Ala Ala Ala
         35                  40                  45

Glu Lys Ala Ala Ala Ala Ala Glu Lys Ala Ala Ala Ala Glu
     50                  55                  60

<210> SEQ ID NO 132
<211> LENGTH: 70
<212> TYPE: PRT
<213> ORGANISM: Artificial Sequence
<220> FEATURE:
<223> OTHER INFORMATION: Fragment

<400> SEQUENCE: 132

Lys Ala Ala Ala Ala Ala Glu Lys Ala Ala Ala Ala Glu Lys Ala
1               5                   10                  15

Ala Ala Ala Ala Glu Lys Ala Ala Ala Ala Glu Lys Ala Ala Ala
                 20                  25                  30

Ala Ala Glu Lys Ala Ala Ala Ala Glu Lys Ala Ala Ala Ala
         35                  40                  45

Glu Lys Ala Ala Ala Ala Glu Lys Ala Ala Ala Ala Glu Lys
     50                  55                  60

Ala Ala Ala Ala Ala Glu
65                  70

<210> SEQ ID NO 133
<211> LENGTH: 77
<212> TYPE: PRT
<213> ORGANISM: Artificial Sequence
<220> FEATURE:
<223> OTHER INFORMATION: Fragment

<400> SEQUENCE: 133

Lys Ala Ala Ala Ala Ala Glu Lys Ala Ala Ala Ala Glu Lys Ala
1               5                   10                  15

Ala Ala Ala Ala Glu Lys Ala Ala Ala Ala Glu Lys Ala Ala Ala
                 20                  25                  30

Ala Ala Glu Lys Ala Ala Ala Ala Glu Lys Ala Ala Ala Ala
         35                  40                  45

Glu Lys Ala Ala Ala Ala Glu Lys Ala Ala Ala Ala Glu Lys
     50                  55                  60

Ala Ala Ala Ala Glu Lys Ala Ala Ala Ala Glu
65                  70                  75

<210> SEQ ID NO 134
<211> LENGTH: 84
<212> TYPE: PRT
<213> ORGANISM: Artificial Sequence
<220> FEATURE:
<223> OTHER INFORMATION: Fragment

<400> SEQUENCE: 134

Lys Ala Ala Ala Ala Ala Glu Lys Ala Ala Ala Ala Glu Lys Ala
1               5                   10                  15

Ala Ala Ala Ala Glu Lys Ala Ala Ala Ala Glu Lys Ala Ala Ala
                 20                  25                  30

Ala Ala Glu Lys Ala Ala Ala Ala Glu Lys Ala Ala Ala Ala
         35                  40                  45

Glu Lys Ala Ala Ala Ala Glu Lys Ala Ala Ala Ala Glu Lys
     50                  55                  60
```

```
Ala Ala Ala Ala Ala Glu Lys Ala Ala Ala Ala Glu Lys Ala Ala
 65                  70                  75                  80

Ala Ala Ala Glu

<210> SEQ ID NO 135
<211> LENGTH: 8
<212> TYPE: PRT
<213> ORGANISM: Artificial Sequence
<220> FEATURE:
<223> OTHER INFORMATION: Fragment

<400> SEQUENCE: 135

Glu Ala Ala Lys Ala Ala Lys Ala
1               5

<210> SEQ ID NO 136
<211> LENGTH: 8
<212> TYPE: PRT
<213> ORGANISM: Artificial Sequence
<220> FEATURE:
<223> OTHER INFORMATION: Fragment

<400> SEQUENCE: 136

Ala Lys Ala Ala Lys Ala Ala Glu
1               5

<210> SEQ ID NO 137
<211> LENGTH: 73
<212> TYPE: PRT
<213> ORGANISM: Artificial Sequence
<220> FEATURE:
<223> OTHER INFORMATION: Fusion molecule
<220> FEATURE:
<221> NAME/KEY: Xaa
<222> LOCATION: (37)..(37)
<223> OTHER INFORMATION: Any amino acid sequence

<400> SEQUENCE: 137

Glu Ala Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Lys
                20                  25                  30

Ala Ala Lys Ala Xaa Ala Lys Ala Ala Lys Ala Glu Lys Ala Ala
            35                  40                  45

Ala Ala Ala Glu Lys Ala Ala Ala Ala Glu Lys Ala Ala Ala Ala
        50                  55                  60

Ala Glu Lys Ala Ala Ala Ala Ala Glu
 65                  70

<210> SEQ ID NO 138
<211> LENGTH: 30
<212> TYPE: PRT
<213> ORGANISM: Artificial Sequence
<220> FEATURE:
<223> OTHER INFORMATION: Fragment

<400> SEQUENCE: 138

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys
                20                  25                  30

<210> SEQ ID NO 139
```

```
<211> LENGTH: 30
<212> TYPE: PRT
<213> ORGANISM: Artificial Sequence
<220> FEATURE:
<223> OTHER INFORMATION: Fragment

<400> SEQUENCE: 139

Lys Ala Ala Ala Glu Lys Ala Ala Ala Glu Lys Ala Ala Ala Glu Lys
1               5                   10                  15

Ala Ala Ala Glu Lys Ala Ala Ala Glu Lys Ala Ala Ala Glu
            20                  25                  30

<210> SEQ ID NO 140
<211> LENGTH: 63
<212> TYPE: PRT
<213> ORGANISM: Artificial Sequence
<220> FEATURE:
<223> OTHER INFORMATION: Fusion molecule

<400> SEQUENCE: 140

Glu Ala Ala Ala Lys Glu Ala Ala Ala Lys Glu Ala Ala Ala Lys Glu
1               5                   10                  15

Ala Ala Ala Lys Glu Ala Ala Lys Glu Ala Ala Ala Lys Ser Gly
            20                  25                  30

Ser Lys Ala Ala Ala Glu Lys Ala Ala Ala Glu Lys Ala Ala Ala Glu
        35                  40                  45

Lys Ala Ala Ala Glu Lys Ala Ala Ala Glu Lys Ala Ala Ala Glu
    50                  55                  60

<210> SEQ ID NO 141
<211> LENGTH: 36
<212> TYPE: PRT
<213> ORGANISM: Artificial Sequence
<220> FEATURE:
<223> OTHER INFORMATION: Fragment

<400> SEQUENCE: 141

Glu Ala Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Lys
            20                  25                  30

Ala Ala Lys Ala
        35

<210> SEQ ID NO 142
<211> LENGTH: 75
<212> TYPE: PRT
<213> ORGANISM: Artificial Sequence
<220> FEATURE:
<223> OTHER INFORMATION: Fusion molecule

<400> SEQUENCE: 142

Glu Ala Ala Ala Ala Lys Glu Ala Ala Ala Ala Lys Glu Ala
1               5                   10                  15

Ala Ala Ala Lys Glu Ala Ala Ala Ala Lys Glu Ala Ala Lys
            20                  25                  30

Ala Ala Lys Ala Ser Gly Ser Ala Lys Ala Ala Lys Ala Ala Glu Lys
        35                  40                  45

Ala Ala Ala Ala Ala Glu Lys Ala Ala Ala Ala Glu Lys Ala Ala
    50                  55                  60

Ala Ala Ala Glu Lys Ala Ala Ala Ala Ala Glu
65                  70                  75
```

<210> SEQ ID NO 143
<211> LENGTH: 264
<212> TYPE: PRT
<213> ORGANISM: Artificial Sequence
<220> FEATURE:
<223> OTHER INFORMATION: Fusion molecule

<400> SEQUENCE: 143

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Asp Tyr Tyr Asp Ser Ser Gly Tyr Tyr Pro Ile Asp
            100                 105                 110

Ala Phe Asp Ile Trp Gly Gln Gly Thr Thr Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Ala Ser Val Ser Ala Ser Pro Gly Gln Ser Ile
145                 150                 155                 160

Thr Ile Ser Cys Thr Gly Thr Ser Ser Asp Val Gly Ala Tyr Asp Trp
                165                 170                 175

Val Ser Trp Tyr Gln Gln His Pro Gly Lys Ala Pro Lys Leu Leu Ile
            180                 185                 190

Phe Asp Val Asn Asn Arg Pro Ser Gly Val Ser His Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Ala Ser Ala Thr Leu Leu Asp Thr
225                 230                 235                 240

Tyr Val Phe Gly Thr Gly Thr Lys Val Thr Val Leu Gly Asp Gln Glu
                245                 250                 255

Pro Lys Ser Ser Asp Lys Thr His
            260

<210> SEQ ID NO 144
<211> LENGTH: 70
<212> TYPE: PRT
<213> ORGANISM: Artificial Sequence
<220> FEATURE:
<223> OTHER INFORMATION: Binding fragment

<400> SEQUENCE: 144

Met Gly Ser Ser His His His His His His Leu Gln Val Asp Asn Lys
1               5                   10                  15

Phe Asn Lys Glu Met Arg Asn Ala Tyr Trp Glu Ile Ala Leu Leu Pro
            20                  25                  30

Asn Leu Asn Asn Gln Gln Lys Arg Ala Phe Ile Arg Ser Leu Tyr Asp

```
              35                  40                  45

Asp Pro Ser Gln Ser Ala Asn Leu Leu Ala Glu Ala Lys Lys Leu Asn
    50                  55                  60

Asp Ala Gln Ala Pro Lys
65                  70

<210> SEQ ID NO 145
<211> LENGTH: 12
<212> TYPE: PRT
<213> ORGANISM: Artificial Sequence
<220> FEATURE:
<223> OTHER INFORMATION: Fragment

<400> SEQUENCE: 145

Met Gly Ser Ser His His His His His His Leu Gln
1               5                   10

<210> SEQ ID NO 146
<211> LENGTH: 35
<212> TYPE: PRT
<213> ORGANISM: Artificial Sequence
<220> FEATURE:
<223> OTHER INFORMATION: Binding fragment

<400> SEQUENCE: 146

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr
        35

<210> SEQ ID NO 147
<211> LENGTH: 23
<212> TYPE: PRT
<213> ORGANISM: Artificial Sequence
<220> FEATURE:
<223> OTHER INFORMATION: Fragment

<400> SEQUENCE: 147

Asp Asp Pro Ser Gln Ser Ala Asn Leu Leu Ala Glu Ala Lys Lys Leu
1               5                   10                  15

Asn Asp Ala Gln Ala Pro Lys
            20

<210> SEQ ID NO 148
<211> LENGTH: 90
<212> TYPE: PRT
<213> ORGANISM: Artificial Sequence
<220> FEATURE:
<223> OTHER INFORMATION: Fusion molecule

<400> SEQUENCE: 148

Met Gly Ser Ser His His His His His His Leu Gln Val Asp Asn Lys
1               5                   10                  15

Phe Asn Lys Glu Met Arg Asn Ala Tyr Trp Glu Ile Ala Leu Leu Pro
            20                  25                  30

Asn Leu Asn Asn Gln Gln Lys Arg Ala Phe Ile Arg Ser Leu Tyr Asp
        35                  40                  45

Asp Pro Ser Gln Ser Ala Asn Leu Leu Ala Glu Ala Lys Leu Asn Asp
    50                  55                  60

Leu Leu Pro Asn Leu Asn Asn Gln Ser Ala Asn Leu Leu Ala Glu Ala
```

```
                65                  70                  75                  80

Lys Glu Leu Asn Asp Ala Gln Ala Pro Lys
                85                  90

<210> SEQ ID NO 149
<211> LENGTH: 28
<212> TYPE: PRT
<213> ORGANISM: Artificial Sequence
<220> FEATURE:
<223> OTHER INFORMATION: Fragment

<400> SEQUENCE: 149

Asn Asp Leu Leu Pro Asn Leu Asn Asn Gln Ser Ala Asn Leu Leu Ala
1               5                   10                  15

Glu Ala Lys Glu Leu Asn Asp Ala Gln Ala Pro Lys
            20                  25

<210> SEQ ID NO 150
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: the sequence (Glu Ala Ala Ala Lys) can be
      repeated n times, wherein n is the number of repeats ranging from
      6 to 12

<400> SEQUENCE: 150

Glu Ala Ala Ala Lys
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: the sequence (Lys Ala Ala Ala Glu) can be
      repeated n times, wherein n is the number of repeats ranging from
      6 to 12

<400> SEQUENCE: 151

Lys Ala Ala Ala Glu
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: the sequence (Glu Ala Ala Ala Ala Lys) can be
      repeated n times, wherein n is the number of repeats ranging from
      6 to 12

<400> SEQUENCE: 152

Glu Ala Ala Ala Ala Lys
1               5
```

```
<210> SEQ ID NO 153
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: the sequence (Lys Ala Ala Ala Ala Glu) can be
      repeated n times, wherein n is the number of repeats ranging from
      6 to 12

<400> SEQUENCE: 153

Lys Ala Ala Ala Ala Glu
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: the sequence (Glu Ala Ala Ala Ala Ala Lys) can
      be repeated n times, wherein n is the number of repeats ranging
      from 6 to 12

<400> SEQUENCE: 154

Glu Ala Ala Ala Ala Ala Lys
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: the sequence (Lys Ala Ala Ala Ala Ala Glu) can
      be repeated n times, wherein n is the number of repeats ranging
      from 6 to 12

<400> SEQUENCE: 155

Lys Ala Ala Ala Ala Ala Glu
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positive charged at
      physiological pH condition
<220> FEATURE:
<221> NAME/KEY: MISC_FEATURE
<222> LOCATION: (1)..(5)
<223> OTHER INFORMATION: the sequence (Xaa Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (5)..(5)
<223> OTHER INFORMATION: Xaa is negatively or positive charged at
      physiological pH condition
```

<400> SEQUENCE: 156

Xaa Ala Ala Ala Xaa
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positively charged at
      physiological pH condition
<220> FEATURE:
<221> NAME/KEY: MISC_FEATURE
<222> LOCATION: (1)..(6)
<223> OTHER INFORMATION: the sequence (Xaa Ala Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (6)..(6)
<223> OTHER INFORMATION: Xaa is negatively or positively charged at
      physiological pH condition

<400> SEQUENCE: 157

Xaa Ala Ala Ala Ala Xaa
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positively charged at
      physiological pH condition
<220> FEATURE:
<221> NAME/KEY: MISC_FEATURE
<222> LOCATION: (1)..(7)
<223> OTHER INFORMATION: the sequence (Xaa Ala Ala Ala Ala Ala Xaa) can
      be repeated n times, wherein n is an integer selected from 1, 2,
      3, 4, 5, 6, 7, 8, 9, 10, 11, 12, 13, and 14
<220> FEATURE:
<221> NAME/KEY: MISC_FEATURE
<222> LOCATION: (7)..(7)
<223> OTHER INFORMATION: Xaa is negatively or positively charged at
      physiological pH condition

<400> SEQUENCE: 158

Xaa Ala Ala Ala Ala Ala Xaa
1               5

<210> SEQ ID NO 159
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is hydrophilic at physiological pH
<220> FEATURE:
<221> NAME/KEY: MISC_FEATURE
<222> LOCATION: (1)..(5)
<223> OTHER INFORMATION: the sequence (Xaa Ala Ala Ala Xaa) can be

```
       repeated n times, wherein n is an integer selected from 1, 2, 3,
       4, 5, 6, 7, 8, 9, 10, 11, 12, 13, and 14
<220> FEATURE:
<221> NAME/KEY: MISC_FEATURE
<222> LOCATION: (5)..(5)
<223> OTHER INFORMATION: Xaa is hydrophilic at physiological pH
<220> FEATURE:
<221> NAME/KEY: MISC_FEATURE
<222> LOCATION: (6)..(6)
<223> OTHER INFORMATION: Xaa is negatively or positively charged at
       physiological pH
<220> FEATURE:
<221> NAME/KEY: MISC_FEATURE
<222> LOCATION: (6)..(10)
<223> OTHER INFORMATION: the sequence (Xaa Ala Ala Ala Xaa) can be
       repeated n times, wherein n is an integer selected from 1, 2, 3,
       4, 5, 6, 7, 8, 9, 10, 11, 12, 13, and 14
<220> FEATURE:
<221> NAME/KEY: MISC_FEATURE
<222> LOCATION: (10)..(10)
<223> OTHER INFORMATION: Xaa is negatively or positively charged at
       physiological pH

<400> SEQUENCE: 159

Xaa Ala Ala Ala Xaa Xaa Ala Ala Ala Xaa
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positive charged at
       physiological pH condition
<220> FEATURE:
<221> NAME/KEY: MISC_FEATURE
<222> LOCATION: (1)..(5)
<223> OTHER INFORMATION: the sequence (Xaa Ala Ala Ala Xaa) can be
       repeated n times, wherein n is an integer selected from 1, 2, 3,
       4, 5, 6, 7, 8, 9, 10, 11, 12, 13, and 14
<220> FEATURE:
<221> NAME/KEY: MISC_FEATURE
<222> LOCATION: (5)..(5)
<223> OTHER INFORMATION: Xaa is negatively or positive charged at
       physiological pH condition
<220> FEATURE:
<221> NAME/KEY: MISC_FEATURE
<222> LOCATION: (6)..(6)
<223> OTHER INFORMATION: Xaa is hydrophilic at physiological pH
<220> FEATURE:
<221> NAME/KEY: MISC_FEATURE
<222> LOCATION: (6)..(10)
<223> OTHER INFORMATION: the sequence (Xaa Ala Ala Ala Xaa) can be
       repeated n times, wherein n is an integer selected from 1, 2, 3,
       4, 5, 6, 7, 8, 9, 10, 11, 12, 13, and 14
<220> FEATURE:
<221> NAME/KEY: MISC_FEATURE
<222> LOCATION: (10)..(10)
<223> OTHER INFORMATION: Xaa is hydrophilic at physiological pH

<400> SEQUENCE: 160

Xaa Ala Ala Ala Xaa Xaa Ala Ala Ala Xaa
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa is hydrophilic at physiological pH
<220> FEATURE:
<221> NAME/KEY: MISC_FEATURE
<222> LOCATION: (1)..(6)
<223> OTHER INFORMATION: the sequence (Xaa Ala Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (6)..(6)
<223> OTHER INFORMATION: Xaa is hydrophilic at physiological pH
<220> FEATURE:
<221> NAME/KEY: MISC_FEATURE
<222> LOCATION: (7)..(7)
<223> OTHER INFORMATION: Xaa is negatively or positively charged at
      physiological pH condition
<220> FEATURE:
<221> NAME/KEY: MISC_FEATURE
<222> LOCATION: (7)..(12)
<223> OTHER INFORMATION: the sequence (Xaa Ala Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (12)..(12)
<223> OTHER INFORMATION: Xaa is negatively or positively charged at
      physiological pH condition

<400> SEQUENCE: 161

Xaa Ala Ala Ala Ala Xaa Xaa Ala Ala Ala Ala Xaa
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positively charged at
      physiological pH condition
<220> FEATURE:
<221> NAME/KEY: MISC_FEATURE
<222> LOCATION: (1)..(6)
<223> OTHER INFORMATION: the sequence (Xaa Ala Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (6)..(6)
<223> OTHER INFORMATION: Xaa is negatively or positively charged at
      physiological pH condition
<220> FEATURE:
<221> NAME/KEY: MISC_FEATURE
<222> LOCATION: (7)..(7)
<223> OTHER INFORMATION: Xaa is hydrophilic charged at physiological pH
<220> FEATURE:
<221> NAME/KEY: MISC_FEATURE
<222> LOCATION: (7)..(12)
<223> OTHER INFORMATION: the sequence (Xaa Ala Ala Ala Ala Xaa) can be
      repeated n times, wherein n is an integer selected from 1, 2, 3,
      4, 5, 6, 7, 8, 9, 10, 11, 12, 13, and 14
<220> FEATURE:
<221> NAME/KEY: MISC_FEATURE
<222> LOCATION: (12)..(12)
<223> OTHER INFORMATION: Xaa is hydrophilic charged at physiological pH

<400> SEQUENCE: 162

Xaa Ala Ala Ala Ala Xaa Xaa Ala Ala Ala Ala Xaa
1               5                   10
```

```
<210> SEQ ID NO 163
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is hydrophilic at physiological pH
      condition
<220> FEATURE:
<221> NAME/KEY: MISC_FEATURE
<222> LOCATION: (1)..(7)
<223> OTHER INFORMATION: the sequence (Xaa Ala Ala Ala Ala Ala Xaa) can
      be repeated n times, wherein n is an integer selected from 1, 2,
      3, 4, 5, 6, 7, 8, 9, 10, 11, 12, 13, and 14
<220> FEATURE:
<221> NAME/KEY: MISC_FEATURE
<222> LOCATION: (7)..(7)
<223> OTHER INFORMATION: Xaa is hydrophilic at physiological pH
<220> FEATURE:
<221> NAME/KEY: MISC_FEATURE
<222> LOCATION: (8)..(8)
<223> OTHER INFORMATION: Xaa is negatively or positively charged at
      physiological pH condition
<220> FEATURE:
<221> NAME/KEY: MISC_FEATURE
<222> LOCATION: (8)..(14)
<223> OTHER INFORMATION: the sequence (Xaa Ala Ala Ala Ala Ala Xaa) can
      be repeated n times, wherein n is an integer selected from 1, 2,
      3, 4, 5, 6, 7, 8, 9, 10, 11, 12, 13, and 14
<220> FEATURE:
<221> NAME/KEY: MISC_FEATURE
<222> LOCATION: (14)..(14)
<223> OTHER INFORMATION: Xaa is negatively or positively charged at
      physiological pH condition

<400> SEQUENCE: 163

Xaa Ala Ala Ala Ala Ala Xaa Xaa Ala Ala Ala Ala Ala Xaa
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is negatively or positively charged at
      physiological pH condition
<220> FEATURE:
<221> NAME/KEY: MISC_FEATURE
<222> LOCATION: (1)..(7)
<223> OTHER INFORMATION: the sequence (Xaa Ala Ala Ala Ala Ala Xaa) can
      be repeated n times, wherein n is an integer selected from 1, 2,
      3, 4, 5, 6, 7, 8, 9, 10, 11, 12, 13, and 14
<220> FEATURE:
<221> NAME/KEY: MISC_FEATURE
<222> LOCATION: (7)..(7)
<223> OTHER INFORMATION: Xaa is negatively or positively charged at
      physiological pH condition
<220> FEATURE:
<221> NAME/KEY: MISC_FEATURE
<222> LOCATION: (8)..(8)
<223> OTHER INFORMATION: Xaa is hydrophilic at physiological pH
<220> FEATURE:
<221> NAME/KEY: MISC_FEATURE
<222> LOCATION: (8)..(14)
<223> OTHER INFORMATION: the sequence (Xaa Ala Ala Ala Ala Ala Xaa) can
      be repeated n times, wherein n is an integer selected from 1, 2,
      3, 4, 5, 6, 7, 8, 9, 10, 11, 12, 13, and 14
<220> FEATURE:
<221> NAME/KEY: MISC_FEATURE
<222> LOCATION: (14)..(14)
```

-continued

```
<223> OTHER INFORMATION: Xaa is hydrophilic at physiological pH

<400> SEQUENCE: 164

Xaa Ala Ala Ala Ala Xaa Xaa Ala Ala Ala Ala Xaa
1               5                   10
```